(12) United States Patent
Schilling et al.

(10) Patent No.: US 8,338,120 B2
(45) Date of Patent: Dec. 25, 2012

(54) METHOD OF TREATING INFLAMMATION WITH GLUTAMINYL CYCLASE INHIBITORS

(75) Inventors: Stephan Schilling, Halle/Saale (DE); Holger Cynis, Halle/Saale (DE); Torsten Hoffman, Halle/Saale (DE); Hans-Ulrich Demuth, Halle/Saale (DE)

(73) Assignee: Probiodrug AG, Halle (Saale) (DE)

( * ) Notice: Subject to any disclaimer, the term of this patent is extended or adjusted under 35 U.S.C. 154(b) by 0 days.

(21) Appl. No.: 12/039,066

(22) Filed: Feb. 28, 2008

(65) Prior Publication Data

US 2009/0068699 A1 Mar. 12, 2009

Related U.S. Application Data

(63) Continuation-in-part of application No. 11/685,881, filed on Mar. 14, 2007, now Pat. No. 7,732,162, which is a continuation-in-part of application No. 10/839,017, filed on May 5, 2004, now Pat. No. 7,381,537.

(60) Provisional application No. 60/892,265, filed on Mar. 1, 2007, provisional application No. 60/512,038, filed on Oct. 15, 2003, provisional application No. 60/468,014, filed on May 5, 2003, provisional application No. 60/468,043, filed on May 5, 2003.

(51) Int. Cl.
*C12Q 1/34* (2006.01)

(52) U.S. Cl. .......................................... 435/18

(58) Field of Classification Search .................. 435/69.2, 435/18
See application file for complete search history.

(56) References Cited

U.S. PATENT DOCUMENTS

| | | | |
|---|---|---|---|
| 5,100,909 A | 3/1992 | Moon et al. | |
| 7,381,537 B2* | 6/2008 | Demuth et al. | 435/18 |
| 2003/0166644 A1 | 9/2003 | Ebdrup et al. | |
| 2004/0224875 A1 | 11/2004 | Schilling et al. | |
| 2007/0191366 A1 | 8/2007 | Hoffmann et al. | |
| 2008/0286231 A1* | 11/2008 | Buchholz et al. | 424/85.2 |
| 2009/0068699 A1* | 3/2009 | Schilling et al. | 435/29 |

FOREIGN PATENT DOCUMENTS

| | | |
|---|---|---|
| WO | WO 97-43278 | 11/1997 |
| WO | WO 02-096869 | 12/2002 |
| WO | WO 03-022273 | 3/2003 |
| WO | 2004098591 | 11/2004 |
| WO | 2005039548 | 5/2005 |
| WO | 2005049027 | 6/2005 |
| WO | 2005075436 | 8/2005 |

OTHER PUBLICATIONS

Buchholz et al., The First Potent Inhibitors for Human Glutaminyl Cyclase: Synthesis and Structure—Activity Relationship, J Medicinal Chemistry 2006, 49, 664-677.
Bhatia et al., Treatment with bindarit, a blocker of MMP-1 synthesis, protects mice against acute pancreatitis, Am J Physiol Gastrointest Liver Physiol, 2005, pp. G1259-G1265, vol. 288.
European Office Action dated Jun. 6, 2011 in related Application No. 08717208.6, 7 pages.
Galimberti et al., Serum MCP-1 levels are increased in mild cognitive impairment and mild Alzheimer's disease, Neurobiology of Aging, 2006, pp. 1763-1768, vol. 27.
Marra, Renaming cytokines: MCP-1, Major Chemokine in Pancreatitis, Gut, 2005, pp. 1679-1681, vol. 54, No. 12.
Mori et al., Essential Role of Monocyte Chemoattractant Protein-1 in Development of Restenotic Changes (Neointimal Hyperplasia and Constrictive Remodeling) After Balloon Angioplasty in Hypercholesterolemic Rabbits, Circulation, 2002, pp. 1763-1768, vol. 105, No. 24.
Schilling et al., Glutaminyl cyclases unfold glutaminyl cyclase activity under mild acid conditions, FEBS Letters, 2004, pp. 191-196, vol. 563.

* cited by examiner

*Primary Examiner* — Ralph Gitomer
(74) *Attorney, Agent, or Firm* — SNR Denton US LLP

(57) ABSTRACT

Provided herein are methods for the treatment and/or prevention of an inflammatory disease or disorder through administration of an inhibitor of a glutaminyl peptide cyclotransferase. Inflammatory diseases or disorders treated or prevented by methods disclosed herein include mild cognitive impairment (MCI), rheumatoid arthritis, atherosclerosis, restenosis and pancreatitis.

16 Claims, 49 Drawing Sheets

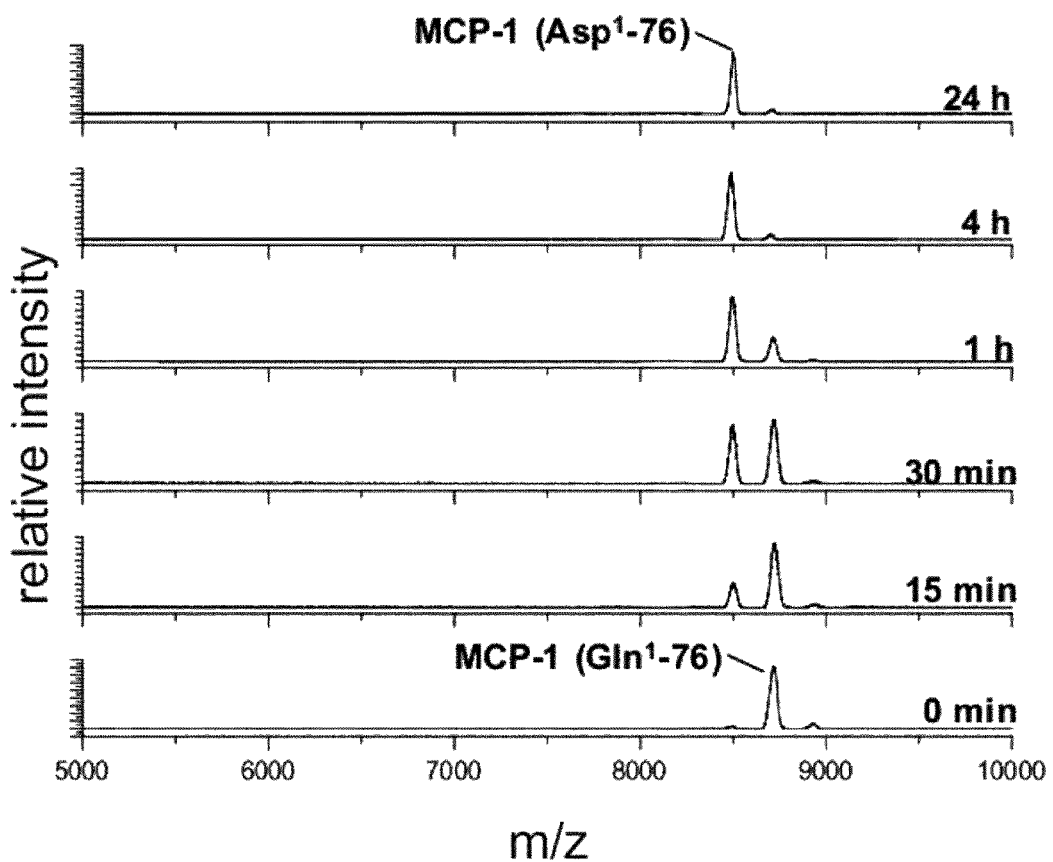

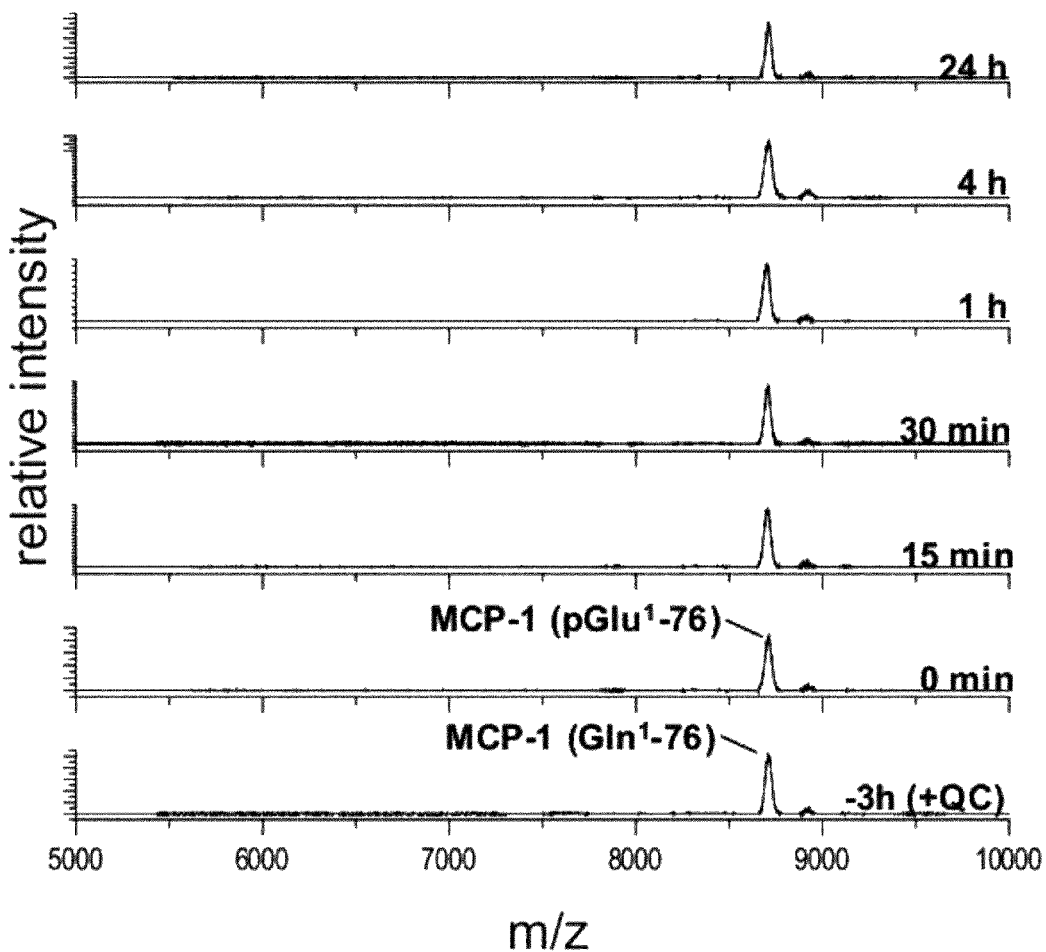

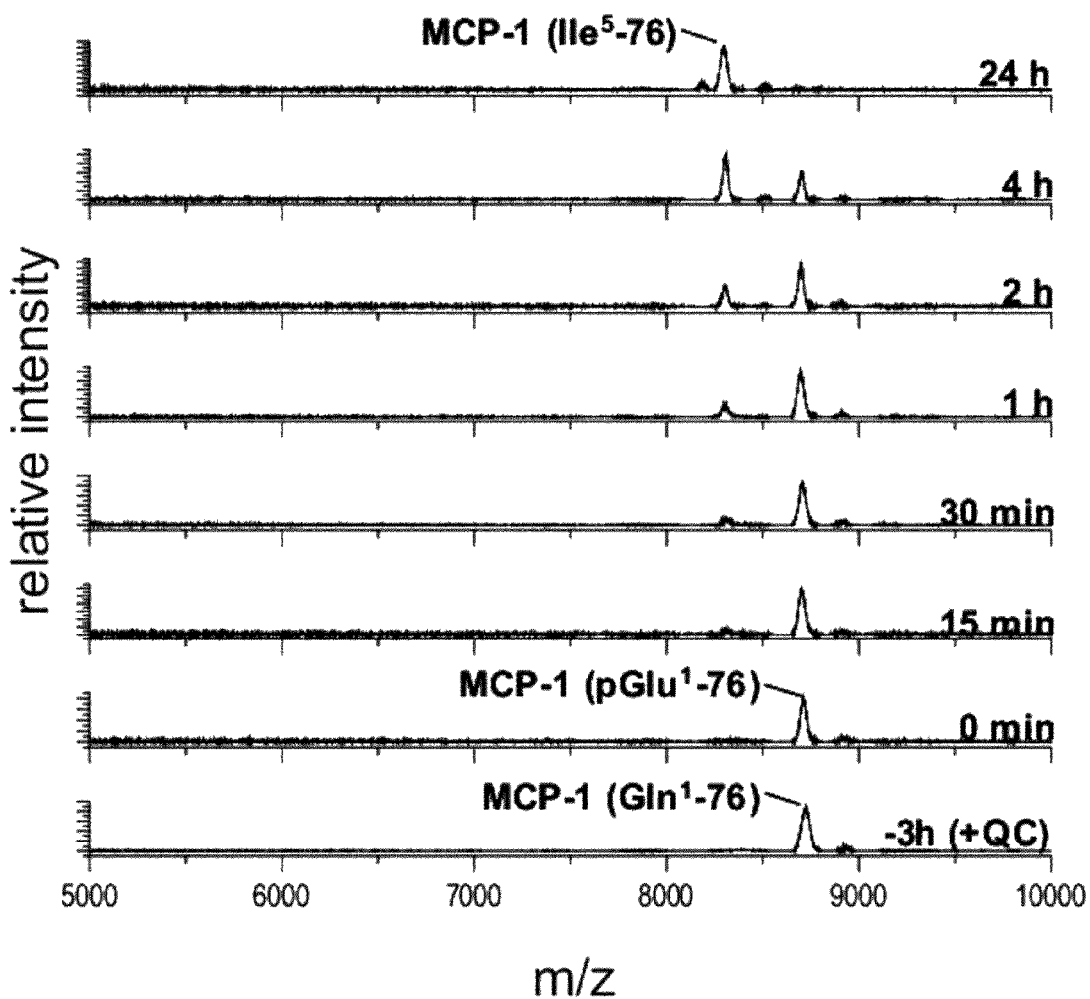

Figure 5A

```
                              ATGAAAGTCTCTGCCGCCCTTCTGTGCCT
                              :::::::::::::::::::::::::::::
                              ATGAAAGTCTCTGCCGCCCTTCTGTGCCT

GCTGCTCATAGCAGCCACCTTCATTCCCCAAGGGCTCGCTCAGCCAGATGCAATCAATGC
::::::::::::::::::::::::::::::::::::::::::::::::::::::::::::
GCTGCTCATAGCAGCCACCTTCATTCCCCAAGGGCTCGCTCAGCCAGATGCAATCAATGC

CCCAGTCACCTGCTGCTATAACTTCACCAATAGGAAGATCTCAGTGCAGAGGCTCGCGAG
:::::::::::::::: :::::::::::::::::::::::::::::::::::::::::::
CCCAGTCACCTGCTGTTATAACTTCACCAATAGGAAGATCTCAGTGCAGAGGCTCGCGAG

CTATAGAAGAATCACCAGCAGCAAGTGTCCCAAAGAAGCTGTGATCTTCAAGACCATTGT
::::::::::::::::::::::::::::::::::::::::::::::::::::::::::::
CTATAGAAGAATCACCAGCAGCAAGTGTCCCAAAGAAGCTGTGATCTTCAAGACCATTGT

GGCCAAGGAGATCTGTGCTGACCCCAAGCAGAAGTGGGTTCAGGATTCCATGGACCACCT
::::::::::::::::::::::::::::::::::::::::::::::::::::::::::::
GGCCAAGGAGATCTGTGCTGACCCCAAGCAGAAGTGGGTTCAGGATTCCATGGACCACCT

GGACAAGCAAACCCAAACTCCGAAGACTTGA
:::::::::::::::::::::::::::::::
GGACAAGCAAACCCAAACTCCGAAGACTTGA
```

Figure 5B

SY5Y       MKVSAALLCLLLIAATFIPQGLAQPDAINAPVTCCYNFTNRKISVQRL
WT         MKVSAALLCLLLIAATFIPQGLAQPDAINAPVTCCYNFTNRKISVQRL
           ************************************************

SY5Y       ASYRRITSSKCPKEAVIFKTIVAKEICADPKQKWVQDSMDHLDKQTQTPKT
WT         ASYRRITSSKCPKEAVIFKTIVAKEICADPKQKWVQDSMDHLDKQTQTPKT
           **************************************************

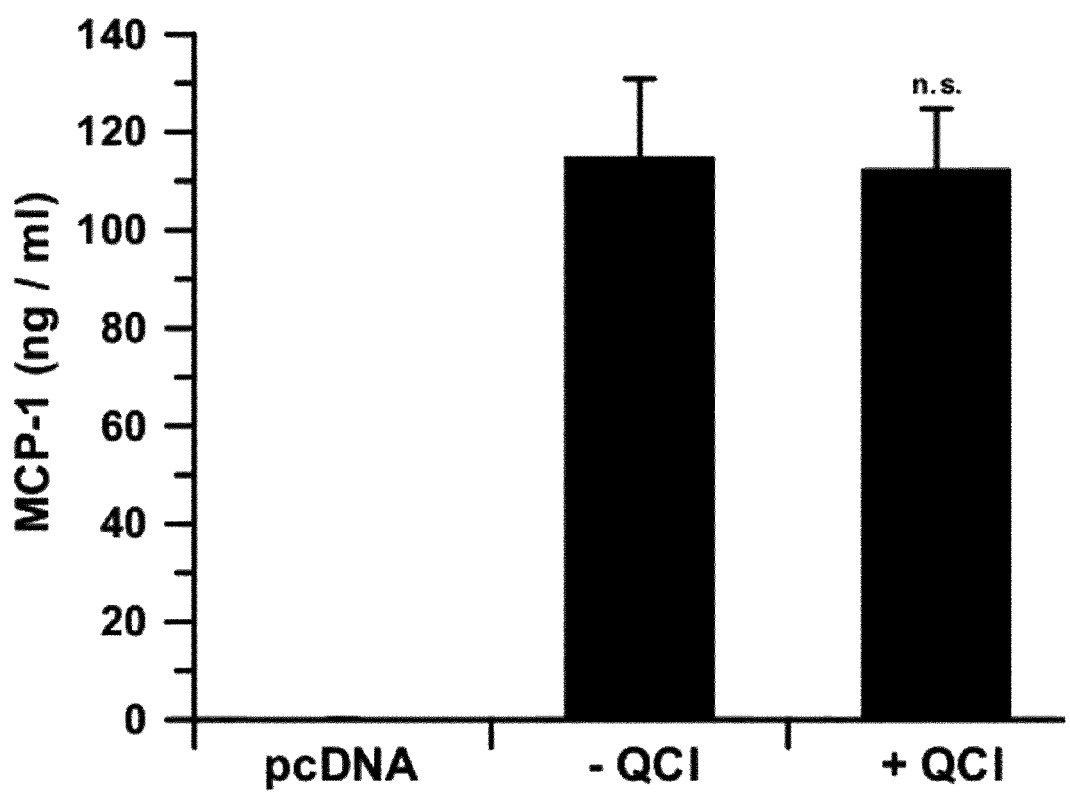

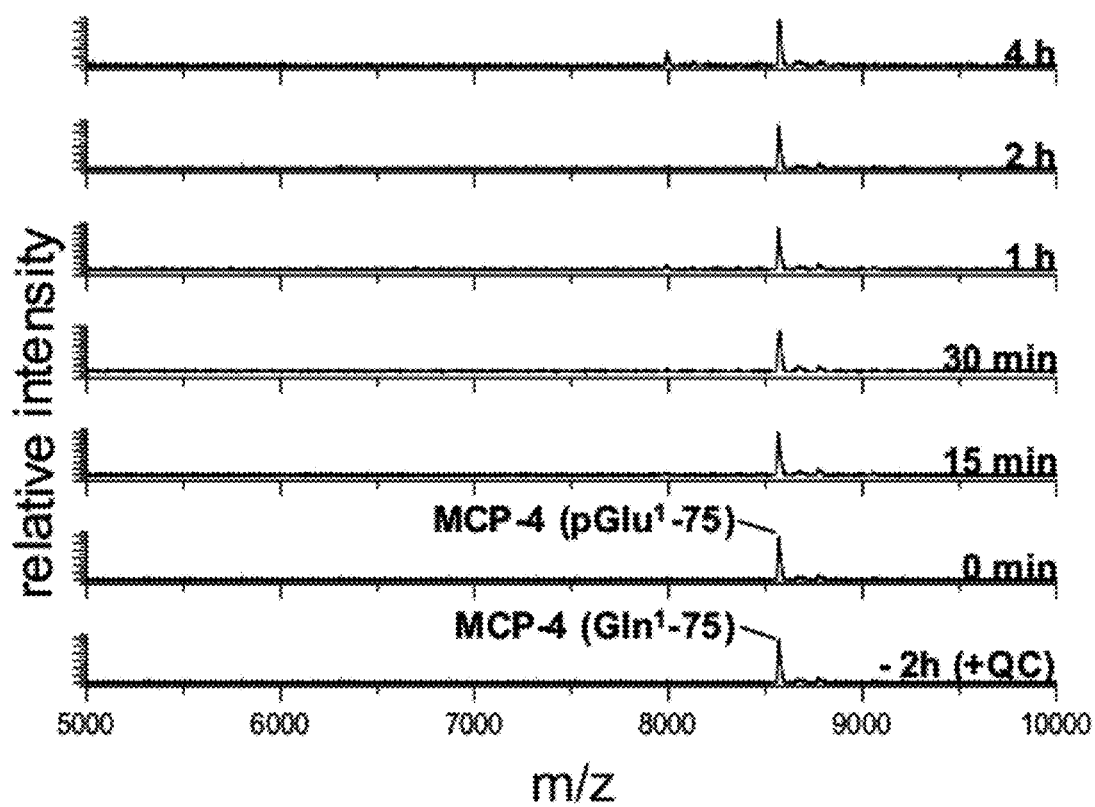

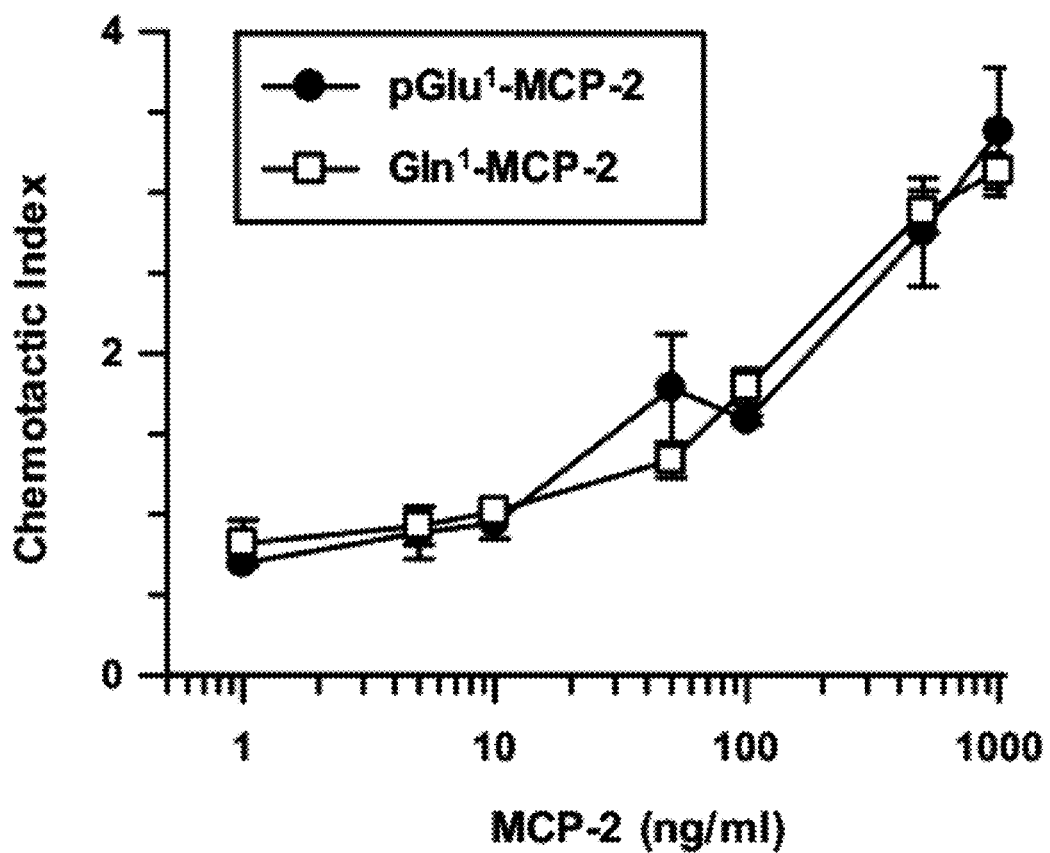

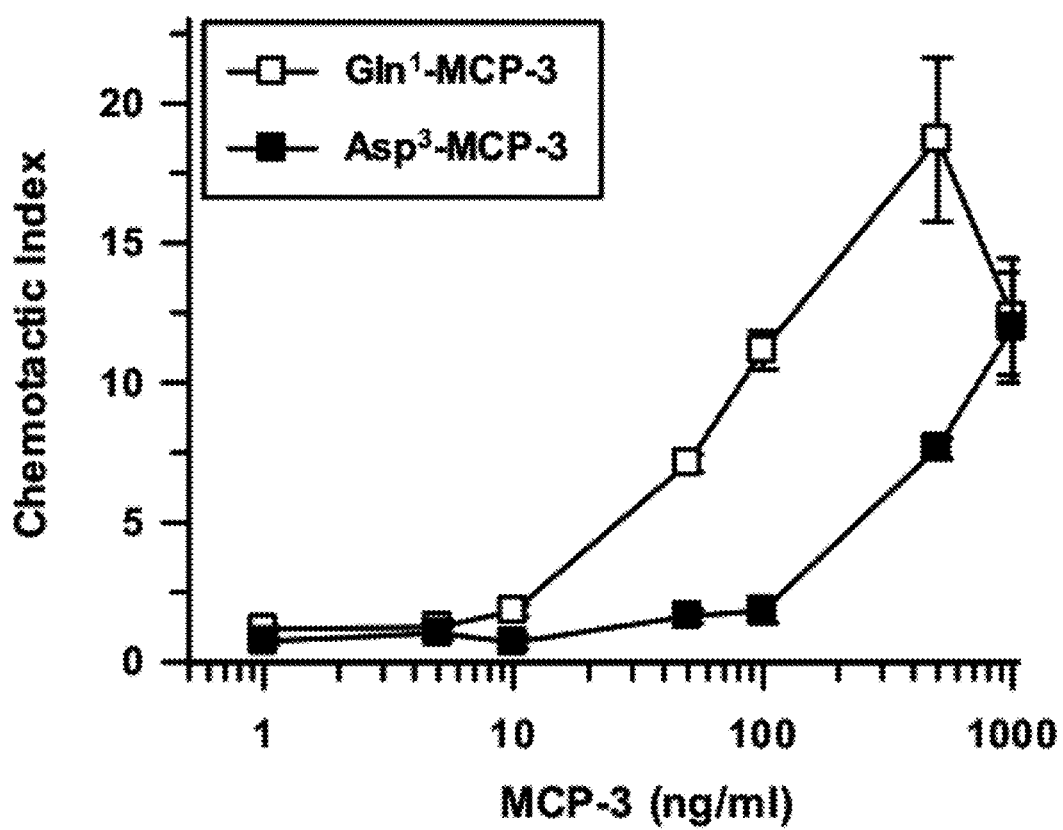

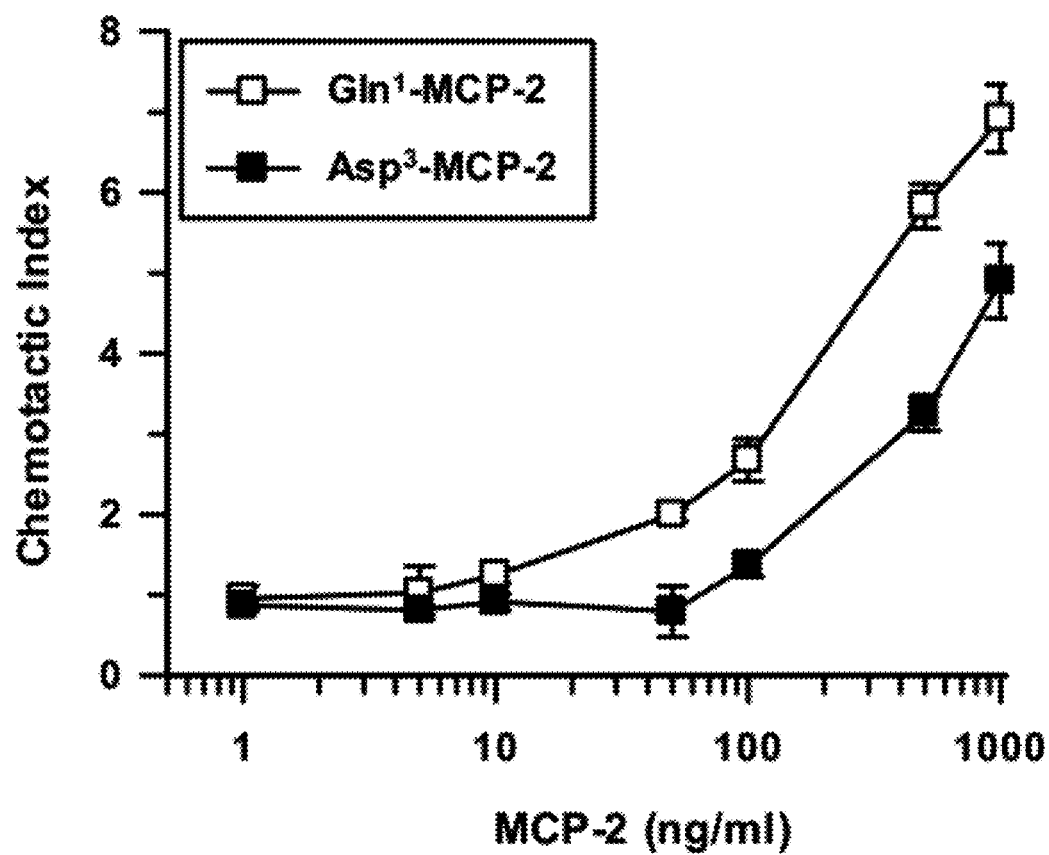

METHOD OF TREATING INFLAMMATION WITH GLUTAMINYL CYCLASE INHIBITORS

RELATED APPLICATIONS AND INCORPORATION BY REFERENCE

The present application is a continuation in part of U.S. patent application Ser. No. 11/685,881, filed Mar. 14, 2007 (claiming priority to U.S. Provisional Application Ser. No. 60/892,265, filed Mar. 1, 2007), issued as U.S. Pat. No. 7,732,162 on Jun. 8, 2010, which is a continuation in part of U.S. patent application Ser. No. 10/839,017, filed May 5, 2004 (claiming priority to U.S. Provisional Application Ser. No. 60/512,038, filed Oct. 15, 2003; U.S. Provisional Application Ser. No. 60/468,014, filed May 5, 2003; and U.S. Provisional Application Ser. No. 60/468,043, filed May 5, 2003), issued as U.S. Pat. No. 7,381,537 on Jun. 3, 2008, which are fully incorporated herein by reference to the extent permitted by law.

The present application also is a continuation in part of U.S. patent application Ser. No. 11/685,881, filed Mar. 14, 2007, fully incorporated herein by reference to the extent permitted by law. U.S. patent application Ser. No. 11/685,881 is a continuation in part of U.S. patent application Ser. No. 10/839,017.

This application also claims priority to United State Provisional Application 60/892,265, filed Mar. 1, 2007.

SEQUENCE LISTING

The accompanying sequence listing is fully incorporated herein by reference for all purposes.

BACKGROUND OF THE INVENTION

The present invention relates in general to an inhibitor of a glutaminyl peptide cyclotransferase, and the use thereof for the treatment and/or prevention of a disease or disorder selected from the group consisting of rheumatoid arthritis, atherosclerosis, restenosis, lung fibrosis, liver fibrosis, renal fibrosis, pancreatitis, mild cognitive impairment, Alzheimer's disease, neurodegeneration in Down Syndrome, Familial British Dementia, Familial Danish Dementia, neuropathic pain, graft rejection/graft failure/graft vasculopathy, hypertension, HIV infections/AIDS, gestosis, cancer/hemangioendothelioma proliferation, tuberous sclerosis, and gastric carcinomas.

Further, the present invention pertains to diagnostic kits and methods based on the use of a glutaminyl cyclase inhibitor.

Glutaminyl cyclase (QC, EC 2.3.2.5) catalyzes the intramolecular cyclization of N-terminal glutaminyl residues into pyroglutamic acid (5-oxo-proline, pGlu*) under liberation of ammonia and the intramolecular cyclization of N-terminal glutamyl residues into pyroglutamic acid under liberation of water.

A QC was first isolated by Messer from the Latex of the tropical plant *Carica papaya* in 1963 (Messer, M. 1963 Nature 4874, 1299). 24 years later, a corresponding enzymatic activity was discovered in animal pituitary (Busby, W. H. J. et al. 1987 *J Biol Chem* 262, 8532-8536; Fischer, W. H. and Spiess, J. 1987 *Proc Natl Acad Sci USA* 84, 3628-3632).

For the mammalian QCs, the conversion of Gln into pGlu by QC could be shown for the precursors of TRH and GnRH (Busby, W. H. J. et al. 1987 *J Biol Chem* 262, 8532-8536; Fischer, W. H. and Spiess, J. 1987 *Proc Natl Acad Sci USA* 84, 3628-3632). In addition, initial localization experiments of QC revealed a co-localization with its putative products of catalysis in the bovine tractus hypothalamo-hypophysal is further improving the suggested function in peptide hormone maturation (Bockers, T. M. et al. 1995 *J Neuroendocrinol* 7, 445-453). In contrast, the physiological function of the plant QC is less clear. In case of the enzyme from *C. papaya*, a role in the plant defense against pathogenic microorganisms was suggested (El Moussaoui, A. et al. 2001 *Cell Mol Life Sci* 58, 556-570). Putative QCs from other plants were identified by sequence comparisons recently (Dahl, S. W. et al. 2000 *Protein Expr Purif* 20, 27-36). The physiological function of these enzymes, however, is still ambiguous.

The QCs known from plants and animals show a strict specificity for L-Glutamine in the N-terminal position of the substrates and their kinetic behaviour was found to obey the Michaelis-Menten equation (Pohl, T. et al. 1991 *Proc Natl Acad Sci USA* 88, 10059-10063; Consalvo, A. P. et al. 1988 *Anal Biochem* 175, 131-138; Gololobov, M. Y. et al. 1996 *Biol Chem Hoppe Seyler* 377, 395-398). A comparison of the primary structures of the QCs from *C. papaya* and that of the highly conserved QC from mammals, however, did not reveal any sequence homology (Dahl, S. W. et al. (2000) *Protein Expr Purif* 20, 27-36). Whereas the plant QCs appear to belong to a new enzyme family (Dahl, S. W. et al. (2000) *Protein Expr Purif* 20, 27-36), the mammalian QCs were found to have a pronounced sequence homology to bacterial aminopeptidases (Bateman, R. C. et al. 2001 *Biochemistry* 40, 11246-11250), leading to the conclusion that the QCs from plants and animals have different evolutionary origins.

EP 02 011 349.4 discloses polynucleotides encoding insect glutaminyl cyclase, as well as polypeptides encoded thereby. This application further provides host cells comprising expression vectors comprising polynucleotides of the invention. Isolated polypeptides and host cells comprising insect QC are useful in methods of screening for agents that reduce glutaminyl cyclase activity. Such agents are described as useful as pesticides.

Chemotactic cytokines (chemokines) are proteins that attract and activate leukocytes and are thought to play a fundamental role in inflammation. Chemokines are divided into four groups categorized by the appearance of N-terminal cysteine residues ("C"-; "CC"-; "CXC"- and "CX3C"-chemokines). "CXC"-chemokines preferentially act on neutrophils. In contrast, "CC"-chemokines attract preferentially monocytes to sites of inflammation. Monocyte infiltration is considered to be a key event in a number of disease conditions (Gerard, C. and Rollins, B. J. (2001) *Nat. Immunol* 2, 108-115; Bhatia, M., et al., (2005) *Pancreatology*. 5, 132-144; Kitamoto, S., Egashira, K., and Takeshita, A. (2003) *J Pharmacol Sci*. 91, 192-196). The MCP family, as one family of chemokines, consists of four members (MCP-1-4), displaying a preference for attracting monocytes but showing differences in their potential (Luini, W., et al., (1994) *Cytokine* 6, 28-31; Uguccioni, M., et al., (1995) *Eur J Immunol* 25, 64-68). In the following both cDNA as well as amino acid sequences of MCP-1-4 are indicated:

Human MCP-1 (CCL2) (GeneBank Accession: M24545)
cDNA (300 bp)

SEQ ID NO: 2

```
  1 atgaaagtct ctgccgccct tctgtgcctg ctgctcatag cagccacctt cattcccaa
 61 gggctcgctc agccagatgc aatcaatgcc ccagtcacct gctgttataa cttcaccaat
121 aggaagatct cagtgcagag gctcgcgagc tatagaagaa tcaccagcag caagtgtccc
181 aaagaagctg tgatcttcaa gaccattgtg gccaaggaga tctgtgctga ccccaagcag
241 aagtgggttc aggattccat ggaccacctg gacaagcaaa cccaaactcc gaagacttga
```

Protein (Signal Sequence in bold: 23 aa; Mature MCP-1: 76 aa)

SEQ ID NO: 1

MKVSAALLCLLLIAATFIPQGLAQPDAINAPVTCCYNFTNRKISVQRLASYRRITSSKCPKEAVIFKTI

VAKEICADPKQKWVQDSMDHLDKQTQTPKT

Human MCP-2 (CCL8) (GeneBank Accession: Y10802)
cDNA (300 bp)

SEQ ID NO: 12

```
  1 atgaaggttt ctgcagcgct tctgtgcctg ctgctcatgg cagccacttt cagccctcag
 61 ggacttgctc agccagattc agtttccatt ccaatcacct gctgctttaa cgtgatcaat
121 aggaaaattc ctatccagag gctggagagc tacacaagaa tcaccaacat ccaatgtccc
181 aaggaagctg tgatcttcaa gacccaacgg ggcaaggagt ctgtgctga ccccaaggag
241 agatgggtca gggattccat gaagcatctg gaccaaatat ttcaaaatct gaagccatga
```

Protein (Signal Sequence in bold: 23 aa; Mature MCP-2: 76 aa)

SEQ ID NO: 11

MKVSAALLCLLLMAATFSPQGLAQPDSVSIPITCCFNVINRKIPIQRLESYTRITNIQCPKEAVIFKTQ

RGKEVCADPKERWVRDSMKHLDQIFQNLKP

Human MCP-3 (CCL7) (GeneBank Accession: X71087)
cDNA (300 bp)

SEQ ID NO: 14

```
  1 atgaaagcct ctgcagcact tctgtgtctg ctgctcacag cagctgcttt cagcccccag
 61 gggcttgctc agccagttgg gattaatact tcaactacct gctgctacag atttatcaat
121 aagaaaatcc ctaagcagag gctggagagc tacagaagga ccaccagtag ccactgtccc
181 cgggaagctg taatcttcaa gaccaaactg gacaaggaga tctgtgctga ccccacacag
241 aagtgggtcc aggactttat gaagcacctg gacaagaaaa cccaaactcc aaagctttga
```

Protein (Signal Sequence in bold: 23 aa; Mature MCP-3: 76 aa)

SEQ ID NO: 13

MKASAALLCLLLTAAAFSPQGLAQPVGINTSTTCCYRFINKKIPKQRLESYRRTTSSHCPREAVIFKTK

LDKEICADPTQKWVQDFMKHLDKKTQTPKL

Human MCP-4 (CCL13) (GeneBank Accession: U46767)
cDNA (297 bp)

SEQ ID NO: 16

```
  1 atgaaagtct ctgcagtgct tctgtgcctg ctgctcatga cagcagcttt caaccccag
 61 ggacttgctc agccagatgc actcaacgtc ccatctactt gctgcttcac atttagcagt
121 aagaagatct ccttgcagag gctgaagagc tatgtgatca ccaccagcag gtgtccccag
181 aaggctgtca tcttcagaac caaactgggc aaggagatct gtgctgaccc aaaggagaag
241 tgggtccaga attatatgaa acacctgggc cggaaagctc acaccctgaa gacttga
```

Protein (Signal Sequence in bold: 23 aa; Mature MCP-4: 75 aa)

SEQ ID NO: 15

MKVSAVLLCLLLMTAAFNPQGLAQPDALNVPSTCCFTFSSKKISLQRLKSYVITTSRCPQKAVIFRTKL

GKEICADPKEKWVQNYMKHLGRKAHTLKT

A number of studies have underlined in particular the crucial role of MCP-1 for the development of atherosclerosis (Gu, L., et al., (1998) *Mol. Cell* 2, 275-281; Gosling, J., et al., (1999) *J. Clin. Invest* 103, 773-778); rheumatoid arthritis (Gong, J. H., et al., (1997) *J. Exp. Med* 186, 131-137; Ogata, H., et al., (1997) *J Pathol.* 182, 106-114); pancreatitis (Bhatia, M., et al., (2005) *Am. J Physiol Gastrointest. Liver Physiol* 288, G1259-G1265); Alzheimer's disease (Yamamoto, M., et al., (2005) *Am. J Pathol.* 166, 1475-1485); lung fibrosis (Inoshima, I., et al., (2004) *Am. J Physiol Lung Cell Mol. Physiol* 286, L1038-L1044); renal fibrosis (Wada, T., et al., (2004) *J. Am. Soc. Nephrol.* 15, 940-948), and graft rejection (Saiura, A., et al., (2004) *Arterioscler. Thromb. Vasc. Biol.* 24, 1886-1890). Furthermore, MCP-1 might also play a role in gestosis (Katabuchi, H., et al., (2003) *Med Electron Microsc.* 36, 253-262), as a paracrine factor in tumor development (Ohta, M., et al., (2003) *Int. J Oncol.* 22, 773-778; Li, S., et al., (2005) *J. Exp. Med* 202, 617-624), neuropathic pain (White, F. A., et al., (2005) *Proc. Natl. Acad. Sci. U.S.A*) and AIDS (Park, I. W., Wang, J. F., and Groopman, J. E. (2001) *Blood* 97, 352-358; Coll, B., et al., (2006) *Cytokine* 34, 51-55).

The mature form of human and rodent MCP-1 is posttranslationally modified by Glutaminyl Cyclase (QC) to possess an N-terminal pyroglutamyl (pGlu) residue. The N-terminal pGlu modification makes the protein resistant against N-terminal degradation by aminopeptidases, which is of importance, since chemotactic potency of MCP-1 is mediated by its N-terminus (Van Damme, J., et al., (1999) *Chem Immunol* 72, 42-56). Artificial elongation or degradation leads to a loss of function although MCP-1 still binds to its receptor (CCR2) (Proost, P., et al., (1998), *J Immunol* 160, 4034-4041; Zhang, Y. J., et al., 1994, *J. Biol. Chem.* 269, 15918-15924; Masure, S., et al., 1995, *J Interferon Cytokine Res.* 15, 955-963; Hemmerich, S., et al., (1999) *Biochemistry* 38, 13013-13025).

Due to the major role of MCP-1 in a number of disease conditions, an anti-MCP-1 strategy is required. Therefore, small orally available compounds inhibiting the action of MCP-1 are promising candidates for a drug development. Inhibitors of Glutaminyl Cyclase are small orally available compounds, which target the important step of pGlu-formation at the N-terminus of MCP-1 (Cynis, H., et al., (2006) *Biochim. Biophys. Acta* 1764, 1618-1625; Buchholz, M., et al., (2006) *J Med Chem* 49, 664-677). In consequence, caused by QC-inhibition, the N-terminus of MCP-1 is not protected by a pGlu-residue. Instead, the N-terminus possesses a glutamine-proline motif, which is prone to cleavage by dipeptidylpeptidases, e.g. dipeptidylpeptidase 4 and fibroblast activating protein (FAP, Seprase), which are abundant on the endothelium and within the blood circulation. This cleavage results in the formation of N-terminal truncated MCP-1. These molecules unfold, in turn, an antagonistic action at the CCR2 receptor and therefore, monocyte-related disease conditions are inhibited efficiently.

Atherosclerotic lesions, which limit or obstruct coronary blood flow, are the major cause of ischemic heart disease related mortality, resulting in 500,000-600,000 deaths annually. Percutaneous transluminal coronary angioplasty (PTCA) to open the obstructed artery was performed in over 550,000 patients in the U.S. and 945,000+ patients worldwide in 1996 (Lemaitre et al., 1996). A major limitation of this technique is the problem of post-PTCA closure of the vessel, both immediately after PTCA (acute occlusion) and in the long term (restenosis): 30% of patients with subtotal lesions and 50% of patients with chronic total lesions will progress to restenosis after angioplasty. Additionally, restenosis is a significant problem in patients undergoing saphenous vein bypass graft. The mechanism of acute occlusion appears to involve several factors and may result from vascular recoil with resultant closure of the artery and/or deposition of blood platelets along the damaged length of the newly opened blood vessel followed by formation of a fibrin/red blood cell thrombus.

Restenosis after angioplasty is a more gradual process and involves initial formation of a subcritical thrombosis with release from adherent platelets of cell derived growth factors with subsequent proliferation of intimal smooth muscle cells and local infiltration of inflammatory cells contributing to vascular hyperplasia. It is important to note that multiple processes, among those thrombosis, cell proliferation, cell migration and inflammation each seem to contribute to the restenotic process.

In the U.S., a 30-50% restenosis rate translates to 120,000-200,000 U.S. patients at risk from restenosis. If only 80% of such patients elect repeated angioplasty (with the remaining 20% electing coronary artery bypass graft) and this is added to the costs of coronary artery bypass graft for the remaining 20%, the total costs for restenosis treatment easily amounts to billions of dollars in the U.S. Thus, successful prevention of restenosis could result not only in significant therapeutic benefit but also in significant health care savings.

Monocyte chemoattractant protein 1 (MCP-1, CCL2) belongs to a family of potent chemotactic cytokines (CC chemokines), that regulate the trafficking of leukocytes, especially monocytes, macrophages and T-cells, to sites of inflammation (Charo, I. F. and Taubman, M. B. (2004) *Circ. Res.* 95, 858-866). Besides its role in, e.g. vascular disease, compelling evidence points to a role of MCP-1 in Alzheimer's disease (AD) (Xia, M. Q. and Hyman, B. T. (1999) *J Neurovirol.* 5, 32-41). The presence of MCP-1 in senile plaques and in reactive microglia, the residential macrophages of the CNS have been observed in brains of patients suffering from AD (Ishizuka, K., et al., (1997) *Psychiatry Clin. Neurosci.* 51, 135-138). Stimulation of monocytes and microglia with Amyloid-β protein (Aβ) induces chemokine secretion in vitro (Meda, L., et al., (1996) *J Immunol* 157, 1213-1218; Szczepanik, A. M., et al., (2001) *J Neuroimmunol.* 113, 49-62) and intracerebroventricular infusion of $A\beta_{(1-42)}$ into murine hippocampus significantly increases MCP-1 in vivo. Moreover, Aβ deposits attract and activate microglial cells and force them to produce inflammatory mediators such as MCP-1, which in turn leads to a feed back to induce further chemotaxis, activation and tissue damage. At the site of Aβ deposition, activated microglia also phagocytose Aβ peptides leading to an amplified activation (Rogers, J. and Lue, L. F. (2001) *Neurochem. Int.* 39, 333-340).

Examination of chemokine expression in a 3×Tg mouse model for AD revealed that neuronal inflammation precedes plaque formation and MCP-1 is upregulated by a factor of 11. Furthermore, the upregulation of MCP-1 seems to correlate with the occurrence of first intracellular Aβ deposits (Janelsins, M. C., et al., (2005) *J Neuroinflammation.* 2, 23). Crossbreeding of the Tg2575 mouse model for AD with a MCP-1 overexpressing mouse model has shown an increased microglia accumulation around Aβ deposits and that this accumulation was accompanied by increased amount of diffuse plaques compared to single-transgenic Tg2576 littermates (Yamamoto, M., et al. (2005) *Am. J Pathol.* 166, 1475-1485). MCP-1 levels are increased in CSF of AD patients and patients showing mild cognitive impairment (MCI) (Galimberti, D., et al., (2006) *Arch. Neurol.* 63, 538-543). Furthermore, MCP-1 shows an increased level in serum of patients with MCI and early AD (Clerici, F., et al., (2006) *Neurobiol. Aging* 27, 1763-1768).

SUMMARY OF THE INVENTION

The present application discloses inhibitors of a glutaminyl peptide cyclotransferase and the use thereof for the treatment and/or prevention of a disease or disorder selected from the group consisting of inflammatory diseases selected from
a. neurodegenerative diseases, e.g. mild cognitive impairment (MCI), Alzheimer's disease, neurodegeneration in Down Syndrome, Familial British Dementia, Familial Danish Dementia, multiple sclerosis,
b. chronic and acute inflammations, e.g. rheumatoid arthritis, atherosclerosis, restenosis, pancreatitis,
c. fibrosis, e.g. lung fibrosis, liver fibrosis, renal fibrosis,
d. cancer, e.g. cancer/hemangioendothelioma proliferation, gastric carcinomas,
e. metabolic diseases, e.g. hypertension,
f. and other inflammatory diseases, e.g. neuropathic pain, graft rejection/graft failure/graft vasculopathy, HIV infections/AIDS, gestosis, tuberous sclerosis.

BRIEF DESCRIPTION OF THE DRAWINGS

FIG. 1 shows the incubation of MCP-$1_{(1-76)}$ bearing an N-terminal glutaminyl (A) or Pyroglutamyl (5-oxo-L-Prolyl) residue (B) with recombinant human DP4 for 24 h. For cyclization of N-terminal glutamine into pyroglutamate MCP-1 was incubated with recombinant human QC 3 h prior to assay start. The DP4 cleavage products were analyzed after 0 min, 15 min, 30 min, 1 h, 4 h and 24 h using Maldi-TOF mass spectrometry.

FIG. 22 shows the chemotactic potency of human N-terminal MCP-1 variants starting with N-terminal glutamine ($Gln^1$-MCP-1), pyroglutamic acid ($pGlu^1$-MCP-1) (5-oxo-L-Proline), starting with proline 2 ($Pro^2$-MCP-1, the aminopeptidase P cleavage product), starting with aspartic acid 3 ($Asp^3$-MCP-1, the DP4 cleavage product) and starting with isoleucine 5 ($Ile^5$-MCP-1, the MMP-1 cleavage product) towards human THP-1 monocytes.

DETAILED DESCRIPTION OF THE PRESENTLY PREFERRED EMBODIMENTS

Figure 2A:
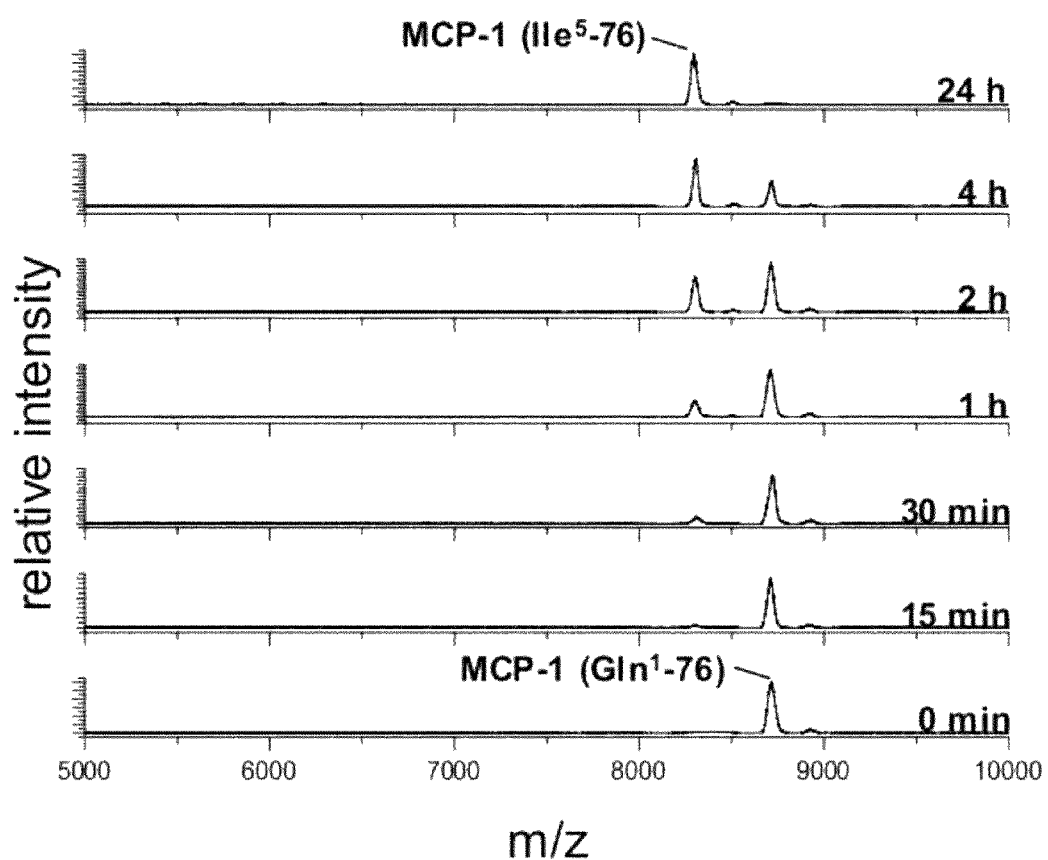
FIG. 2 shows the incubation of MCP-$1_{(1-76)}$ bearing an N-terminal glutaminyl (A) or Pyroglutamyl (5-oxo-L-Prolyl) residue with human synovial fibroblast MMP-1 for 24 h. For cyclization of N-terminal glutamine into pyroglutamate MCP-1 was incubated with recombinant human QC 3 h prior to assay start. The MMP-1 cleavage products were analyzed after 0 min, 15 min, 30 min, 1 h, 2 h, 4 h and 24 h using Maldi-TOF mass spectrometry.
Figure 2B:
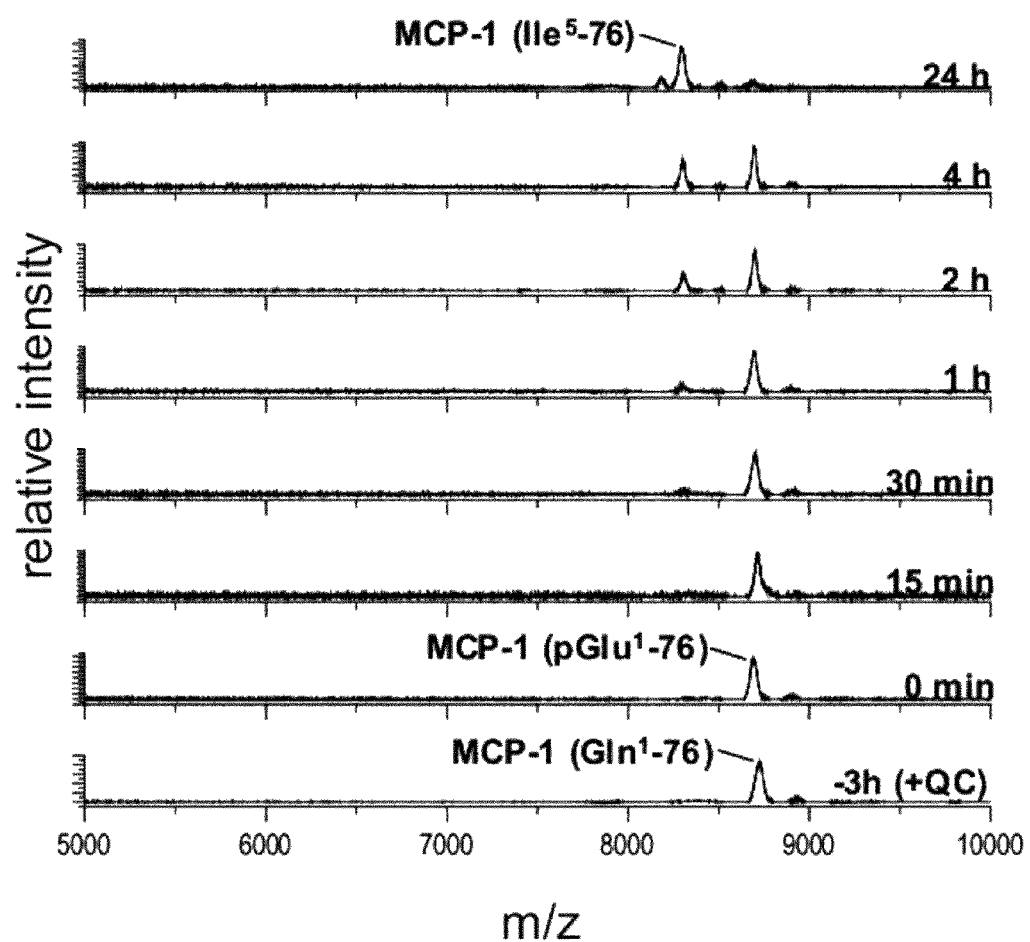

In particular the present invention pertains to the following items:
1. A QC inhibitor for the treatment and/or prevention of an inflammatory disease or condition, selected from
   a. neurodegenerative diseases, comprising mild cognitive impairment (MCI), Alzheimer's disease, neurodegeneration in Down Syndrome, Familial British Dementia, Familial Danish Dementia, and multiple sclerosis,
   b. chronic and acute inflammations, comprising rheumatoid arthritis, atherosclerosis, restenosis, and pancreatitis,
   c. fibrosis, comprising lung fibrosis, liver fibrosis, and renal fibrosis,
   d. cancer, comprising cancer/hemangioendothelioma proliferation, and gastric carcinomas,
   e. metabolic diseases, comprising hypertension,
   f. and other inflammatory diseases, comprising neuropathic pain, graft rejection/graft failure/graft vasculopathy, HIV infections/AIDS, gestosis, tuberous sclerosis.

2. The QC inhibitor according to item 1, wherein the neurodegenerative disease is selected from mild cognitive impairment (MCI), Alzheimer's disease, neurodegeneration in Down Syndrome, Familial British Dementia, Familial Danish Dementia, multiple sclerosis.
3. The QC inhibitor according to item 1 or 2, wherein the disease is mild cognitive impairment.
4. The QC inhibitor according to any of items 1 to 3, wherein the QC inhibitor is administered in combination with a further agent, selected from the group consisting of nootropic agents, neuroprotectants, antiparkinsonian drugs, amyloid protein deposition inhibitors, beta amyloid synthesis inhibitors, antidepressants, anxiolytic drugs, antipsychotic drugs and anti-multiple sclerosis drugs.
5. The QC inhibitor according to item 1, wherein the disease is a chronic or acute inflammation, selected from rheumatoid arthritis, atherosclerosis, restenosis and pancreatitis.
6. The QC inhibitor according to item 1 or 5, wherein the disease is selected from restenosis and pancreatitis.
7. The QC inhibitor according to item 1, 5 or 6, wherein the QC inhibitor is administered in combination with a further agent, selected from the group consisting of inhibitors of the angiotensin converting enzyme (ACE); angiotensin II receptor blockers; diuretics; calcium channel blockers (CCB); beta-blockers; platelet aggregation inhibitors; cholesterol absorption modulators; HMG-Co-A reductase inhibitors; high density lipoprotein (HDL) increasing compounds; renin inhibitors; IL-6 inhibitors; antiinflammatory corticosteroids; antiproliferative agents; nitric oxide donors; inhibitors of extracellular matrix synthesis; growth factor or cytokine signal transduction inhibitors; MCP-1 antagonists and tyrosine kinase inhibitors.
8. Use of a QC inhibitor for the treatment and/or prevention of an inflammatory disease or condition selected from
    a. neurodegenerative diseases, comprising mild cognitive impairment (MCI), Alzheimer's disease, neurodegeneration in Down Syndrome, Familial British Dementia, Familial Danish Dementia, multiple sclerosis,
    b. chronic and acute inflammations, comprising rheumatoid arthritis, atherosclerosis, restenosis, pancreatitis,
    c. fibrosis, comprising lung fibrosis, liver fibrosis, renal fibrosis,
    d. cancer, comprising cancer/hemangioendothelioma proliferation, gastric carcinomas,
    e. metabolic diseases, comprising hypertension,
    f. and other inflammatory diseases, comprising neuropathic pain, graft rejection/graft failure/graft vasculopathy, HIV infections/AIDS, gestosis, tuberous sclerosis.
9. The use according to item 8, wherein the disease is a neurodegenerative disease, selected from mild cognitive impairment (MCI), Alzheimer's disease, neurodegeneration in Down Syndrome, Familial British Dementia, Familial Danish Dementia, multiple sclerosis.
10. The use according to item 8 or 9, wherein the disease is mild cognitive impairment (MCI).
11. The use according to any of items 8 to 10, wherein the QC inhibitor is administered in combination with a further agent, selected from the group consisting of nootropic agents, neuroprotectants, antiparkinsonian drugs, amyloid protein deposition inhibitors, beta amyloid synthesis inhibitors, antidepressants, anxiolytic drugs, antipsychotic drugs and anti-multiple sclerosis drugs.
12. The use according to item 8, wherein the disease is a chronic or acute inflammation, selected from rheumatoid arthritis, atherosclerosis, restenosis and pancreatitis.
13. The use according to item 8 or 12, wherein the disease is selected from restenosis and pancreatitis.
14. The use according to item 8, 12 or 13, wherein the QC inhibitor is administered in combination with a further agent, selected from the group consisting of inhibitors of the angiotensin converting enzyme (ACE); angiotensin II receptor blockers; diuretics; calcium channel blockers (CCB); beta-blockers; platelet aggregation inhibitors; cholesterol absorption modulators; HMG-Co-A reductase inhibitors; high density lipoprotein (HDL) increasing compounds; renin inhibitors; IL-6 inhibitors; antiinflammatory corticosteroids; antiproliferative agents; nitric oxide donors; inhibitors of extracellular matrix synthesis; growth factor or cytokine signal transduction inhibitors; MCP-1 antagonists and tyrosine kinase inhibitors.
15. Use of a QC inhibitor for the preparation of a medicament for treating and/or preventing an inflammatory disease or condition selected from
    a. neurodegenerative diseases, comprising mild cognitive impairment (MCI), Alzheimer's disease, neurodegeneration in Down Syndrome, Familial British Dementia, Familial Danish Dementia, multiple sclerosis,
    b. chronic and acute inflammations, comprising rheumatoid arthritis, atherosclerosis, restenosis, pancreatitis,
    c. fibrosis, comprising lung fibrosis, liver fibrosis, renal fibrosis,
    d. cancer, comprising cancer/hemangioendothelioma proliferation, gastric carcinomas,
    e. metabolic diseases, comprising hypertension,
    f. and other inflammatory diseases, comprising neuropathic pain, graft rejection/graft failure/graft vasculopathy, HIV infections/AIDS, gestosis, tuberous sclerosis.
16. The use according to item 15, wherein the disease is a neurodegenerative disease, selected from mild cognitive impairment (MCI), Alzheimer's disease, neurodegeneration in Down Syndrome, Familial British Dementia, Familial Danish Dementia, multiple sclerosis.
17. The use according to item 15 or 16, wherein the disease is mild cognitive impairment (MCI).
18. The use according to any of items 15 to 17, wherein the QC inhibitor is administered in combination with a further agent, selected from the group consisting of nootropic agents, neuroprotectants, antiparkinsonian drugs, amyloid protein deposition inhibitors, beta amyloid synthesis inhibitors, antidepressants, anxiolytic drugs, antipsychotic drugs and anti-multiple sclerosis drugs.
19. The use according to item 15, wherein the disease is a chronic or acute inflammation, selected from rheumatoid arthritis, atherosclerosis, restenosis and pancreatitis.
20. The use according to item 15 or 19, wherein the disease is selected from restenosis and pancreatitis.
21. The use according to any of items 15, 19 or 20, wherein the QC inhibitor is administered in combination with a further agent, selected from the group consisting of inhibitors of the angiotensin converting enzyme (ACE); angiotensin II receptor blockers; diuretics; calcium channel blockers (CCB); beta-blockers; platelet aggregation inhibitors; cholesterol absorption modulators; HMG-Co-A reductase inhibitors; high density lipoprotein (HDL) increasing compounds; renin inhibitors; IL-6 inhibitors; antiinflammatory corticosteroids; antiproliferative agents; nitric oxide donors; inhibitors of extracellular matrix synthesis; growth factor or cytokine signal transduction inhibitors; MCP-1 antagonists and tyrosine kinase inhibitors.
22. A Method of treatment and/or prevention of an inflammatory disease or condition, selected from
    a. neurodegenerative diseases, comprising mild cognitive impairment (MCI), Alzheimer's disease, neurodegeneration in Down Syndrome, Familial British Dementia, Familial Danish Dementia, multiple sclerosis,
b. chronic and acute inflammations, comprising rheumatoid arthritis, atherosclerosis, restenosis, pancreatitis,
c. fibrosis, comprising lung fibrosis, liver fibrosis, renal fibrosis,
d. cancer, comprising cancer/hemangioendothelioma proliferation, gastric carcinomas,
e. metabolic diseases, comprising hypertension,
f. and other inflammatory diseases, comprising neuropathic pain, graft rejection/graft failure/graft vasculopathy, HIV infections/AIDS, gestosis, tuberous sclerosis,
wherein an effective amount of a QC inhibitor is administered to a subject in need thereof.

23. The method of treatment and/or prevention according to item 22, wherein the disease is a neurodegenerative disease, selected from mild cognitive impairment (MCI), Alzheimer's disease, neurodegeneration in Down Syndrome, Familial British Dementia, Familial Danish Dementia, multiple sclerosis.

24. The method of treatment and/or prevention according to item 23 or 24, wherein the disease is mild cognitive impairment (MCI).

25. The method of treatment and/or prevention according to any of items 23 to 25, wherein the QC inhibitor is administered in combination with a further agent, selected from the group consisting of nootropic agents, neuroprotectants, antiparkinsonian drugs, amyloid protein deposition inhibitors, beta amyloid synthesis inhibitors, antidepressants, anxiolytic drugs, antipsychotic drugs and anti-multiple sclerosis drugs.

26. The method of treatment and/or prevention according to item 23, wherein the disease is a chronic or acute inflammation, selected from rheumatoid arthritis, atherosclerosis, restenosis and pancreatitis.

27. The method of treatment and/or prevention according to item 23 or 26, wherein the disease is selected from restenosis and pancreatitis.

28. The method of treatment and/or prevention according to item 23, 26 or 27 wherein the QC inhibitor is administered in combination with a further agent, selected from the group consisting of inhibitors of the angiotensin converting enzyme (ACE); angiotensin II receptor blockers; diuretics; calcium channel blockers (CCB); beta-blockers; platelet aggregation inhibitors; cholesterol absorption modulators; HMG-Co-A reductase inhibitors; high density lipoprotein (HDL) increasing compounds; renin inhibitors; IL-6 inhibitors; antiinflammatory corticosteroids; antiproliferative agents; nitric oxide donors; inhibitors of extracellular matrix synthesis; growth factor or cytokine signal transduction inhibitors; MCP-1 antagonists and tyrosine kinase inhibitors.

29. The use according to any of items 7 to 21, wherein the disease and/or condition afflict a human being.

30. The method of any of items 22 to 28, wherein the disease and/or condition afflicts a human being.

31. The use or method according to any one of the preceding items, wherein said QC inhibitor is an inhibitor selected from formulae 1, 1*, 1a, 1b, 1c, 1d, 1e, 1f, 1g, 1h, and 1i.

32. The use or method according to any one of items 1 to 31, wherein said QC inhibitor is an inhibitor selected from examples 1 to 141.

33. The use or method according to any one of items 1 to 32, wherein said QC inhibitor is 1-(3-(1H-imidazole-1-yl)propyl)-3-(3,4-dimethoxy-phenyl)thiourea hydrochloride.

34. Diagnostic assay, comprising a QC inhibitor.

35. Diagnostic assay according to item 34, wherein said QC inhibitor is an inhibitor selected from formulae 1, 1*, 1a, 1b, 1c, 1d, 1e, 1f, 1g, 1h, and 1i.

36. Diagnostic assay according to item 34 or 35, wherein said QC inhibitor is an inhibitor selected from examples 1 to 141.

37. Diagnostic assay according to any of items 34 to 36, wherein said QC inhibitor is 1-(3-(1H-imidazole-1-yl)propyl)-3-(3,4-dimethoxy-phenyl)thiourea hydrochloride.

38. A method of diagnosing any one of the diseases and/or conditions as defined in item 1, comprising the steps of collecting a sample from a subject who is suspected to be afflicted with said disease and/or condition,
contacting said sample with a QC inhibitor, and
determining whether or not said subject is afflicted by said disease and/or condition.

39. The method according to item 38, wherein said subject is a human being.

40. The method according to item 38 or 39, wherein said QC inhibitor is an inhibitor selected from formulae 1, 1*, 1a, 1b, 1c, 1d, 1e, 1f, 1g, 1h, and 1i.

41. The method according to any of items 38 to 40, wherein said QC inhibitor is an inhibitor selected from examples 1 to 141.

42. The method according to any of items 38 to 41, wherein said QC inhibitor is 1-(3-(1H-imidazole-1-yl)propyl)-3-(3,4-dimethoxy-phenyl)thiourea hydrochloride.

43. The method of any of items 38 to 42, wherein said sample is a blood sample, a serum sample, a sample of cerebrospinal liquor or a urine sample.

44. Diagnostic kit for carrying out the method of items 38 to 42 comprising as detection means the diagnostic assay of any of items 34 or 37 and a determination means.

45. Pharmaceutical composition, comprising the QC inhibitor according to any of items 1 to 7 or 31 to 33.

In an especially preferred embodiment, the invention relates to the use of a QC inhibitor in methods of treating a chronic or acute inflammation, selected from rheumatoid arthritis, atherosclerosis, restenosis and pancreatitis, particularly restenosis and pancreatitis, most preferably restenosis.

The effect of a QC inhibitor for treating a chronic or acute inflammation, selected from rheumatoid arthritis, atherosclerosis, restenosis and pancreatitis, can be tested using the in vivo assays described in examples 3, 7 and 8 of the present invention.

Even preferred according to the present invention is the use of a QC inhibitor in methods of treating mild cognitive impairment (MCI).

Accordingly, the present invention pertains more preferably to the following items:

1. A QC inhibitor for the treatment and/or prevention of an inflammatory disease or condition, selected from mild cognitive impairment (MCI), restenosis, and pancreatitis.

2. Use of a QC inhibitor for the treatment and/or prevention of an inflammatory disease or condition selected from mild cognitive impairment (MCI), restenosis, and pancreatitis.

3. Use of a QC inhibitor for the preparation of a medicament for treating and/or preventing an inflammatory disease or condition selected from mild cognitive impairment (MCI), restenosis, and pancreatitis.

4. The QC inhibitor or use according to any of items 1 to 3, wherein the disease is mild cognitive impairment (MCI).

5. The QC inhibitor or use according to any of items 1 to 4, wherein the QC inhibitor is administered in combination with a further agent, selected from the group consisting of nootropic agents, neuroprotectants, antiparkinsonian drugs, amyloid protein deposition inhibitors, beta amyloid synthesis inhibitors, antidepressants, anxiolytic drugs, antipsychotic drugs and anti-multiple sclerosis drugs.

6. The QC inhibitor or use according to any of items 1 to 3, wherein the disease is selected from restenosis and pancreatitis.

7. The QC inhibitor or use according to any of items 1 to 3 or 6, wherein the disease is restenosis.

8. The QC-inhibitor or use according to any of items 1 to 3, 6 or 7, wherein the QC inhibitor is administered in combination with a further agent, selected from the group consisting of inhibitors of the angiotensin converting enzyme (ACE); angiotensin II receptor blockers; diuretics; calcium channel blockers (CCB); beta-blockers; platelet aggregation inhibitors; cholesterol absorption modulators; HMG-Co-A reductase inhibitors; high density lipoprotein (HDL) increasing compounds; renin inhibitors; IL-6 inhibitors; antiinflammatory corticosteroids; antiproliferative agents; nitric oxide donors; inhibitors of extracellular matrix synthesis; growth factor or cytokine signal transduction inhibitors; MCP-1 antagonists and tyrosine kinase inhibitors.

9. A Method of treatment and/or prevention of an inflammatory disease or condition, selected from mild cognitive impairment (MCI), restenosis and pancreatitis, wherein an effective amount of a QC inhibitor is administered to a subject in need thereof.

10. The method of treatment and/or prevention according to item 9, wherein the disease is mild cognitive impairment (MCI).

11. The method of treatment and/or prevention according to item 9 or 10, wherein the QC inhibitor is administered in combination with a further agent, selected from the group consisting of nootropic agents, neuroprotectants, antiparkinsonian drugs, amyloid protein deposition inhibitors, beta amyloid synthesis inhibitors, antidepressants, anxiolytic drugs, antipsychotic drugs and anti-multiple sclerosis drugs.

12. The method of treatment and/or prevention according to item 9, wherein the disease is a chronic or acute inflammation, selected from rheumatoid arthritis, atherosclerosis, restenosis and pancreatitis.

13. The method of treatment and/or prevention according to item 9 or 12, wherein the disease is selected from restenosis and pancreatitis.

14. The method of treatment and/or prevention according to any of item 9, 12 or 13, wherein the disease is restenosis.

15. The method of treatment and/or prevention according to any of items 9, or 12 to 14, wherein the QC inhibitor is administered in combination with a further agent, selected from the group consisting of inhibitors of the angiotensin converting enzyme (ACE); angiotensin II receptor blockers; diuretics; calcium channel blockers (CCB); beta-blockers; platelet aggregation inhibitors; cholesterol absorption modulators; HMG-Co-A reductase inhibitors; high density lipoprotein (HDL) increasing compounds; renin inhibitors; IL-6 inhibitors; antiinflammatory corticosteroids; antiproliferative agents; nitric oxide donors; inhibitors of extracellular matrix synthesis; growth factor or cytokine signal transduction inhibitors; MCP-1 antagonists and tyrosine kinase inhibitors.

16. The use according to any of items 2 to 8, wherein the disease and/or condition afflict a human being.

17. The method of any of items 9 to 15, wherein the disease and/or condition afflicts a human being.

18. The QC-inhibitor, use or method according to any one of items 1 to 17, wherein said QC inhibitor is an inhibitor selected from formulae 1, 1*, 1a, 1b, 1c, 1d, 1e, 1f, 1g, 1h, and 1i.

19. The QC-inhibitor, use or method according to any one of items 1 to 18, wherein said QC inhibitor is an inhibitor selected from examples 1 to 141.

20. The QC-inhibitor, use or method according to any one of items 1 to 19, wherein said QC inhibitor is 1-(3-(1H-imidazole-1-yl)propyl)-3-(3,4-dimethoxy-phenyl)thiourea hydrochloride.

21. Diagnostic assay, comprising a QC inhibitor.

22. Diagnostic assay according to item 21, wherein said QC inhibitor is an inhibitor selected from formulae 1, 1*, 1a, 1b, 1c, 1d, 1e, 1f, 1g, 1h, and 1i.

23. Diagnostic assay according to item 21 or 22, wherein said QC inhibitor is an inhibitor selected from examples 1 to 141.

24. Diagnostic assay according to any of items 21 to 23, wherein said QC inhibitor is 1-(3-(1H-imidazole-1-yl)propyl)-3-(3,4-dimethoxy-phenyl)thiourea hydrochloride.

25. A method of diagnosing any one of the diseases and/or conditions as defined in item 1, comprising the steps of collecting a sample from a subject who is suspected to be afflicted with said disease and/or condition, contacting said sample with an inhibitor of a glutaminyl peptide cyclotransferase, and determining whether or not said subject is afflicted by said disease and/or condition.

26. The method according to item 26, wherein said subject is a human being.

27. The method according to item 26 or 27, wherein said QC inhibitor is an inhibitor selected from formulae 1, 1*, 1a, 1b, 1c, 1d, 1e, 1f, 1g, 1h, and 1i.

28. The method according to any of items 25 to 27, wherein said QC inhibitor is an inhibitor selected from examples 1 to 141.

29. The method according to any of items 25 to 28, wherein said QC inhibitor is 1-(3-(1H-imidazole-1-yl)propyl)-3-(3, 4-dimethoxy-phenyl)thiourea hydrochloride.

30. The method of any of items 25 to 29, wherein said sample is a blood sample, a serum sample, a sample of cerebrospinal liquor or a urine sample.

31. Diagnostic kit for carrying out the method of items 25 to 30 comprising as detection means the diagnostic assay of any of items 21 to 24 and a determination means.

32. Pharmaceutical composition, comprising the QC inhibitor according to any of items 1, 4 to 6 or 18 to 20.

DEFINITIONS

Enzyme Inhibitors, in Particular Inhibitors of QC

Reversible enzyme inhibitors: comprise competitive inhibitors, non-competitive reversible inhibitors, slow-binding or tight-binding inhibitors, transition state analogues and multisubstrate analogues.

Competitive Inhibitors Show i) non-covalent interactions with the enzyme, ii) compete with substrate for the enzyme active site.

The principal mechanism of action of a reversible enzyme inhibitor and the definition of the dissociation constant can be visualized as follows:

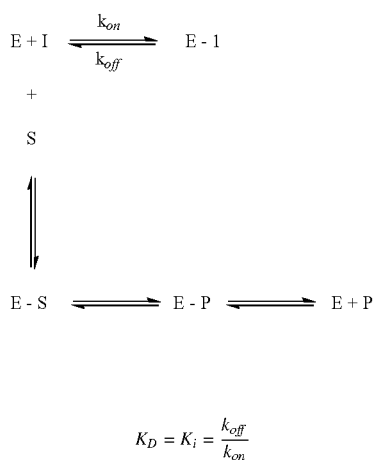

$$K_D = K_i = \frac{k_{off}}{k_{on}}$$

The formation of the enzyme-inhibitor [E-I] complex prevents binding of substrates, therefore the reaction cannot proceed to the normal physiological product, P. A larger inhibitor concentration [I] leads to larger [E-I], leaving less free enzyme to which the substrate can bind.

Non-Competitive Reversible Inhibitors i) bind at a site other than active site (allosteric binding site)
ii) cause a conformational change in the enzyme which decreases or stops catalytic activity.

Slow-Binding or Tight-Binding Inhibitors i) are competitive inhibitors where the equilibrium between inhibitor and enzyme is reached slowly,
ii) ($k_{on}$ is slow), possibly due to conformational changes that must occur in the enzyme or inhibitor
a) are often transition state analogues
b) are effective at concentrations similar to the enzyme concentration (subnanomolar KD values)
c) due to $k_{off}$ values being so low these types of inhibitors are "almost" irreversible.

Transition State Analogues

Are competitive inhibitors which mimic the transition state of an enzyme catalyzed reaction. Enzyme catalysis occurs due to a lowering of the energy of the transition state, therefore, transition state binding is favored over substrate binding.

Multisubstrate Analogues

For a reaction involving two or more substrates, a competitive inhibitor or transition state analogue can be designed which contains structural characteristics resembling two or more of the substrates.

Irreversible enzyme inhibitors: drive the equilibrium between the unbound enzyme and inhibitor and enzyme inhibitor complex (E+I<--->E-I) all the way to the E-1-side with a covalent bond (~100 kcal/mole), making the inhibition irreversible.

Affinity Labeling Agents

Active-site directed irreversible inhibitors (competitive irreversible inhibitor) are recognized by the enzyme (reversible, specific binding) followed by covalent bond formation, and i) are structurally similar to substrate, transition state or product allowing for specific interaction between drug and target enzyme,
ii) contain reactive functional group (e.g. a nucleophile, —COCH$_2$Br) allowing for covalent bond formation.

The reaction scheme below describes an active-site directed reagent with its target enzyme where $K_D$ is the dissociation constant and $k_{inactivation}$ is the rate of covalent bond formation.

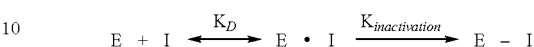

Mechanism-based enzyme inactivators (also called suicide inhibitors) are active-site directed reagents (unreactive) which bind to the enzyme active site where they are transformed to a reactive form (activated) by the enzyme's catalytic capabilities. Once activated, a covalent bond between the inhibitor and the enzyme is formed.

The reaction scheme below shows the mechanism of action of a mechanism based enzyme inactivator, where $K_D$ is the dissociation complex, $k_2$ is the rate of activation of the inhibitor once bound to the enzyme, $k_3$ is the rate of dissociation of the activated inhibitor, P, from the enzyme (product can still be reactive) from the enzyme and $k_4$ is the rate of covalent bond formation between the activated inhibitor and the enzyme.

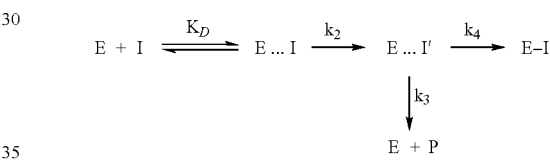

Inactivation (covalent bond formation, $k_4$) must occur prior to dissociation ($k_3$) otherwise the now reactive inhibitor is released into the environment. The partition ratio, $k_3/k_4$: ratio of released product to inactivation should be minimized for efficient inactivation of the system and minimal undesirable side reactions.

A large partition ratio (favors dissociation) leads to non-specific reactions.

Uncompetitive enzyme inhibitors: As a definition of uncompetitive inhibitor (an inhibitor which binds only to ES complexes) the following equilibria equation can be assumed:

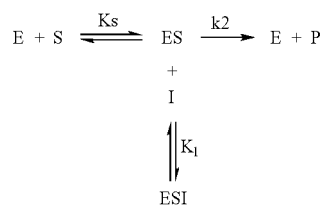

The ES complex dissociates the substrate with a dissociation constant equal to Ks, whereas the ESI complex does not dissociate it (i.e has a Ks value equal to zero). The Km's of Michaelis-Menten type enzymes are expected to be reduced. Increasing substrate concentration leads to increasing ESI concentration (a complex incapable of progressing to reaction products) therefore the inhibition cannot be removed.

Preferred according to the present invention are competitive enzyme inhibitors.

Most preferred are competitive reversible enzyme inhibitors.

The terms "$K_i$" or "$K_I$" and "$K_D$" are binding constants, which describe the binding of an inhibitor to and the subsequent release from an enzyme. Another measure is the "$IC_{50}$" value, which reflects the inhibitor concentration, which at a given substrate concentration results in 50% enzyme activity.

QC

The term "QC" as used herein comprises glutaminyl cyclase (QC) and QC-like enzymes. QC and QC-like enzymes have identical or similar enzymatic activity, further defined as QC activity. In this regard, QC-like enzymes can fundamentally differ in their molecular structure from QC.

The term "QC activity" as used herein is defined as intramolecular cyclization of N-terminal glutaminyl residues into pyroglutamic acid (pGlu*) or of N-terminal L-homoglutaminyl or L-beta-homoglutaminyl to a cyclic pyro-homoglutamine derivative under liberation of ammonia. See schemes 1 and 2 in this regard.

Scheme 1: Cyclization of glutamine by QC

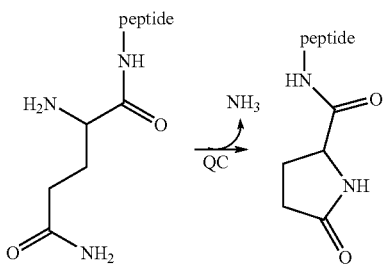

Scheme 2: Cyclization of L-homoglutamine by QC

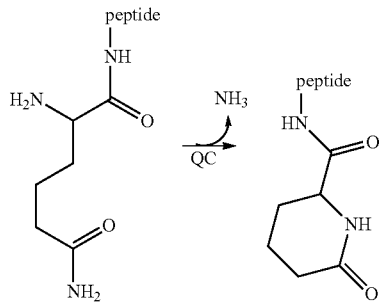

The term "EC" as used herein comprises the side activity of QC and QC-like enzymes as glutamate cyclase (EC), further defined as EC activity.

The term "EC activity" as used herein is defined as intramolecular cyclization of N-terminal glutamyl residues into pyroglutamic acid (pGlu*) by QC. See scheme 3 in this regard.

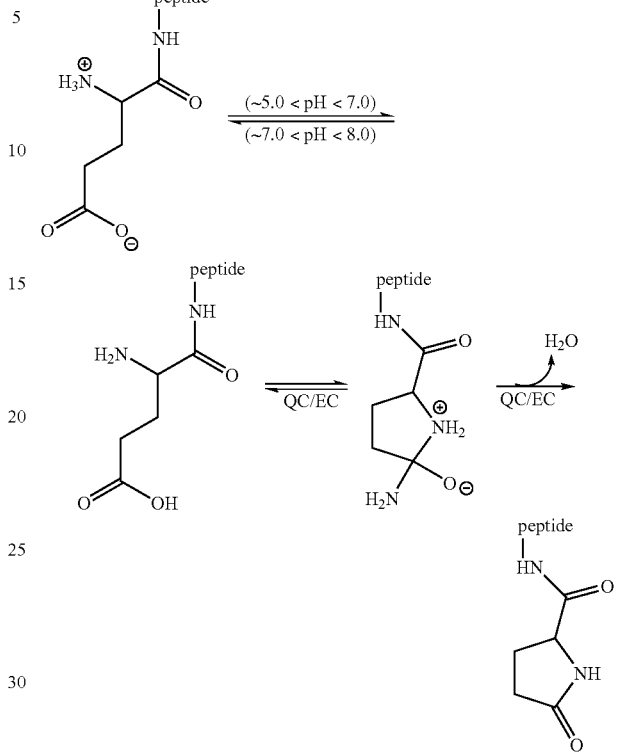

Scheme 3: N-terminal cyclization of uncharged glutamyl peptides by QC (EC)

The term "QC-inhibitor" "glutaminyl cyclase inhibitor" is generally known to a person skilled in the art and means enzyme inhibitors as generally defined above, which inhibit the catalytic activity of glutaminyl cyclase (QC) or its glutamyl cyclase (EC) activity.

Potency of QC Inhibition

In light of the correlation with QC inhibition, in preferred embodiments, the subject method and medical use utilize an agent with a $K_i$ for QC inhibition of 10 μM or less, more preferably of 1 μM or less, even more preferably of 0.1 μM or less or 0.01 μM or less, or most preferably 0.001 μM or less. Indeed, inhibitors with $K_i$ values in the lower micromolar, preferably the nanomolar and even more preferably the picomolar range are contemplated. Thus, while the active agents are described herein, for convenience, as "QC inhibitors", it will be understood that such nomenclature is not intended to limit the subject matter of the invention in any way.

Molecular Weight of QC Inhibitors

In general, the QC inhibitors of the subject method or medical use will be small molecules, e.g., with molecular weights of 1000 g/mole or less, 500 g/mole or less, preferably of 400 g/mole or less, and even more preferably of 350 g/mole or less and even of 300 g/mole or less.

The term "subject" as used herein, refers to an animal, preferably a mammal, most preferably a human, who has been the object of treatment, observation or experiment and/or is suspected of being afflicted with a disease and/or condition as defined in the items.

The term "therapeutically effective amount" as used herein, means that amount of an active compound or a pharmaceutical agent that elicits the biological or medicinal response in a tissue system, animal or human being sought by a researcher, veterinarian, medical doctor or other clinician, which includes alleviation of the symptoms of the disease or disorder being treated.

As used herein, the term "pharmaceutically acceptable" embraces both human and veterinary use: for example the term "pharmaceutically acceptable" embraces a veterinary acceptable compound or a compound acceptable in human medicine and health care.

Pharmaceutically Acceptable Salts:

In view of the close relationship between the free compounds and the compounds in the form of their salts or solvates, whenever a compound or inhibitor, respectively, is referred to in this context, a corresponding salt or solvate is also intended, provided such is possible or appropriate under the circumstances.

Salts and solvates of the inhibitors of the present invention and physiologically functional derivatives thereof which are suitable for use in medicine are those wherein the counter-ion or associated solvent is pharmaceutically acceptable. However, salts and solvates having non-pharmaceutically acceptable counter-ions or associated solvents are within the scope of the present invention, for example, for use as intermediates in the preparation of other compounds and their pharmaceutically acceptable salts and solvates.

Suitable salts according to the invention include those formed with both organic and inorganic acids or bases. Pharmaceutically acceptable acid addition salts include those formed from hydrochloric, hydrobromic, sulphuric, nitric, citric, tartaric, phosphoric, lactic, pyruvic, acetic, trifluoroacetic, triphenylacetic, sulphamic, sulphanilic, succinic, oxalic, fumaric, maleic, malic, mandelic, glutamic, aspartic, oxalacetic, methanesulphonic, ethanesulphonic, arylsulphonic (for example p-toluenesulphonic, benzenesulphonic, naphthalenesulphonic or naphthalene-disulphonic), salicylic, glutaric, gluconic, tricarballylic, cinnamic, substituted cinnamic (for example, phenyl, methyl, methoxy or halo substituted cinnamic, including 4-methyl and 4-methoxycinnamic acid), ascorbic, oleic, naphthoic, hydroxynaphthoic (for example 1- or 3-hydroxy-2-naphthoic), naphthaleneacrylic (for example naphthalene-2-acrylic), benzoic, 4 methoxybenzoic, 2- or 4-hydroxybenzoic, 4-chlorobenzoic, 4-phenylbenzoic, benzeneacrylic (for example 1,4-benzenediacrylic), isethionic acids, perchloric, propionic, glycolic, hydroxyethanesulfonic, pamoic, cyclohexanesulfamic, salicylic, saccharinic and trifluoroacetic acid. Pharmaceutically acceptable base salts include ammonium salts, alkali metal salts such as those of sodium and potassium, alkaline earth metal salts such as those of calcium and magnesium and salts with organic bases such as dicyclohexylamine and N-methyl-D-glutamine.

All pharmaceutically acceptable acid addition salt forms of the inhibitors of the present invention are intended to be embraced by the scope of this invention.

Examples of solvates include hydrates.

Polymorph Crystal Forms:

Furthermore, some of the crystalline forms of the inhibitors may exist as polymorphs and as such are intended to be included in the present invention. In addition, some of the compounds may form solvates with water (i.e. hydrates) or common organic solvents, and such solvates are also intended to be encompassed within the scope of this invention. The inhibitors, including their salts, can also be obtained in the form of their hydrates, or include other solvents used for their crystallization.

Prodrugs:

The present invention further includes within its scope prodrugs of the inhibitors of this invention. In general, such prodrugs will be functional derivatives of the inhibitors, which are readily convertible in vivo into the desired therapeutically active inhibitors. Thus, in these cases, the methods of treatment of the present invention, the term "administering" shall encompass the treatment of the various disorders described with prodrug versions of one or more of the itemed inhibitors, but which converts to the above specified inhibitors in vivo after administration to the subject. Conventional procedures for the selection and preparation of suitable prodrug derivatives are described, for example, in "Design of Prodrugs", ed. H. Bundgaard, Elsevier, 1985 and the patent applications DE 198 28 113, DE 198 28 114, WO 99/67228 and WO 99/67279 which are fully incorporated herein by reference.

Protective Groups:

During any of the processes for preparation of the inhibitors of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991, fully incorporated herein by reference. The protecting groups may be removed at a convenient subsequent stage using methods known from the art.

As used herein, the term "composition" is intended to encompass a product comprising the itemed compounds in the therapeutically effective amounts, as well as any product, which results, directly or indirectly, from combinations of the itemed compounds.

Carriers and Additives for Galenic Formulations:

For liquid oral preparations, such as for example, suspensions, elixirs and solutions, suitable carriers and additives may advantageously include water, glycols, oils, alcohols, flavouring agents, preservatives, colouring agents and the like; for solid oral preparations such as, for example, powders, capsules, gelcaps and tablets, suitable carriers and additives include starches, sugars, diluents, granulating agents, lubricants, binders, disintegrating agents and the like.

Carriers, which can be added to the mixture, include necessary and inert pharmaceutical excipients, including, but not limited to, suitable binders, suspending agents, lubricants, flavorants, sweeteners, preservatives, coatings, disintegrating agents, dyes and colouring agents.

Soluble polymers as targetable drug carriers can include polyvinylpyrrolidone, pyran copolymer, polyhydroxypropylmethacrylamidephenol, polyhydroxyethylaspartamidephenol, or polyethyleneoxidepolyllysine substituted with palmitoyl residue(s). Furthermore, the inhibitors of the present invention may be coupled to a class of biodegradable polymers useful in achieving controlled/sustained release of a drug, for example, poly acetic acid, poly-epsilon caprolactone, polyhydroxy butyric acid, polyorthoesters, polyacetals, polydihydropyrans, polycyanoacrylates and cross-linked or amphipathic block copolymers of hydrogels.

Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like.

Disintegrating agents include, without limitation, starch, methyl cellulose, agar, bentonite, xanthan gum and the like.

Examples of QC-Inhibitors

QC-inhibitors, which are suitable for uses and methods according to the present invention are disclosed in WO 2005/

075436, which is incorporated herein in its entirety with regard to the structure, synthesis and methods of use of the QC-inhibitors.

The present invention provides novel inhibitors of QC (EC) of the formula 1,

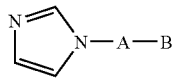

formula 1 wherein:

A is either:
an alkyl chain, alkenyl chain or alkynyl chain;
or A is a group selected from:

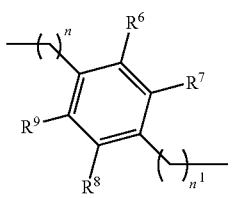
(I)

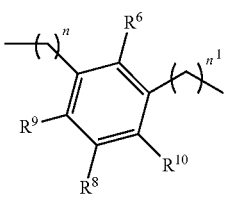
(II)

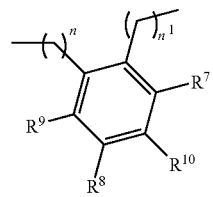
(III)

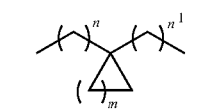
(IV)

(V)

wherein:
$R^6$, $R^7$, $R^8$, $R^9$ and $R^{10}$ are independently H or an alkyl chain, alkenyl chain, alkynyl chain, cycloalkyl, a carbocycle, aryl, heteroaryl, or a heterocycle;
n and $n^1$ are independently 1-5;
m is 1-5;
o is 0-4;

and B is a group selected from (VI)-(XIV):

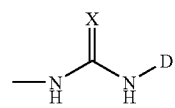
(VI)

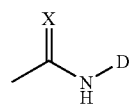
(VIa)

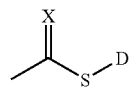
(VIb)

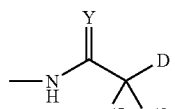
(VII)

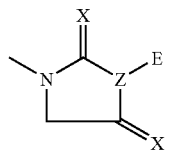
(VIII)

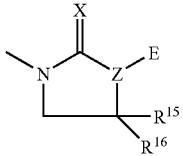
(IX)

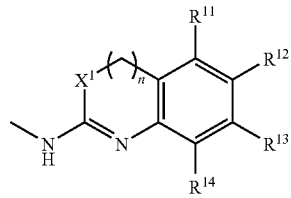
(X)

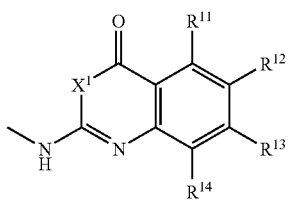
(XI)

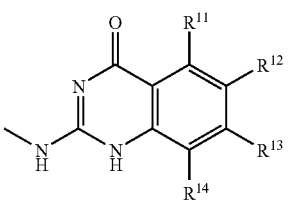
(XII)

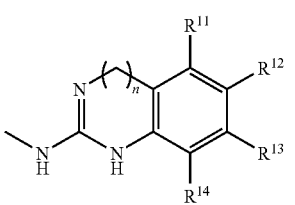
(XIII)

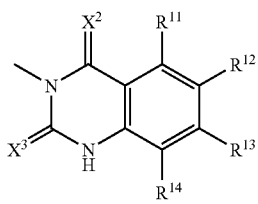

(XIV)

wherein:

D and E independently represent an alkyl chain, alkenyl chain, alkynyl chain, a cycloalkyl, carbocycle, aryl, -alkylaryl, heteroaryl, -alkylheteroaryl, acyl or a heterocycle.

X represents $CR^{20}R^{21}$, O, S, $NR^{19}$, with the proviso for formulas (VIII) and (IX) that, if Z=CH, X is O or S;

$R^{19}$ is selected from the group consisting of H, alkyl, cycloalkyl, aryl, heteroaryl, -oxyalkyl, -oxyaryl, carbonyl, amido, hydroxy, $NO_2$, $NH_2$, CN;

$R^{20}$ and $R^{21}$ are independently selected from H, alkyl, cycloalkyl, heterocycle, aryl, heteroaryl, -oxyalkyl, -oxyaryl, carbonyl, amido, $NO_2$, $NH_2$, CN, $CF_3$;

$X^1$, $X^2$ and $X^3$ are independently O or S provided that $X^2$ and $X^3$ are not both O;

Y is O or S, with the proviso that Y may not be O, when the carbocycle formed by $R^{17}$ and $R^{18}$ has 3 members in the ring;

Z is CH or N;

$R^{11}$, $R^{12}$, $R^{13}$ and $R^{14}$ can be independently selected from H, an alkyl chain, an alkenyl chain, an alkynyl chain, cycloalkyl, carbocycle, aryl, heteroaryl, a heterocycle, halogen, alkoxy-, -thioalkyl, carboxyl, carboxylic acid ester, carbonyl, carbamide, carbimide, thiocarbamide or thiocarbonyl, $NH_2$, $NO_2$;

$R^{15}$ and $R^{16}$ are independently of each other H or a branched or unbranched alkyl chain, or a branched or unbranched alkenyl chain;

$R^{17}$ and $R^{18}$ are independently selected from H or an alkyl chain, alkenyl chain, a alkynyl chain, a carbocycle, aryl, heteroaryl, heteroalkyl or can be connected to form a carbocycle with up to 6 ring atoms;

n is 0 or 1;

In one proviso, the following compounds:

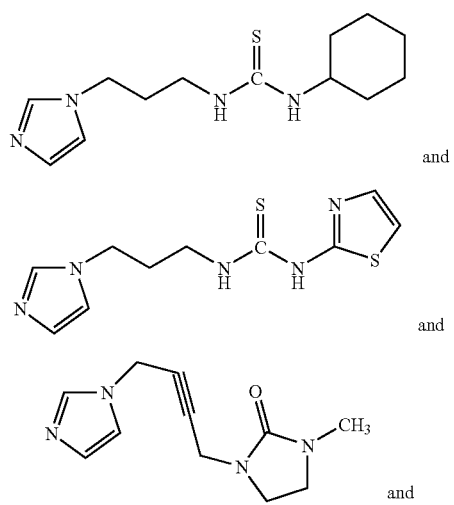

(a)

(b)

(c)

and

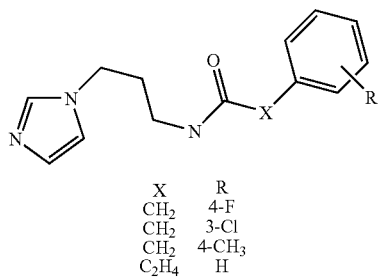

(d)

| X | R |
|---|---|
| $CH_2$ | 4-F |
| $CH_2$ | 3-Cl |
| $CH_2$ | 4-$CH_3$ |
| $C_2H_4$ | H | are excluded from formula 1.

When A is selected from an alkyl chain, alkenyl chain or alkynyl chain, preferably A is a $C_1$-$C_7$ alkyl chain, $C_1$-$C_7$ alkenyl chain or a $C_1$-$C_7$ alkynyl chain. In one embodiment of the invention A is an unbranched $C_{2-5}$ alkyl chain, in particular an unbranched $C_{3-4}$ alkyl chain, especially an unbranched $C_3$ alkyl chain. In a second embodiment of the invention A represents a $C_3$ alkyl chain which is substituted at the 2 position by one (i.e. in S or R configuration) or two methyl groups.

When A is selected from the formulae (I) to (V), preferably A is selected from groups (I) to (IV). In one embodiment of the invention A represents a group of formula (IV), wherein $n^1$ are each equal to 1 and m=1-4, especially m=1. In a second embodiment of the invention A represents a group of formula (I), (II) or (III), wherein n and $n^1$ are each equal to 1 and $R^6$, $R^7$, $R^8$, $R^9$ and $R^{10}$ represent H.

Preferably $R^6$, $R^7$, $R^8$, $R^9$ and $R^{10}$ represent H or methyl.

In one embodiment of the invention the group B is chosen from (VI), (VIa), (VIb), (VII), (X), (XI), (XII), (XIII) and (XIV). In a second embodiment of the invention group B represents formula (VI). In a third embodiment of the invention group B represents formula (VIa). In a fourth embodiment of the invention group B represents formula (VIb). In a fifth embodiment of the invention group B represents formula (VII). In a sixth embodiment of the invention group B represents formula (X). In a seventh embodiment of the invention group B represents formula (XI). In an eighth embodiment of the invention group B represents formula (XII). In another embodiment of the invention group B represents formula (XIII). In a further embodiment of the invention group B represents formula (XIV). In a preferred embodiment of the invention B represents a group of formula (VI) or (VII).

When B represents a group (IX) suitably A does not represent alkynyl.

Preferably D and E independently represent benzyl, aryl, heteroaryl or a heterocycle.

In one embodiment of the invention D and E represent aryl, in particular phenyl or napthyl, especially substituted phenyl. Preferred substituent groups when D represents phenyl include alkoxy-, -thioalkyl, halogen, or a carboxylic acid alkyl or aryl ester. Also preferred are fluoro, chloro, bromo, iodo, trifluoromethyl, trifluoromethoxy, methoxy, ethoxy, benzyloxy, cyano, acetyl, dimethyl amino, methylsulphanyl, nitro, oxazolyl, pyrazolyl, isopropyl, ethyl and methoxycarbonyl. Where a phenyl group is mono-substituted it is preferred that substitution is in the 4-position. Other suitable aryl groups, which D and E may represent include dihydrobenzodioxine, benzodioxole, benzodithiole dihydrobenzodithiine, benzooxathiole and dihydrobenzooxathiine. A particularly preferred group, which D or E may represent is 3,4-(dimethoxy)-phenyl, Preferably $R^{20}$ and $R^{21}$ represent $NO_2$, CN, $CF_3$ or, if $R^{20}$ is H, $R^{21}$ is $NO_2$, CN, $CF_3$, or, if $R^{21}$ is H, $R^{20}$ is $NO_2$, CN, $CF_3$.

In one embodiment, X or Y is S, O or NR$^1$. Preferably X or Y is S.

Preferably Z represents N.

In a preferred embodiment, R$^{11}$ and R$^{14}$ are H.

In a further preferred embodiment, R$^{12}$ and R$^{13}$ are independently selected from oxyalkyl or thioalkyl, halogen, or carboxylic acid alkyl ester or phenyl.

In a preferred embodiment, at least one of R$^{15}$ and R$^{16}$ is H, more preferably, R$^{15}$ and R$^{16}$ are both H.

In a preferred embodiment, one of R$^{17}$ and R$^{18}$ is H and the other is Me. Also preferred are compounds wherein one of R$^{17}$ and R$^{18}$ is H and the other is phenyl. Additionally preferred are compounds where R$^{17}$ and R$^{18}$ form a carbocycle with up to 6 members in the ring atoms.

Preferred compounds include those defined by Examples 13, 119 and 125 below.

The present invention provides compounds of formula 1 for use as a pharmaceutical. In one embodiment regarding the use of the compounds of formula 1 as a pharmaceutical, the compounds:

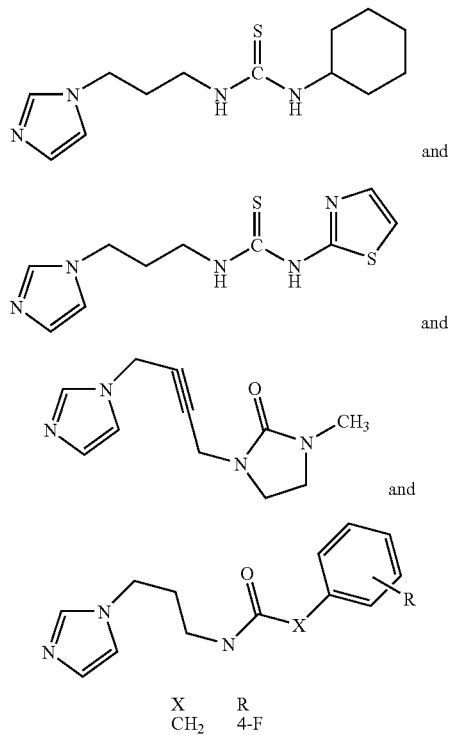

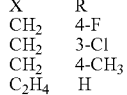

are excluded from formula 1.

The compound (a) of the proviso above is disclosed as compound 7 in Ganellin et al (1995) J Med Chem 38(17) 3342-3350. This paper discloses said compound as a weak inhibitor of the histamine H3 receptor.

The compound of proviso (b) is disclosed as compound 7 in Venkatachalam et al (2001) Bioorganic Med Chem Lett 11, 523-528. This discloses said compound as an HIV1 reverse transcriptase inhibitor.

The compound of proviso (c) is disclosed as compound 19b in Moon et al (1991) J Med Chem 34, 2314-2327. This paper discloses said compound as a cholinergic agonist with potential use in the treatment of Alzheimer's disease.

The compounds of proviso (d) are disclosed as compounds 99, 100 and 102-103 in Wright et al (1986) J Med Chem 29, 523-530. This paper discloses said compounds as thromoxane synthetase inhibitors.

Certain compounds which would be embraced by formula 1 if it were not for the proviso "provided that X$^2$ and X$^3$ are not both O" are disclosed in Wright et al (1987) J Med Chem 30, 2277-2283 as thromboxane synthetase inhibitors.

Certain compounds which would be embraced by formula 1 if it were not for the proviso "that Y may not be O, when the carbocycle formed by R$^{17}$ and R$^{18}$ has 3 members in the ring" are disclosed in EP 0 117 462 A2 as thromboxane synthetase inhibitors.

In particular:

A suitable compound, that of formula 1* shown below, is a inhibitor of QC:

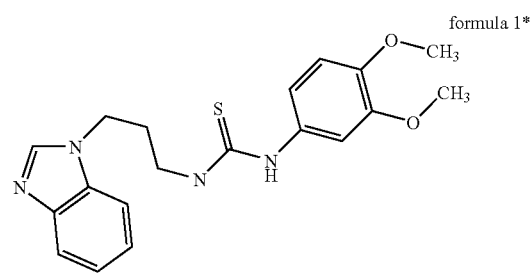

In a further embodiment, the inhibitors of QC (EC) are those of formula 1a,

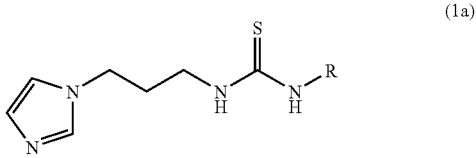

wherein R is defined in examples 1 to 53.

| Example | R | ESI-MS (M + H) | Res. Act. (%) | IC$_{50}$ (μM) | K$_i$ (μM) |
|---|---|---|---|---|---|
| 1 | Methyl | 199.3 | 4.3 | | 13 |
| 2 | tert-Butyl | 241.4 | 60.7 | | 14.7 |
| 3 | Benzyl | 275.4 | 60.9 | | 5.67 |
| 4 | Phenyl | 261.4 | 42.3 | | 4.4 |
| 5 | 4-(fluoro)-phenyl | 279.35 | 42.0 | | 4.73 |
| 6 | 4-(chloro)-phenyl | 295.80 | | | 1.2 |
| 7 | 4-(ethyl)-phenyl | 289.41 | 28.7 | | 2.78 |
| 8 | 4-(trifluoromethyl)-phenyl | 329.4 | 38.5 | | 3.93 |
| 9 | 4-(methoxy-carbonyl)-Phenyl | 319.4 | | | 1.19 |
| 10 | 4-(acetyl)-phenyl | 303.4 | 17.0 | | 1.70 |
| 11 | 4-(methoxy)-phenyl | 291.4 | 9.7 | | 0.70 |
| 12 | bicyclo[2.2.1]hept-5-en-2-yl | 277.5 | 16.0 | | |
| 13 | 3,4-(dimethoxy)-phenyl | 321.5 | 0.7 | 0.22 | 0.06 |
| 14 | 2,4-(dimethoxy)-phenyl | 321.5 | 2.2 | | 0.57 |
| 15 | 3,5-(dimethoxy)-phenyl | 321.5 | 2.86 | | 0.75 |

| Example | R | ESI-MS (M + H) | Res. Act. (%) | IC$_{50}$ (µM) | K$_i$ (µM) |
|---|---|---|---|---|---|
| 16 | 2-(methoxy-carbonyl)-Phenyl | 319.4 | | | |
| 17 | 4-(oxazol-5-y)-phenyl | 328.5 | 3.64 | | 0.86 |
| 18 | 4-(pyrazol-1-yl)-phenyl | 327.4 | | | |
| 19 | 4-(isopropyl)-phenyl | 303.5 | 8.7 | | |
| 20 | 4-(piperidine-1-sulfonyl)-Phenyl | 408.6 | 8.5 | | 2.27 |
| 21 | 4-(morpholin-4-yl)-phenyl | 346.5 | 9.0 | | |
| 22 | 4-(cyano)-phenyl | 286.4 | 9.0 | | 2.89 |
| 23 | 2,3-dihydro-benzo[1,4]dioxin-6-yl | 319.4 | 4.17 | | 1.12 |
| 24 | benzo[1,3]dioxol-5-yl | 305.4 | 16.7 | | 5.66 |
| 25 | 3,4,5(trimethoxy)-phenyl | 351.5 | 1.7 | | 0.34 |
| 26 | 3-(methoxy)-phenyl | 291.4 | 6.8 | | 1.86 |
| 27 | 4-(ethoxy)-phenyl | 305.5 | 7.2 | | 0.89 |
| 28 | 4-(benzyloxy)-phenyl | 367.5 | | | 0.98 |
| 29 | 4-(methoxy)-benzyl | 305.5 | | | 3.93 |
| 30 | 3,4-(dimethoxy)-benzyl | 335.5 | | | 1.55 |
| 31 | 2-(methoxy-carbonyl)-thiophene-3-yl | 325.5 | | | |
| 32 | 3-(ethoxy-carbonyl)-4,5,6,7-tetrahydrobenzo[b]thiophene2-yl | 392.6 | | | |
| 33 | 2-(methoxy-carbonyl)-4-(methyl)-thiophene-3-yl | 339.5 | | | |
| 34 | Benzo[c][1,2,5]thiazol-4-yl | 319.5 | | | |
| 35 | Benzo[c][1,2,5]thiazol-5-yl | 319.5 | 4.4 | | 1.37 |
| 36 | 5-(methyl)-3-(phenyl)-isooxazol-4-yl | 342.5 | | | |
| 37 | 3,5-(dimethyl)-isooxazol-4-yl | 280.4 | | | |
| 38 | 4-(iodo)-phenyl | 387.3 | 23.5 | | 2.12 |
| 39 | 4-(bromo)-phenyl | 340.3 | | | 2.52 |
| 40 | 4-(methyl)-phenyl | 275.4 | 31.3 | | 2.14 |
| 41 | Naphthalen-1-yl | 311.5 | 26.7 | | 2.79 |
| 42 | 4-(nitro)-phenyl | 306.4 | 31.1 | | 2.68 |
| 43 | Butyl | 241.4 | 53.8 | 14.0 | |
| 44 | Cyclooctyl | 295.5 | 33.1 | 9.1 | |
| 45 | Furan-2-ylmethyl | 265.4 | 61.4 | 10.0 | |
| 46 | Tetrahydrofuran-2-ylmethyl | 269.4 | 46.0 | 12.8 | |
| 47 | Benzo[1,3]dioxol-5-ylmethyl | 319.4 | 42.7 | | 6.1 |
| 48 | 2-(morpholin-4-yl)-ethyl | 298.5 | 55.0 | 13.3 | |
| 49 | 4-(methylsulfanyl)-phenyl | 307.5 | 19.1 | | 1.66 |
| 50 | 4-(dimethylamino)-phenyl | 304.5 | | | 2.03 |
| 51 | 4-(trifluoromethoxy)-phenyl | 345.4 | 14.2 | | |
| 52 | Benzoyl | 288.3 | | | |
| 53 | Pyridin-4-yl | 261.1 | | | |

Further suitable inhibitors of QC (EC) are those of formula 1b,

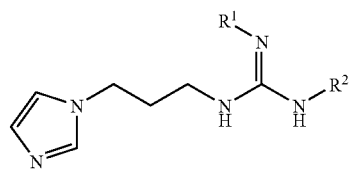

(1b)

wherein R$^1$ and R$^2$ are defined in examples 54 to 95.

| Example | R$^1$ | R$^2$ | ESI-MS (M + H) | Res. Act. (%) | K$_i$ (µM) |
|---|---|---|---|---|---|
| 54 | Cyano | Methyl | 207.3 | | 1.5 |
| 55 | Cyano | 3,4-(dimethoxy)-phenyl | 329.4 | | 1.36 |
| 56 | Cyano | 2,4-(dimethoxy)-phenyl | 329.4 | | |
| 57 | Cyano | 3,5-(dimethoxy)-phenyl | 329.4 | | 0.91 |
| 58 | Cyano | 2,3-dihydrobenzo[b][1,4]dioxin-7-yl | 327.4 | | 0.64 |
| 59 | Cyano | Benzo[d][1,3]dioxol-6-yl | 313.4 | | 0.73 |
| 60 | Cyano | 3,4,5-(trimethoxy)-phenyl | 359.4 | | 0.88 |
| 61 | Cyano | 3-(methoxy)-phenyl | 299.4 | | |
| 62 | Cyano | 4-(ethoxy)-phenyl | 313.4 | | |
| 63 | Cyano | 4-(benzyloxy)-phenyl | 375.5 | | |
| 64 | Cyano | Phenyl | 269.4 | | 1.02 |
| 65 | Cyano | 4-(methoxy)-phenyl | 299.4 | | 0.70 |
| 66 | Cyano | 4-(acetyl)-phenyl | 311.4 | | |
| 67 | Cyano | 4-(nitro)-phenyl | 314.4 | | |
| 68 | Cyano | Benzyl | 283.4 | 22.5 | 8.17 |
| 69 | Cyano | Naphthalen-1-yl | 319.4 | | |

-continued

| Example | R¹ | R² | ESI-MS (M + H) | Res. Act. (%) | $K_i$ (μM) |
|---|---|---|---|---|---|
| 70 | Cyano | 4-(fluoro)-phenyl | 387.3 | | |
| 71 | Cyano | 4-(iodo)-phenyl | 395.3 | | |
| 72 | Cyano | 4-(bromo)-phenyl | 348.3 | | |
| 73 | Cyano | Cyclooctyl | 289.4 | | |
| 74 | Cyano | tert-butyl | 249.3 | | |
| 75 | Cyano | 4-(methyl)-phenyl | 283.3 | | 1.34 |
| 76 | Cyano | 4-(methylthio)-phenyl | 315.5 | | |
| 77 | Cyano | 4-(ethyl)-phenyl | 297.4 | | |
| 78 | Cyano | 4-(dimethylamino)-phenyl | 312.4 | | |
| 79 | Cyano | Butyl | 249.4 | | |
| 80 | Cyano | Trityl | 435.6 | | |
| 81 | Cyano | (Benzo[d][1,3]dioxol-6yl)methyl | 327.4 | | 1.53 |
| 82 | Cyano | (tetrahydrofuran-2yl)methyl | 277.4 | | |
| 83 | Cyano | 4-(trifluoromethyl)-phenyl | 334.4 | | |
| 84 | Cyano | (furan-2-yl)methyl | 273.4 | | |
| 85 | Cyano | 2-(morpholin-4-yl)-ethyl | 306.4 | | |
| 86 | Cyano | 4-(oxazol-5yl)-phenyl | 336.4 | | |
| 87 | Cyano | Pyridin-3-yl | 270.4 | | |
| 88 | Cyano | 4-(cyano)-phenyl | 294.4 | | |
| 89 | Cyano | 4-(trifluoromethoxy)-phenyl | 353.4 | | |
| 90 | Cyano | 4-(piperidinosulfonyl)-phenyl | 416.6 | | |
| 91 | Cyano | 4-(1H-pyrazol-1-yl)phenyl | 335.4 | | |
| 92 | H | 3,4-(dimethoxy)-phenyl | 304.4 | | 204.5 |
| 93 | Methyl | 3,4-(dimethoxy)-phenyl | 318.4 | | 3.62 |
| 94 | Cyano | 2,3,4-(trimethoxy)-phenyl | 358.1 | | |
| 95 | Cyano | Cycloheptyl | 288.2 | | |

Further suitable inhibitors of QC (EC) are those of formula 1c,

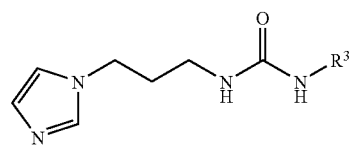

wherein R³ is defined in examples 96 to 102.

| Example | R³ | ESI-MS (M + H) | Res. Act. (%) | IC₅₀ (μM) | $K_i$ (μM) |
|---|---|---|---|---|---|
| 96 | Ethyl | 197.3 | | | 19.2 |
| 97 | 6-fluoro-4H-benzo[d][1,3]dioxin-8-yl | 321.4 | 19.0 | 12.0 | |
| 98 | 3-(cylopentyloxy)-4-(methoxy)-phenyl | 359.4 | 2.87 | | 0.62 |
| 99 | 4-(heptyloxy)-phenyl | 359.5 | 5.6 | 9.9 | |
| 100 | 3,4-dihydro-2H-benzo[b][1,4]dioxepin-7-yl | 317.4 | | | |
| 101 | 4-(butoxy)-phenyl | 317.4 | | | |
| 102 | 3,4-(dimethoxy)-phenyl | 305.4 | | | 0.46 |

Further suitable inhibitors of QC (EC) are those of formula 1d,

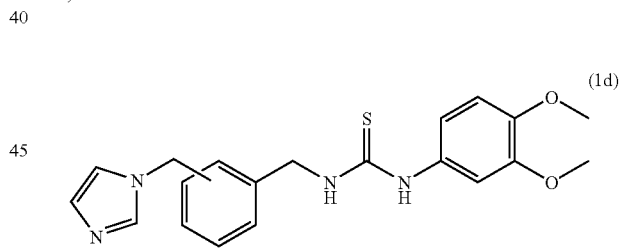

wherein the position on the ring is defined in examples 103 to 105.

| Example | Position of the Benzyl-substitution | ESI-MS (M + H) | Res. Act. (%) | $K_i$ (μM) |
|---|---|---|---|---|
| 103 | 2 | 383.5 | 16.27 | 4.84 |
| 104 | 3 | 383.5 | | 3.52 |
| 105 | 4 | 383.5 | | 1.86 |

Further suitable inhibitors of QC (EC) are those of formula 1e,

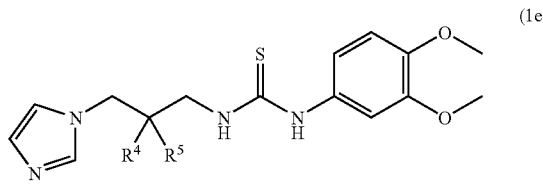

wherein $R^4$ and $R^5$ are defined in examples 106 to 109.

| Example | $R^4$ | $R^5$ | ESI-MS (M + H) | Res. Act. (%) | $IC_{50}$ (μM) | $K_i$ (μM) |
|---|---|---|---|---|---|---|
| 106 (S) | H | Methyl | 335.5 | | | 0.76 |
| 107 (R) | Methyl | H | 335.5 | | | 0.35 |
| 108 | Methyl | Methyl | 349.5 | | | |
| 109 | —CH$_2$—CH$_2$— | | 347.5 | | | 7.85 |

Further suitable inhibitors of QC (EC) are those of formula 1f,

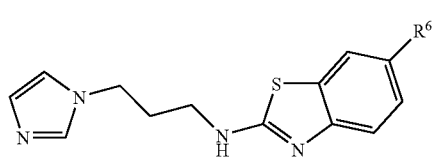

wherein $R^6$ is defined in examples 110 to 112.

| Example | $R^6$ | ESI-MS (M + H) | Res. Act. (%) | $IC_{50}$ (μM) | $K_i$ (μM) |
|---|---|---|---|---|---|
| 110 | H | 259.4 | | | 3.00 |
| 111 | Chloro | 293.8 | | | 3.35 |
| 112 | Methoxy | 289.4 | | | 1.57 |

Further suitable inhibitors of QC (EC) are those of formula 1g,

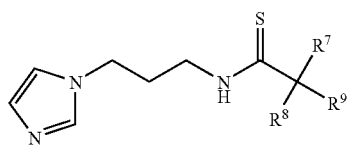

wherein $R^7$, $R^8$ and $R^9$ are defined in examples 113 to 132.

| Example | $R^7$ | $R^8$ | $R^9$ | ESI-MS (M + H) | Res. Act. (%) | $K_i$ (μM) |
|---|---|---|---|---|---|---|
| 113 | Phenyl | H | H | 260.4 | | 4.62 |
| 114 | Thiophen-2-yl | H | H | 266.5 | | 3.29 |
| 115 (R) | Phenyl | Methyl | H | 274.5 | 21.2 | 7.34 |
| 116 (S) | Phenyl | H | Methyl | 274.5 | 8.1 | 3.51 |
| 117 | Phenyl | H | Ethyl | 288.5 | | 3.57 |
| 118 | Phenyl | H | Phenyl | 336.5 | 13.5 | 4.48 |
| 119 | 3,4-(dimethoxy)-Phenyl | H | H | 320.5 | | 0.39 |
| 120 | 3,4-(dimethoxy)-Phenyl | Methyl | Methyl | 347.2 | | |
| 121 | 4-(chloro)-phenyl | —CH$_2$—CH$_2$—CH$_2$— | | 334.9 | | 4.88 |
| 122 | 4-(chloro)-phenyl | —CH$_2$—C$_2$H$_4$—CH$_2$— | | 349.0 | | 7.3 |
| 123 | 4-(methoxy)-phenyl | —CH$_2$—C$_3$H$_6$—CH$_2$— | | 358.6 | | 2.78 |
| 124 | 4-(methoxy)-phenyl | —CH$_2$—CH$_2$— | | 316.5 | | 0.39 |
| 125 | 3,4-(dimethoxy)-Phenyl | —CH$_2$—CH$_2$— | | 346.5 | | 0.09 |
| 126 | 3,4,5-(trimethoxy)-Phenyl | —CH$_2$—CH$_2$— | | 376.6 | | |
| 127 | 2,3,4-(trimethoxy)-Phenyl | —CH$_2$—CH$_2$— | | 376.6 | | |
| 128 | 2-(methoxy)-phenyl | —CH$_2$—CH$_2$— | | 316.5 | | |
| 129 | 3-(methoxy)-phenyl | —CH$_2$—CH$_2$— | | 316.5 | | |
| 130 | 2,3-(dimethoxy)-Phenyl | —CH$_2$—CH$_2$— | | 346.5 | | |

| Example | R⁷ | R⁸ | R⁹ | ESI-MS (M + H) | Res. Act. (%) | $K_i$ (μM) |
|---|---|---|---|---|---|---|
| 131 | 3,5-(dimethoxy)-Phenyl | | —CH₂—CH₂— | 346.5 | | |
| 132 | 2,5-(dimethoxy)-Phenyl | | —CH₂—CH₂— | 346.5 | | |

Further suitable inhibitors of QC (EC) are those of formula 1h,

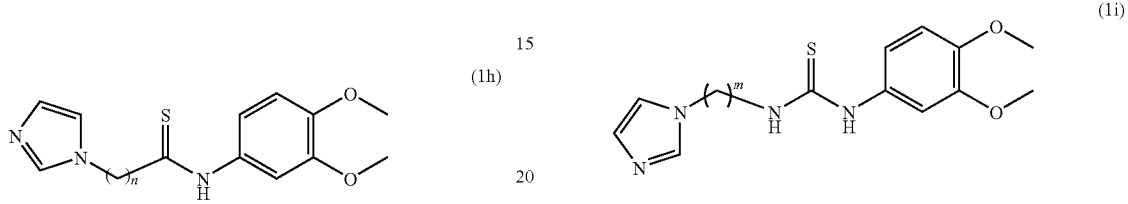

wherein n is defined in examples 133 to 135.

wherein m is defined in examples 136 and 137.

| Example | N | ESI-MS (M + H) | $K_i$ (μM) |
|---|---|---|---|
| 133 | 3 | 306.4 | |
| 134 | 4 | 320.5 | 0.99 |
| 135 | 5 | 334.5 | |

| Example | m | ESI-MS (M + H) | Res. Act. (%) | $K_i$ (μM) |
|---|---|---|---|---|
| 136 | 2 | 307.4 | | 17.6 |
| 137 | 4 | 335.5 | 2.19 | 0.55 |

Further suitable inhibitors of QC (EC) are those of formula 1i,

Further suitable inhibitors of QC (EC) are those of formula 138 to 141.

| Example | Structure | ESI-MS (M + H) | Res. Act. (%) | IC₅₀ (μM) | $K_i$ (μM) |
|---|---|---|---|---|---|
| 138 | 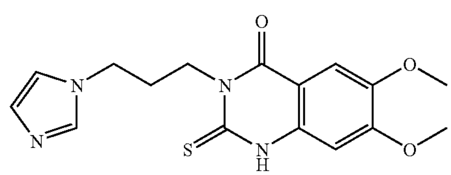 | 347.5 | | | |
| 139 | 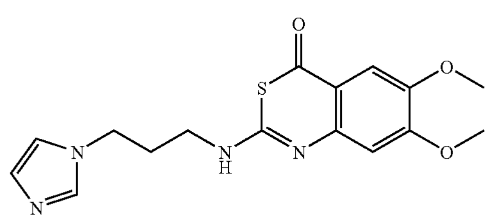 | 347.2 | | | |
| 140 | 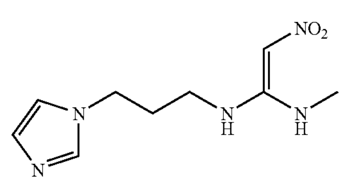 | 226.3 | 13.8 | | 20.5 |

| Example | Structure | ESI-MS (M + H) | Res. Act. (%) | IC$_{50}$ (µM) | K$_i$ (µM) |
|---|---|---|---|---|---|
| 141 | 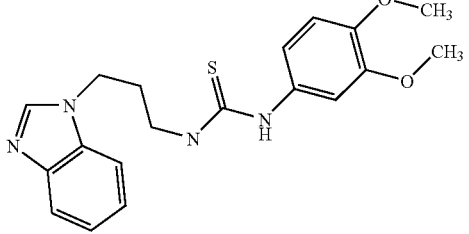 | 370.4 | | | |

A preferred inhibitor of glutaminyl peptide cyclotransferase is 1-(3-(1H-imidazol-1-yl)propyl)-3-(3,4-dimethoxyphenyl)thiourea hydrochloride (further named as QCI)

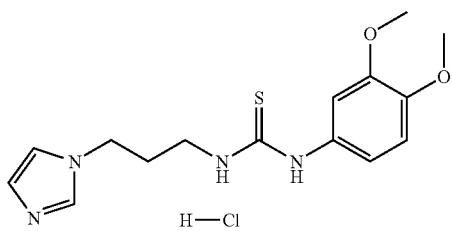

In a preferred embodiment, the present invention provides a composition, preferably a pharmaceutical composition, comprising at least one QC inhibitor optionally in combination with at least one other agent selected from the group consisting of nootropic agents, neuroprotectants, antiparkinsonian drugs, amyloid protein deposition inhibitors, beta amyloid synthesis inhibitors, antidepressants, anxiolytic drugs, antipsychotic drugs and anti-multiple sclerosis drugs.

More specifically, the aforementioned other agent is selected from the group consisting of beta-amyloid antibodies, cysteine protease inhibitors, PEP-inhibitors, LiCl, acetylcholinesterase (AChE) inhibitors, PIMT enhancers, inhibitors of beta secretases, inhibitors of gamma secretases, inhibitors of neutral endopeptidase, inhibitors of Phosphodiesterase-4 (PDE-4), TNFalpha inhibitors, muscarinic M1 receptor antagonists, NMDA receptor antagonists, sigma-1 receptor inhibitors, histamine H3 antagonists, immunomodulatory agents, immunosuppressive agents, MCP-1 antagonists or an agent selected from the group consisting of antegren (natalizumab), Neurelan (fampridine-SR), campath (alemtuzumab), IR 208, NBI 5788/MSP 771 (tiplimotide), paclitaxel, Anergix.MS (AG 284), SH636, Differin (CD 271, adapalene), BAY 361677 (interleukin-4), matrix-metalloproteinase-inhibitors (e.g. BB 76163), interferon-tau (trophoblastin) and SAIK-MS.

Furthermore, the other agent may be, for example, an anti-anxiety drug or antidepressant selected from the group consisting of
(a) Benzodiazepines, e.g. alprazolam, chlordiazepoxide, clobazam, clonazepam, clorazepate, diazepam, fludiazepam, loflazepate, lorazepam, methaqualone, oxazepam, prazepam, tranxene,
(b) Selective serotonin re-uptake inhibitors (SSRI's), e.g. citalopram, fluoxetine, fluvoxamine, escitalopram, sertraline, paroxetine,
(c) Tricyclic antidepressants, e.g. amitryptiline, clomipramine, desipramine, doxepin, imipramine
(d) Monoamine oxidase (MAO) inhibitors,
(e) Azapirones, e.g. buspirone, tandopsirone,
(f) Serotonin-norepinephrine reuptake inhibitors (SNRI's), e.g. venlafaxine, duloxetine,
(g) Mirtazapine,
(h) Norepinephrine reuptake inhibitors (NRI's), e.g. reboxetine,
(i) Bupropione,
(j) Nefazodone,
(k) beta-blockers,
(l) NPY-receptor ligands: NPY agonists or antagonists.

In a further embodiment, the other agent may be, for example, an anti-multiple sclerosis drug selected from the group consisting of
a) dihydroorotate dehydrogenase inhibitors, e.g. SC-12267, teriflunomide, MNA-715, HMR-1279 (syn. to HMR-1715, MNA-279),
b) autoimmune suppressant, e.g. laquinimod,
c) paclitaxel,
d) antibodies, e.g. AGT-1, anti-granulocyte-macrophage colony-stimulating factor (GM-CSF) monoclonal antibody, Nogo receptor modulators, ABT-874, alemtuzumab (CAMPATH), anti-OX40 antibody, CNTO-1275, DN-1921, natalizumab (syn. to AN-100226, Antegren, VLA-4 Mab), daclizumab (syn. to Zenepax, Ro-34-7375, SMART anti-Tac), J-695, priliximab (syn. to Centara, CEN-000029, cM-T412), MRA, Dantes, anti-IL-12-antibody,
e) peptide nucleic acid (PNA) preparations, e.g. reticulose,
f) interferon alpha, e.g. Alfaferone, human alpha interferon (syn. to Omniferon, Alpha Leukoferon),
g) interferon beta, e.g. Frone, interferon beta-1a like Avonex, Betron (Rebif), interferon beta analogs, interferon beta-transferrin fusion protein, recombinant interferon beta-1b like Betaseron,
h) interferon tau,
i) peptides, e.g. AT-008, AnergiX.MS, Immunokine (alpha-Immunokine-NNSO3), cyclic peptides like ZD-7349,
j) therapeutic enzymes, e.g. soluble CD8 (sCD8),
k) multiple sclerosis-specific autoantigen-encoding plasmid and cytokine-encoding plasm1d, e.g. BHT-3009;
l) inhibitor of TNF-alpha, e.g. BLX-1002, thalidomide, SH-636,
m) TNF antagonists, e.g. solimastat, lenercept (syn. to RO-45-2081, Tenefuse), onercept (sTNFR1), CC-1069,
n) TNF alpha, e.g. etanercept (syn. to Enbrel, TNR-001)
o) CD28 antagonists, e.g. abatacept,
p) Lck tyrosine kinase inhibitors, q) cathepsin K inhibitors,
r) analogs of the neuron-targeting membrane transporter protein taurine and the plant-derived calpain inhibitor leupeptin, e.g. Neurodur,
s) chemokine receptor-1 (CCR1) antagonist, e.g. BX-471,
t) CCR2 antagonists,
u) AMPA receptor antagonists, e.g. ER-167288-01 and ER-099487, E-2007, talampanel,
v) potassium channel blockers, e.g. fampridine,
w) tosyl-proline-phenylalanine small-molecule antagonists of the VLA-4/VCAM interaction, e.g. TBC-3342,
x) cell adhesion molecule inhibitors, e.g. TBC-772,
y) antisense oligonucleotides, e.g. EN-101,
z) antagonists of free immunoglobulin light chain (IgLC) binding to mast cell receptors, e.g. F-991,
aa) apoptosis inducing antigens, e.g. Apogen MS,
bb) alpha-2 adrenoceptor agonist, e.g. tizanidine (syn. to Zanaflex, Ternelin, Sirdalvo, Sirdalud, Mionidine),
cc) copolymer of L-tyrosine, L-lysine, L-glutamic acid and L-alanine, e.g. glatiramer acetate (syn. to Copaxone, COP-1, copolymer-1),
dd) topoisomerase II modulators, e.g. mitoxantrone hydrochloride,
ee) adenosine deaminase inhibitor, e.g. cladribine (syn. to Leustatin, Mylinax, RWJ-26251),
ff) interleukin-10, e.g. ilodecakin (syn. to Tenovil, Sch-52000, CSIF),
gg) interleukin-12 antagonists, e.g. lisofylline (syn. to CT-1501R, LSF, lysofylline),
hh) Ethanaminum, e.g. SRI-62-834 (syn. to CRC-8605, NSC-614383),
ii) immunomodulators, e.g. SAIK-MS, PNU-156804, alpha-fetoprotein peptide (AFP), IPDS,
jj) retinoid receptor agonists, e.g. adapalene (syn. to Differin, CD-271),
kk) TGF-beta, e.g. GDF-1 (growth and differentiation factor 1),
ll) TGF-beta-2, e.g. BetaKine,
mm) MMP inhibitors, e.g. glycomed,
nn) phosphodiesterase 4 (PDE4) inhibitors, e.g. RPR-122818,
oo) purine nucleoside phosphorylase inhibitors, e.g. 9-(3-pyridylmethyl)-9-deazaguanine, peldesine (syn. to BCX-34, TO-200),
pp) alpha-4/beta-1 integrin antagonists, e.g. ISIS-104278,
qq) antisense alpha4 integrin (CD49d), e.g. ISIS-17044, ISIS-27104,
rr) cytokine-inducing agents, e.g. nucleosides, ICN-17261,
ss) cytokine inhibitors,
tt) heat shock protein vaccines, e.g. HSPPC-96,
uu) neuregulin growth factors, e.g. GGF-2 (syn. to neuregulin, glial growth factor 2),
vv) cathepsin S-inhibitors,
ww) bropirimine analogs, e.g. PNU-56169, PNU-63693,
xx) Monocyte chemoattractant protein-1 inhibitors, e.g. benzimidazoles like MCP-1 inhibitors, LKS-1456, PD-064036, PD-064126, PD-084486, PD-172084, PD-172386.

Further, the present invention provides pharmaceutical compositions e.g. for parenteral, enteral or oral administration, comprising at least one QC inhibitor, optionally in combination with at least one of the other aforementioned agents.

These combinations provide a particularly beneficial effect. Such combinations are therefore shown to be effective and useful for the treatment of the aforementioned diseases. Accordingly, the invention provides a method for the treatment of these conditions.

The method comprises either co-administration of at least one QC inhibitor and at least one of the other agents or the sequential administration thereof.

Co-administration includes administration of a formulation, which comprises at least one QC inhibitor and at least one of the other agents or the essentially simultaneous administration of separate formulations of each agent.

Beta-amyloid antibodies and compositions containing the same are described, e.g. in WO 2006/137354, WO 2006/118959, WO 2006/103116, WO 2006/095041, WO 2006/081171, WO 2006/066233, WO 2006/066171, WO 2006/066089, WO 2006/066049, WO 2006/055178, WO 2006/046644, WO 2006/039470, WO 2006/036291, WO 2006/026408, WO 2006/016644, WO 2006/014638, WO 2006/014478, WO 2006/008661, WO 2005/123775, WO 2005/120571, WO 2005/105998, WO 2005/081872, WO 2005/080435, WO 2005/028511, WO 2005/025616, WO 2005/025516, WO 2005/023858, WO 2005/018424, WO 2005/011599, WO 2005/000193, WO 2004/108895, WO 2004/098631, WO 2004/080419, WO 2004/071408, WO 2004/069182, WO 2004/067561, WO 2004/044204, WO 2004/032868, WO 2004/031400, WO 2004/029630, WO 2004/029629, WO 2004/024770, WO 2004/024090, WO 2003/104437, WO 2003/089460, WO 2003/086310, WO 2003/077858, WO 2003/074081, WO 2003/070760, WO 2003/063760, WO 2003/055514, WO 2003/051374, WO 2003/048204, WO 2003/045128, WO 2003/040183, WO 2003/039467, WO 2003/016466, WO 2003/015691, WO 2003/014162, WO 2003/012141, WO 2002/088307, WO 2002/088306, WO 2002/074240, WO 2002/046237, WO 2002/046222, WO 2002/041842, WO 2001/062801, WO 2001/012598, WO 2000/077178, WO 2000/072880, WO 2000/063250, WO 1999/060024, WO 1999/027944, WO 1998/044955, WO 1996/025435, WO 1994/017197, WO 1990/014840, WO 1990/012871, WO 1990/012870, WO 1989/006242.

The beta-amyloid antibodies may be selected from, for example, polyclonal, monoclonal, chimenic or humanited antibodies. Furthermore, said antibodies may be useful to develop active and passive immune therapies, i.e. vaccines and monoclonal antibodies.

Suitable examples of beta-amyloid antibodies are ACU-5A5, huC091 (Acumen/Merck); PF-4360365, RI-1014, RI-1219, RI-409, RN-1219 (Rinat Neuroscience Corp (Pfizer Inc)); the nanobody therapeutics of Ablynx/Boehringer Ingelheim; beta-amyloid-specific humanized monoclonal antibodies of Intellect Neurosciences/IBL; m266, m266.2 (Eli Lilly & Co.); AAB-02 (Elan); bapineuzumab (Elan); BAN-2401 (Bioarctic Neuroscience AB); ABP-102 (Abiogen Pharma SpA); BA-27, BC-05 (Takeda); R-1450 (Roche); ESBA-212 (ESBATech AG); AZD-3102 (AstraZeneca) and beta-amyloid antibodies of Mindset BioPharmaceuticals Inc.

Especially preferred are antibodies, which recognize the N-terminus of the Aβ peptide. A suitable antibody, which recognize the Aβ-N-Terminus is, for example Acl-24 (AC immune CA). A monoclonal antibody against beta-amyloid peptide is disclosed in WO 2007/068412. Respective chimenic and humanized antibodies are disclosed in WO 2008/011348. A method for producing a vaccine composition for treating an amyloid-associated disease is disclosed in WO 2007/068411.

Suitable cysteine protease inhibitors are for example inhibitors of cathepsin B. Inhibitors of cathepsin B and compositions containing such inhibitors are described, e.g. in WO 2006/060473, WO 2006/042103, WO 2006/039807, WO 2006/021413, WO 2006/021409, WO 2005/097103, WO 2005/007199, WO2004/084830, WO 2004/078908, WO 2004/026851, WO 2002/094881, WO 2002/027418, WO 2002/021509, WO 1998/046559, WO 1996/021655.

Examples of suitable PIMT enhancers are 10-aminoaliphatyl-dibenz[b,f] oxepines described in WO 98/15647 and WO 03/057204, respectively. Further useful according to the present invention are modulators of PIMT activity described in WO 2004/039773.

Inhibitors of beta secretase and compositions containing such inhibitors are described, e.g. in WO 03/059346, WO 2006/099352, WO 2006/078576, WO 2006/060109, WO 2006/057983, WO 2006/057945, WO 2006/055434, WO 2006/044497, WO 2006/034296, WO 2006/034277, WO 2006/029850, WO 2006/026204, WO 2006/014944, WO 2006/014762, WO 2006/002004, U.S. Pat. No. 7,109,217, WO 2005/113484, WO 2005/103043, WO 2005/103020, WO 2005/065195, WO 2005/051914, WO 2005/044830, WO 2005/032471, WO 2005/018545, WO 2005/004803, WO 2005/004802, WO 2004/062625, WO 2004/043916, WO 2004/013098, WO 03/099202, WO 03/043987, WO 03/039454, U.S. Pat. No. 6,562,783, WO 02/098849 and WO 02/096897.

Suitable examples of beta secretase inhibitors for the purpose of the present invention are WY-25105 (Wyeth); Posiphen, (+)-phenserine (TorreyPines/NIH); LSN-2434074, LY-2070275, LY-2070273, LY-2070102 (Eli Lilly & Co.); PNU-159775A, PNU-178025A, PNU-17820A, PNU-33312, PNU-38773, PNU-90530 (Elan/Pfizer); KMI-370, KMI-358, kmi-008 (Kyoto University); OM-99-2, OM-003 (Athenagen Inc.); AZ-12304146 (AstraZeneca/Astex); GW-840736X (GlaxoSmithKline plc.) and DNP-004089 (De Novo Pharmaceuticals Ltd.).

Inhibitors of gamma secretase and compositions containing such inhibitors are described, e.g. in WO 2005/008250, WO 2006/004880, U.S. Pat. No. 7,122,675, U.S. Pat. No. 7,030,239, U.S. Pat. No. 6,992,081, U.S. Pat. No. 6,982,264, WO 2005/097768, WO2005/028440, WO 2004/101562, U.S. Pat. No. 6,756,511, U.S. Pat. No. 6,683,091, WO 03/066592, WO 03/014075, WO 03/013527, WO 02/36555, WO 01/53255, U.S. Pat. No. 7,109,217, U.S. Pat. No. 7,101,895, U.S. Pat. No. 7,049,296, U.S. Pat. No. 7,034,182, U.S. Pat. No. 6,984,626, WO 2005/040126, WO 2005/030731, WO 2005/014553, U.S. Pat. No. 6,890,956, EP 1334085, EP 1263774, WO 2004/101538, WO 2004/00958, WO 2004/089911, WO 2004/073630, WO 2004/069826, WO 2004/039370, WO 2004/031139, WO 2004/031137, U.S. Pat. No. 6,713,276, U.S. Pat. No. 6,686,449, WO 03/091278, U.S. Pat. No. 6,649,196, U.S. Pat. No. 6,448,229, WO 01/77144 and WO 01/66564.

Suitable gamma secretase inhibitors for the purpose of the present invention are GSI-953, WAY-GSI-A, WAY-GSI-B (Wyeth); MK-0752, MRK-560, L-852505, L-685-458, L-852631, L-852646 (Merck & Co. Inc.); LY-450139, LY-411575, AN-37124 (Eli Lilly & Co.); BMS-299897, BMS-433796 (Bristol-Myers Squibb Co.); E-2012 (Eisai Co. Ltd.); EHT-0206, EHT-206 (ExonHit Therapeutics SA); and NGX-555 (TorreyPines Therapeutics Inc.).

Suitable beta amyloid synthesis inhibitors for the purpose of the present invention are for example Bisnorcymserine (Axonyx Inc.); (R)-flurbiprofen (MCP-7869; Flurizan) (Myriad Genetics); nitroflurbiprofen (NicOx); BGC-20-0406 (Sankyo Co. Ltd.) and BGC-20-0466 (BTG plc.).

Suitable amyloid protein deposition inhibitors for the purpose of the present invention are for example SP-233 (Samaritan Pharmaceuticals); AZD-103 (Ellipsis Neurotherapeutics Inc.); AAB-001 (Bapineuzumab), AAB-002, ACC-001 (Elan Corp plc.); Colostrinin (ReGen Therapeutics plc.); Tramiprosate (Neurochem); AdPEDI-(amyloid-beta1-6)11) (Vaxin Inc.); MPI-127585, MPI-423948 (Mayo Foundation); SP-08 (Georgetown University); ACU-5A5 (Acumen/Merck); Transthyretin (State University of New York); PTI-777, DP-74, DP 68, Exebryl (ProteoTech Inc.); m266 (Eli Lilly & Co.); EGb-761 (Dr. Willmar Schwabe GmbH); SPI-014 (Satori Pharmaceuticals Inc.); ALS-633, ALS-499 (Advanced Life Sciences Inc.); AGT-160 (ArmaGen Technologies Inc.); TAK-070 (Takeda Pharmaceutical Co. Ltd.); CHF-5022, CHF-5074, CHF-5096 and CHF-5105 (Chiesi Farmaceutici SpA.).

Suitable PDE-4 inhibitors for the purpose of the present invention are for example Doxofylline (Instituto Biologico Chemioterapica ABC SpA.); idudilast eye drops, tipelukast, ibudilast (Kyorin Pharmaceutical Co. Ltd.); theophylline (Elan Corp.); cilomilast (GlaxoSmithKline plc.); Atopik (Barrier Therapeutics Inc.); tofimilast, CI-1044, PD-189659, CP-220629, PDE 4d inhibitor BHN (Pfizer Inc.); arofylline, LAS-37779 (Almirall Prodesfarma SA.); roflumilast, hydroxypumafentrine (Altana AG), tetomilast (Otska Pharmaceutical Co. Ltd.); tipelukast, ibudilast (Kyorin Pharmaceutical), CC-10004 (Celgene Corp.); HT-0712, IPL-4088 (Inflazyme Pharmaceuticals Ltd.); MEM-1414, MEM-1917 (Memory Pharmaceuticals Corp.); oglemilast, GRC-4039 (Glenmark Pharmaceuticals Ltd.); AWD-12-281, ELB-353, ELB-526 (Elbion AG); EHT-0202 (ExonHit Therapeutics SA.); ND-1251 (Neuro3d SA.); 4AZA-PDE4 (4 AZA Bioscience NV.); AVE-8112 (Sanofi-Aventis); CR-3465 (Rottapharm SpA.); GP-0203, NCS-613 (Centre National de la Recherche Scientifique); KF-19514 (Kyowa Hakko Kogyo Co. Ltd.); ONO-6126 (Ono Pharmaceutical Co. Ltd.); OS-0217 (Dainippon Pharmaceutical Co. Ltd.); IBFB-130011, IBFB-150007, IBFB-130020, IBFB-140301 (IBFB Pharma GmbH); IC-485 (ICOS Corp.); RBx-14016 and RBx-11082 (Ranbaxy Laboratories Ltd.). A preferred PDE-4-inhibitor is Rolipram.

MAO inhibitors and compositions containing such inhibitors are described, e.g. in WO 2006/091988, WO 2005/007614, WO 2004/089351, WO 01/26656, WO 01/12176, WO 99/57120, WO 99/57119, WO 99/13878, WO 98/40102, WO 98/01157, WO 96/20946, WO 94/07890 and WO 92/21333.

Suitable MAO-inhibitors for the purpose of the present invention are for example Linezolid (Pharmacia Corp.); RWJ-416-457 (RW Johnson Pharmaceutical Research Institute); budipine (Altana AG); GPX-325 (BioResearch Ireland); isocarboxazid; phenelzine; tranylcypromine; indantadol (Chiesi Farmaceutici SpA.); moclobemide (Roche Holding AG); SL-25.1131 (Sanofi-Synthelabo); CX-1370 (Burroughs Wellcome Co.); CX-157 (Krenitsky Pharmaceuticals Inc.); desoxypeganine (HF Arzneimittelforschung GmbH & Co. KG); bifemelane (Mitsubishi-Tokyo Pharmaceuticals Inc.); RS-1636 (Sankyo Co. Ltd.); esuprone (BASF AG); rasagiline (Teva Pharmaceutical Industries Ltd.); ladostigil (Hebrew University of Jerusalem); safinamide (Pfizer) and NW-1048 (Newron Pharmaceuticals SpA.).

Suitable histamine H3 antagonists for the purpose of the present invention are, e.g. ABT-239, ABT-834 (Abbott Laboratories); 3874-H1 (Aventis Pharma); UCL-2173 (Berlin Free University), UCL-1470 (BioProjet, Societe Civile de Recherche); DWP-302 (Daewoong Pharmaceutical Co Ltd); GSK-189254A, GSK-207040A (GlaxoSmithKline Inc.); cipralisant, GT-2203 (Gliatech Inc.); Ciproxifan (INSERM), 1S,2S)-2-(2-Aminoethyl)-1-(1H-imidazol-4-yl)cyclopropane (Hokkaido University); JNJ-17216498, JNJ-5207852 (Johnson & Johnson); NNC-0038-0000-1049 (Novo Nordisk A/S); and Sch-79687 (Schering-Plough).

PEP inhibitors and compositions containing such inhibitors are described, e.g. in JP 01042465, JP 03031298, JP 04208299, WO 00/71144, U.S. Pat. No. 5,847,155; JP 09040693, JP 10077300, JP 05331072, JP 05015314, WO 95/15310, WO 93/00361, EP 0556482, JP 06234693, JP 01068396, EP 0709373, U.S. Pat. No. 5,965,556, U.S. Pat. No. 5,756,763, U.S. Pat. No. 6,121,311, JP 63264454, JP 64000069, JP 63162672, EP 0268190, EP 0277588, EP 0275482, U.S. Pat. No. 4,977,180, U.S. Pat. No. 5,091,406, U.S. Pat. No. 4,983,624, U.S. Pat. No. 5,112,847, U.S. Pat. No. 5,100,904, U.S. Pat. No. 5,254,550, U.S. Pat. No. 5,262,431, U.S. Pat. No. 5,340,832, U.S. Pat. No. 4,956,380, EP 0303434, JP 03056486, JP 01143897, JP 1226880, EP 0280956, U.S. Pat. No. 4,857,537, EP 0461677, EP 0345428, JP 02275858, U.S. Pat. No. 5,506,256, JP 06192298, EP 0618193, JP 03255080, EP 0468469, U.S. Pat. No. 5,118,811, JP 05025125, WO 93/3065, JP 05201970, WO 9412474, EP 0670309, EP 0451547, JP 06339390, U.S. Pat. No. 5,073,549, U.S. Pat. No. 4,999,349, EP 0268281, U.S. Pat. No. 4,743,616, EP 0232849, EP 0224272, JP 62114978, JP 62114957, U.S. Pat. No. 4,757,083, U.S. Pat. No. 4,810,721, U.S. Pat. No. 5,198,458, U.S. Pat. No. 4,826,870, EP 0201742, EP 0201741, U.S. Pat. No. 4,873,342, EP 0172458, JP 61037764, EP 0201743, U.S. Pat. No. 4,772,587, EP 0372484, U.S. Pat. No. 5,028,604, WO 91/18877, JP 04009367, JP 04235162, U.S. Pat. No. 5,407,950, WO 95/01352, JP 01250370, JP 02207070, U.S. Pat. No. 5,221,752, EP 0468339, JP 04211648, WO 99/46272, WO 2006/058720 and WO 2006/120104.

Suitable prolyl endopeptidase inhibitors for the purpose of the present invention are, e.g. Fmoc-Ala-Pyrr-CN, Z-Phe-Pro-Benzothiazole (Probiodrug), Z-321 (Zeria Pharmaceutical Co Ltd.); ONO-1603 (Ono Pharmaceutical Co Ltd); JTP-4819 (Japan Tobacco Inc.) and S-17092 (Servier).

Other suitable compounds that can be used according to the present invention in combination with QC-inhibitors are NPY, an NPY mimetic or an NPY agonist or antagonist or a ligand of the NPY receptors.

Preferred according to the present invention are antagonists of the NPY receptors.

Suitable ligands or antagonists of the NPY receptors are 3a,4,5,9b-tetrahydro-1 h-benz[e]indol-2-yl amine-derived compounds as disclosed in WO 00/68197.

NPY receptor antagonists which may be mentioned include those disclosed in European patent applications EP 0 614 911, EP 0 747 357, EP 0 747 356 and EP 0 747 378; international patent applications WO 94/17035, WO 97/19911, WO 97/19913, WO 96/12489, WO 97/19914, WO 96/22305, WO 96/40660, WO 96/12490, WO 97/09308, WO 97/20820, WO 97/20821, WO 97/20822, WO 97/20823, WO 97/19682, WO 97/25041, WO 97/34843, WO 97/46250, WO 98/03492, WO 98/03493, WO 98/03494 and WO 98/07420; WO 00/30674, U.S. Pat. Nos. 5,552,411, 5,663,192 and 5,567,714; 6,114,336, Japanese patent application JP 09157253; international patent applications WO 94/00486, WO 93/12139, WO 95/00161 and WO 99/15498; U.S. Pat. No. 5,328,899; German patent application DE 393 97 97; European patent applications EP 355 794 and EP 355 793; and Japanese patent applications JP 06116284 and JP 07267988. Preferred NPY antagonists include those compounds that are specifically disclosed in these patent documents. More preferred compounds include amino acid and non-peptide-based NPY antagonists. Amino acid and non-peptide-based NPY antagonists which may be mentioned include those disclosed in European patent applications EP 0 614 911, EP 0 747 357, EP 0 747 356 and EP 0 747 378; international patent applications WO 94/17035, WO 97/19911, WO 97/19913, WO 96/12489, WO 97/19914, WO 96/22305, WO 96/40660, WO 96/12490, WO 97/09308, WO 97/20820, WO 97/20821, WO 97/20822, WO 97/20823, WO 97/19682, WO 97/25041, WO 97/34843, WO 97/46250, WO 98/03492, WO 98/03493, WO 98/03494, WO 98/07420 and WO 99/15498; U.S. Pat. Nos. 5,552,411, 5,663,192 and 5,567,714; and Japanese patent application JP 09157253. Preferred amino acid and non-peptide-based NPY antagonists include those compounds that are specifically disclosed in these patent documents.

Particularly preferred compounds include amino acid-based NPY antagonists. Amino acid-based compounds, which may be mentioned include those disclosed in international patent applications WO 94/17035, WO 97/19911, WO 97/19913, WO 97/19914 or, preferably, WO 99/15498. Preferred amino acid-based NPY antagonists include those that are specifically disclosed in these patent documents, for example BIBP3226 and, especially, (R)—N2-(diphenylacetyl)-(R)—N-[1-(4-hydroxy-phenyl)ethyl]arginine amide (Example 4 of international patent application WO 99/15498).

M1 receptor agonists and compositions containing such inhibitors are described, e.g. in WO 2004/087158, WO 91/10664.

Suitable M1 receptor antagonists for the purpose of the present invention are for example CDD-0102 (Cognitive Pharmaceuticals); Cevimeline (Evoxac) (Snow Brand Milk Products Co. Ltd.); NGX-267 (TorreyPines Therapeutics); sabcomeline (GlaxoSmithKline); alvameline (H Lundbeck A/S); LY-593093 (Eli Lilly & Co.); VRTX-3 (Vertex Pharmaceuticals Inc.); WAY-132983 (Wyeth) and CI-101 7/(PD-151832) (Pfizer Inc.).

Acetylcholinesterase inhibitors and compositions containing such inhibitors are described, e.g. in WO 2006/071274, WO 2006/070394, WO 2006/040688, WO 2005/092009, WO 2005/079789, WO 2005/039580, WO 2005/027975, WO 2004/084884, WO 2004/037234, WO 2004/032929, WO 03/101458, WO 03/091220, WO 03/082820, WO 03/020289, WO 02/32412, WO 01/85145, WO 01/78728, WO 01/66096, WO 00/02549, WO 01/00215, WO 00/15205, WO 00/23057, WO 00/33840, WO 00/30446, WO 00/23057, WO 00/15205, WO 00/09483, WO 00/07600, WO 00/02549, WO 99/47131, WO 99/07359, WO 98/30243, WO 97/38993, WO 97/13754, WO 94/29255, WO 94/20476, WO 94/19356, WO 93/03034 and WO 92/19238.

Suitable acetylcholinesterase inhibitors for the purpose of the present invention are for example Donepezil (Eisai Co. Ltd.); rivastigmine (Novartis AG); (−)-phenserine (TorreyPines Therapeutics); ladostigil (Hebrew University of Jerusalem); huperzine A (Mayo Foundation); galantamine (Johnson & Johnson); Memoquin (Universita di Bologna); SP-004 (Samaritan Pharmaceuticals Inc.); BGC-20-1259 (Sankyo Co. Ltd.); physostigmine (Forest Laboratories Inc.); NP-0361 (Neuropharma SA); ZT-1 (Debiopharm); tacrine (Warner-Lambert Co.); metrifonate (Bayer Corp.) and INM-176 (WhanIn).

NMDA receptor antagonists and compositions containing such inhibitors are described, e.g. in WO 2006/094674, WO 2006/058236, WO 2006/058059, WO 2006/010965, WO 2005/000216, WO 2005/102390, WO 2005/079779, WO 2005/079756, WO 2005/072705, WO 2005/070429, WO 2005/055996, WO 2005/035522, WO 2005/009421, WO 2005/000216, WO 2004/092189, WO 2004/039371, WO 2004/028522, WO 2004/009062, WO 03/010159, WO 02/072542, WO 02/34718, WO 01/98262, WO 01/94321, WO 01/92204, WO 01/81295, WO 01/32640, WO 01/10833, WO 01/10831, WO 00/56711, WO 00/29023, WO 00/00197, WO 99/53922, WO 99/48891, WO 99/45963, WO 99/01416, WO 99/07413, WO 99/01416, WO 98/50075, WO 98/50044, WO 98/10757, WO 98/05337, WO 97/32873, WO 97/23216, WO 97/23215, WO 97/23214, WO 96/14318, WO 96/08485, WO 95/31986, WO 95/26352, WO 95/26350, WO 95/26349, WO 95/26342, WO 95/12594, WO 95/02602, WO 95/02601, WO 94/20109, WO 94/13641, WO 94/09016 and WO 93/25534.

Suitable NMDA receptor antagonists for the purpose of the present invention are for example Memantine (Merz & Co. GmbH); topiramate (Johnson & Johnson); AVP-923 (Neurodex) (Center for Neurologic Study); EN-3231 (Endo Pharmaceuticals Holdings Inc.); neramexane (MRZ-2/579) (Merz and Forest); CNS-5161 (CeNeS Pharmaceuticals Inc.); dexanabinol (HU-211; Sinnabidol; PA-50211) (Pharmos); Epi-Cept NP-1 (Dalhousie University); indantadol (V-3381; CNP-3381) (Vernalis); perzinfotel (EAA-090, WAY-126090, EAA-129) (Wyeth); RGH-896 (Gedeon Richter Ltd.); traxoprodil (CP-101606), besonprodil (PD-196860, CI-1041) (Pfizer Inc.); CGX-1007 (Cognetix Inc.); delucemine (NPS-1506) (NPS Pharmaceuticals Inc.); EVT-101 (Roche Holding AG); acamprosate (Synchroneuron LLC.); CR-3991, CR-2249, CR-3394 (Rottapharm SpA.); AV-101 (4-Cl-kynurenine (4-Cl-KYN)), 7-chloro-kynurenic acid (7-Cl-KYNA) (VistaGen); NPS-1407 (NPS Pharmaceuticals Inc.); YT-1006 (Yaupon Therapeutics Inc.); ED-1812 (Sosei R&D Ltd.); himantane (hydrochloride N-2-(adamantly)-hexamethylen-imine) (RAMS); Lancicemine (AR-R-15896) (AstraZeneca); EVT-102, Ro-25-6981 and Ro-63-1908 (Hoffmann-La Roche AG/Evotec).

Furthermore, the present invention relates to combination therapies useful for the treatment of atherosclerosis, restenosis, pancreatitis or arthritis, administering a QC inhibitor in combination with another therapeutic agent selected from the group consisting of inhibitors of the angiotensin converting enzyme (ACE); angiotensin II receptor blockers; diuretics; calcium channel blockers (CCB); beta-blockers; platelet aggregation inhibitors; cholesterol absorption modulators; HMG-Co-A reductase inhibitors; high density lipoprotein (HDL) increasing compounds; renin inhibitors; IL-6 inhibitors; antiinflammatory corticosteroids; antiproliferative agents; nitric oxide donors; inhibitors of extracellular matrix synthesis; growth factor or cytokine signal transduction inhibitors; MCP-1 antagonists and tyrosine kinase inhibitors providing beneficial or synergistic therapeutic effects over each monotherapy component alone.

Angiotensin II receptor blockers are understood to be those active agents that bind to the AT1-receptor subtype of angiotensin II receptor but do not result in activation of the receptor. As a consequence of the blockade of the AT1 receptor, these antagonists can, e.g. be employed as antihypertensive agents.

Suitable angiotensin II receptor blockers which may be employed in the combination of the present invention include AT$_1$ receptor antagonists having differing structural features, preferred are those with non-peptidic structures. For example, mention may be made of the compounds that are selected from the group consisting of valsartan (EP 443983), losartan (EP 253310), candesartan (EP 459136), eprosartan (EP 403159), irbesartan (EP 454511), olmesartan (EP 503785), tasosartan (EP 539086), telmisartan (EP 522314), the compound with the designation E-41 77 of the formula

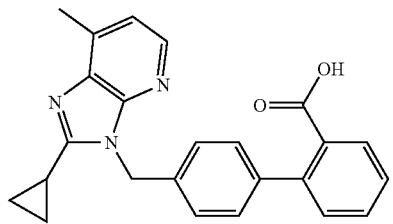

the compound with the designation SC-52458 of the following formula

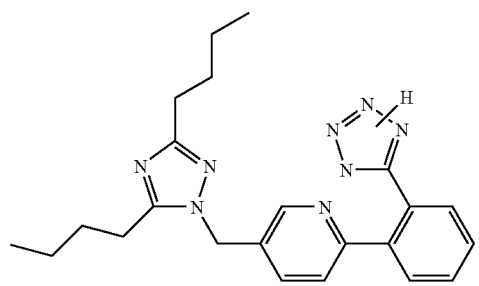

and the compound with the designation the compound ZD-8731 of the formula

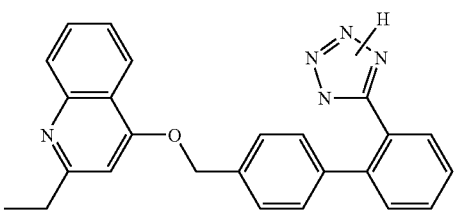

or, in each case, a pharmaceutically acceptable salt thereof.

Preferred AT1-receptor antagonists are those agents that have been approved and reached the market, most preferred is valsartan, or a pharmaceutically acceptable salt thereof.

The interruption of the enzymatic degradation of angiotensin to angiotensin II with ACE inhibitors is a successful variant for the regulation of blood pressure and thus also makes available a therapeutic method for the treatment of hypertension.

A suitable ACE inhibitor to be employed in the combination of the present invention is, e.g. a compound selected from the group consisting alacepril, benazepril, benazeprilat; captopril, ceronapril, cilazapril, delapril, enalapril, enaprilat, fosinopril, imidapril, lisinopril, moveltopril, perindopril, quinapril, ramipril, spirapril, temocapril and trandolapril, or in each case, a pharmaceutically acceptable salt thereof.

Preferred ACE inhibitors are those agents that have been marketed, most preferred are benazepril and enalapril.

A diuretic is, for example, a thiazide derivative selected from the group consisting of chlorothiazide, hydrochlorothiazide, methylclothiazide, and chlorothalidon. The most preferred diuretic is hydrochlorothiazide. A diuretic furthermore comprises a potassium sparing diuretic such as amiloride or triameterine, or a pharmaceutically acceptable salt thereof.

The class of CCBs essentially comprises dihydropyridines (DHPs) and non-DHPs, such as diltiazem-type and verapamil-type CCBs.

A CCB useful in said combination is preferably a DHP representative selected from the group consisting of amlodipine, felodipine, ryosidine, isradipine, lacidipine, nicardipine, nifedipine, niguldipine, niludipine, nimodipine, nisoldipine, nitrendipine and nivaldipine, and is preferably a non-DHP representative selected from the group consisting of flunarizine, prenylamine, diltiazem, fendiline, gallopamil, mibefradil, anipamil, tiapamil and verapamil, and in each case, a pharmaceutically acceptable salt thereof. All these CCBs are therapeutically used, e.g. as anti-hypertensive, anti-angina pectoris or anti-arrhythmic drugs.

Preferred CCBs comprise amlodipine, diltiazem, isradipine, nicardipine, nifedipine, nimodipine, nisoldipine, nitrendipine and verapamil or, e.g. dependent on the specific CCB, a pharmaceutically acceptable salt thereof. Especially preferred as DHP is amlodipine or a pharmaceutically acceptable salt thereof, especially the besylate. An especially preferred representative of non-DHPs is verapamil or a pharmaceutically acceptable salt, especially the hydrochloride, thereof.

Beta-blockers suitable for use in the present invention include beta-adrenergic blocking agents (beta-blockers), which compete with epinephrine for beta-adrenergic receptors and interfere with the action of epinephrine. Preferably, the beta-blockers are selective for the beta-adrenergic receptor as compared to the alpha-adrenergic receptors, and so do not have a significant alpha-blocking effect. Suitable beta-blockers include compounds selected from acebutolol, atenolol, betaxolol, bisoprolol, carteolol, carvedilol, esmolol, labetalol, metoprolol, nadolol, oxprenolol, penbutolol, pindolol, propranolol, sotalol and timolol. Where the beta-blocker is an acid or base or otherwise capable of forming pharmaceutically acceptable salts or prodrugs, these forms are considered to be encompassed herein, and it is understood that the compounds may be administered in free form or in the form of a pharmaceutically acceptable salt or a prodrug, such as a physiologically hydrolyzable and acceptable ester. For example, metoprolol is suitably administered as its tartrate salt, propranolol is suitably administered as the hydrochloride salt, and so forth.

Platelet aggregation inhibitors include PLAVIX® (clopidogrel bisulfate), PLETAL® (cilostazol) and aspirin.

Cholesterol absorption modulators include ZETIA® (ezetimibe) and KT6-971 (Kotobuki Pharmaceutical Co. Japan).

HMG-Co-A reductase inhibitors (also called beta-hydroxy-beta-methylglutaryl-co-enzyme-A reductase inhibitors or statins) are understood to be those active agents which may be used to lower lipid levels including cholesterol in blood.

The class of HMG-Co-A reductase inhibitors comprises compounds having differing structural features. For example, mention may be made of the compounds, which are selected from the group consisting of atorvastatin, cerivastatin, fluvastatin, lovastatin, pitavastatin, pravastatin, rosuvastatin and simvastatin, or in each case, a pharmaceutically acceptable salt thereof.

Preferred HMG-Co-A reductase inhibitors are those agents, which have been marketed, most preferred is atorvastatin, pitavastatin or simvastatin, or a pharmaceutically acceptable salt thereof.

HDL-increasing compounds include, but are not limited to, cholesterol ester transfer protein (CETP) inhibitors. Examples of CETP inhibitors include JTT7O5 disclosed in Example 26 of U.S. Pat. No. 6,426,365 issued Jul. 30, 2002, and pharmaceutically acceptable salts thereof.

Inhibition of interleukin 6 mediated inflammation may be achieved indirectly through regulation of endogenous cholesterol synthesis and isoprenoid depletion or by direct inhibition of the signal transduction pathway utilizing interleukin-6 inhibitor/antibody, interleukin-6 receptor inhibitor/antibody, interleukin-6 antisense oligonucleotide (ASON), gp130 protein inhibitor/antibody, tyrosine kinase inhibitors/antibodies, serine/threonine kinase inhibitors/antibodies, mitogen-activated protein (MAP) kinase inhibitors/antibodies, phosphatidylinositol 3-kinase (PI3K) inhibitors/antibodies, Nuclear factor kappaB (NF-κB) inhibitors/antibodies, IκB kinase (IKK) inhibitors/antibodies, activator protein-1 (AP-1) inhibitors/antibodies, STAT transcription factors inhibitors/antibodies, altered IL-6, partial peptides of IL-6 or IL-6 receptor, or SOCS (suppressors of cytokine signaling) protein, PPAR gamma and/or PPAR beta/delta activators/ligands or a functional fragment thereof.

A suitable antiinflammatory corticosteroid is dexamethasone.

Suitable antiproliferative agents are cladribine, rapamycin, vincristine and taxol.

A suitable inhibitor of extracellular matrix synthesis is halofuginone.

A suitable growth factor or cytokine signal transduction inhibitor is, e.g. the ras inhibitor R115777.

A suitable tyrosine kinase inhibitor is tyrphostin.

Suitable renin inhibitors are described, e.g. in WO 2006/116435. A preferred renin inhibitor is aliskiren, preferably in the form of the hemi-fumarate salt thereof.

MCP-1 antagonists may, e.g. be selected from anti-MCP-1 antibodies, preferably monoclonal or humanized monoclonal antibodies, MCP-1 expression inhibitors, CCR2-antagonists, TNF-alpha inhibitors, VCAM-1 gene expression inhibitors and anti-C5a monoclonal antibodies.

MCP-1 antagonists and compositions containing such inhibitors are described, e.g. in WO 02/070509, WO 02/081463, WO 02/060900, US 2006/670364, US 2006/677365, WO 2006/097624, US 2006/316449, WO 2004/056727, WO 03/053368, WO 00/198289, WO 00/157226, WO 00/046195, WO 00/046196, WO 00/046199, WO 00/046198, WO 00/046197, WO 99/046991, WO 99/007351, WO 98/006703, WO 97/012615, WO 2005/105133, WO 03/037376, WO 2006/125202, WO 2006/085961, WO 2004/024921, WO 2006/074265.

Suitable MCP-1 antagonists are, for instance, C-243 (Telik Inc.); NOX-E36 (Noxxon Pharma AG); AP-761 (Actimis Pharmaceuticals Inc.); ABN-912, NIBR-177 (Novartis AG); CC-11006 (Celgene Corp.); SSR-150106 (Sanofi-Aventis); MLN-1202 (Millenium Pharmaceuticals Inc.); AGI-1067, AGIX-4207, AGI-1096 (AtherioGenics Inc.); PRS-211095, PRS-211092 (Pharmos Corp.); anti-C5a monoclonal antibodies, e.g. neutrazumab (G2 Therapies Ltd.); AZD-6942 (AstraZeneca plc.); 2-mercaptoimidazoles (Johnson & Johnson); TEI-E00526, TEI-6122 (Deltagen); RS-504393 (Roche Holding AG); SB-282241, SB-380732, ADR-7 (GlaxoSmithKline); anti-MCP-1 monoclonal antibodies (Johnson & Johnson).

Combinations of QC-inhibitors with MCP-1 antagonists may be useful for the treatment of inflammatory diseases in general, including neurodegenerative diseases.

Combinations of QC-inhibitors with MCP-1 antagonists are preferred for the treatment of Alzheimer's disease.

Most preferably the QC inhibitor is combined with one or more compounds selected from the following group:

PF-4360365, m266, bapineuzumab, R-1450, Posiphen, (+)-phenserine, MK-0752, LY-450139, E-2012, (R)-flurbiprofen, AZD-103, AAB-001 (Bapineuzumab), Tramiprosate, EGb-761, TAK-070, Doxofylline, theophylline, cilomilast, tofimilast, roflumilast, tetomilast, tipelukast, ibudilast, HT-0712, MEM-1414, oglemilast, Linezolid, budipine, isocarboxazid, phenelzine, tranylcypromine, indantadol, moclobemide, rasagiline, ladostigil, safinamide, ABT-239, ABT-834, GSK-189254A, Ciproxifan, JNJ-17216498, Fmoc-Ala-Pyrr-CN, Z-Phe-Pro-Benzothiazole, Z-321, ONO-1603, JTP-4819, S-17092, BIBP3226; (R)—N2-(diphenylacetyl)-(R)—N-[1-(4-hydroxyphenyl)ethyl]arginine amide, Cevimeline, sabcomeline, (PD-151832), Donepezil, rivastigmine, (-)-phenserine, ladostigil, galantamine, tacrine, metrifonate, Memantine, topiramate, AVP-923, EN-3231, neramexane, valsartan, benazepril, enalapril, hydrochlorothiazide, amlodipine, diltiazem, isradipine, nicardipine, nifedipine, nimodipine, nisoldipine, nitrendipine, verapamil, amlodipine, acebutolol, atenolol, betaxolol, bisoprolol, carteolol, carvedilol, esmolol, labetalol, metoprolol, nadolol, oxprenolol, penbutolol, pindolol, propranolol, sotalol, timolol, PLAVIX® (clopidogrel bisulfate), PLETAL® (cilostazol), aspirin, ZETIA® (ezetimibe) and KT6-971, statins, atorvastatin, pitavastatin or simvastatin; dexamethasone, cladribine, rapamycin, vincristine, taxol, aliskiren, C-243, ABN-912, SSR-150106, MLN-1202 and betaferon.

In particular, the following combinations are considered:
- a QC inhibitor, in particular QCI, in combination with Atorvastatin for the treatment and/or prevention of atherosclerosis
- a QC inhibitor, in particular QCI, in combination with immunosuppressive agents, preferably rapamycin for the prevention and/or treatment of restenosis
- a QC inhibitor, in particular QCI, in combination with immunosuppressive agents, preferably paclitaxel for the prevention and/or treatment of restenosis
- a QC inhibitor, in particular QCI, in combination with AChE inhibitors, preferably Donepezil, for the prevention and/or treatment of Alzheimer's disease
- a QC inhibitor, in particular QCI, in combination with interferones, preferably Aronex, for the prevention and/or treatment of multiple sclerosis
- a QC inhibitor, in particular QCI, in combination with interferones, preferably betaferon, for the prevention and/or treatment of multiple sclerosis
- a QC inhibitor, in particular QCI, in combination with interferones, preferably Rebif, for the prevention and/or treatment of multiple sclerosis
- a QC inhibitor, in particular QCI, in combination with Copaxone, for the prevention and/or treatment of multiple sclerosis
- a QC inhibitor, in particular QCI, in combination with dexamethasone, for the prevention and/or treatment of restenosis
- a QC inhibitor, in particular QCI, in combination with dexamethasone, for the prevention and/or treatment of atherosclerosis
- a QC inhibitor, in particular QCI, in combination with dexamethasone, for the prevention and/or treatment of rheumatoid arthritis
- a QC inhibitor, in particular QCI, in combination with HMG-Co-A-reductase inhibitors, for the prevention and/or treatment of restenosis, wherein the HMG-Co-A-reductase inhibitor is selected from atorvastatin, cerivastatin, fluvastatin, lovastatin, pitavastatin, pravastatin, rosuvastatin and simvastatin
- a QC inhibitor, in particular QCI, in combination with HMG-Co-A reductase inhibitors, for the prevention and/or treatment of atherosclerosis wherein the HMG-Co-A-reductase inhibitor is selected from atorvastatin, cerivastatin, fluvastatin, lovastatin, pitavastatin, pravastatin, rosuvastatin and simvastatin
- a QC inhibitor, in particular QCI, in combination with HMG-Co-A reductase inhibitors, for the prevention and/or treatment of rheumatoid arthritis wherein the HMG-Co-A-reductase inhibitor is selected from atorvastatin, cerivastatin, fluvastatin, lovastatin, pitavastatin, pravastatin, rosuvastatin and simvastatin Such a combination therapy is in particular useful for AD, FAD, FDD and neurodegeneration in Down syndrome as well as atherosclerosis, rheumatoid arthritis, restenosis and pancreatitis.

Such combination therapies might result in a better therapeutic effect (less proliferation as well as less inflammation, a stimulus for proliferation) than would occur with either agent alone.

With regard to the specific combination of inhibitors of QC and further compounds it is referred in particular to WO 2004/098625 in this regard, which is incorporated herein by reference.

In a further embodiment the present invention provides a method for preventing or treating a disease or condition, selected from a group consisting of inflammatory diseases selected from
a. neurodegenerative diseases, e.g. mild cognitive impairment (MCI), Alzheimer's disease, neurodegeneration in Down Syndrome, Familial British Dementia, Familial Danish Dementia, multiple sclerosis,
b. chronic and acute inflammations, e.g. rheumatoid arthritis, atherosclerosis, restenosis, pancreatitis,
c. fibrosis, e.g. lung fibrosis, liver fibrosis, renal fibrosis,
d. cancer, e.g. cancer/hemangioendothelioma proliferation, gastric carcinomas,
e. metabolic diseases, e.g. hypertension,
f. and other inflammatory diseases, e.g. neuropathic pain, graft rejection/graft failure/graft vasculopathy, HIV infections/AIDS, gestosis, tuberous sclerosis.

Additionally, the present invention includes the use of the compounds of this invention and their corresponding pharmaceutically acceptable acid salt forms for the preparation of a medicament for the prevention or treatment of any of the above diseases or conditions.

Most preferably, the present QC inhibitors are used for the treatment of the above-mentioned neurodegenerative diseases. Even preferred is the use of the QC inhibitors of the present invention for the treatment of a disease selected from restenosis, pancreatitis, rheumatoid arthritis and atherosclerosis, most preferably restenosis or pancreatitis.

The compound may be administered to a patient by any conventional route of administration, including, but not limited to, intravenous, oral, subcutaneous, intramuscular, intradermal, parenteral and combinations thereof.

In a further preferred form of implementation, the invention relates to pharmaceutical compositions, that is to say, medicaments, that contain at least one compound of the invention or salts thereof, optionally in combination with one or more pharmaceutically acceptable carriers and/or solvents.

The pharmaceutical compositions may, for example, be in the form of parenteral or enteral formulations and contain appropriate carriers, or they may be in the form of oral formulations that may contain appropriate carriers suitable for oral administration. Preferably, they are in the form of oral formulations.

The inhibitors of QC activity administered according to the invention may be employed in pharmaceutically administrable formulations or formulation complexes as inhibitors or in combination with inhibitors, substrates, pseudosubstrates, inhibitors of QC expression, binding proteins or antibodies of those enzyme proteins that reduce the QC protein concentration in mammals. The compounds of the invention make it possible to adjust treatment individually to patients and diseases, it being possible, in particular, to avoid individual intolerances, allergies and side-effects.

The compounds also exhibit differing degrees of activity as a function of time. The physician providing treatment is thereby given the opportunity to respond differently to the individual situation of patients: he is able to adjust precisely, on the one hand, the speed of the onset of action and, on the other hand, the duration of action and especially the intensity of action.

The compounds may be advantageously administered, for example, in the form of pharmaceutical preparations that contain the active ingredient in combination with customary additives like diluents, excipients and/or carriers known from the prior art. For example, they can be administered parenterally (for example i.v. in physiological saline solution) or enterally (for example orally, formulated with customary carriers).

Depending on their endogenous stability and their bioavailability, one or more doses of the compounds can be given per day in order to achieve the desired reduction of MCP activity. For example, such a dosage range in humans may be in the range of from about 0.01 mg to 250.0 mg per day, preferably in the range of about 0.01 to 100 mg of compound per kilogram of body weight per day.

The compounds used according to the invention can accordingly be converted in a manner known per se into conventional formulations, such as, for example, tablets, (bitable) capsules, dragées, pills, suppositories, granules, aerosols, syrups, drops, liquid, solid and cream-like emulsions and suspensions and/or also as suppositories or as nasal sprays solutions, using inert, non-toxic, pharmaceutically suitable carriers and additives or solvents. In each of those formulations, the therapeutically effective compounds are preferably present in a concentration of approximately from 0.1 to 80% by weight, more preferably from 1 to 50% by weight, of the total mixture, that is to say, in amounts sufficient for the mentioned dosage latitude to be obtained.

The formulations may be advantageously prepared, for example, by extending the active ingredient with solvents and/or carriers, optionally with the use of emulsifiers and/or dispersants, it being possible, for example, in the case where water is used as diluent, for organic solvents to be optionally used as auxiliary solvents.

Examples of excipients useful in connection with the present invention include: water, non-toxic organic solvents, such as paraffins (for example natural oil fractions), vegetable oils (for example rapeseed oil, groundnut oil, sesame oil), alcohols (for example ethyl alcohol, glycerol), glycols (for example propylene glycol, polyethylene glycol); solid carriers, such as, for example, natural powdered minerals (for example highly dispersed silica, silicates), sugars (for example raw sugar, lactose and dextrose); emulsifiers, such as non-ionic and anionic emulsifiers (for example polyoxyethylene fatty acid esters, polyoxyethylene fatty alcohol ethers, alkylsulphonates and arylsulphonates), dispersants (for example lignin, sulphite liquors, methylcellulose, starch and polyvinylpyrrolidone) and lubricants (for example magnesium stearate, talcum, stearic acid and sodium lauryl sulphate) and optionally flavourings.

Administration may be carried out in the usual manner, preferably enterally or parenterally, especially orally. In the case of enteral administration, tablets may contain in addition to the mentioned carriers further additives such as sodium citrate, calcium carbonate and calcium phosphate, together with various additives, such as starch, preferably potato starch, gelatin and the like. Furthermore, lubricants, such as magnesium stearate, sodium lauryl sulphate and talcum, can be used concomitantly for tabletting. In the case of aqueous suspensions and/or elixirs intended for oral administration, various taste correctives or colourings can be added to the active ingredients in addition to the above-mentioned excipients.

In the case of parenteral administration, solutions of the active ingredients using suitable liquid carriers can be employed. In general, it has been found advantageous to administer, in the case of intravenous administration, amounts of approximately from 0.01 to 2.0 mg/kg, preferably approximately from 0.01 to 1.0 mg/kg, of body weight per day to obtain effective results and, in the case of enteral administration, the dosage is approximately from 0.01 to 2 mg/kg, preferably approximately from 0.01 to 1 mg/kg, of body weight per day.

It may nevertheless be necessary in some cases to deviate from the stated amounts, depending upon the body weight of the experimental animal or the patient or upon the type of administration route, but also on the basis of the species of animal and its individual response to the medicament or the interval at which administration is carried out. Accordingly, it may be sufficient in some cases to use less than the above-mentioned minimum amount, while, in other cases, the mentioned upper limit will have to be exceeded. In cases where relatively large amounts are being administered, it may be advisable to divide those amounts into several single doses over the day. For administration in human medicine, the same dosage latitude is provided. The above remarks apply analogously in that case.

The above disclosure describes the present invention in general. A more complete understanding can be obtained by reference to the following figures and examples. These examples are described solely for purposes of illustration and are not intended to limit the scope of the invention. Although specific terms have been employed herein, such terms are intended in a descriptive sense and not for purposes of limitation.

Reference Example 1

Preparation of Human QC

Host Strains and Media

*Pichia pastoris* strain X33 (AOX1, AOX2), used for the expression of human QC was grown, transformed and analyzed according to the manufacturer's instructions (Invitrogen). The media required for *P. pastoris*, i.e. buffered glycerol (BMGY) complex or methanol (BMMY) complex medium, and the fermentation basal salts medium were prepared according to the manufacturer's recommendations.

Molecular Cloning of Plasmid Vectors Encoding the Human QC

All cloning procedures were done applying standard molecular biology techniques. For expression in yeast, the vector pPICZαB (Invitrogen) was used. The pQE-31 vector (Qiagen) was used to express the human QC in *E. coli*. The cDNA of the mature QC starting with codon 38 was fused in frame with the plasmid encoded 6× histidine tag. After amplification utilizing the primers pQCyc-1 and pQCyc-2 (WO 2004/098625) and subcloning, the fragment was inserted into the expression vector employing the restriction sites of SphI and HindIII.

Transformation of *P. pastoris* and Mini-Scale Expression

Plasmid DNA was amplified in *E. coli* JM109 and purified according to the recommendations of the manufacturer (Qiagen). In the expression plasmid used, pPICZαB, three restriction sites are provided for linearization. Since SacI and BstXI cut within the QC cDNA, PmeI was chosen for linearization. 20-30 μg plasmid DNA was linearized with PmeI, precipitated by ethanol, and dissolved in sterile, deionized water. 10 μg of the DNA was then applied for transformation of competent *P. pastoris* cells by electroporation according to the manufacturer's instructions (BioRad). Selection was done using plates containing 150 μg/ml Zeocin. One transformation using the linearized plasmid yielded several hundred transformants.

In order to test the recombinant yeast clones for QC expression, recombinants were grown for 24 h in 10 ml conical tubes containing 2 ml BMGY. Afterwards, the yeast was centrifuged and resuspended in 2 ml BMMY containing 0.5% methanol. This concentration was maintained by addition of methanol every 24 h up to 72 h. Subsequently, QC activity in the supernatant was determined. The presence of the fusion protein was confirmed by western blot analysis using an antibody directed against the 6× histidine tag (Qiagen). Clones that displayed the highest QC activity were chosen for further experiments and fermentation.

Large-Scale Expression in a Fermenter

Expression of the QC was performed in a 5 l reactor (Biostat B, B. Braun biotech), essentially as described in the "*Pichia* fermentation process guidelines" (Invitrogen). Briefly, the cells were grown in the fermentation basal salts medium supplemented with trace salts, and with glycerol as the sole carbon source (pH 5.5). During an initial batch phase for about 24 h and a subsequent fed-batch phase for about 5 h, cell mass was accumulated. Once a cell wet weight of 200 g/l was achieved, induction of QC expression was performed using methanol applying a three-step feeding profile for an entire fermentation time of approximately 60 h. Subsequently, cells were removed from the QC-containing supernatant by centrifugation at 6000×g, 4° C. for 15 min. The pH was adjusted to 6.8 by addition of NaOH, and the resultant turbid solution was centrifuged again at 37000×g, 4° C. for 40 min. In cases of continued turbidity, an additional filtration step was applied using a cellulose membrane (pore width 0.45 μm).

Purification of 6× Histidine Tagged QC Expressed in *P. pastoris*

The His-tagged QC was first purified by immobilized metal affinity chromatography (IMAC). In a typical purification, 1000 ml of culture supernatant were applied to a $Ni^{2+}$-loaded Chelating Sepharose FF column (1.6×20 cm, Pharmacia), that was equilibrated with 50 mM phosphate buffer, pH 6.8, containing 750 mM NaCl, at a flow rate of 5 ml/min. After washing with 10 column volumes of equilibration buffer and 5 column volumes of equilibration buffer containing 5 mM histidine, the bound protein was eluted by a shift to 50 mM phosphate buffer, pH 6.8, containing 150 mM NaCl and 100 mM histidine. The resulting eluate was dialyzed against 20 mM Bis-Tris/HCl, pH 6.8, at 4° C. overnight. Subsequently, the QC was further purified by anion exchange chromatography an a Mono Q6 column (BioRad), equilibrated with dialysis buffer. The QC-containing fraction was loaded onto the column using a flow rate of 4 ml/min. The column was then washed with equilibration buffer containing 100 mM NaCl. The elution was performed by two gradients resulting in equilibration buffer containing 240 mM and 360 mM NaCl in 30 or 5 column volumes, respectively. Fractions of 6 ml were collected and the purity was analyzed by SDS-PAGE. Fractions containing homogenous QC were pooled and concentrated by ultrafiltration. For long-term storage (−200° C.), glycerol was added to a final concentration of 50%. Protein was quantified according to the methods of Bradford or Gill and von Hippel (Bradford, M. M. 1976 Anal Biochem 72, 248-254; Gill, S. C. and von Hippel, P. H. 1989 Anal Biochem 182, 319-326.).

Expression and Purification of QC in *E. coli*

The construct encoding the QC was transformed into M15 cells (Qiagen) and grown an selective LB agar plates at 37° C. Protein expression was carried out in LB medium containing 1% glucose and 1% ethanol at room temperature. When the culture reached an $OD_{600}$ of approximately 0.8, expression was induced with 0.1 mM IPTG overnight. After one cycle of freezing and thawing, cells were lysed at 4° C. by addition of 2.5 mg/ml lysozyme in 50 mM phosphate buffer, pH 8.0, containing 300 mM NaCl and 2 mM histidine for approximately 30 min. The solution was clarified by centrifugation at 37000×g, 4° C. for 30 min, followed by a filtration applying a glass frit (DNA separation) and two additional filtration steps applying cellulose filters for crude and fine precipitates. The supernatant (approx. 500 ml) was applied onto a $Ni^{2+}$-affinity column (1.6×20 cm) at a flow rate of 1 ml/min. Elution of QC was carried out with 50 mM phosphate buffer containing 150 mM NaCl and 100 mM histidine. The QC-containing fraction was concentrated by ultrafiltration.

Reference Example 2

MALDI-TOF Mass Spectrometry

Matrix-assisted laser desorption/ionization mass spectrometry was carried out using the Voyager De-Pro (Applied Biosystems, Darmstadt) with a linear time of flight analyzer. The instrument was equipped with a 337 nm nitrogen laser, a potential acceleration source and a 1.4 m flight tube. Detector operation was in the positive-ion mode. Samples (5 μl) were mixed with equal volumes of the matrix solution. For matrix solution we used sinapinic acid, prepared by solving 20 mg sinapinic acid (Sigma-Aldrich) in 1 ml acetonitrile/0.1% TFA in water (1/1, v/v). A small volume (≈1 μl) of the matrix-analyte-mixture was transferred to a probe tip.

For long-term testing of $Glu^1$-cyclization, Aβ-derived peptides were incubated in 100 μl 0.1 M sodium acetate buffer, pH 5.2 or 0.1 M Bis-Tris buffer, pH 6.5 at 30° C. Peptides were applied in 0.5 mM [β3-11a] or 0.15 mM [Aβ3-21a] concentrations, and 0.2 U QC was added all 24 hours. In case of Aβ3-21a, the assays contained 1% DMSO. At different times, samples were removed from the assay tube, peptides extracted using ZipTips (Millipore) according to the manufacturer's recommendations, mixed with matrix solution (1:1 v/v) and subsequently the mass spectra recorded. Negative controls contained either no QC or heat deactivated enzyme. For the inhibitor studies the sample composition was the same as described above, with exception of the inhibitory compound added (5 mM benzimidazole or 2 mM 1,10-phenanthroline).

Example 1

Preparation and Expression of human MCP-1 in Mammalian Cell Culture

Cell Lines and Media

Human neuroblastoma cell line SH-SY5Y, human embryonic kidney cell line HEK293 and human monocyte cell line THP-1 were cultured in appropriate cell culture media (DMEM, 10% FBS for SH-SY5Y and HEK293), (RPMI1640, 10% FBS for THP-1), in a humidified atmosphere of 5% $CO_2$ (HEK293, THP-1) or 10% $CO_2$ (SH-SY5Y) at 37° C.

Isolation of Human MCP-1

Full-length cDNA of human MCP-1 was isolated from SH-SY5Y cells using RT-PCR. Total RNA of SH-SY5Y cells was reversely transcribed by SuperScript II (Invitrogen) and subsequently, human MCP-1 was amplified on a 1:12.5 dilution of generated cDNA product in a 25 µl reaction with Pfu-DNA-Polymerase (Promega) using primers hMCP-1-1 (sense) and hMCP-1-2 (antisense) (Table 1). The resulting PCR-product was cloned into vector pcDNA 3.1 using the HindIII and NotI restriction sites and the sequence confirmed by DNA-sequencing.

Site-Directed Mutagenesis of Human MCP-1

Deletions of the first (ΔQ1) and first and second (ΔQ1P2) amino acids of the mature human MCP-1 were generated by site-directed mutagenesis using primer ΔQ1-1 and ΔQ1-2 for ΔQ1 (Table 1) and primers ΔQ1P2-1 and ΔQ1P2-2 for ΔQ1P2 (Table 1). Parental DNA was digested with Dpn I. The pcDNA 3.1 plasmids with the deletions ΔQ1 and ΔQ1P2 of the mature human MCP-1 were transformed into E. coli JM109. Ampicillin-resistant clones were confirmed by sequencing and subsequently isolated for cell culture purposes using the EndoFree Maxi Kit (Qiagen).

Expression of N-Terminal Variants of Human MCP-1 in HEK293 Cells

For expression of N-terminal variants of human MCP-1, HEK293 cells were cultured in collagen I coated 6-well dishes and grown until 80% confluency, transfected using Lipofectamin2000 (Invitrogen) according to manufacturer's manual and incubated in the transfection solution for 5 hours. Afterwards, cells were allowed to recover in normal growth media over night. The next day, cells were incubated another 24 h in growth media. For analysis of efficacy of QC-inhibition, cells were incubated for 24 h in absence or presence of the specific inhibitor. After 24 h, the media containing the human MCP-1 variants were collected and investigated in a migration assay for chemotactic potency. Furthermore, an aliquot of cell culture supernatant was stored at −80° C. for quantification of human MCP-1 concentration using a human MCP-1-ELISA (Pierce).

TransWell Chemotaxis Assay

The chemotaxis assay was performed using 24 well TransWell plates with a pore size of 5 µm (Corning). Media containing the human MCP-1 variants expressed in HEK293 were used as chemoattractant. To this avail, 600 µl of the culture media of N-terminal human MCP-1 variants was applied undiluted or in dilutions 1:3, 1:10 and 1:30 in RPMI1640 to the lower chamber of the TransWell plate. Furthermore, undiluted media of HEK293 cells transfected with vector control were applied as negative control to the lower chamber. THP-1 cells were harvested and resuspended in RPMI1640 in a concentration of $1*10^6$ cells/100 µl and applied in 100 µl aliquots to the upper chamber. Cells were allowed to migrate towards the chemoattractant for 2 h at 37° C. Subsequently, cells from the upper chamber were discarded and the lower chamber was mixed with 50 µl 70 mM EDTA in PBS and incubated for 15 min at 37° C. to release cells attached to the membrane. Afterwards, cells migrated to the lower chamber were counted using a cell counter system (Schärfe System). The chemotactic index was calculated by dividing cells migrated to the stimulus from cells migrated to the negative control.

Example 2

Investigations on the Proteolytic Degradation of Human MCP-1$_{(1-76)}$

Methods

N-Terminal Degradation by Recombinant Human DP4

Full length recombinant human MCP-1$_{(1-76)}$ (SEQ ID NO: 1) encoded by the nucleic acid sequence as shown in SEQ ID NO: 2, obtained in Example 1 above, starting with an N-terminal glutamine (Peprotech) was dissolved in 25 mM Tris/HCl pH 7.6 in a concentration of 10 µg/ml. The MCP-1 solution was either pre-incubated with recombinant human QC (0.0006 mg/ml) (obtained according to Reference Example 1 above, SEQ ID No: 3 for nucleic acid sequence and SEQ ID No: 4 for amino acid sequence) for 3 h at 30° C. and subsequently incubated with recombinant human DP4 (0.0012 mg/ml) at 30° C. (see FIG. 1) or incubated with DP4 without prior QC application. Resulting DP4 cleavage products were analyzed after 0 min, 15 min, 30 min, 1 h, 4 h and 24 h using Maldi-TOF mass spectrometry.

N-Terminal Degradation by Human Rheumatoid Synovial Fibroblast MMP-1

Human recombinant MCP-1 carrying an N-terminal glutaminyl instead of a pyroglutamyl residue (Peprotech) was dissolved in 25 mM Tris/HCl, pH 7.6, in a concentration of 10 µg/ml. The MMP-1 proenzyme from human rheumatoid synovial fibroblasts (Calbiochem) was activated using 25 mM p-aminophenylmercuric acetate (APMA), dissolved in 0.1 N NaOH at 37° C. for 3 h in a APMA:enzyme-mixture of 10:1. MCP-1 was either pre-incubated with recombinant human QC (0.0006 mg/ml) for 3 h at 30° C. and subsequently incubated with MMP-1 at 30° C. or incubated with MMP-1 without prior QC application. Resulting MMP-1 cleavage products were analyzed after 0 min, 15 min, 30 min, 1 h, 2 h, 4 h and 24 h using Maldi-TOF mass spectrometry.

N-Terminal Degradation by Human Rheumatoid Synovial Fibroblast MMP-1 and Recombinant Human DP4

Human recombinant MCP-1 starting with a N-terminal glutamine (Peprotech) was dissolved in 25 mM Tris/HCl, pH 7.6, in a concentration of 10 µg/ml. MMP-1 proenzyme from human rheumatoid synovial fibroblasts (Calbiochem) was activated using 25 mM p-aminophenylmercuric acetate (APMA) dissolved in 0.1 N NaOH. The APMA:enzyme-mixture of 10:1 was incubated at 37° C. for 3 h. MCP-1 solution was either pre-incubated with recombinant human QC (0.0006 mg/ml) for 3 h at 30° C. and subsequently incubated with MMP-1 and DP4 at 30° C. or incubated with MMP-1 and DP4 without QC application. Resulting MMP-1 cleavage products were analyzed after 0 min, 15 min, 30 min, 1 h, 2 h, 4 h and 24 h using Maldi-TOF mass spectrometry.

Example 3

Effect of QC Specific Inhibitor 1-(3-(1H-imidazol-1-yl)propyl)-3-(3,4-dimethoxyphenyl)thiourea hydrochloride (in the Following Also Designated as QCI) on Cuff-Induced Accelerated Atherosclerosis in ApoE3*Leiden Mice Timeline 30 male ApoE3*Leiden mice (age 12 weeks) were fed a mildly hypercholesterolemic diet for 3 weeks prior to surgical cuff placement.

After 3 weeks, the mice underwent surgical non-constricting cuff placement (day 0) and were divided into 2 groups, matched for plasma cholesterol levels. The mice either received control (acidified) drinking water or drinking water containing the QC specific inhibitor 1-(3-(1H-imidazol-1-yl)propyl)-3-(3,4-dimethoxyphenyl)thiourea hydrochloride in a concentration of 2.4-mg/ml. 7 days after start of treatment, the inhibitor concentration was reduced to 1.2 mg/ml. 5 Mice of each group were sacrificed after 2 days for analysis of monocyte adhesion and infiltration, and 10 mice were sacrificed after 2 weeks for histomorphometric analysis to quantify the inhibition of accelerated atherosclerotic lesions and neointima formation.

Surgical Procedure of Cuff Placement

At the time of surgery, mice were anaesthetized with an intraperitoneal injection of 5 mg/kg Dormicum, 0.5 mg/kg Domitor and 0.05 mg/kg Fentanyl. This cocktail gives complete narcosis for at least one hour and can be quickly antagonized with Antisedan 2.5 mg/kg and Anexate 0.5 mg/kg.

A longitudinal 1 cm incision is made in the internal side of the leg and the femoral artery is dissected for 3 mm length from the femoral nerve and femoral vein. The femoral artery is looped with a ligature and a non-constrictive fine bore polyethylene tubing (0.4 mm inner diameter, 0.8 mm outer diameter, length 2 mm) is longitudinally opened and sleeved loosely around the femoral artery. The cuff is closed up with two ligature knots. The skin is closed with a continued suture.

After surgery, the animals were antagonized and placed in a clean cage on top of a heating pad for a few hours.

Sacrifice of the Animals

For histological analysis, animals were sacrificed either 2 days or 14 days after cuff placement. After anaesthesia, the thorax was opened and a mild pressure-perfusion (100 mmHg) with 4% formaldehyde was performed for 3 minutes by cardiac puncture. After perfusion, a longitudinal 2 cm incision was made in the internal side of the leg and the cuffed femoral artery was harvested as a whole and fixed overnight in 4% formaldehyde and processed to paraffin.

Analysis of Monocyte Adhesion and MCP-1 Expression

Adhesion of leukocytes in general and monocytes/macrophages in particular to the activated endothelium of the cuffed vessel wall was analyzed by microscopic analysis of cross sections harvested 2 days after cuff placement. The number of adhering and/or infiltrating leukocytes in general, identified as adhering cells at the luminal side of the vessel segment, and monocytes/macrophages in particular was counted and illustrated as cells per cross-section or as defined areas per cross section. Monocytes were identified by specific immunohistochemical staining by the polyclonal rabbit AIA31240 antibody, recognizing monocytes and macrophages. In addition on these sections a specific immunohistochemical staining for MCP-1 was performed.

Analysis of Vascular Remodeling and Accelerated Atherosclerosis

Vessel wall remodeling, accelerated atherosclerosis and neointima formation were analyzed morphometrically in all mice sacrificed after 14 days. A full comparison between the two groups was performed for all relevant vessel wall parameters (neointima formation, vascular circumference (i.e. outward remodelling), media thickness, lumen stenosis). Accelerated atherosclerosis was analyzed by immunohistochemical staining for macrophages and foam cells in the lesion area by AIA31240 antibody. Furthermore, these sections were also stained for MCP-1.

Example 4

Proteolytic Degradation of Human MCP-$1_{(1-76)}$ by Dipeptidyl-Peptidase 4 (DP4), Aminopeptidase P, and by Proteases Present in Human Serum N-Terminal Degradation by Recombinant Human Aminopeptidase P Human recombinant MCP-1 carrying an N-terminal glutaminyl instead of a pyroglutamyl residue (Peprotech) was dissolved in 25 mM Tris/HCl, pH 7.6 in a concentration of 10 µg/ml. MCP-1 was incubated with 30 µg/ml Aminopeptidase P (R&D Systems) at 30° C. $Gln^1$-MCP-1 was either used without pGlu-modification or was pre-incubated with recombinant human QC (6 µg/ml) for 3 h at 30° C. in order to generate pGlu. Resulting Aminopeptidase P cleavage products were analyzed using Maldi-TOF mass spectrometry after 0 min, 15 min, 30 min, 1 h, 2 h, 4 h and 24 h.

N-Terminal Degradation of MCP-1 by Recombinant Human DP4 in Absence and Presence of a QC-Specific Inhibitor Recombinant human MCP-$1_{(1-76)}$ (SEQ ID NO: 1) encoded by the nucleic acid sequence as shown in SEQ ID NO: 2, obtained in Example 1 above, starting with an N-terminal glutamine (Peprotech) was dissolved in 25 mM Tris/HCl pH 7.6 in a concentration of 10 µg/ml. The MCP-1 solution was either pre-incubated with recombinant human QC (0.0006 mg/ml) (obtained according to Reference Example 1 above) for 3 h at 30° C. and subsequently incubated with recombinant human DP4 (0.0012 mg/ml) at 30° C. (see FIG. 1) or incubated with DP4 without prior QC application. In addition, the incubation of $Gln^1$-MCP-1 with recombinant human QC was carried out in presence of 10 µM of 1-(3-(1H-imidazol-1-yl)propyl)-3-(3,4-dimethoxyphenyl)thiourea hydrochloride. Resulting DP4 cleavage products were analyzed using Maldi-TOF mass spectrometry after 0 min, 15 min, 30 min, 1 h, 2 h and 4 h.

N-Terminal Degradation of Human MCP-1 in Human Serum

Human recombinant MCP-1 carrying an N-terminal glutaminyl instead of a pyroglutamyl residue (Peprotech) was dissolved in 25 mM Tris/HCl, pH 7.6, in a concentration of 100 µg/ml. MCP-1 was either pre-incubated with recombinant human QC (0.006 mg/ml) for 3 h at 30° C. and subsequently incubated with human serum at 30° C. or incubated with human serum without addition of QC. The cleavage products were analyzed using Maldi-TOF mass spectrometry after 0 min, 10 min, 30 min, 1 h, 2 h, 3 h 5 h and 7 h for $Gln^1$-MCP-1 and 0 min, 30 min, 1 h, 2 h, 3 h 5 h, 7 h and 24 h for $pGlu^1$-MCP-1.

Example 5

Degradation of Human MCP-2, MCP-3 and MCP-4

N-Terminal Degradation of Human MCP-2 by DP4

Human recombinant MCP-2 carrying an N-terminal glutaminyl instead of a pyroglutamyl residue (Peprotech) was dissolved in 25 mM Tris/HCl, pH 7.6, in a concentration of 10 μg/ml. MCP-2 was either pre-incubated with recombinant human QC (0.0006 mg/ml) for 3 h at 30° C. and subsequently incubated with recombinant human DP4 (0.0012 mg/ml) at 30° C. or incubated with recombinant human DP4 (0.0012 mg/ml) without pre-incubation with QC. Resulting DP4 cleavage products were analyzed using Maldi-TOF mass spectrometry after 0 min, 15 min, 30 min, 1 h, 2 h, 4 h and 24 h.
N-Terminal Degradation of Human MCP-3 by DP4

Human recombinant MCP-3 carrying an N-terminal glutaminyl instead of a pyroglutamyl residue (Peprotech) was dissolved in 25 mM Tris/HCl, pH 7.6, in a concentration of 10 μg/ml. MCP-3 was either pre-incubated with recombinant human QC (0.0006 mg/ml) for 3 h at 30° C. and subsequently incubated with recombinant human DP4 (0.00012 mg/ml) at 30° C. or incubated with recombinant human DP4 (0.00012 mg/ml) without prior QC application. Resulting DP4 cleavage products were analyzed using Maldi-TOF mass spectrometry after 0 min, 15 min, 30 min, 1 h, 2 h, 4 h and 24 h.
N-Terminal Degradation of Human MCP-4 by DP4

Human recombinant MCP-4 carrying an N-terminal glutaminyl instead of a pyroglutamyl residue (Peprotech) was dissolved in 25 mM Tris/HCl, pH 7.6, in a concentration of 10 μg/ml. MCP-4 was either pre-incubated with recombinant human QC (0.0006 mg/ml) for 3 h at 30° C. and subsequently incubated with recombinant human DP4 (0.00006 mg/ml) at 30° C. or incubated with recombinant human DP4 (0.00006 mg/ml) without prior QC application. Resulting DP4 cleavage products were analyzed using Maldi-TOF mass spectrometry after 0 min, 15 min, 30 min, 1 h, 2 h, 4 h and 24 h.

Example 6

Chemotactic Potency of Different N-Terminal Variants of Human MCP-1, MCP-2, MCP-3, MCP-4

Chemotactic Potency of N-Terminal Variants of Human MCP-1

MCP-1 starting with glutamine 1 (Gln$^1$-MCP-1) (Peprotech) was incubated with (i) recombinant human QC to generate pGlu$^1$-MCP-1, (ii) human recombinant DP4 to generate Asp$^3$-MCP-1, (iii) human synovial fibroblast MMP-1 to generate Ile$^5$-MCP-1 and human recombinant Aminopeptidase P to generate Pro$^2$-MCP-1. Concentrations of 1, 5, 10, 50, 100, 500 and 1000 ng/ml of the generated MCP-1 variants were tested using the THP-1 chemotaxis assay (n=3).
Chemotactic Potency of Human MCP-1 in Absence or Presence of a QC-Inhibitor MCP-1 with N-terminal glutamine (Gln$^1$-MCP-1) (Peprotech) was incubated with recombinant human QC and DP4 (Gln$^1$-MCP-1+QC+DP4), human recombinant DP4 alone (Gln$^1$-MCP+DP4) and with recombinant human QC in combination with 10 μM of QC-inhibitor 1-(3-(1H-imidazol-1-yl)propyl)-3-(3,4-dimethoxyphenyl)thiourea hydrochloride and DP4 (Gln$^1$-MCP-1+QC+QCI+DP4). Concentrations of 1, 5, 10, 50, 100, 500 and 1000 ng/ml of generated MCP-1 variants were tested using chemotaxis assay (n=3).
Comparison of the Chemotactic Potency of Variants of Human MCP-1, MCP-2, MCP-3 and MCP-4 Possessing an N-Terminal Glutaminyl or Pyroglutamyl Residue.

Human MCP-1, MCP-2, MCP-3 and MCP-4 with an N-terminal glutamine (Peprotech) or pyroglutamyl-residue (incubation of Gln$^1$-MCPs with human recombinant QC at a dilution of 1:100 for 2 h at 30° C.) were tested for chemotactic potency. Concentrations of 1, 5, 10, 50, 100, 500 and 1000 ng/ml of a particular MCP were tested using chemotaxis assay (n=3).
Comparison of the Chemotactic Potency of Variants of Human MCP-1, MCP-2, MCP-3 and MCP-4 Possessing an N-Terminal Glutaminyl Residue with the Respective DP4 Cleavage Product The human MCP-1, MCP-2, MCP-3 and MCP-4 starting with an N-terminal glutamine (Peprotech) was directly applied to the chemotaxis assay and compared to chemotactic potency of the DP4 cleavage products of MCP-1, MCP-2, MCP-3 and MCP-4. For the generation of the DP4 cleavage product, the respective MCPs were incubated with human recombinant DP4 at a 1:100 dilution for 2 h at 30° C. prior to assay. Concentrations of 1, 5, 10, 50, 100, 500 and 1000 ng/ml of a particular MCP were tested using chemotaxis assay (n=3).

Example 7

Application of a QC-Inhibitor to a Model of LPS-Induced Sepsis in Rats

Preparation
The QC-inhibitor 1-(3-(1H-imidazol-1-yl)propyl)-3-(3,4-dimethoxyphenyl)thiourea hydrochloride was formulated using 0.9% (w/v) saline at the highest concentration required. Lower doses were obtained by serial dilution using 0.9% (w/v) saline. In addition, a stock solution (1 mg/mL) of LPS was prepared using 0.9% (w/v) saline and diluted using 0.9% (w/v) saline to provide the required concentration for dosing.
Concentrations
Dose levels were expressed in terms of the amount of inhibitor administered without regard to purity or active content.
Species
Male Han Wistar rats were obtained from Charles River (UK) Ltd., Margate, Kent.
Acclimatisation and Health Procedures
On arrival, all animals were examined for ill-health. Animals were acclimatised for a period of at least 5 days prior to dosing. During this time animals were identified by their cage labels. A veterinary examination was performed before the start of any experimental procedures to ensure their suitability for the study.
Experimental Design
The study was performed over two days (five animals from each treatment group on each day).
Food and water was available ad libitum, except when the animals are removed from the home cage for the study procedures. Each animal received two single intravenous administrations of vehicle or QC-inhibitor 1-(3-(1H-imidazol-1-yl)propyl)-3-(3,4-dimethoxyphenyl)thiourea in a low, intermediate and high dose (Table 2) at 3.5 hours and 0.5 hours before LPS administration, using a constant dose volume of 2 mL/kg as a slow bolus.
Thirty minutes following the last administration of vehicle or test article each animal received an intraperitoneal injection of LPS or saline, using a constant dose volume of 5 mL/kg. Individual dose volumes were based on the individual body weights obtained on the day of dosing. The treatment groups employed for the study are depicted in Table 2.
Sampling and TNFα Determination
A terminal blood sample was collected at 2 hours post-LPS. Blood samples were centrifuged at 2300×g for 10 minutes at 4° C. and subsequently analyzed for TNFα. Samples were analysed using a quantitative sandwich enzyme immunoassay.

Example 8

Evaluation of a QC-Inhibitor in a Mouse Model of Thioglycollate-Induced Peritonitis Animals For each experiment C57/Bl6J wild type mice were purchased from Charles River Laboratories Inc. For each experiment the mice were age- and sex-matched.

Induction of Thioglycollate-Induced Peritonitis

For induction of peritonitis mice were injected intraperitoneally (i.p.) with 25 ml/kg body weight of sterile 8% (w/v) thioglycollate (Sigma-Aldrich; time: t=0). At different time points before and after thioglycollate application, mice were injected i.p. with various concentrations of QC-inhibitor. For lavage of the peritoneum, the animals were anesthesized using 2% isofluran. Peritoneal exudates were collected at time points (4, 24 hours) after thioglycollate injection by washing the peritoneum with 8 ml of sterile phosphate-buffered saline (PBS). Subsequently, the lavage fluids were centrifuged to pellet the cells and stained for FACS analysis.

Analysis of Cellular Composition of Collected Exudates Using FACS-Analysis

Samples were stained for BD Trucount tubes (BD Trucount tubes; catalog no. 340334; BD Biosciences) according to the manufacturer's instructions. Cells were blocked with CD16/32 (Caltag) and stained with the following antibodies for 15 min: CD3-FITC (Caltag)/CD13-PE (BD)/F4/80-APC (Caltag); Moma2-FITC (Acris) and IgG1-PE (BD)/IgG2a-APC (Caltag) as isotype controls. After staining, cells were lysed with BD FACSLyse (BD) for 15 min in the dark at room temperature. Flow cytometric analysis of 5000 beads per sample as reference standard was performed on a BD FACSCalibur (BD Biosciences).

Results

Preparation and Expression of Human MCP-1 in Mammalian Cell Culture

Amplification of human MCP-1 from human neuroblastoma cell line SH-SY5Y RNA resulted in a PCR-product of 300 bp. Sequencing of the isolated cDNA revealed a silent single nucleotide polymorphism of codon 105 coding for cysteine 35.

Figure 4:
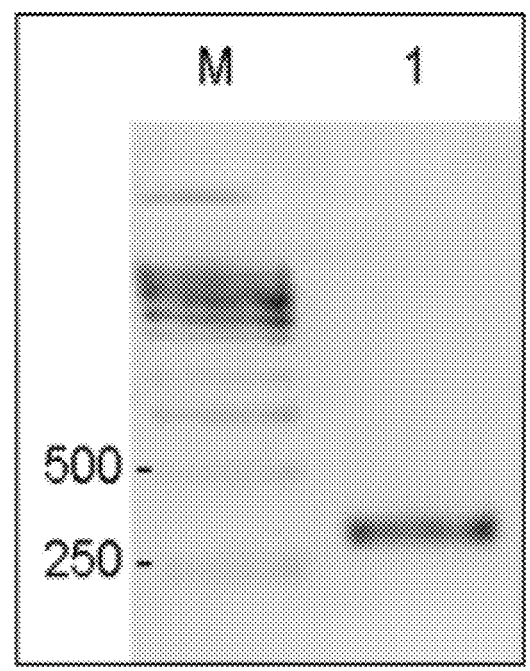
FIG. 4 shows the isolation of human MCP-1 from human neuroblastoma cell line SH-SY5Y. (M:DNA standard in bp; 1: full length human MCP-1 isolated from SH-SY5Y)

Expression of human MCP-1 variants in HEK293 leads to elevated levels within cell culture supernatant as monitored by human MCP-1 ELISA. Thereby, the level between the expressions of MCP-1 (WT) and MCP-1 ($\Delta$Q1) (FIG. 5C), and MCP-1 (WT) in absence or presence of 10 µM 1-(3-(1H-imidazol-1-yl)propyl)-3-(3,4-dimethoxyphenyl)thiourea hydrochloride (FIG. 7A) are not significantly changed. However, the expression of MCP-1 ($\Delta$Q1P2) is reduced by 28% compared to MCP-1 (WT). The supernatant was collected and applied in TransWell migration assays (see FIGS. 4 and 5 C and D in this regard).

TransWell Chemotaxis Assay

Purified human MCP-1 displays a bell-shaped chemotactic dose response curve, when attracting, e.g. monocytes, showing an optimum at approx. 1-50 ng/ml. Therefore, the generated cell culture supernatants containing MCP 1 variants were sequentially diluted in order to achieve the optimal working concentration of MCP-1 for chemotaxis assay attracting THP-1 monocytes.

Figure 5C:
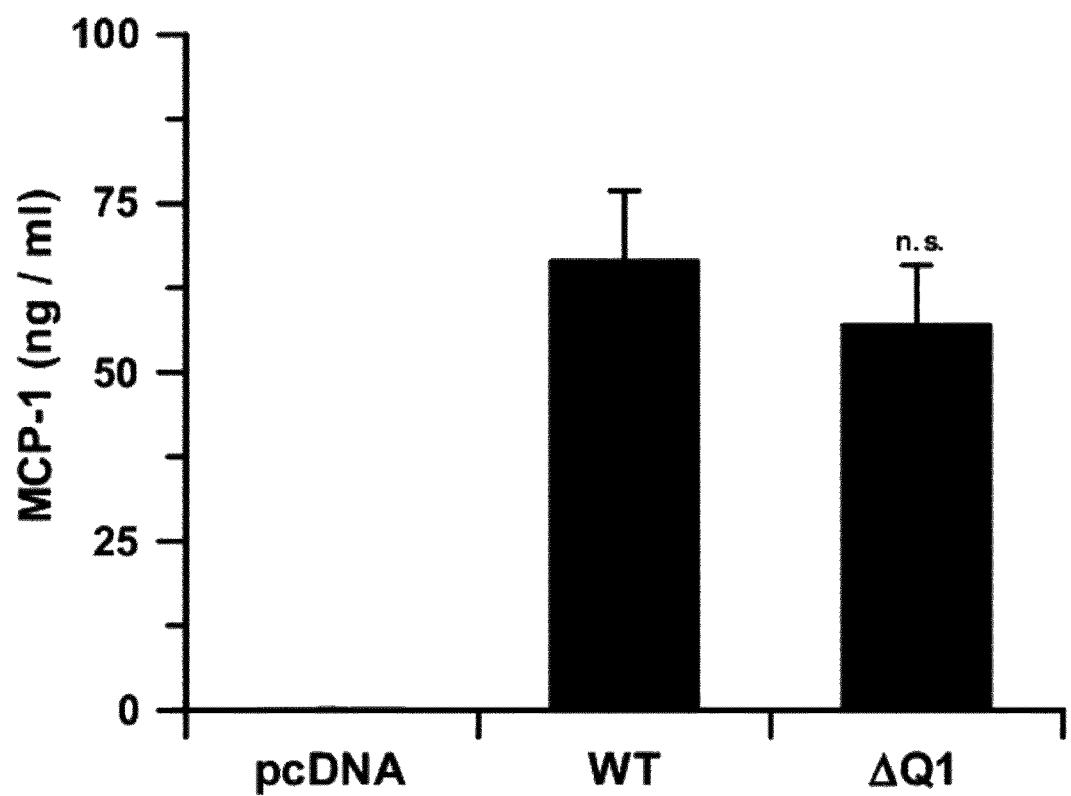
FIG. 5 shows the nucleotide (A) and amino acid (B) alignment of human MCP-1 isolated from SH-SY5Y (upper lane) and human MCP-1 genebank accession M24545 (lower lane). Single nucleotide polymorphism is depicted in bold. C: shows the concentration of human MCP-$1_{(1-76)}$ (WT) and mutant human MCP-1 lacking the N-terminal pGlu residue (ΔQ1) in the supernatant of transfected HEK293 cells in comparison to vector transfected control (pcDNA). (n.s.: not significant, Student's t-test; n=6) D: Migration of THP-1 monocytes towards the generated supernatant of transfected HEK293 cells in dilutions 1:1, 1:3, 1:10 and 1:30. (*, $P<0.05$; , $P<0.01$; *, $P<0.001$; Student's t-test, n=3).
Figure 5D:
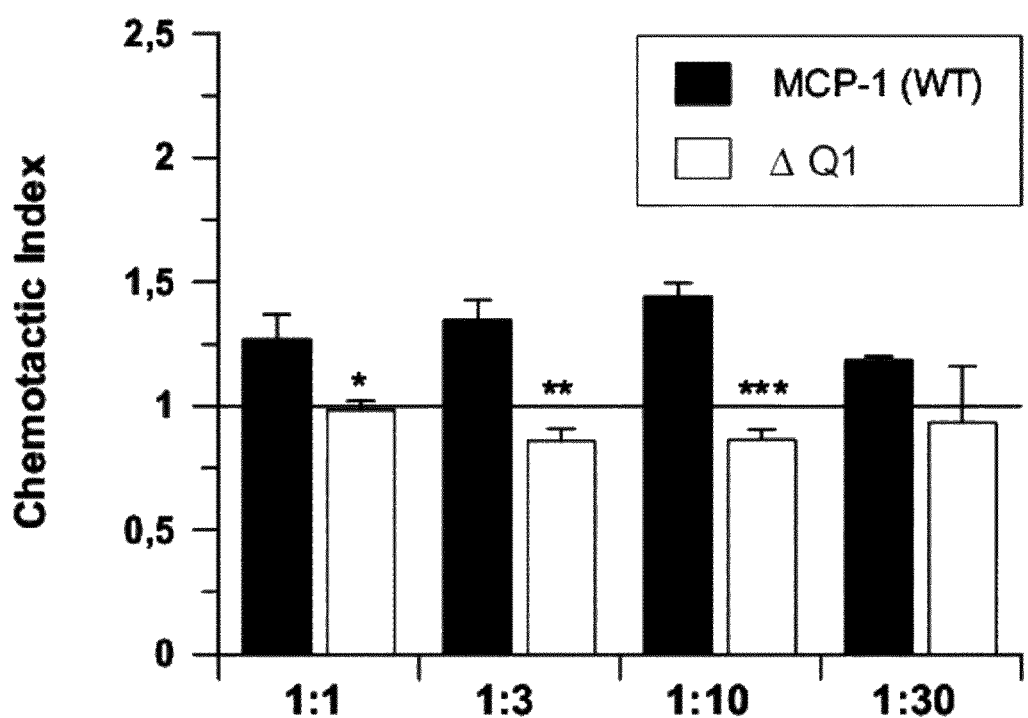
Figure 6A:
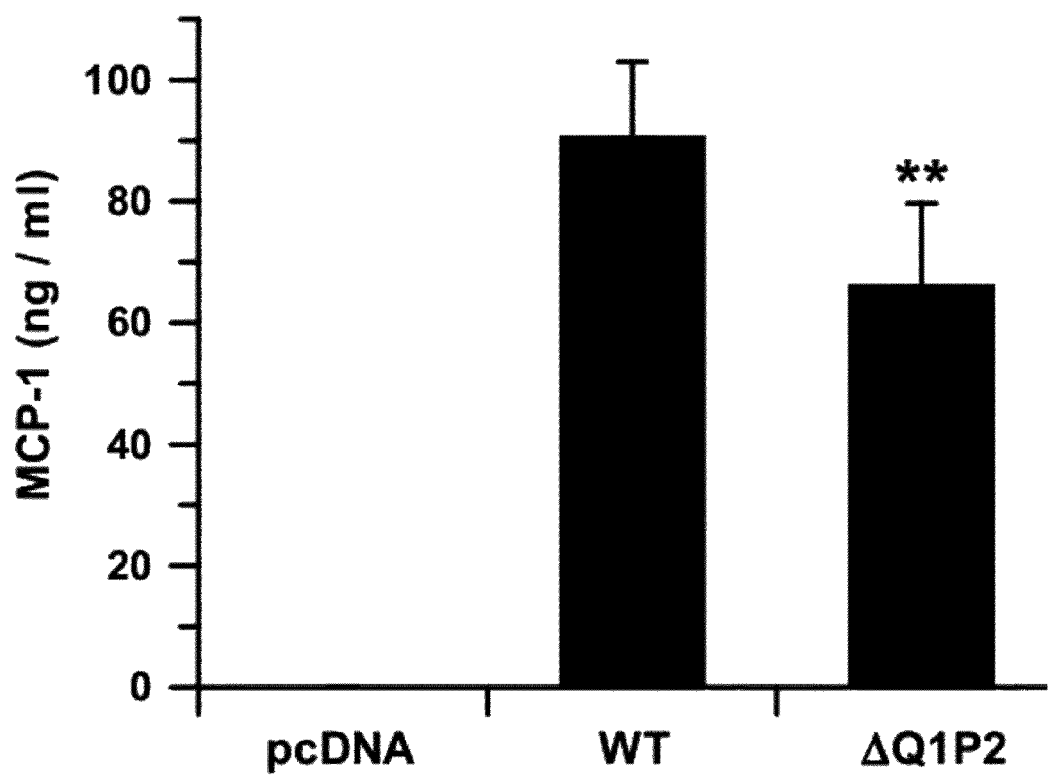
FIG. 6 A: shows the concentration of human MCP-$1_{(1-76)}$ (WT) and mutant human MCP-1 lacking the two N-terminal amino acids (ΔQ1P2) in the supernatant of transfected HEK293 cells in comparison to vector transfected control (pcDNA). (**, $P<0.01$; Student's t-test; n=6) B: Migration of THP-1 monocytes towards the generated supernatant of transfected HEK293 cells in dilutions 1:1, 1:3, 1:10 and 1:30. (*, $P<0.05$; , $P<0.01$; *, $P<0.001$; Student's t-test, n=3).
Figure 6B:
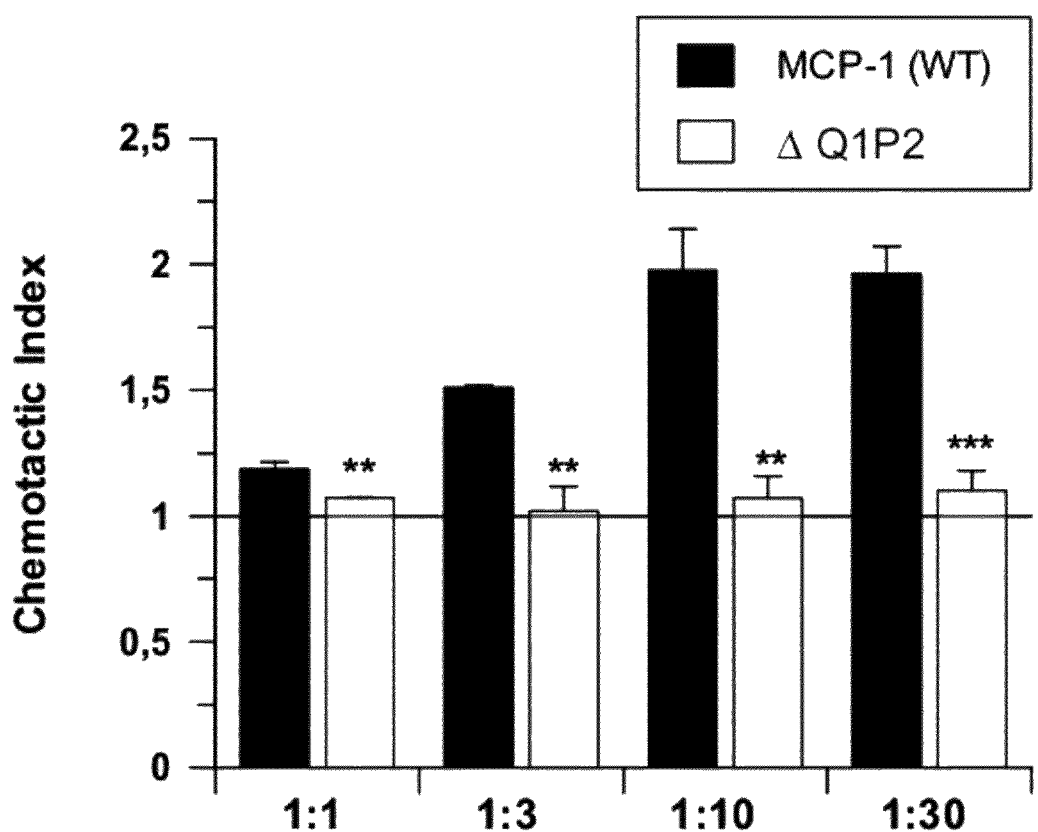
Figure 7B:
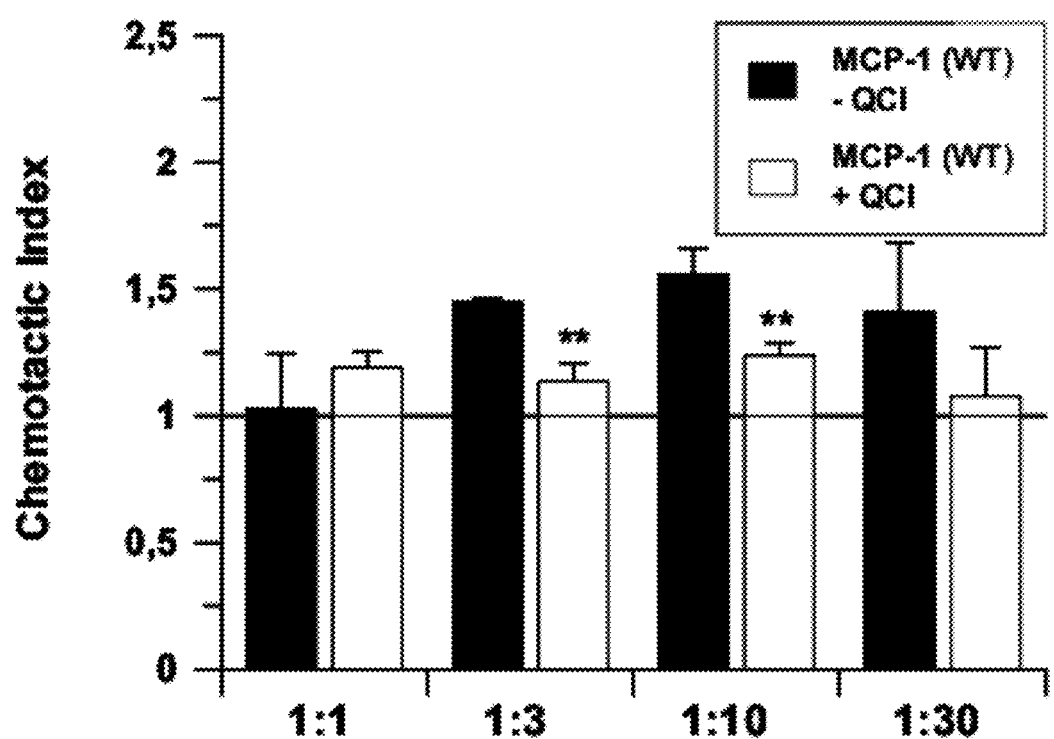
FIG. 7 A: shows the concentration of human MCP-1(1-76) (WT) in the supernatant of transfected HEK293 cells in absence and presence of 10 μM 1-(3-(1H-imidazol-1-yl)propyl)-3-(3,4-dimethoxyphenyl)thiourea hydrochloride in comparison to vector transfected control (pcDNA). (n.s.: not significant; Student's t-test; n=6) B: Migration of THP-1 monocytes towards the generated supernatant of transfected HEK293 cells in absence or presence of 10 μM1-(3-(1H-imidazol-1-yl)propyl)-3-(3,4-dimethoxyphenyl)thiourea hydrochloride in dilutions of 1:1, 1:3, 1:10 and 1:30. (**, $P<0.01$; Student's t-test, n=3).

After expression of MCP-1 (WT) and MCP-1 ($\Delta$Q1), the concentrations of MCP-1 variants did not significantly differ (FIG. 5C). Application of MCP-1 (WT) to the chemotaxis assay led to a chemotactic response of THP-1 cells (FIG. 5D), implied by the elevated chemotactic index. However, MCP-1 ($\Delta$Q1) failed to induce chemotaxis of THP-1 (FIG. 5D) suggested by a chemotactic index of approx. 1. These results support previous results, that N-truncated MCP-1 is inactive. This finding is further substantiated by the inability of MCP-1 ($\Delta$Q1P2) to induce chemotaxis of THP-1 cells (FIG. 6B). Expression of MCP-1 (WT) in HEK293 cells has no influence on MCP-1 concentration in absence or presence of chemotactic cytokines (chemokines). However, the application of chemokines leads to significantly lower chemotaxis of THP 1 cells at dilutions 1:3 and 1:10 (FIG. 7B). This suggests a prevention of N-terminal pGlu-formation of MCP-1 (WT) by QC-specific inhibitor 1-(3-(1H-imidazol-1-yl)propyl)-3-(3, 4-dimethoxyphenyl)thiourea hydrochloride and, therefore, an inactivation of MCP-1 (WT), either by N-terminal proteolytic degradation or by the sole prevention of pGlu formation.

Investigations on the Proteolytic Degradation of Human MCP-1(1-76)

Figure 3A:
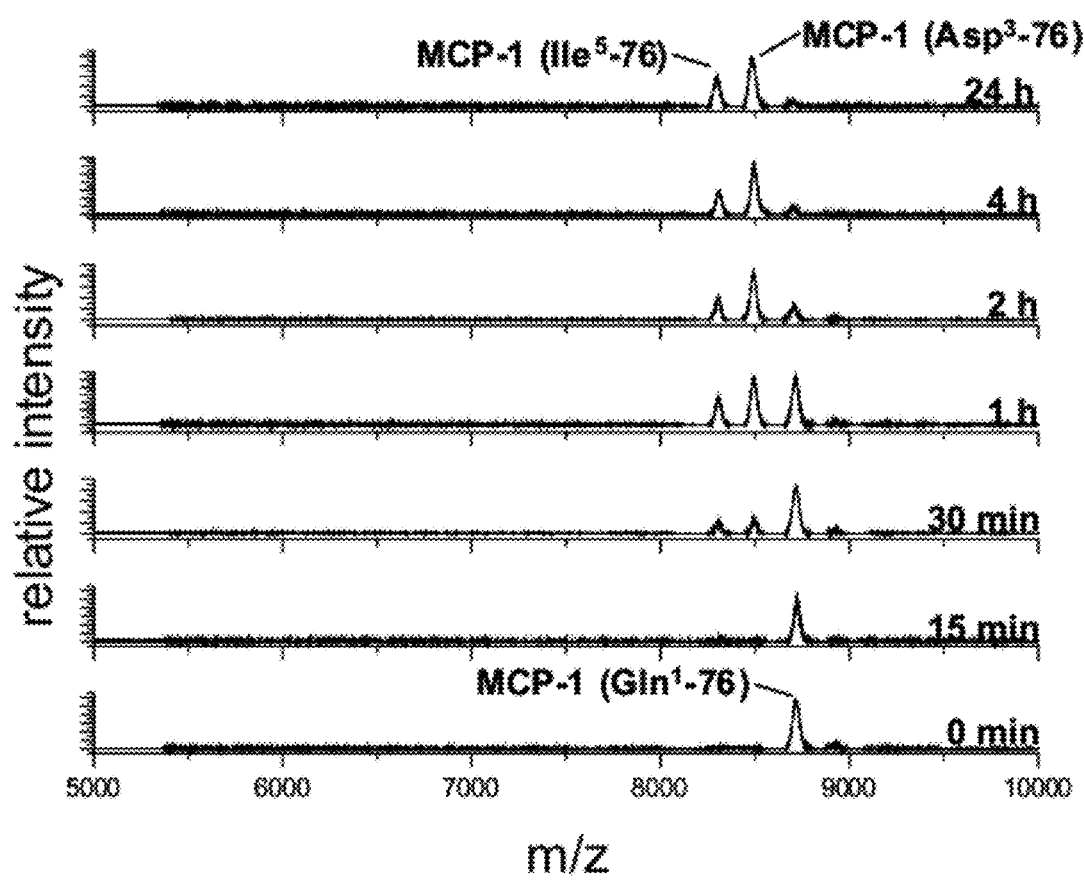
FIG. 3 shows the incubation of MCP-$1_{(1-76)}$ carrying an N-terminal glutaminyl (A) or Pyroglutamyl (5-oxo-L-Prolyl) with human synovial fibroblast MMP-1 and recombinant human DP4 for 24 h. For cyclization of N-terminal glutamine into pyroglutamate, MCP-1 was incubated with recombinant human QC 3 h prior to assay start. Resulting MMP-1 cleavage products were analyzed after 0 min, 15 min, 30 min, 1 h, 2 h, 4 h and 24 h using Maldi-TOF mass spectrometry

Within the circulation, MCP-1 is protected by a N-terminal pGlu-residue, which confers resistance against N-terminal cleavage by aminopeptidases, e.g. DP4. As a result of QC inhibitor administration, the unprotected N-terminus is readily cleaved by DP4. The N-terminal truncation, in turn, leads to inactivation of human MCP-1 (FIGS. 5 and 6). MMP-1 inactivates mature MCP-1 by cleavage of the 4 N-terminal amino acids (pE/Q-P-D-A). The reaction is independent from the presence of a N-terminal pGlu residue. This process reflects the situation of MCP-1 inactivation within the circulation. The resulting cleavage product MCP $1_{(5-76)}$ has been shown to be present within plasma and resembles a naturally occurring CCR2 receptor antagonist. The present experiments point to the finding that MMP-1 cleavage is slightly faster in case of a N-terminal glutamine residue (FIG. 2A: 2 h, 4 h vs. 2B: 2 h, 4 h). Furthermore, incubation of human MCP-1 carrying an N-terminal Gln residue (FIG. 3A) with human DP4 and human MMP-1 shows an accelerated degradation in comparison to pGlu-MCP-1 (FIG. 3B).

Taken together, the results imply that the N-terminal pGlu formation represents a mechanism of protection, conferring resistance against N-terminal degradation by post-proline cleaving enzymes, e.g. DP4, aminopeptidases and, as implied by the results with MMP-1, to a certain extent also endoproteases. Prevention of N-terminal pGlu formation by QC inhibitor application leads to a faster inactivation of human MCP-1.

Figure 8A:
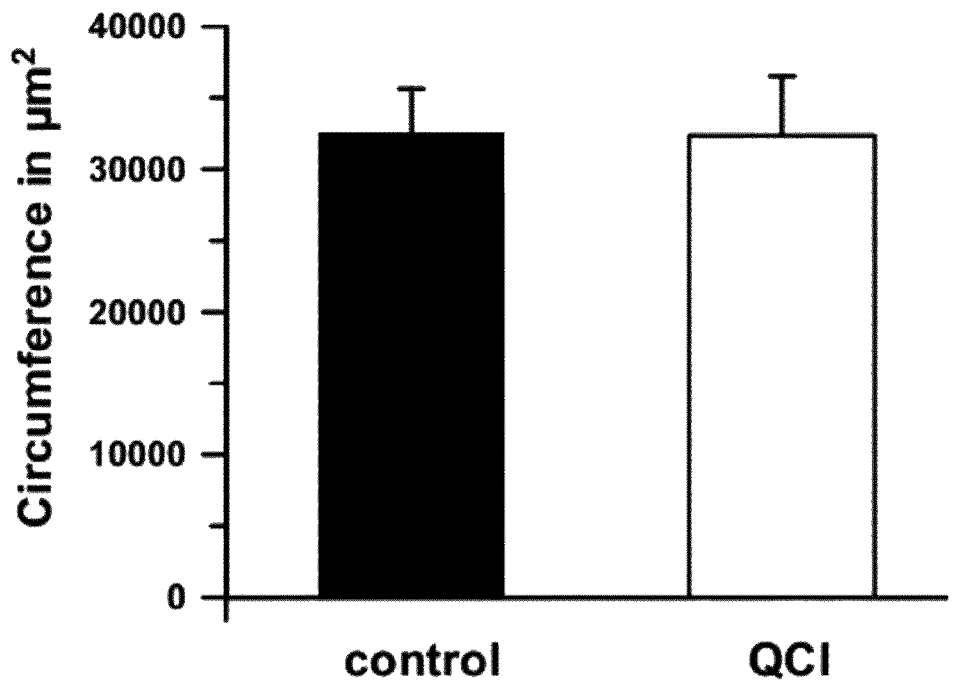
FIG. 8 shows the quantification of the vascular remodeling of the cuffed vessel wall segments of untreated ApoE3 Leiden mice (black bars) and mice, which were treated (open bars) with 1-(3-(1H-imidazol-1-yl)propyl)-3-(3,4-dimethoxyphenyl)thiourea hydrochloride. Mice were sacrificed 14 days after cuff placement. Expressed is the vascular circumference (A) i.e. the total area within the outer diameter of the vessel segment and the remaining lumen (B) in 1 $\mu m^2$.
Figure 8B:
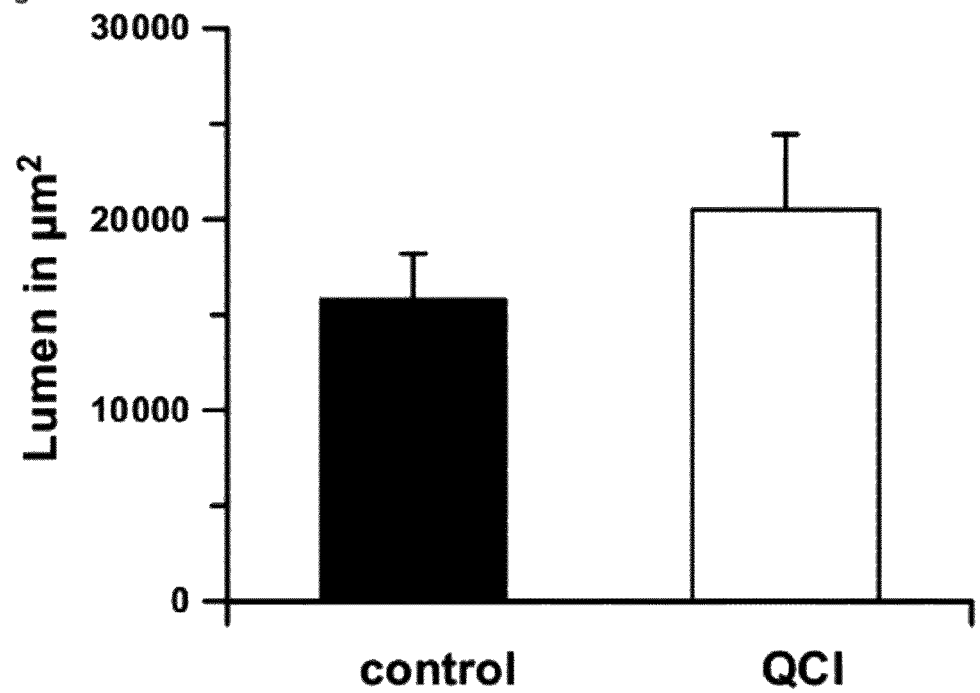
Figure 9A:
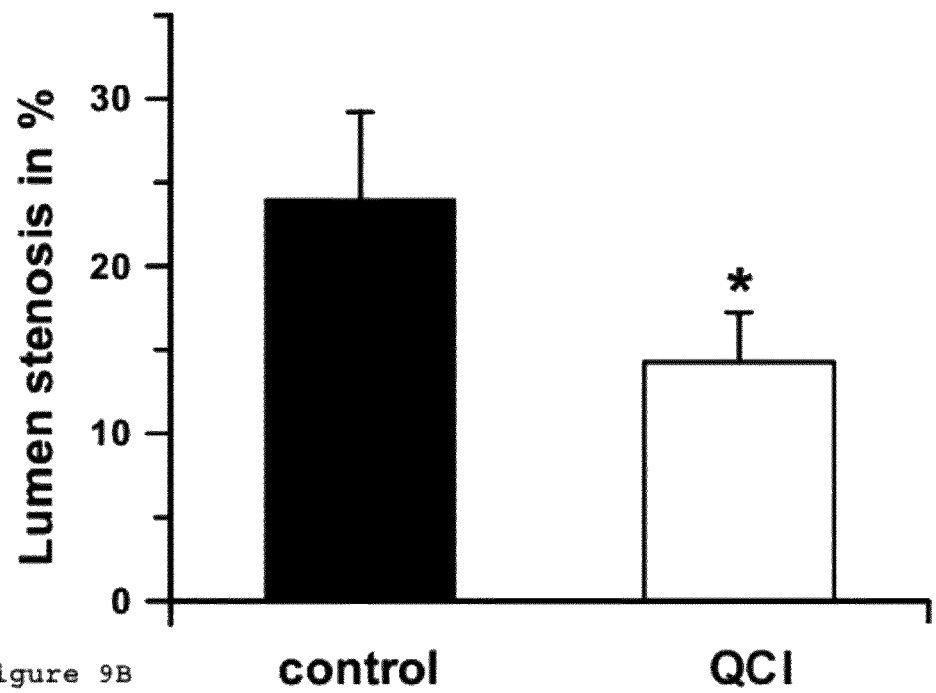
FIG. 9 shows the quantification of the vascular remodeling of the cuffed vessel wall segments of untreated ApoE3 Leiden mice (black bars) or mice treated with (open bars) 1-(3-(1H-imidazol-1-yl)propyl)-3-(3,4-dimethoxyphenyl)thiourea hydrochloride. Mice were sacrificed 14 days after cuff placement. Expressed is the lumen stenosis A in % and the area of neointima B in 1 $\mu m^2$. (*, $P<0.05$, Student's t-test).
Figure 9B:
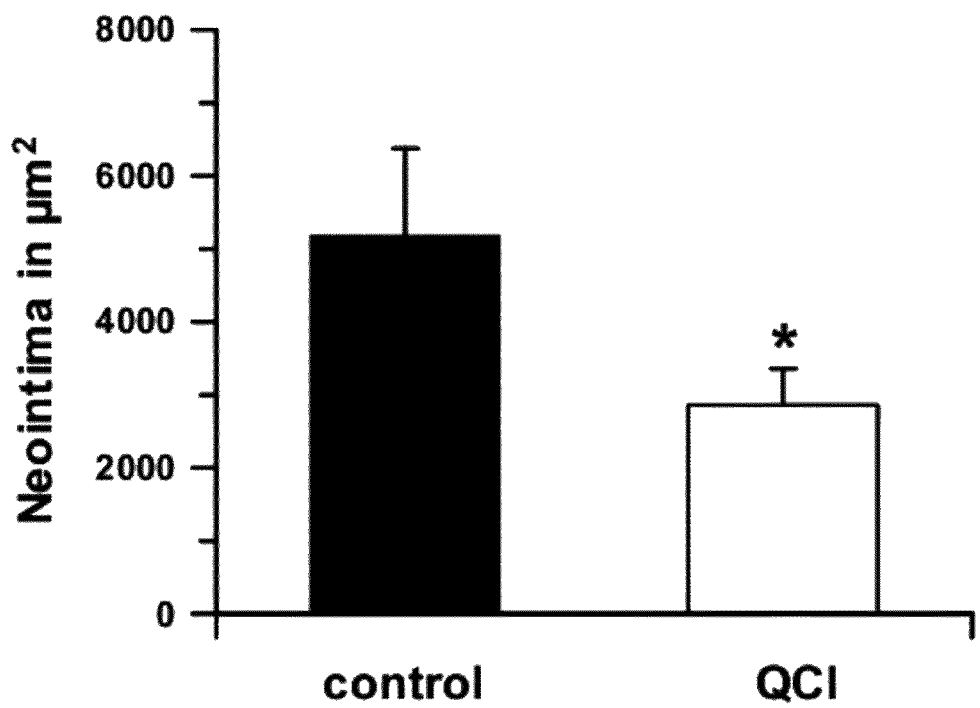
Figure 10A:
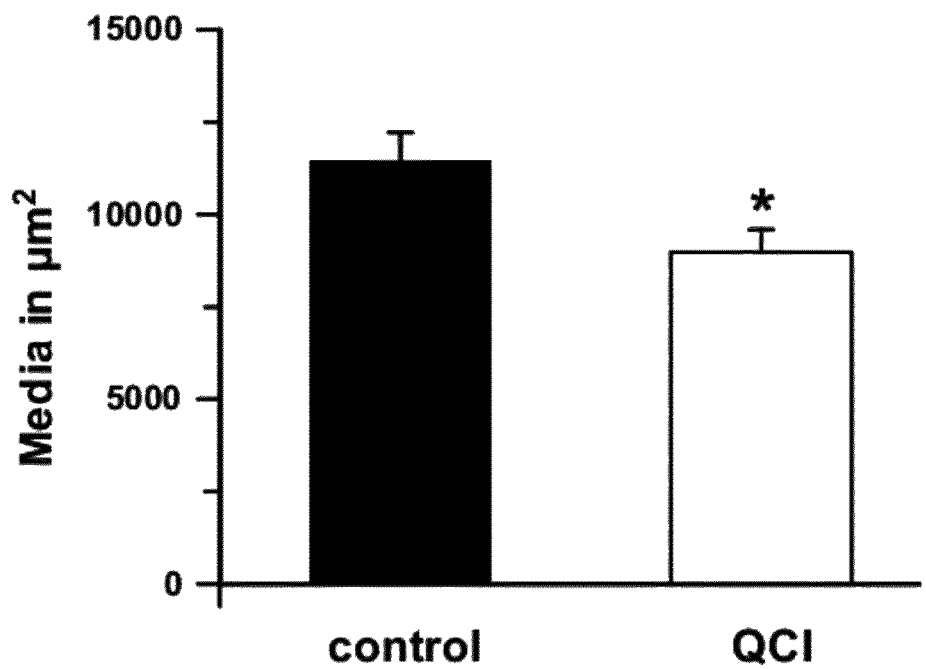
FIG. 10 shows the quantification of the vascular remodeling of the cuffed vessel wall segments of untreated ApoE3 Leiden mice (black bars) or mice, which were treated with (open bars) of 1-(3-(1H-imidazol-1-yl)propyl)-3-(3,4-dimethoxyphenyl)thiourea hydrochloride. Mice were sacrificed 14 days after cuff placement. Expressed is the area of the media A in 1 $\mu m^2$ and the intima/media ratio B. (*, $P<0.05$, Student's t-test).
Figure 10B:
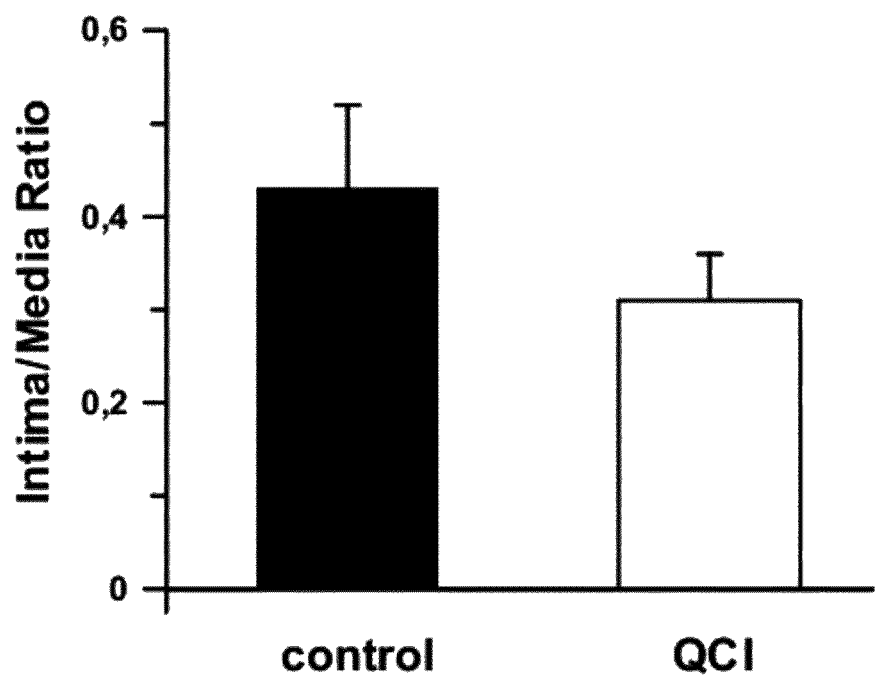

Analysis of Vascular Remodeling and Accelerated Atherosclerosis in ApoE3*Leiden Mice Treatment of cuff-induced accelerated atherosclerosis in ApoE3*Leiden mice had no effect on the total area within the outer diameter of the vessel segment (FIG. 8A) and no statistically significant effect on the remaining lumen (FIG. 8 B), although a slight increase in the remaining lumen can be observed. However, 1-(3-(1H-imidazol-1-yl)propyl)-3-(3,4-dimethoxyphenyl)thiourea hydrochloride shows a profound reduction of 40% on the percentage of lumen stenosis (FIG. 9A) and 45% reduction of the area of neointima formation (FIG. 9B). Both values are statistically significant. Furthermore, the inhibitor also reduced the area of the media (FIG. 10 A) and the intima/media ratio (FIG. 10B), although the reduction in intima/media ration lacks statistically significance (P<0.102).

Figure 15A:
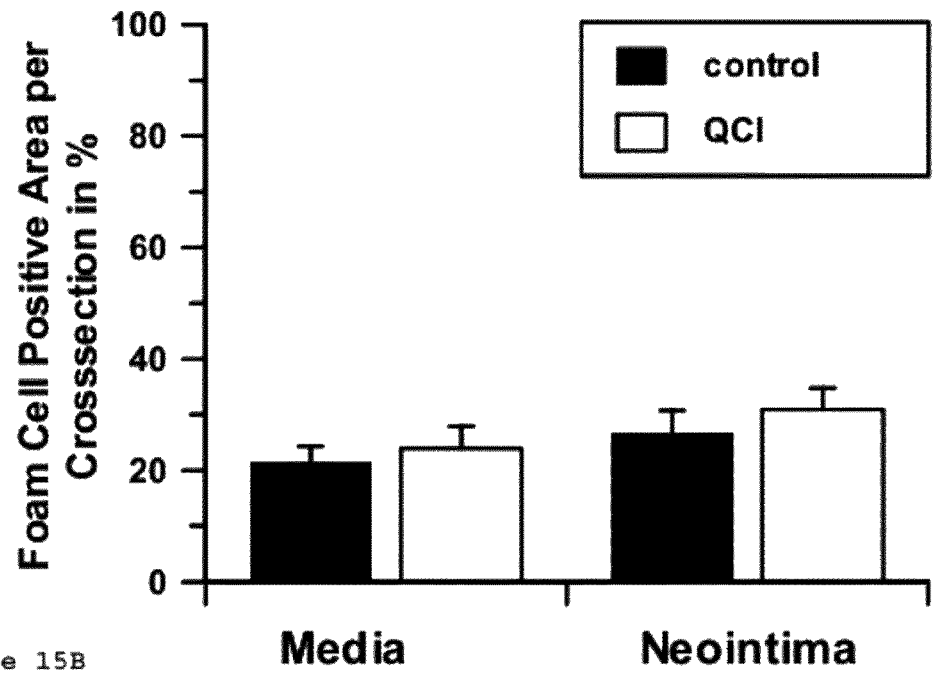
FIG. 15 shows the quantification of the accelerated atherosclerosis in the vessel wall based on the quantification of monocyte/macrophage staining using marker AIA31240. Presented are cross sections of mice sacrificed at the late time point (14 days) treated in absence (black bars) and presence (open bars) of 1-(3-(1H-imidazol-1-yl)propyl)-3-(3,4-dimethoxyphenyl)thiourea hydrochloride. Foam cell accumulation is illustrated as (A) foam cell positive area/cross section in % and (B) foam cell positive area/cross section in $\mu m^2$.
Figure 15B:
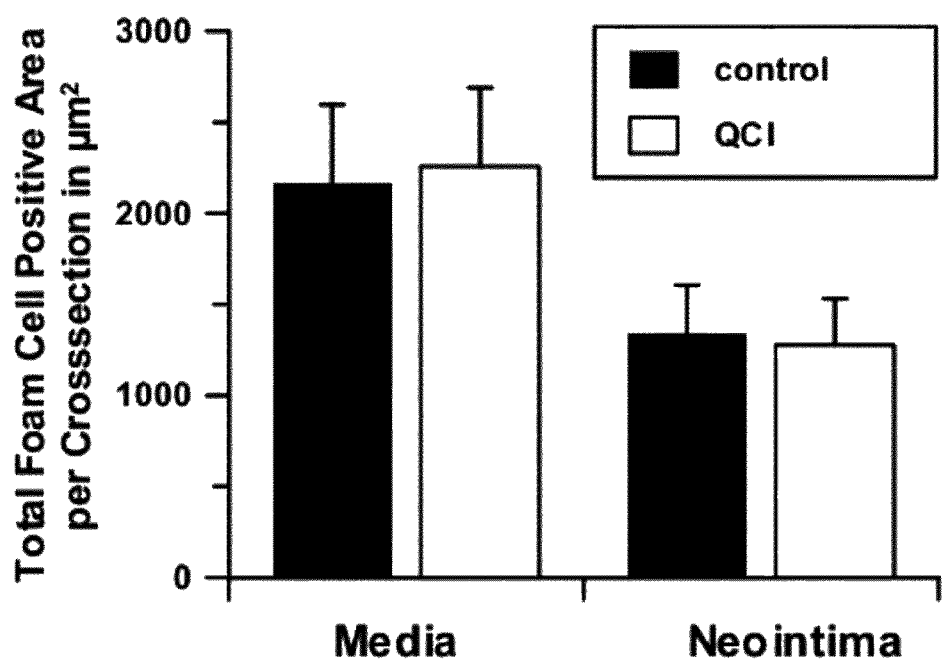

The analysis of the cellular composition in the specific vessel wall layers shows no differences in relative contribution of smooth muscle cells and macrophages/foam cells to the composition of both the media and the adventitia after 2 days and 14 days (FIG. 15). Although one could expect a more specific effect on monocyte/macrophage content in the vessel wall due to the effect of 1-(3-(1H-imidazol-1-yl)propyl)-3-(3,4-dimethoxyphenyl)thiourea hydrochloride on MCP-1, and therefore on monocyte attraction, it should be noted that MCP-1 also has a direct effect on smooth muscle cell proliferation as recently has been discovered and published by Schepers, A. 2006 *Arterioscler Thromb Vasc Biol.* 26, 2063-2069.

Analysis of Monocyte Adhesion and MCP-1 Expression

Figure 11:
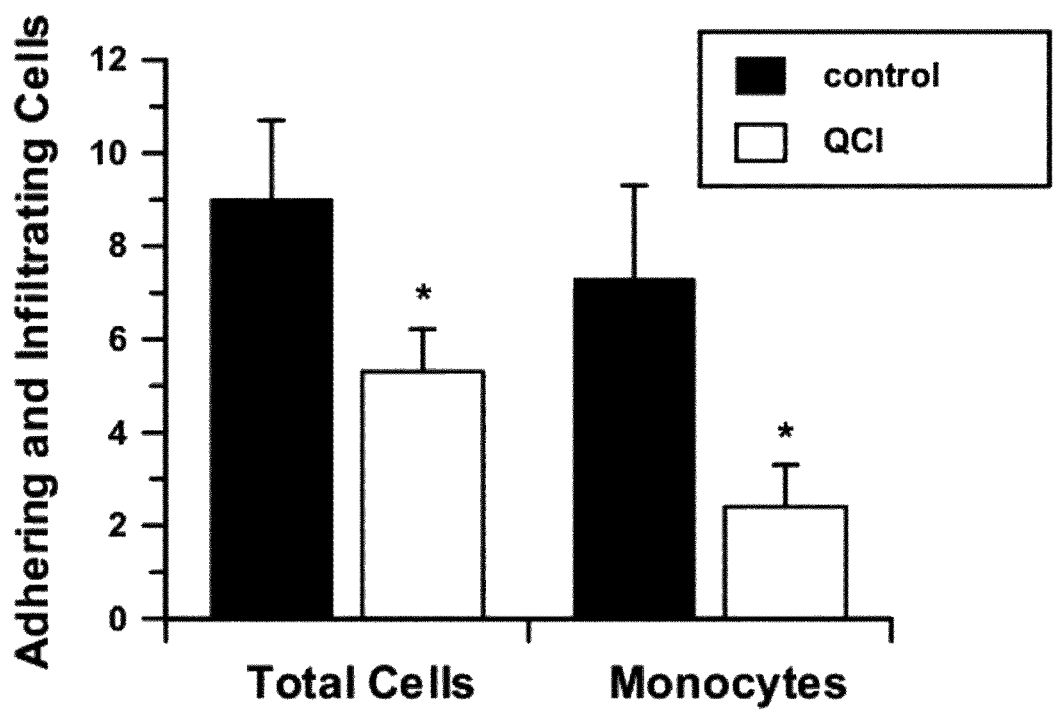
FIG. 11 shows adhering and infiltrating cells per cross section in absence (black bars) or presence (open bars) of 1-(3-(1H-imidazol-1-yl)propyl)-3-(3,4-dimethoxyphenyl) thiourea hydrochloride treatment. Total number of adhering cells per cross section was counted in the cross section of the cuffed femoral arteries harvested two days after cuff placement. Within the total population of adhering cells a specific staining for monocytes/macrophages was used to identify the adhering and infiltrating monocytes. (*, $P<0.05$, Student's t-test).

Treatment of the mildly hypercholesterolemic ApoE3*Leiden mice (plasma cholesterol levels 12-15 mM) with 1-(3-(1H-imidazol-1-yl)propyl)-3-(3,4-dimethoxyphenyl)thiourea hydrochloride resulted in a profound reduction of total adhering cells by 45%, (p<0.05) after 2 days. Specific analysis of adhering monocytes revealed an even stronger reduction of 67% (p<0.05) to the treated cuffed vessel segments (FIG. 11).

Figure 12:
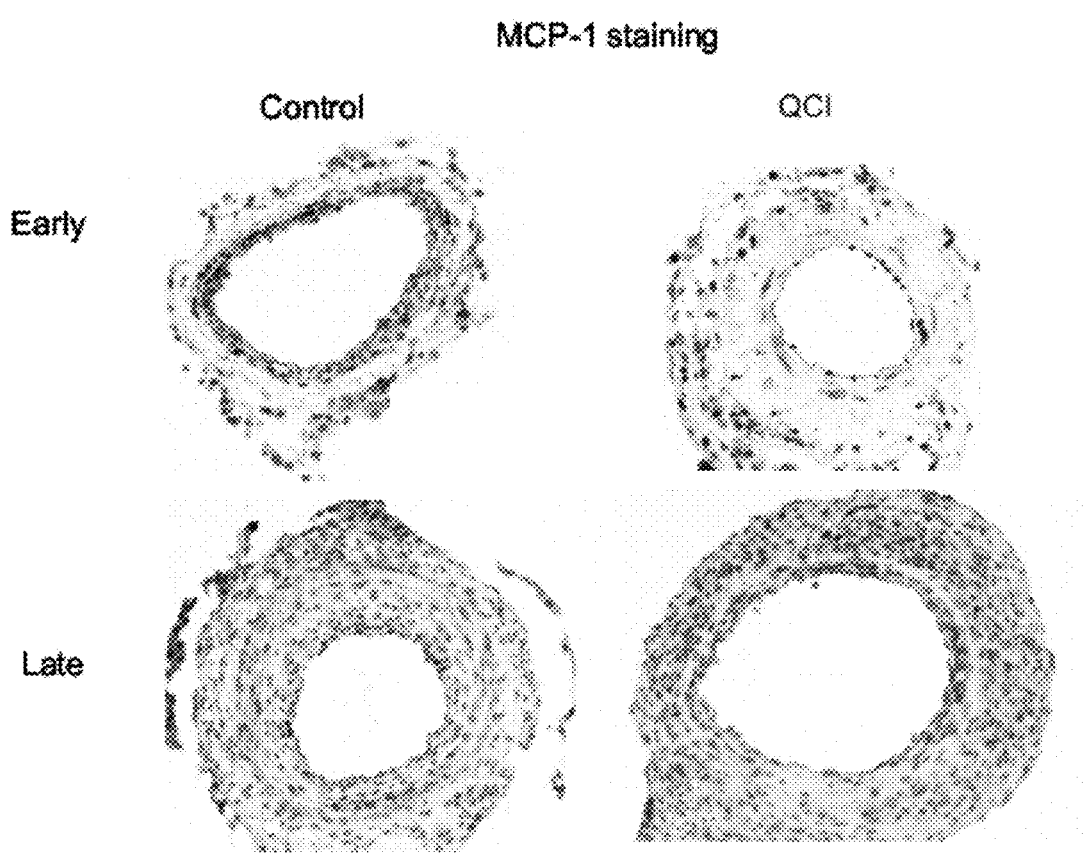
FIG. 12 shows examples of MCP-1 staining by immunohistochemistry of lesions at the early time point (2 days) and the late time point (14 days) in untreated mice (control) and mice, which were treated with 1-(3-(1H-imidazol-1-yl)propyl)-3-(3,4-dimethoxyphenyl)thiourea hydrochloride.
Figure 13A:
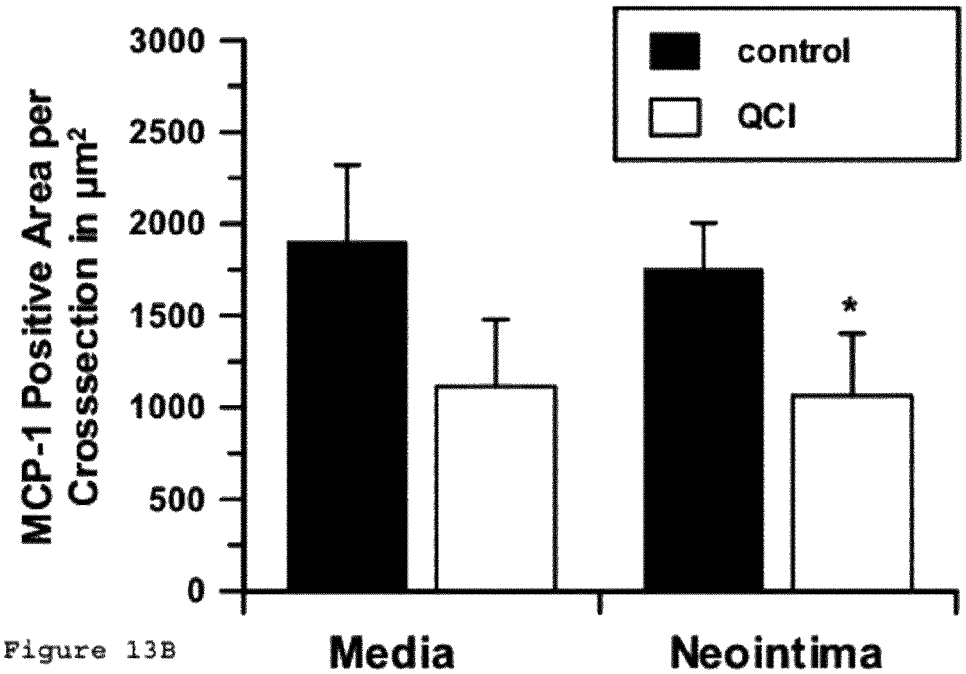
FIG. 13 shows the quantification of MCP-1 staining in cross sections of mice sacrificed after 2 days (early time point) A or after 14 days (late time point) B within the media and neointima in absence (black bars) and presence (open bars) of 1-(3-(1H-imidazol-1-yl)propyl)-3-(3,4-dimethoxyphenyl)thiourea hydrochloride treatment. (*, $P<0.05$; Student's t-test).
Figure 14A:
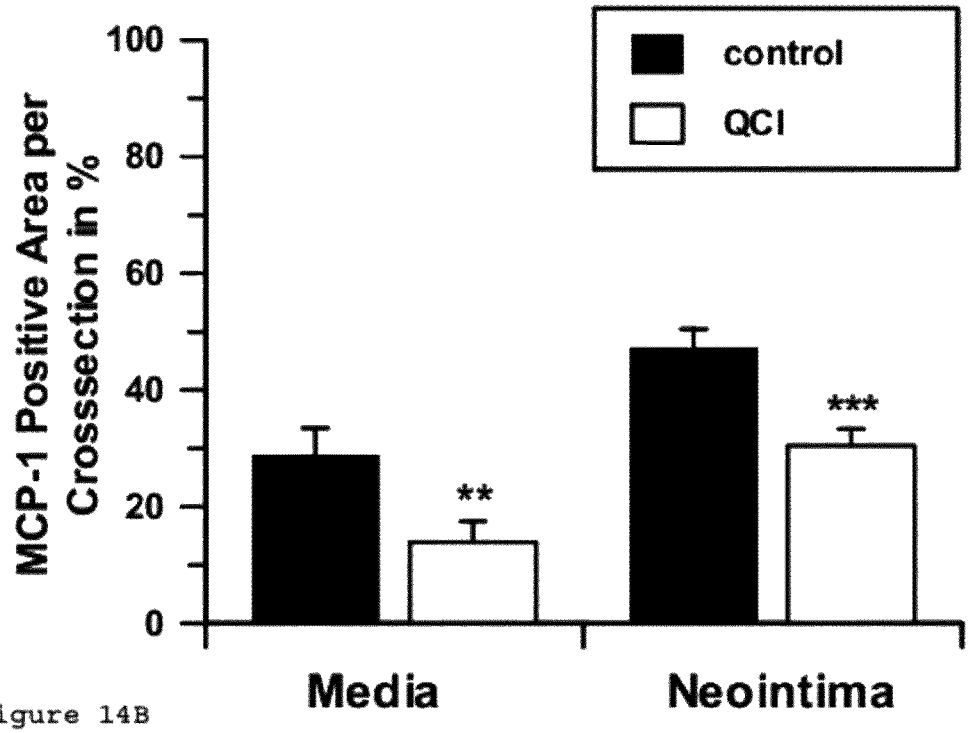
FIG. 14 shows the relative amount of MCP-1 staining (%) in cross sections of mice sacrificed after 2 days (early time point) (A) or after 14 days (late time point) (B) within the media and neointima in absence (black bars) and presence (open bars) of 1-(3-(1H-imidazol-1-yl)propyl)-3-(3,4-dimethoxyphenyl)thiourea hydrochloride treatment. (*, $P<0.05$; Student's t-test).

MCP-1 expression was reduced in the vessel segments of 1-(3-(1H-imidazol-1-yl)propyl)-3-(3,4-dimethoxyphenyl)thiourea hydrochloride treated mice 2 days after surgery, the moment of the highest elevation of MCP-1 expression in the model used (FIG. 12, 13A, 14A). These results indicate that early after vascular injury within the lesions a reduction of MCP-1 expression can be detected in both the media and the intima (i.e inside the Lamina elastica interna) of the vessel wall segment, when 1-(3-(1H-imidazol-1-yl)propyl)-3-(3,4-dimethoxyphenyl)thiourea hydrochloride is administered. Analysis of the relative area of the cross sections positive for MCP-1 revealed a 52% (P=0.01) reduction of MCP 1 expression in the media and a 36% (P=0.001) reduction in the intima (FIG. 14A). Analysis of the absolute area positive for MCP-1 (expressed in $\mu m^2$ positive per cross section) reveals a similar reduction of MCP-1 expression in the media (41% reduction, p=0.09) and the intima (40% reduction, p=0.05), although the reduction within the media is statistically not significant (Student's T-test) (FIG. 13A).

Figure 13B:
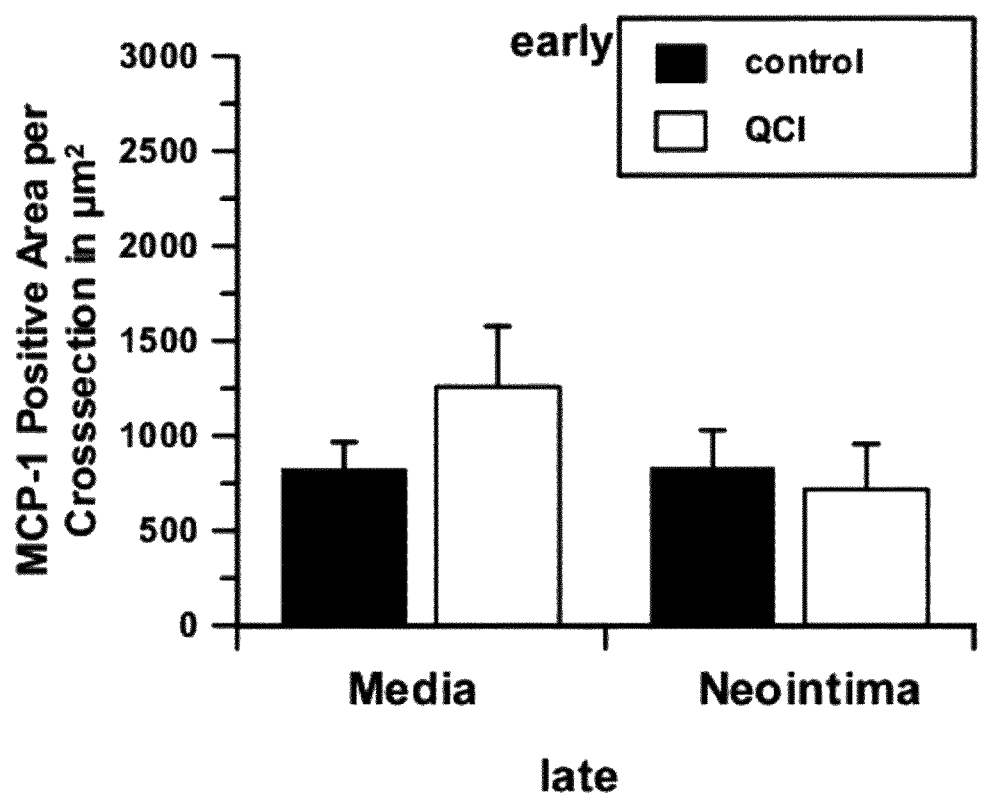
Figure 14B:
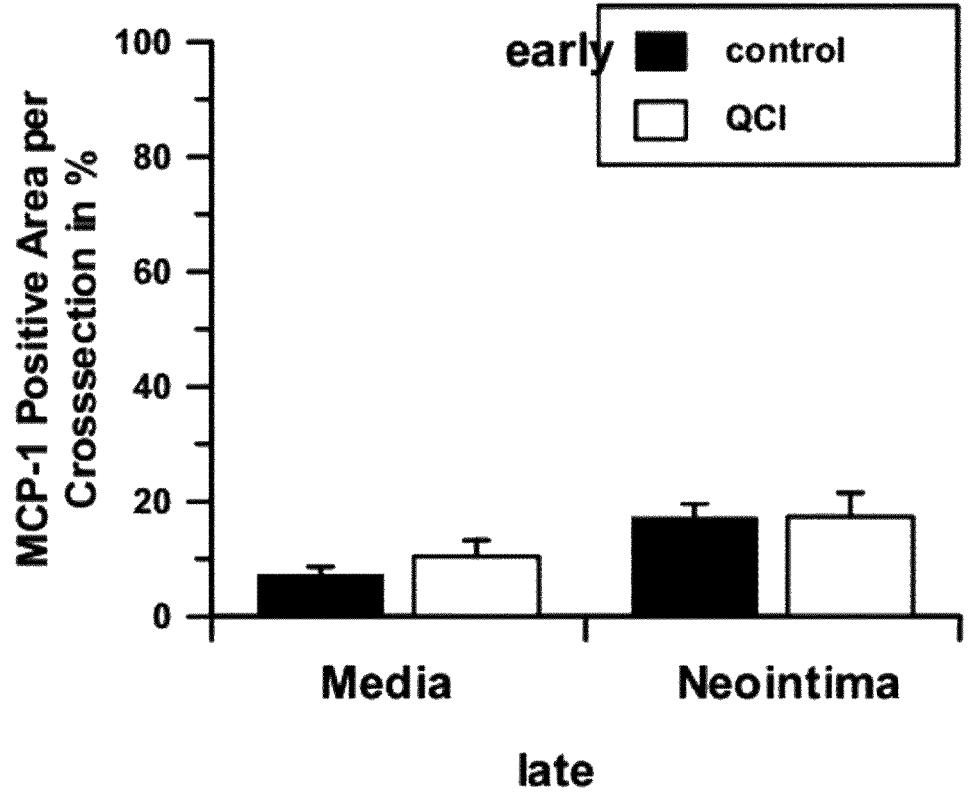

At the later time point of 14 days, when the neointima formation/accelerated atherosclerosis has progressed, the overall MCP-1 expression is lower than observed for the early time point and in contrast, no reduction of MCP-1 expression can be monitored, in the media or in the neointima (FIG. 13B, 14B) suggesting an effect of 1-(3-(1H-imidazol-1-yl)propyl)-3-(3,4-dimethoxyphenyl)thiourea hydrochloride only for the time of strong induction of MCP-1.

Taken together, these data indicate that oral dosing of 1-(3-(1H-imidazol-1-yl)propyl)-3-(3,4-dimethoxyphenyl)thiourea hydrochloride has a beneficial effect on post interventional vascular remodelling and accelerated atherosclerosis in the ApoE3*Leiden cuff model.

Figure 17A:
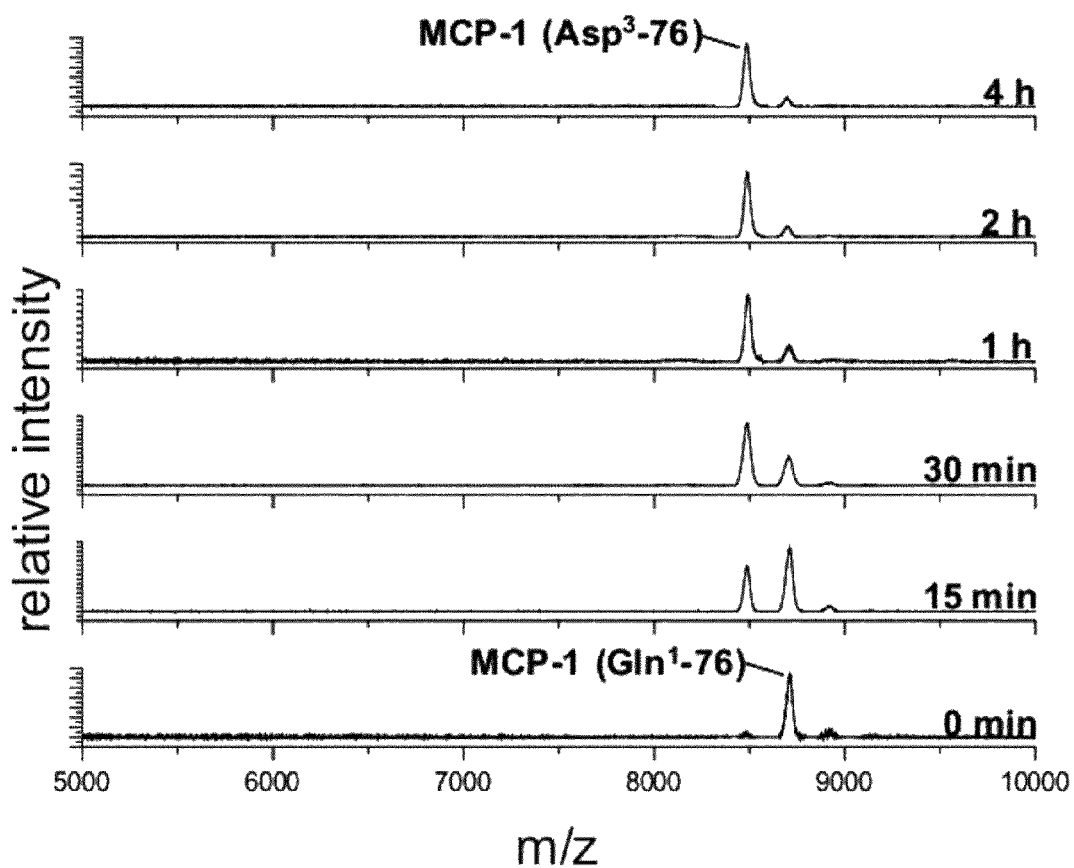
FIG. 17 illustrates the cleavage of human MCP-$1_{(1-76)}$ bearing an N-terminal glutaminyl (A) or pyroglutamyl (5-oxo-L-Prolyl) residue (B) by recombinant human DP4 for 4 h. The pyroglutamate formation at the N-Terminus was accomplished by incubation of MCP-1 with recombinant human QC for 3 h prior to assay. In addition, the incubation of $Gln^1$-MCP-1 with recombinant human QC was carried out in presence of 10 µM QC-specific inhibitor 1-(3-(1H-imidazol-1-yl)propyl)-3-(3,4-dimethoxyphenyl)thiourea hydrochloride. The DP4 cleavage products were analyzed using Maldi-TOF mass spectrometry after 0 min, 15 min, 30 min, 1 h, 2 h and 4 h.
Figure 17B:
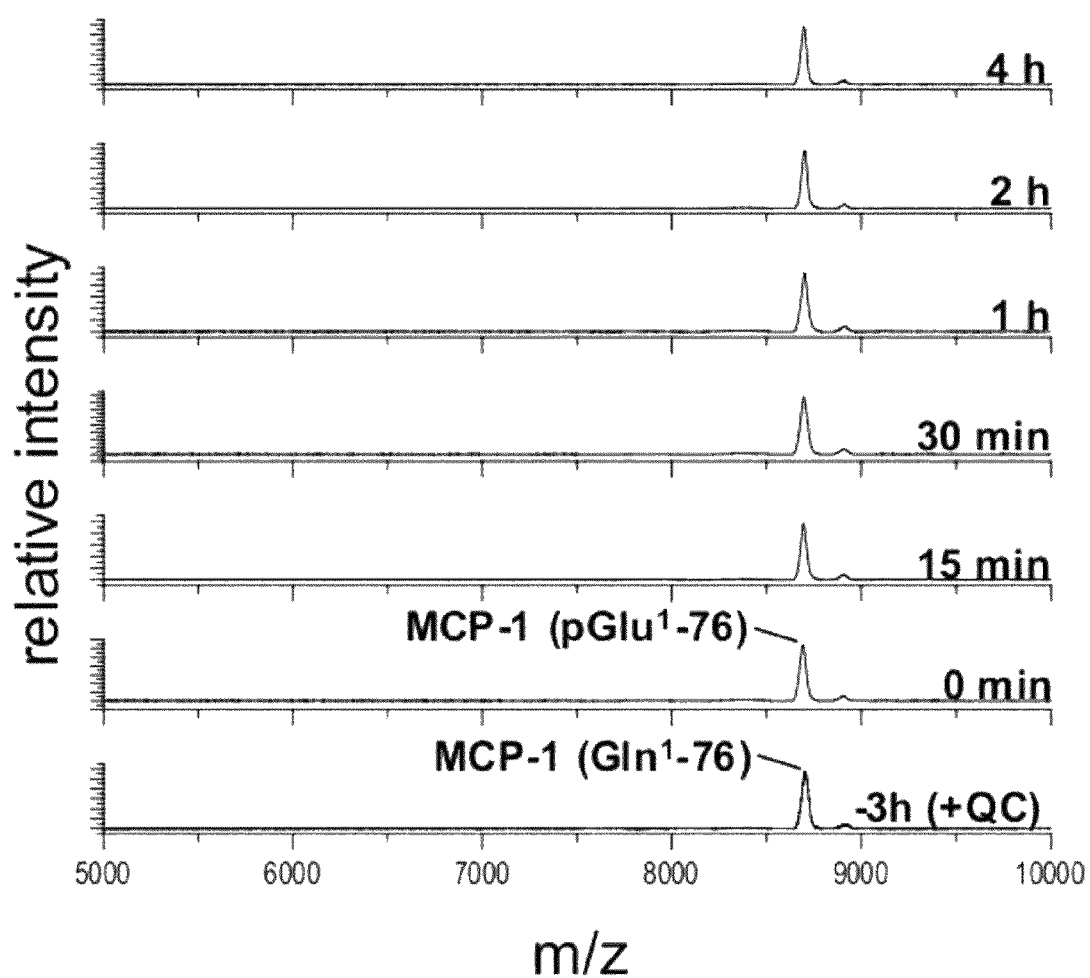
Figure 17C:
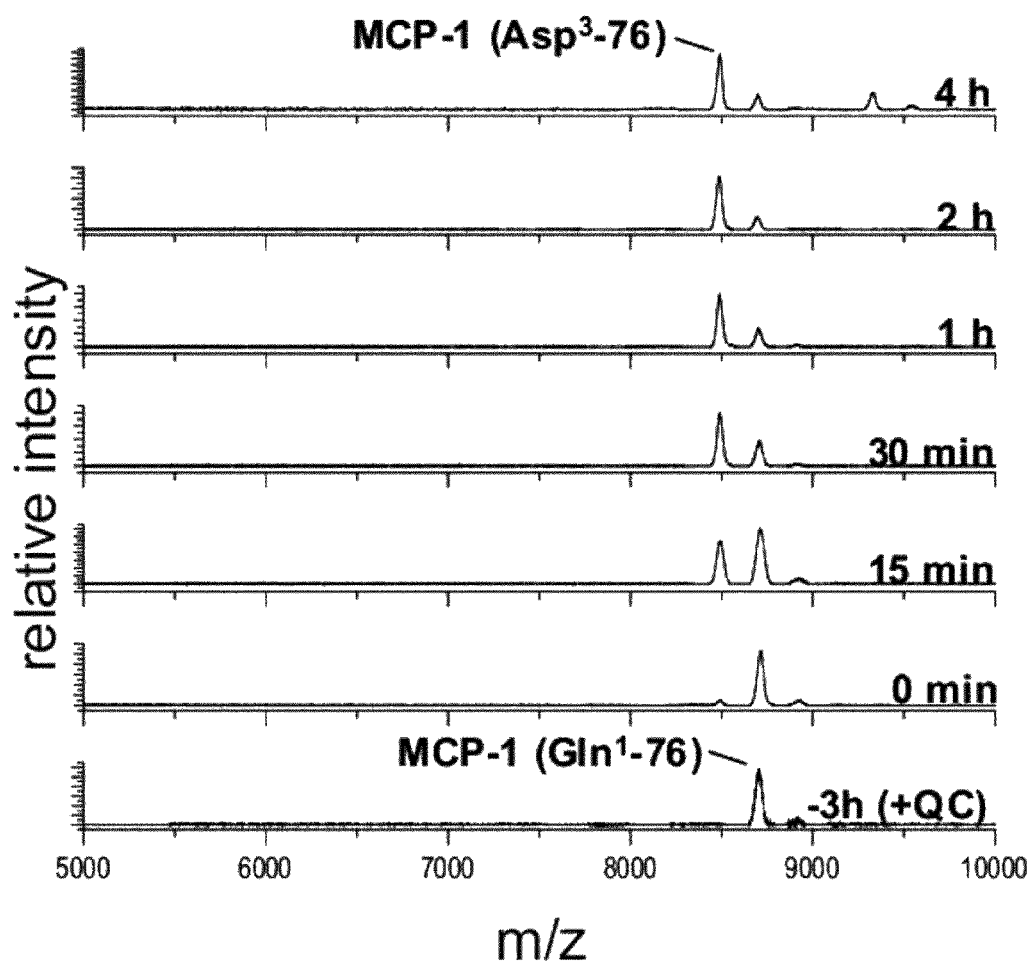

Proteolytic Degradation of Human MCP-$1_{(1-76)}$ by Human Aminopeptidases and Human Serum in Combination with a QC-Specific Inhibitor For further illustration of the effect of the QC-inhibitor 1-(3-(1H-imidazol-1-yl)propyl)-3-(3,4-dimethoxyphenyl)thiourea hydrochloride on the generation of the N-terminal pGlu-residue and its subsequent impact on proteolytic stability, human MCP-1 carrying either N-terminal glutamine (FIG. 17 A) or pyroglutamic acid (FIG. 17 B) was incubated with DP4. N-terminal pGlu-formation was achieved by pre-incubation of the precursor with human QC, reflecting the physiological maturation process. As expected, in absence of the pre-incubation with human QC, MCP-1 is susceptible to DP4 cleavage (FIG. 17 A). In contrast, the pre-incubation with human QC leads to the formation of the N-terminal pGlu-residue and, therefore, to its protection against DP4 cleavage (FIG. 17 B). In addition, the pre-incubation of human MCP-1 with human QC in presence of the QC-inhibitor 1-(3-(1H-imidazol-1-yl)propyl)-3-(3,4-dimethoxyphenyl)thiourea hydrochloride results in the inhibition of QC and, therefore, to a prevention of pGlu-MCP-1 formation. The prevention of pGlu-MCP-1 formation by 1-(3-(1H-imidazol-1-yl)propyl)-3-(3,4-dimethoxyphenyl)thiourea hydrochloride renders the MCP-1 peptide again susceptible to DP4 cleavage (FIG. 17 C). Thus, the inhibition of QC leads to the de-stabilization of the N-Terminus of MCP-1 in vitro and in vivo.

Figure 16A:
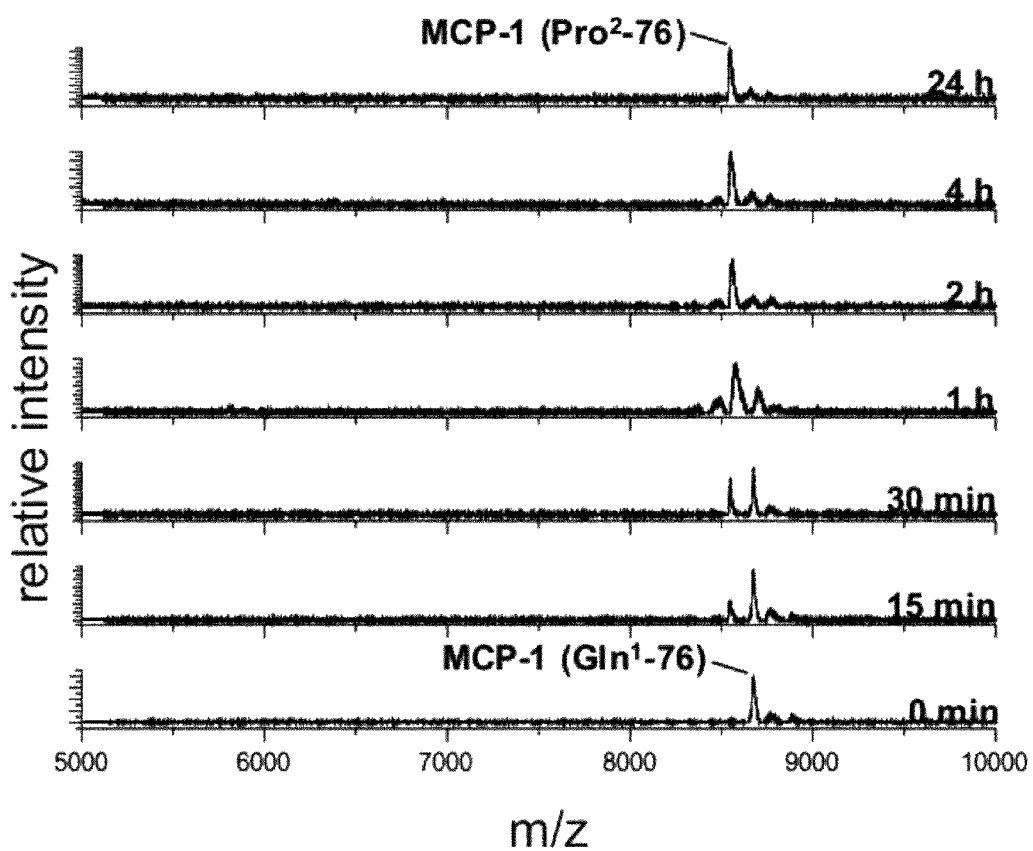
FIG. 16 illustrates cleavage of human MCP-$1_{(1-76)}$ bearing an N-terminal glutaminyl (A) or pyroglutamyl (5-oxo-L-Prolyl) residue (B) by recombinant human Aminopeptidase P for 24 h. The pyroglutamate formation at the N-Terminus was accomplished by incubation of MCP-1 with recombinant human QC for 3 h prior to the assay. The DP4 cleavage products were analyzed after 0 min, 15 min, 30 min, 1 h, 2 h, 4 h and 24 h using Maldi-TOF mass spectrometry.
Figure 16B:
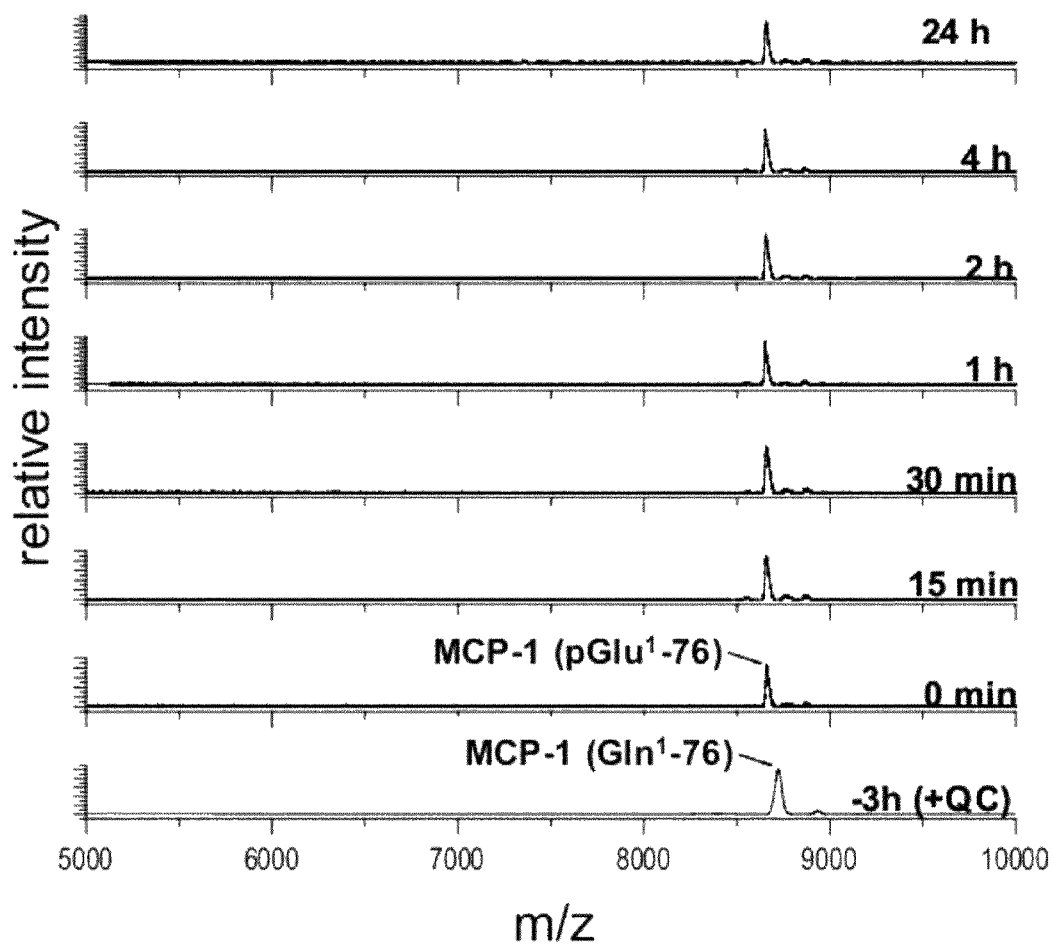

In analogy to the N-terminal truncation of human MCP-1 by DP4, the incubation of $Gln^1$-MCP-1 with recombinant human aminopeptidase P leads to the cleavage of the unprotected N-Terminus. Thereby, aminopeptidase P cleaves between the N-terminal amino acids $Gln^1$ and $Pro^2$ and liberates the N-terminal glutaminyl residue (FIG. 16 A). However, pre-incubation of $Gln^1$-MCP-1 with human QC causes the formation of the N-terminal pGlu-residue and, therefore, the protection against aminopeptidase P cleavage (FIG. 16 B). Thus, the formation of the N-terminal pGlu-residue is also a protection mechanism against aminopeptidase P cleavage and against the cleavage of presumably all other proline-specific aminopeptidases.

Figure 18A:
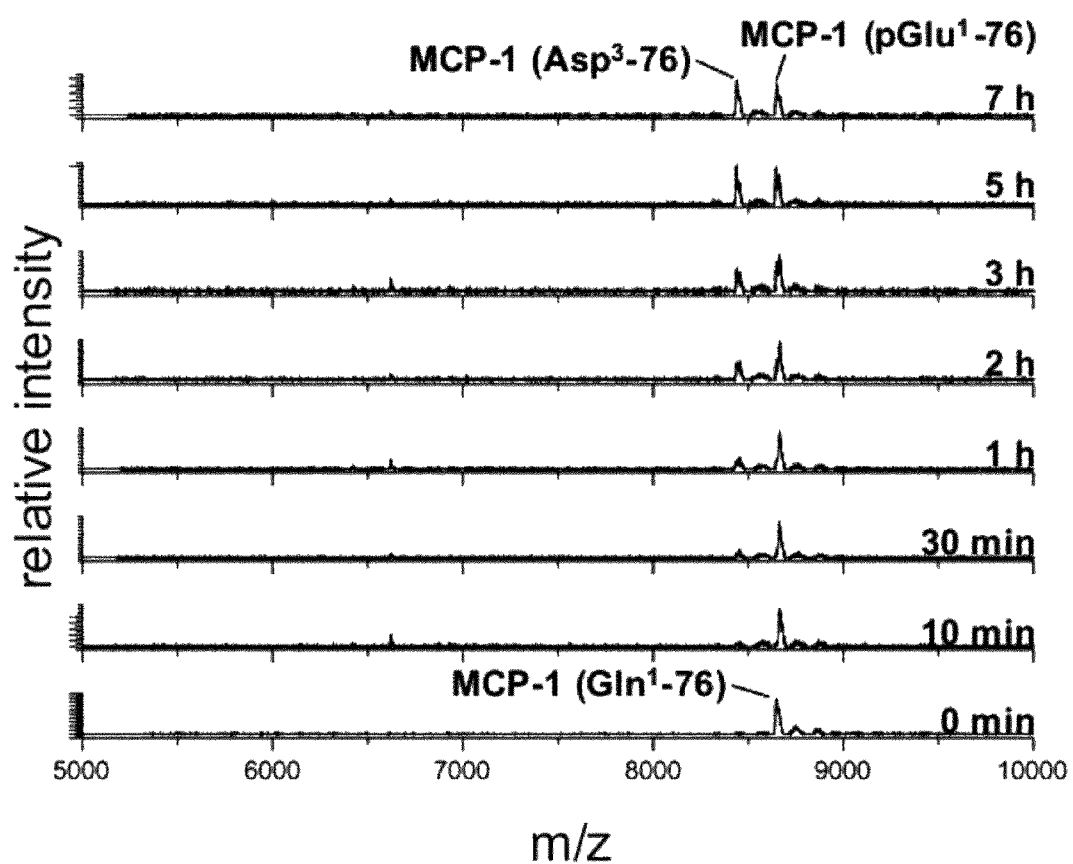
FIG. 18 shows the degradation of human MCP-$1_{(1-76)}$ carrying an N-terminal glutaminyl residue (A) or pyroglutamyl (5-oxo-L-Prolyl) residue (B) in human serum for 7 and 24 h, respectively. For cyclization of the N-terminal glutamine residue into pyroglutamate, MCP-1 was incubated with recombinant human QC for 3 h prior to assay start. In addition, $Gln^1$-MCP-1 was incubated in human serum in the presence of 9.6 µM DP4 Inhibitor Isoleucyl-Thiazolidine (P32/98) for 24 h (C). The cleavage products were analyzed after 0 min, 10 min, 30 min, 1 h, 2 h, 3 h 5 h and 7 h for $Gln^1$-MCP-1, 0 min, 30 min, 1 h, 2 h, 3 h 5 h, 7 h and 24 h for $pGlu^1$-MCP-1 and 0 min, 1 h, 2 h, 3 h, 5 h, 7 h and 24 h for $Gln^1$-MCP-1 in combination with Isoleucyl-Thiazolidine using Maldi-TOF mass spectrometry.
Figure 18B:
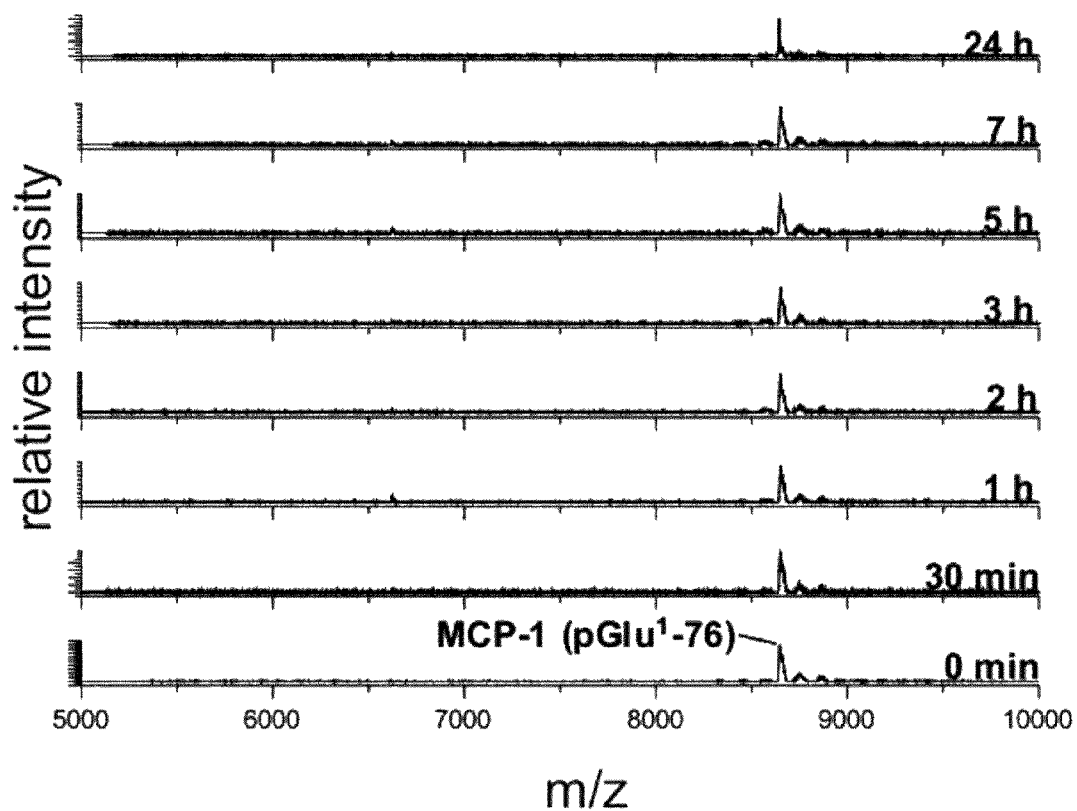
Figure 18C:
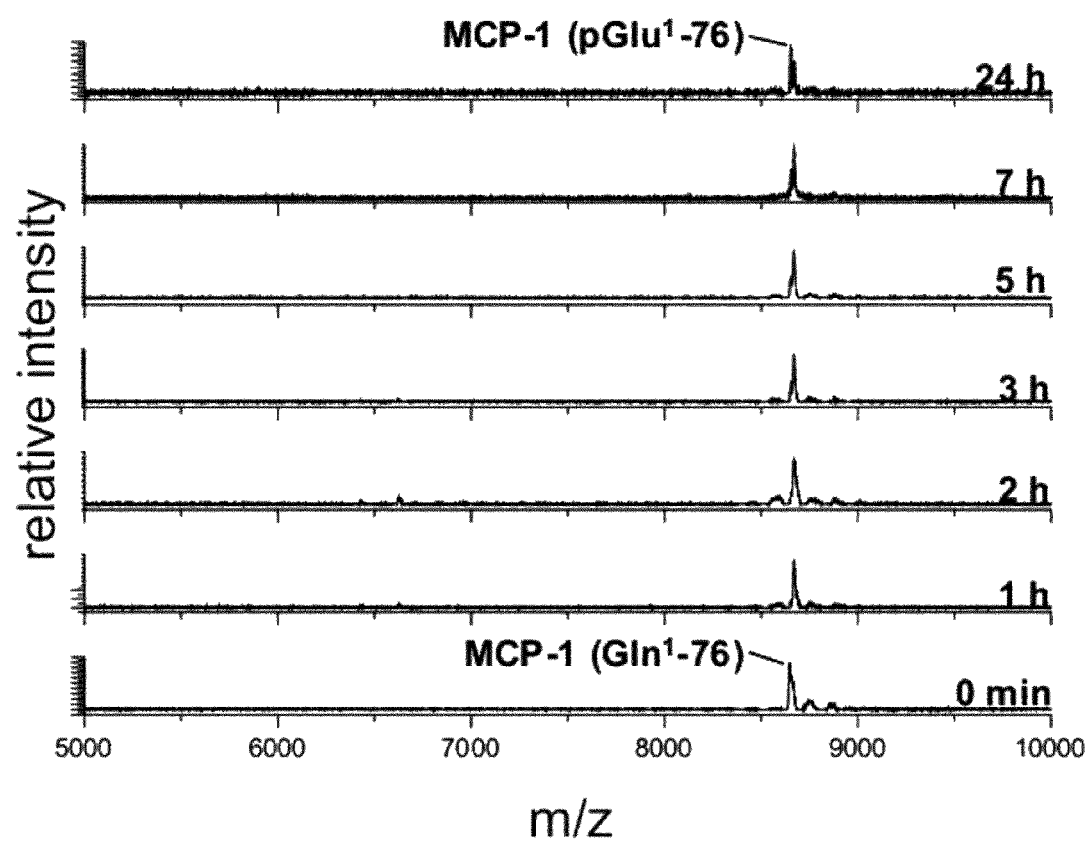

For further investigations on the proteolytic stability of human MCP-1, the data obtained by incubation of MCP-1 with the purified proteases, were substantiated by the incubation of human MCP-1 with human serum. The incubation of human $Gln^1$-MCP-1 with human serum shows the N-terminal truncation of the substrate and the liberation of the first 2 amino acids ($Gln^1 Pro^2$). In addition, QC activity in plasma competes with the N-terminal proteolysis and stabilizes MCP-1, ending at a final ratio of approx. 60% truncated $Asp^3$-MCP-1 and 40% full-length $pGlu^1$-MCP-1 (FIG. 18 A). Furthermore, the pre-incubation of human MCP-1 with human QC leads to the formation of the N-terminal pGlu-residue and, thus, to the stabilization of human MCP-1. At least in the chosen time-frame and dilution of the serum, no degradation of $pGlu^1$-MCP-1 was observed (FIG. 18 B). In addition, the incubation of MCP-1 in serum in presence of 9.6 µM of the DP4-inhibitor Isoleucyl-Thiyzolidide also prevents the N-terminal degradation, proving, that MCP-1 is degraded by DP4 or a DP4-like activity in human serum (FIG. 18 C).

Proteolytic Degradation of Human MCP-2, MCP-3 and MCP-4

Figure 19A:
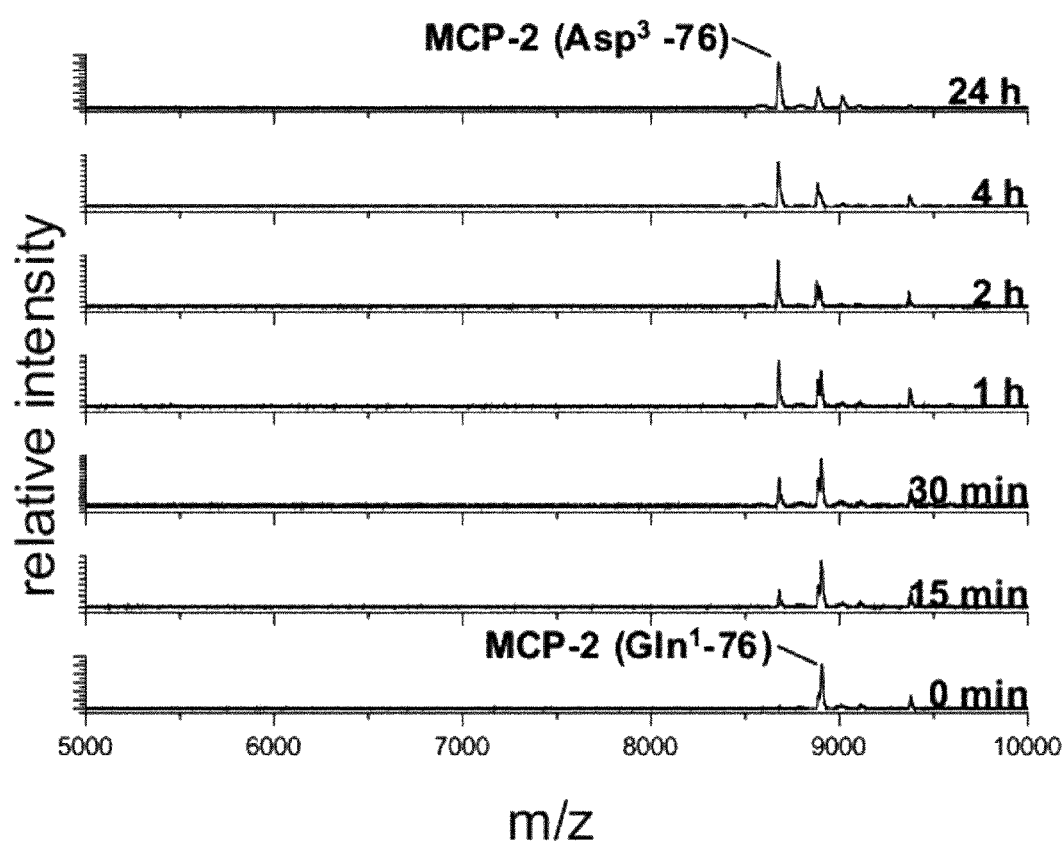
FIG. 19 shows the degradation of human MCP-$2_{(1-76)}$ bearing an N-terminal glutaminyl (A) or pyroglutamyl (5-oxo-L-Prolyl) residue (B) by recombinant human DP4 for 24 h. For cyclization of N-terminal glutamine into pyroglutamate, MCP-2 was incubated with recombinant human QC for 3 h prior to assay start. The DP4 cleavage products were analyzed using Maldi-TOF mass spectrometry after 0 min, 15 min, 30 min, 1 h, 2 h, 4 h and 24 h.
Figure 19B:
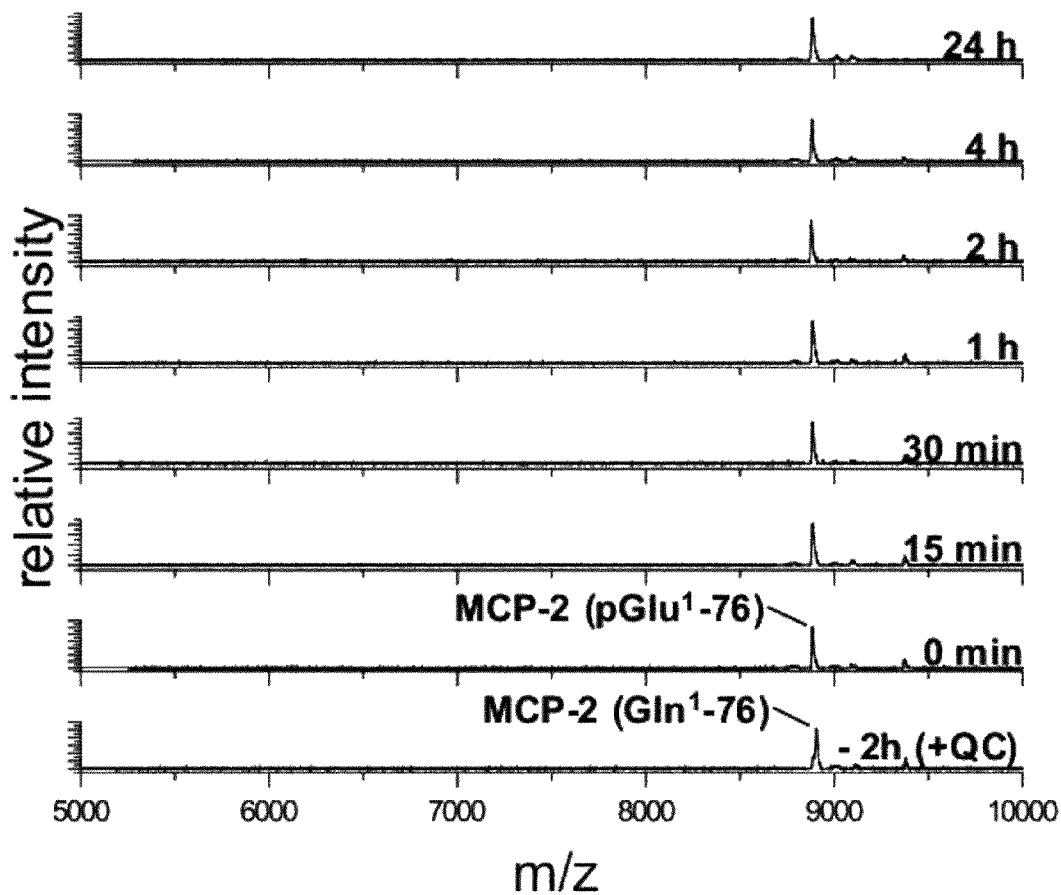
Figure 20A:
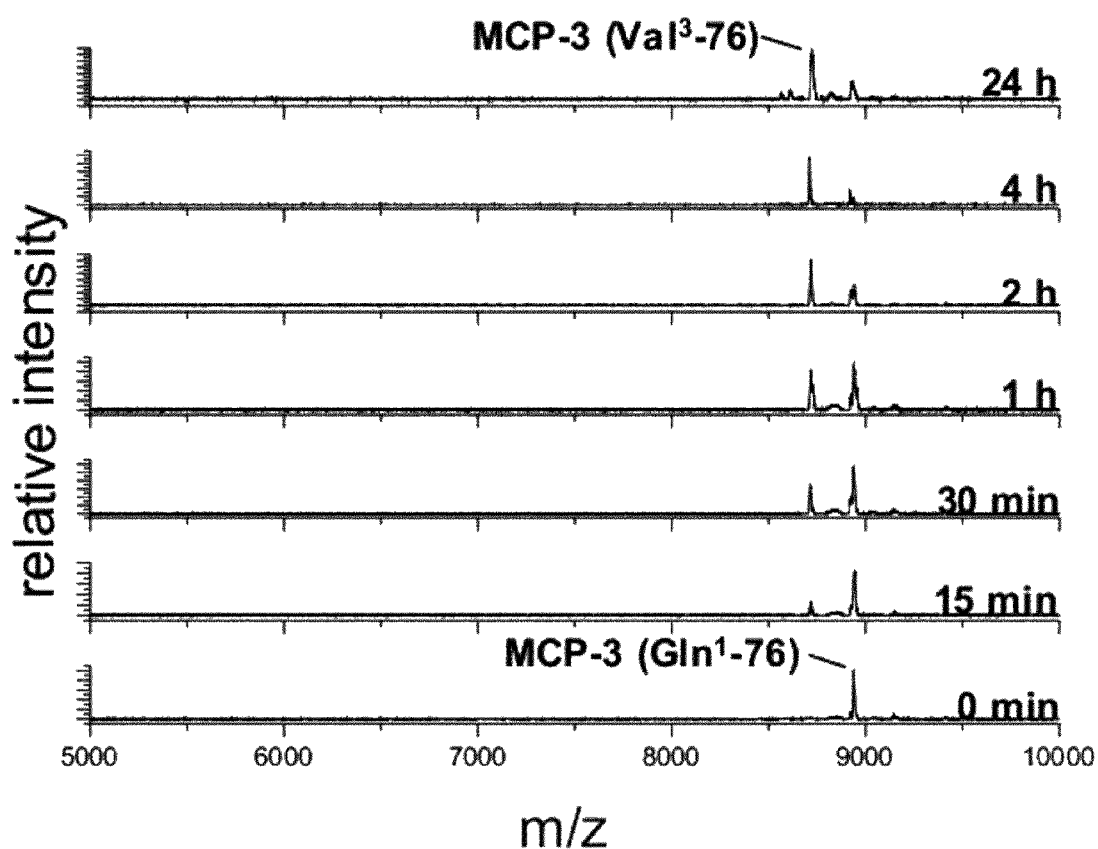
FIG. 20 shows the degradation of human MCP-$3_{(1-76)}$ carrying an N-terminal glutaminyl (A) or pyroglutamyl (5-oxo-L-Prolyl) residue (B) by recombinant human DP4 for 24 h. For cyclization of N-terminal glutamine into pyroglutamate, MCP-3 was incubated with recombinant human QC for 3 h prior to assay start. The DP4 cleavage products were analyzed using Maldi-TOF mass spectrometry after 0 min, 15 min, 30 min, 1 h, 2 h, 4 h and 24 h.
Figure 20B:
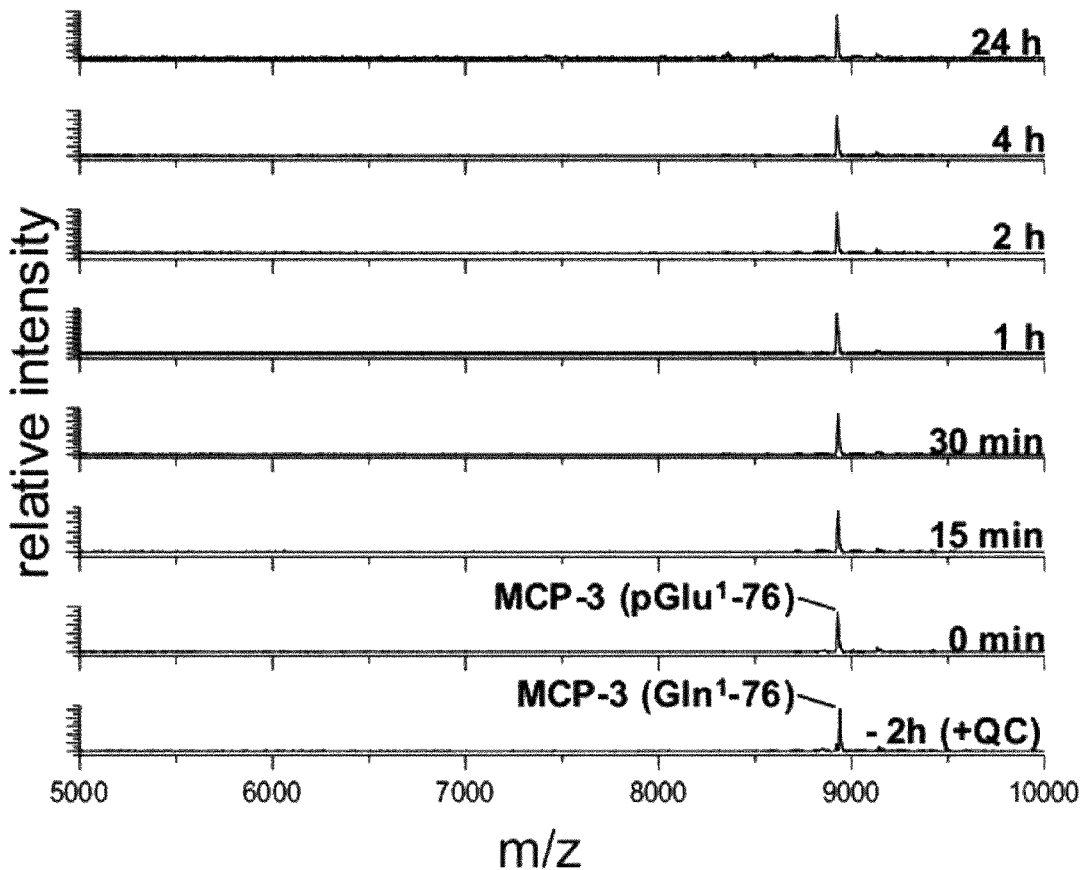
Figure 21A:
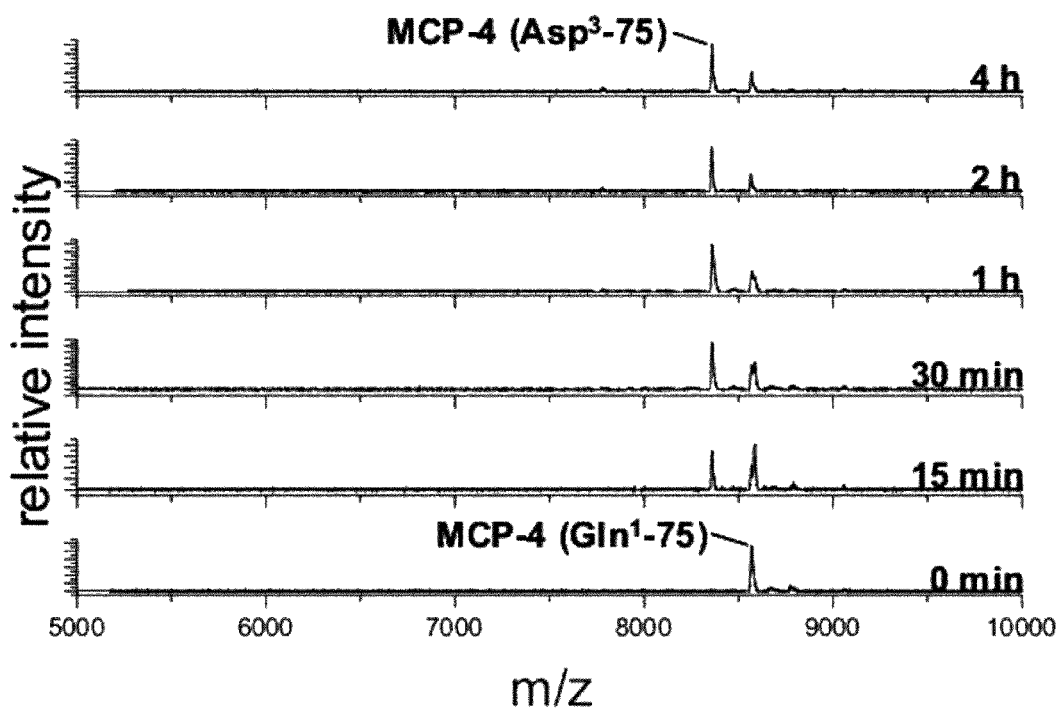
FIG. 21 illustrates the cleavage of human MCP-$4_{(1-75)}$ bearing an N-terminal glutaminyl (A) or pyroglutamyl (5-oxo-L-Prolyl) residue (B) by recombinant human DP4 for 4 hours. For cyclization of N-terminal glutamine into pyroglutamate, MCP-4 was incubated with recombinant human QC for 3 h prior to assay start. The DP4 cleavage products were analyzed using Maldi-TOF mass spectrometry after 0 min, 15 min, 30 min, 1 h, 2 h, and 4 h.
Figure 32:
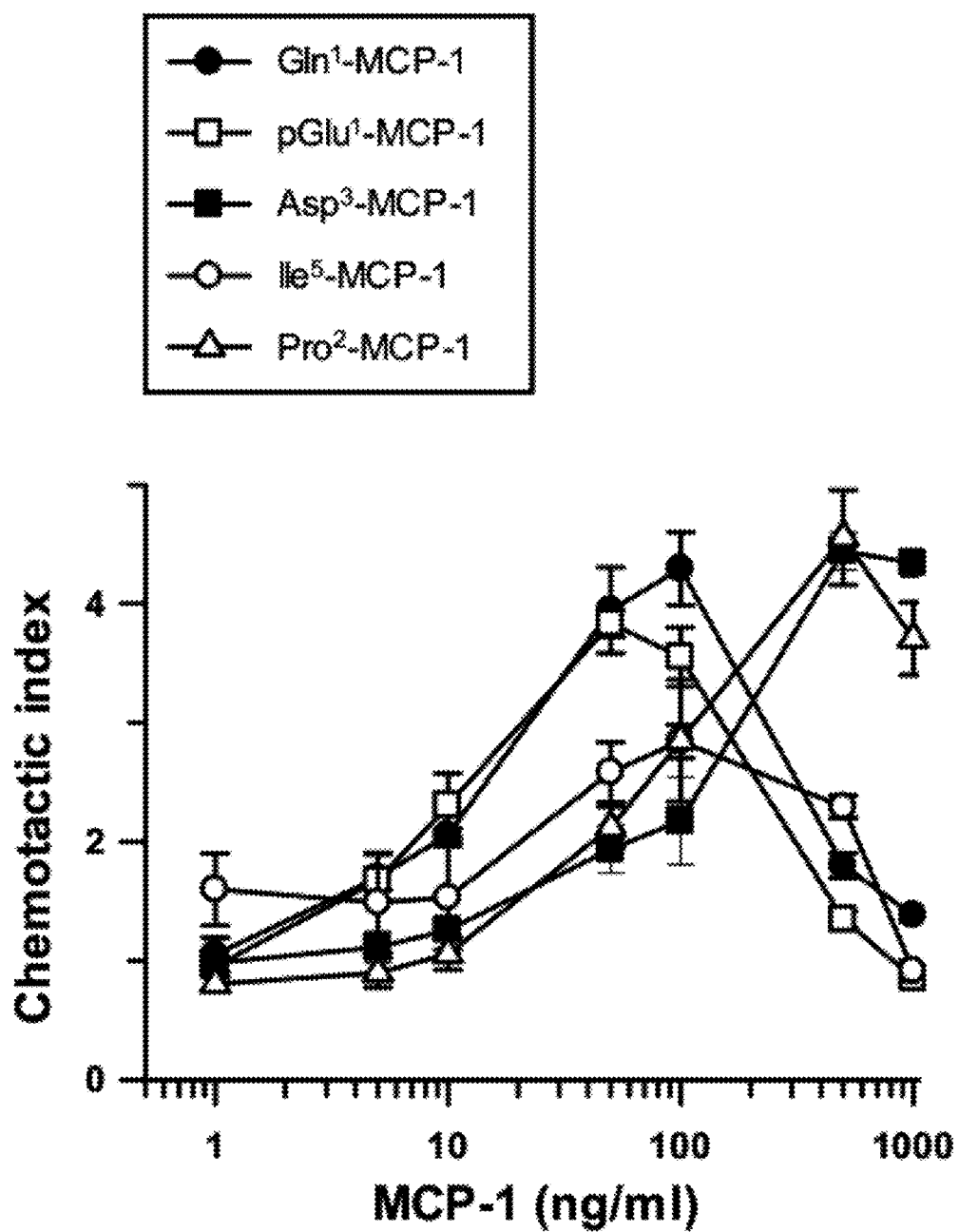

In analogy to the N-terminal degradation of human MCP-1, the susceptibility of other human MCPs, namely MCP-2, MCP-3 and MCP-4, against N-terminal truncation by DP4 was investigated. As observed for MCP-1 before, the N-terminal pGlu-residue protects MCP-2 (FIG. 19 B), MCP-3 (FIG. 20 B) and MCP-4 (FIG. 21 B) against proteolytic degradation by DP4. However, the uncyclized variants, starting with an N-terminal glutamine are readily truncated by DP4 as shown for $Gln^1$-MCP-2 (FIG. 19 A), $Gln^1$-MCP-3 (FIG. 20 A) and $Gln^1$-MCP-4 (FIG. 21 A). Therefore, the N-terminal pGlu-residue stabilizes all MCPs against truncation by aminopeptidases, such as DP4. Thus, the presented concept, to reduce QC activity in vivo in order to provoke accelerated turnover and diminished chemotaxis and receptor activation, applies for all members of the MCP-family.

Chemotactic Potency of Different N-Terminal Variants of Human MCP-1, MCP-2, MCP-3, MCP-4

In order to investigate the influence of different N-terminal variants of MCP-1 on the ability to attract human THP-1 monocytes, $Gln^1$-MCP-1, $pGlu^1$-MCP-1, the aminopeptidase P cleavage product $Pro^2$-MCP-1, the DP4 cleavage product $Asp^3$-MCP-1 and the MMP-1 cleavage product $Ile^5$-MCP-1 were tested in a chemotaxis assay in vitro. The full-length MCP-1 possessing an N-terminal glutaminyl or pyroglutamyl-residue were found to be equally potent in attracting THP-1 monocytes with a maximum response between 50 ng/ml and 100 ng/ml. In contrast, the truncation of MCP-1 by aminopeptidase P (Pro$^2$-MCP-1) and DP4 (Asp$^3$-MCP-1) leads to a loss of potency of the respective variant. The dose-response-curve shifts to higher concentrations needed to elicit the maximum response, which corresponds to an inactivation of MCP-1 by N-terminal truncation. The MMP-1 cleavage product (Ile$^5$-MCP-1) has an equal maximum as Glu$^1$-MCP-1 and pGlu$^1$-MCP-1 between 50 ng/ml and 100 ng/ml, however, the amount of cells migrating to this variant, ie. the chemotactic potency, is much lower, compared to full-length MCP-1 (FIG. 22).

Figure 23:
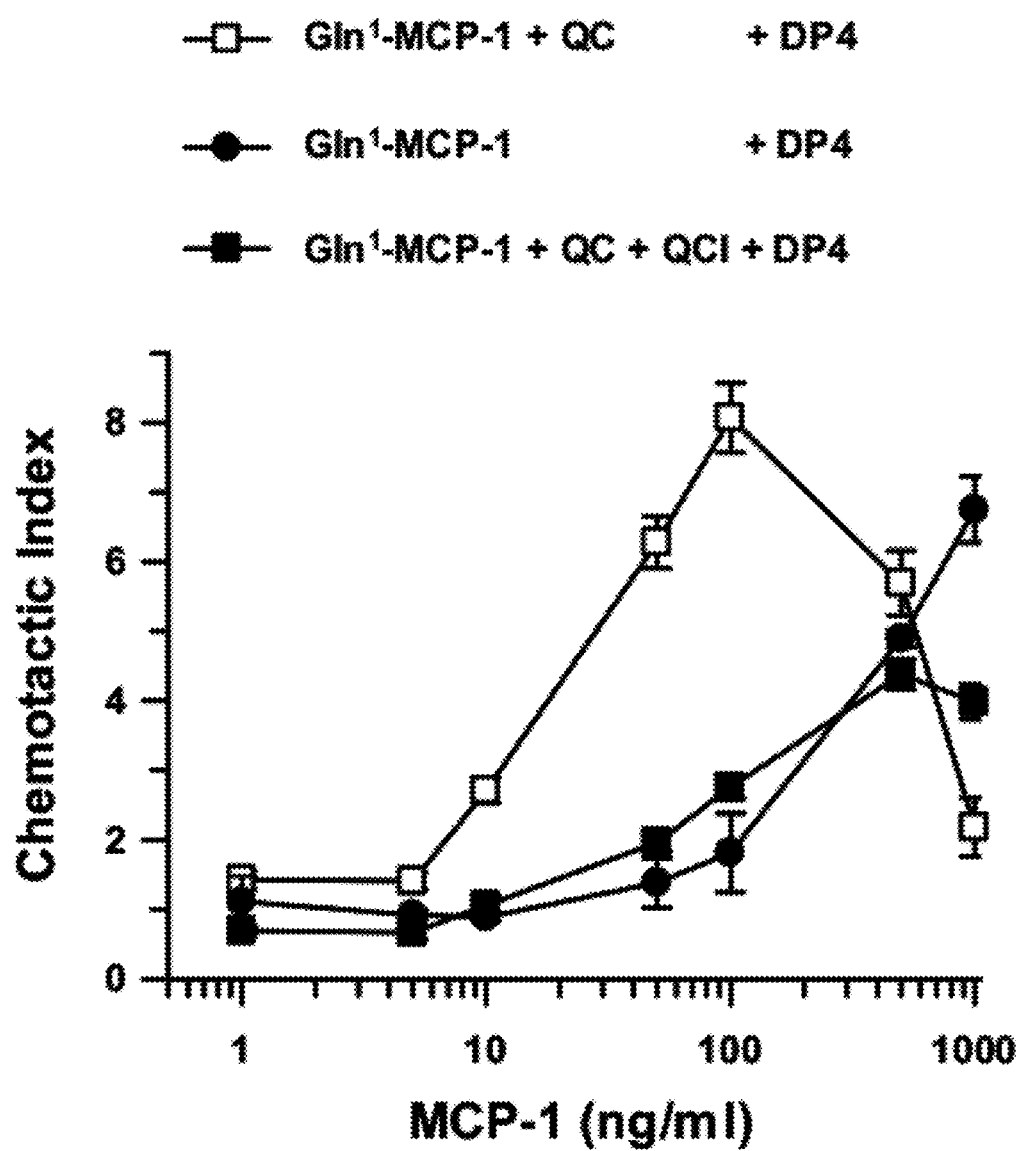
FIG. 23 shows the analysis of chemotactic potency of human MCP-1, which was incubated with human recombinant DP4 in presence ($Gln^1$-MCP-1+QC+DP4) and absence ($Gln^1$-MCP-1+DP4) of QC-mediated pGlu formation. In addition, the influence of the QC-inhibitor 1-(3-(1H-imidazol-1-yl)propyl)-3-(3,4-dimethoxyphenyl)thiourea hydrochloride (QCI) (10 µM) on the formation of the N-terminal pGlu-residue, followed by subsequent DP4 cleavage ($Gln^1$-MCP-1+QC+QCI+DP4) is shown.

To further investigate the role of QC in stabilizing MCP-1 and its impact on the migration of THP-1 monocytes, Gln$^1$-MCP-1 was incubated with human DP4. In parallel samples, MCP-1 was pre-incubated with human QC prior to DP4 application. As expected, the obtained dose-response curves imply a proteolytic stability of pGlu$^1$-MCP-1 reflected by a maximum response at 50-100 ng/ml. In contrast, in absence of QC, Gln$^1$-MCP-1 is truncated by DP4, which leads to a shift of the dose-response curve to higher MCP-1 concentrations (500-1000 ng/ml) needed to elicit the maximum response. In addition, the pre-incubation of Gln$^1$-MCP-1 with QC and the QC-inhibitor 1-(3-(1H-imidazol-1-yl)propyl)-3-(3,4-dimethoxyphenyl)thiourea hydrochloride prevents pGlu-formation and, thus, renders the peptide vulnerable to DP4 cleavage, as observed by the shift of the dose-response curve to higher MCP-1 concentrations compared to pGlu$^1$-MCP-1 (FIG. 23). Therefore, the inhibition of QC leads to the N-terminal destabilization of MCP-1 through degradation by DP4 and, thus, to its inactivation with respect to the monocyte chemotactic activity.

Figure 24A:
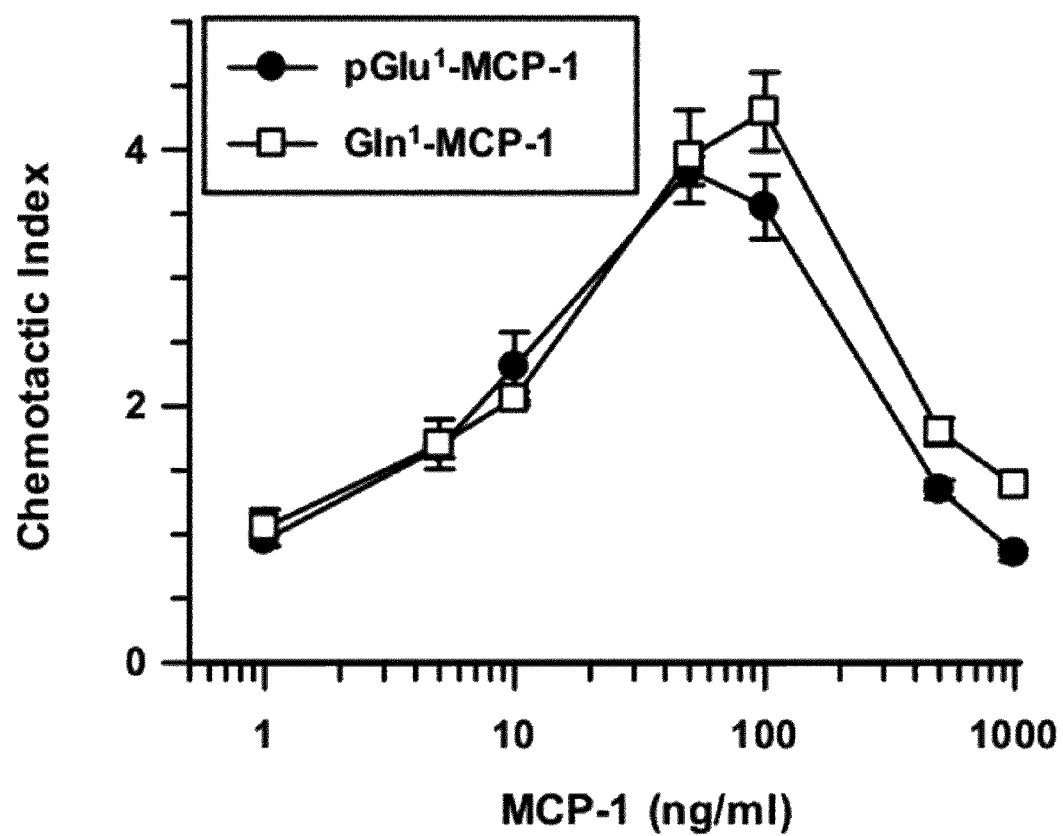
FIG. 24 shows the chemotactic potency of human MCP-1 (A), MCP-2 (B), MCP-3 (C) and MCP-4 (D) in absence or presence of the N-terminal pyroglutamyl residue.
Figure 24C:
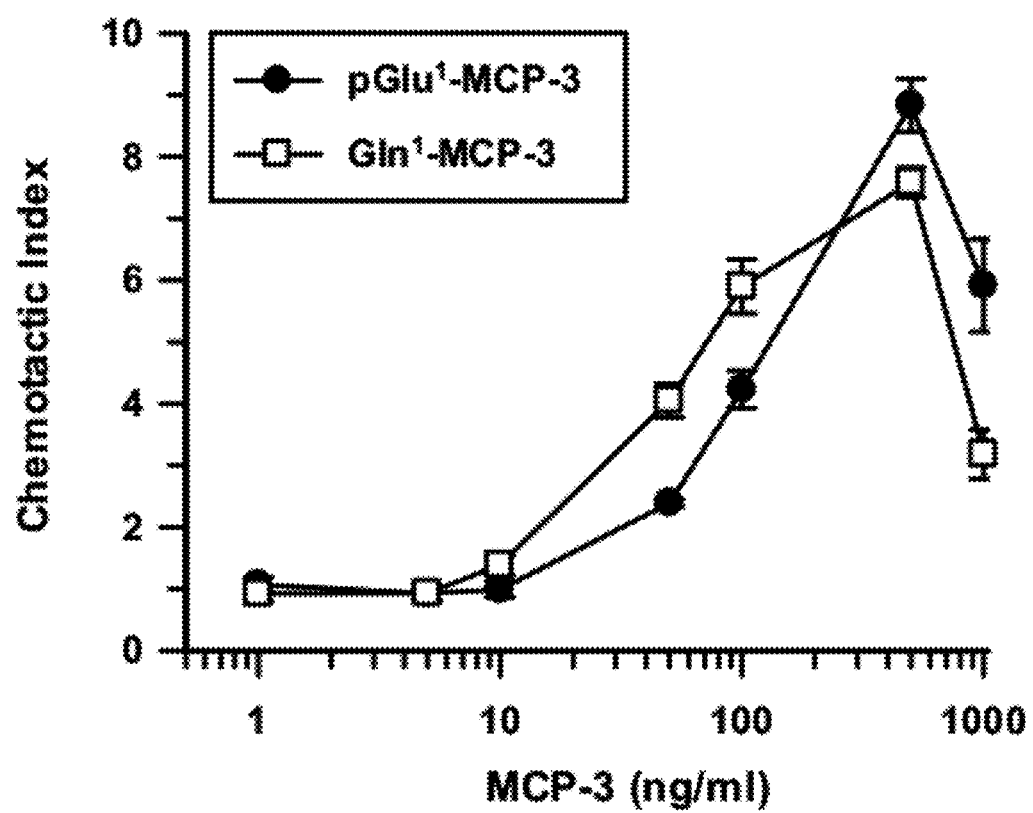
Figure 24D:
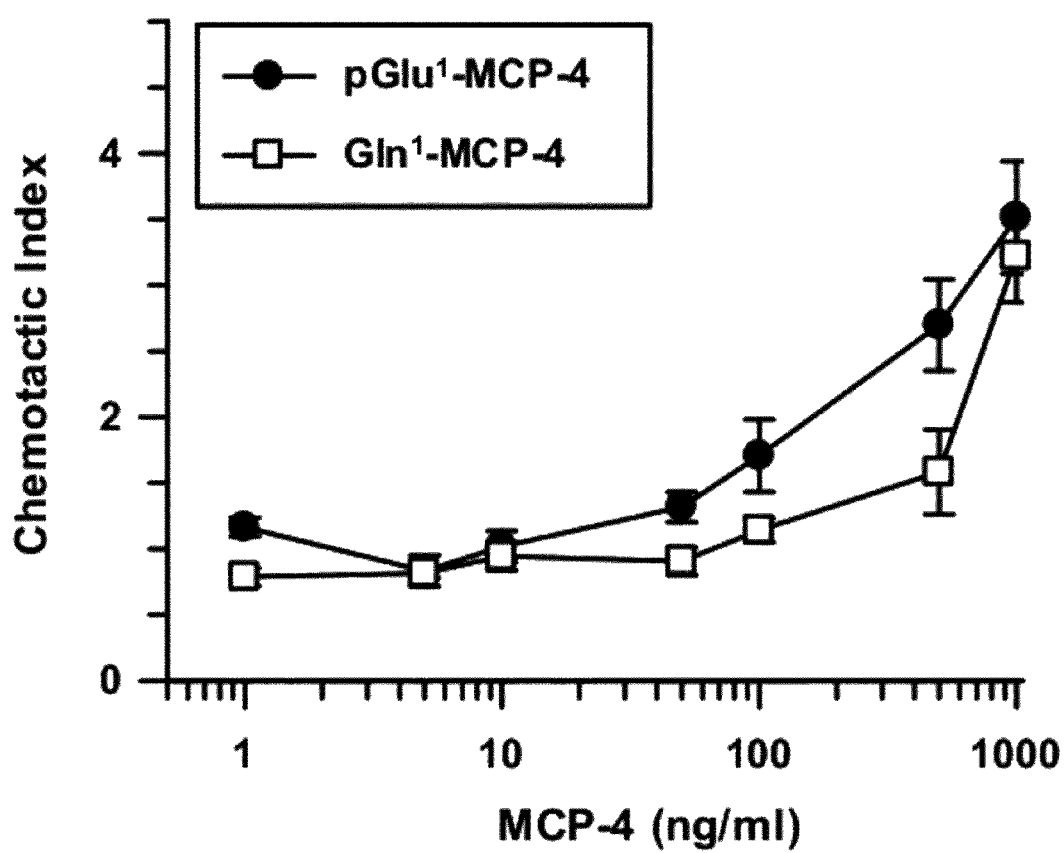
Figure 25A:
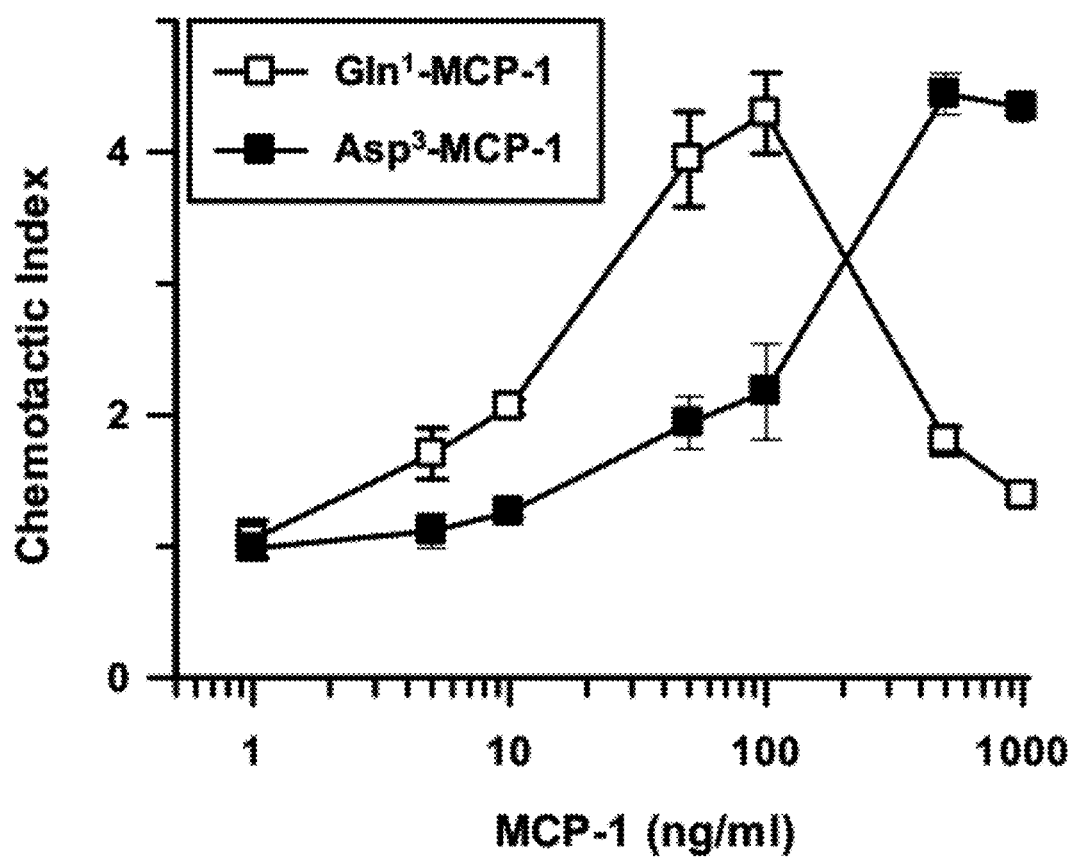
FIG. 25 shows the chemotactic potency of full-length human MCP-1 (A), MCP-3 (B), MCP-2 (C) and MCP-4 (D) starting with an N-terminal glutamine in comparison to their respective DP4 cleavage products.
Figure 25D:
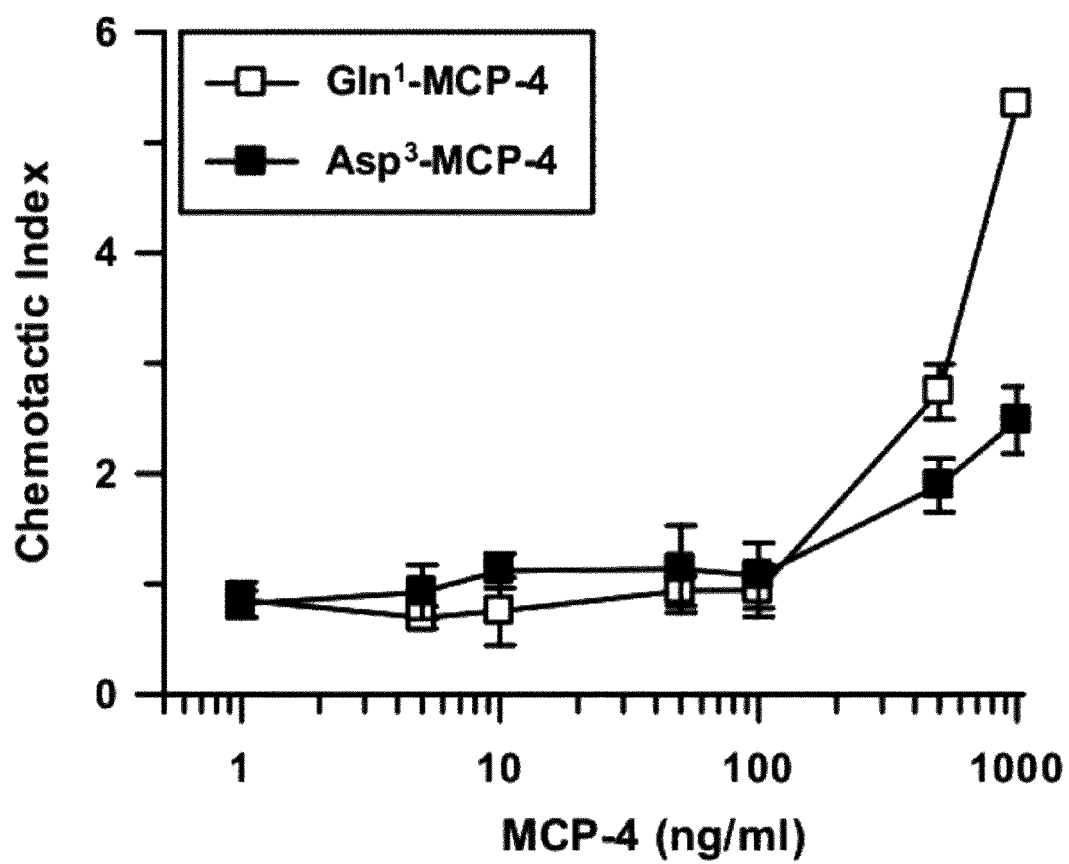

In addition, the ability of MCP-2, MCP-3 and MCP-4 possessing an N-terminal glutamine or pyroglutamate to attract human THP-1 monocytes was investigated. In analogy to MCP-1, the pGlu-formation at the N-terminus of MCP-2 and MCP-3 has no influence on the potency, compared to the respective glutamine-precursors. However, for MCP-4 the pGlu-formation slightly increases the potency of the peptide (FIG. 24). However, since the glutaminyl-precursors are cleaved by DP4 (FIGS. 19, 20 21), also the potencies of the N-truncated DP4 cleavage products of MCP-2, MCP-3 and MCP-4 were investigated using the chemotaxis assay. For all three variants, the truncation by 2 amino acids leads to a partial inactivation of the chemokines (FIG. 25). Therefore, the pGlu-formation at the N-Terminus of all known MCPs not only protects against N-terminal truncation, but also protects against the loss of chemotactic potency. The presented approach to alleviate the activity of MCP-1 by suppression of N-terminal maturation therefore applies for all members of the MCP family in human beings.

Application of a QC-Inhibitor to a Model of LPS-Induced Sepsis in Rats

Figure 26:
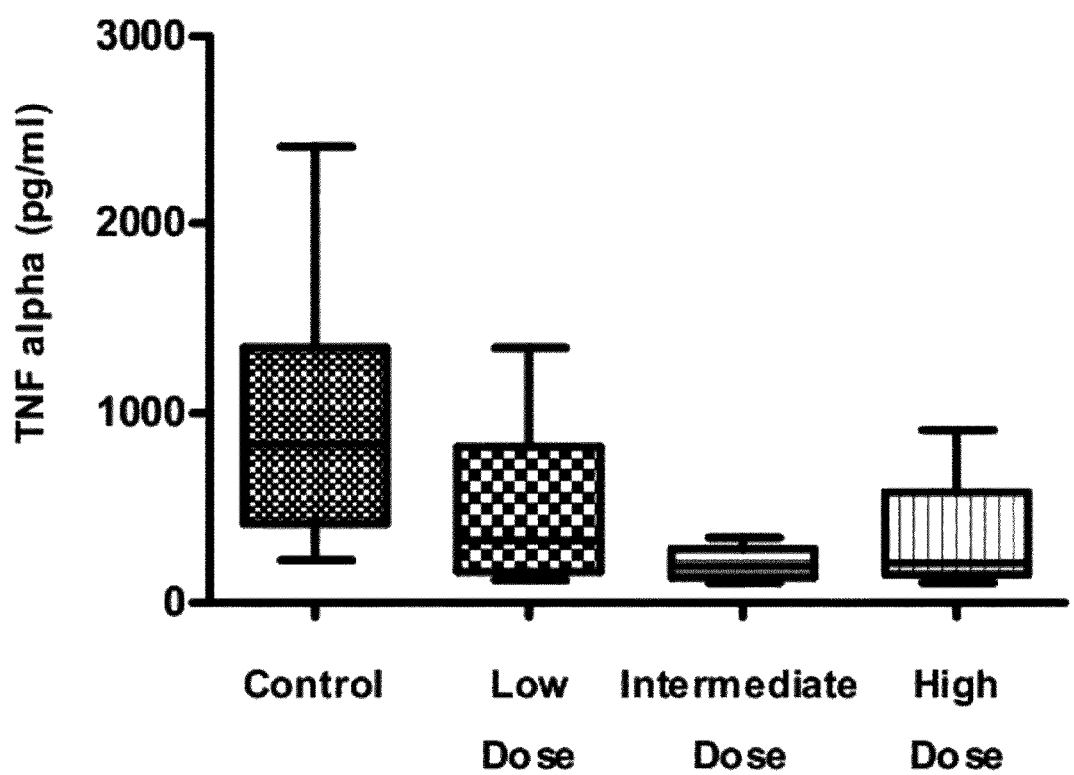
FIG. 26 shows the significant reduction of TNFα-levels after application of QC-inhibitor 1-(3-(1H-imidazol-1-yl)propyl)-3-(3,4-dimethoxyphenyl)thiourea hydrochloride in a model of LPS-induced sepsis in rats (ANOVA, P<0.05).

In order to investigate the general anti-inflammatory properties of 1-(3-(1H-imidazol-1-yl)propyl)-3-(3,4-dimethoxyphenyl)thiourea hydrochloride, the inhibitor was applied to a model of LPS-induced sepsis in rats. As a marker for the initiated inflammatory response, the levels of the cytokine TNFα were determined depending on QC-inhibitor treatment. As depicted in FIG. 26, the application of 1-(3-(1H-imidazol-1-yl)propyl)-3-(3,4-dimethoxyphenyl)thiourea hydrochloride leads to a dose-dependent reduction in TNFα levels ranging from the low dose (5 mg/kg) to the intermediate dose (20 mg/kg). In addition, also the highest dose (80 mg/kg) reduces the TNFα-level in plasma, however, a slight increase was observed compared to the intermediate dose. Therefore, QC-inhibitor application is able to significantly reduce the inflammatory responses shown here exemplarily for TNFα. The experiment shows, that, although the effect of QC-inhibitors is highly specific for the de-stabilization of the N-Terminus of MCPs, the inactivation of this chemokines has an impact also on other inflammatory parameters such as TNFα. Therefore, suppression of other pro-inflammatory cytokines is a further result of the presented concept of destabilizing MCPs. The approach is therefore suitable to develop medications for different inflammatory disorders with varying degree of MCP action.

Figure 27:
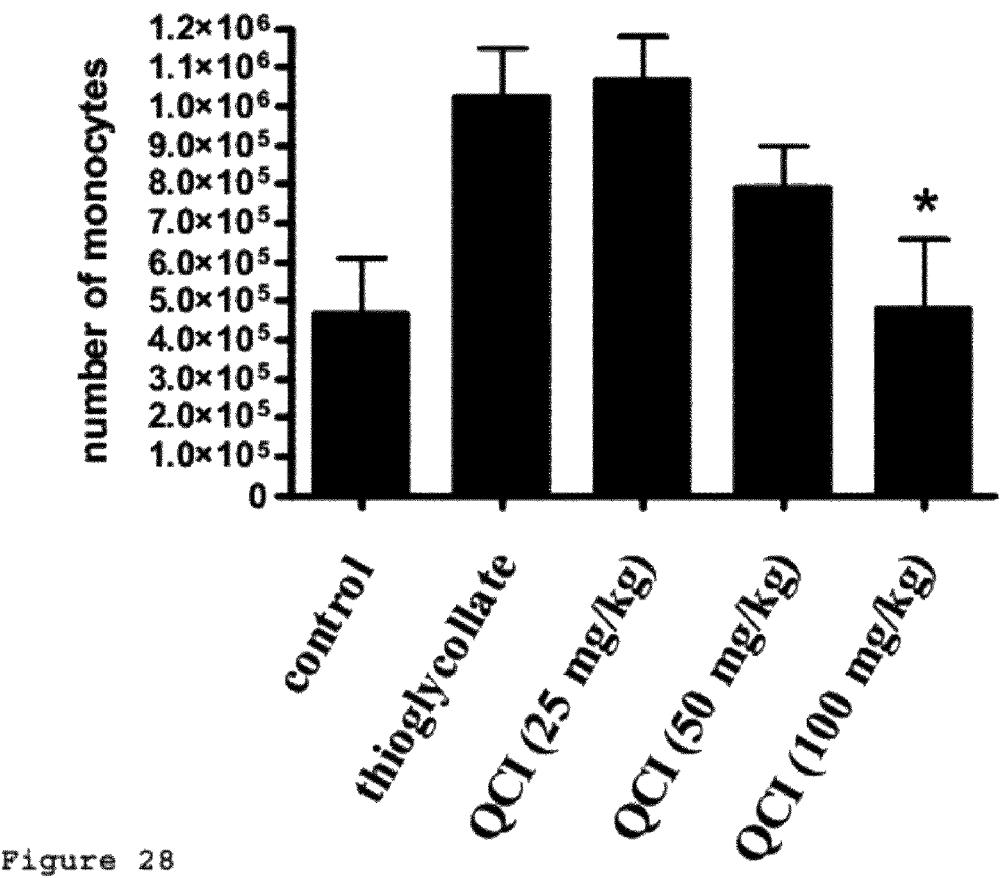
FIG. 27 shows the dose-dependent reduction of infiltrating monocytes to the peritoneum in a model of thioglycollate-induced peritonitis in mice, caused by a QC-inhibitor. Thioglycollate and QCI (1-(3-(1H-imidazol-1-yl)propyl)-3-(3,4-dimethoxyphenyl)thiourea hydrochloride) in three different concentrations of 25 mg/kg, 50 mg/kg and 100 mg/kg were injected. Cells infiltrating the peritoneum, were classified using FACS analysis 4 h after inducing the peritonits. (*, P<0.05, Student's t-test).
Figure 28:
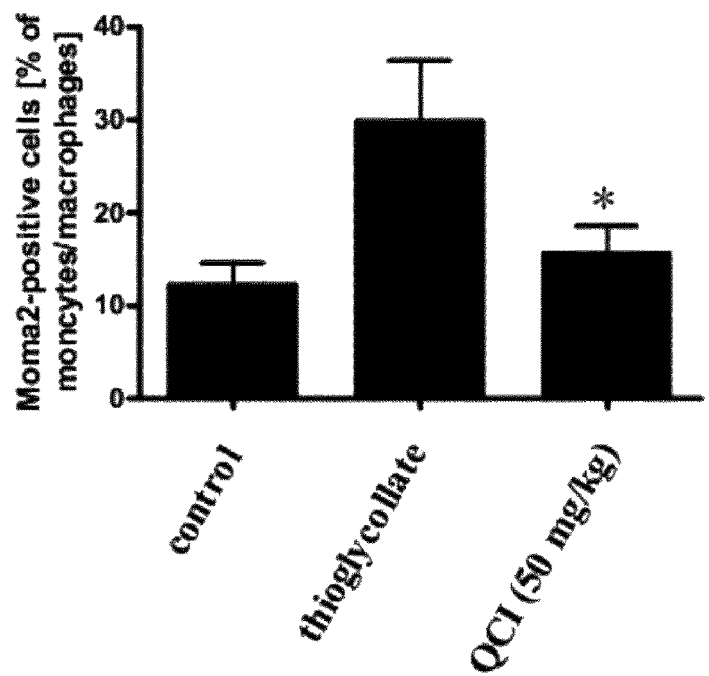
FIG. 28 shows the reduction of Moma2-positive cells in the peritoneal lavage fluid of mice, which received a thioglycollate challenge in combination with the QC-specific inhibitor QCI (1-(3-(1H-imidazol-1-yl)propyl)-3-(3,4-dimethoxyphenyl)thiourea), compared to animals receiving no QCI (*, P<0.05, Student's t-test).

Application of a QC-Inhibitor to a Model of thioglycollate-Induced peritonitis in Mice To further investigate the effect of QC-inhibitor administration on the migration of immune cells in vivo, 1-(3-(1H-imidazol-1-yl)propyl)-3-(3,4-dimethoxyphenyl)thiourea hydrochloride was applied to a model of thioglycollate-induced peritonitis in mice. The cellular composition of the peritoneal lavage fluid was determined with special emphasis on infiltrating monocytes 4 h and 24 hours after thioglycollate-challenge. As shown in FIG. 27, the QC-inhibitor 1-(3-(1H-imidazol-1-yl)propyl)-3-(3,4-dimethoxy phenyl)thiourea hydrochloride reduced the number of infiltrating monocytes to the peritoneum dose-dependently after 4 h. In addition, the presence of Moma2-positive monocytes/macrophages was assessed 24 h after thioglycollate application. As depicted in FIG. 28, the QC-inhibitor 1-(3-(1H-imidazol-1-yl)propyl)-3-(3,4-dimethoxy-phenyl)thiourea hydrochloride also significantly reduced the number of Moma2-positive cells. Therefore, the inhibition of QC destabilizes the N-Terminus of MCPs in vivo.

The experiment proves the applicability of MCP destabilization by QC inhibition to observe a therapeutic effect. The recruitment of monocytes, which is a general feature of several inflammatory disorders, for instance, but not limited to atherosclerosis and restenosis, is suppressed. The experiment therefore provides a method for characterizing QC inhibitors for their applicability in different inflammatory disorders.

TABLE 1

Utilized primers

| Primer | Sequence (5'→3') | Application | SEQ ID NO |
|---|---|---|---|
| hMCP-1-1 | ATAT AAGCTT ATGAAAGTCTCTGCCGCCCTTC | Isolation of human MCP-1 | 5 |
| hMCP-1-2 | ATAT GCGGCCGC TCAAGTCTTCGGAGTTTGGG | Isolation of human MCP-1 | 6 |

TABLE 1-continued

Utilized primers

| Primer | Sequence (5'→3') | Application | SEQ ID NO |
|---|---|---|---|
| ΔQ1-1 | CATTCCCCAAGGGCTCGCTCCAGATGCAATCAATGCC | Site-directed mutagenesis ΔQ1 | 7 |
| ΔQ1-2 | GGCATTGATTGCATCTGGAGCGAGCCCTTGGGGAATG | Site-directed mutagenesis ΔQ1 | 8 |
| ΔQ1P2-1 | CATTCCCCAAGGGCTCGCTGATGCAATCAATGCCCCAG | Site-directed mutagenesis ΔQ1P2 | 9 |
| ΔQ1P2-2 | CTGGGGCATTGATTGCATCAGCGAGCCCTTGGGGAATG | Site-directed mutagenesis ΔQ1P2 | 10 |

TABLE 2

Dosing of a QC-inhibitor in LPS-induced sepsis in rats

| Group | Intravenous Treatment 1 | Dose level (mg/kg) | Formulation concentration (mg/mL) | Intra-Peritoneal Treatment 2 | Dose level (μg/kg) | Formulation concentration (μg/mL) | Number of animals |
|---|---|---|---|---|---|---|---|
| 1 | Vehicle | — | — | Saline | — | — | 10 |
| 2 | Vehicle | — | — | LPS | 100 | 20 | 10 |
| 3 | QCI | 5 | 2.5 | LPS | 100 | 20 | 10 |
| 4 | QCI | 20 | 10 | LPS | 100 | 20 | 10 |
| 5 | QCI | 80 | 40 | LPS | 100 | 20 | 10 |

Synthesis of the QC Inhibitors

Synthesis scheme 1: Synthesis of the examples 1-53, 96-102, 136-137

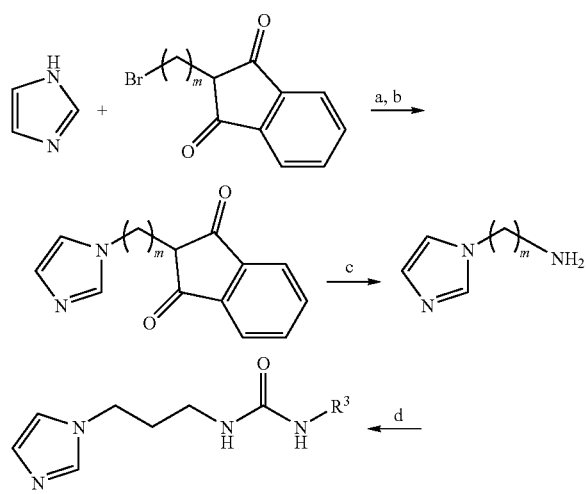

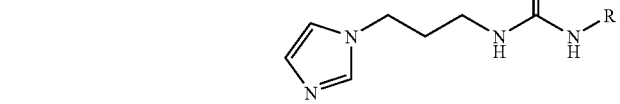

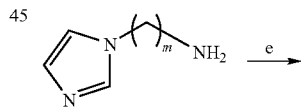

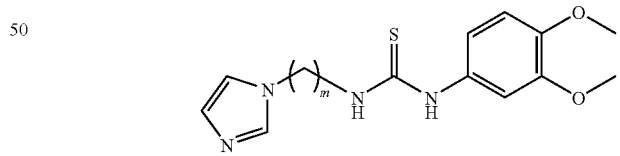

Reagents and conditions: (a) NaH, DMF, 4 h, rt.; (b), 8 h, 100° C.; (c) $H_2N$—$NH_2$, EtOH, 8 h, reflux then 4N HCl, 6 h, reflux, (d) $R^3$—NCO, EtOH, 6 h, reflux (e) 3, 4 dimethoxy-phenyl-isothiocyanate, Synthesis scheme 2: Synthesis of the examples 54-95

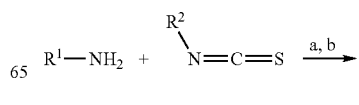

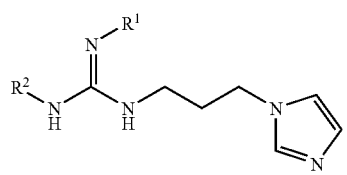

Reagents and conditions: (a) R—NCS, EtOH, 6 h, reflux;
(b) WSCD, 1H-imidazole-1-propanamine, DMF, 2 h, r.t.

Synthesis scheme 3: Synthesis of the examples 103-105

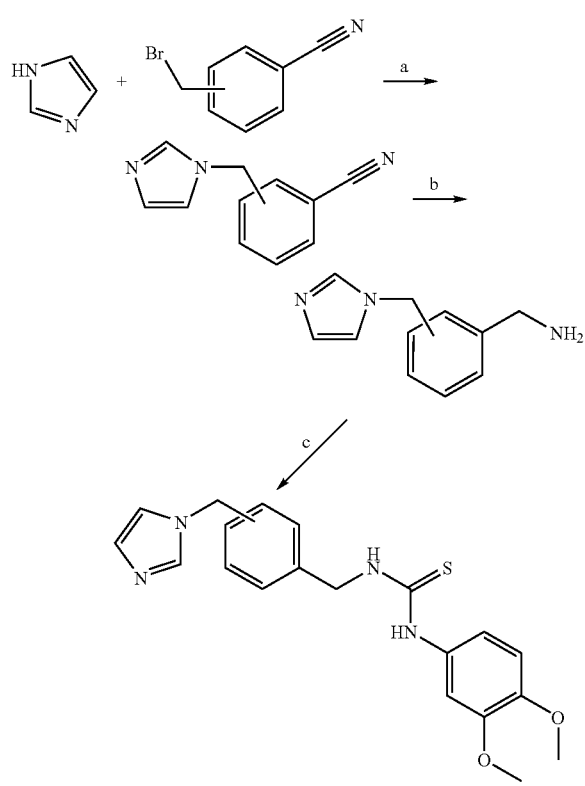

Reagents and conditions: (a) NaH, DMF, rt., 3 h; (b) LiAlH₄, dioxane, reflux, 1 h; (c) R—NCS, EtOH, reflux 6 h, Synthesis scheme 4: Synthesis of the examples 106-109

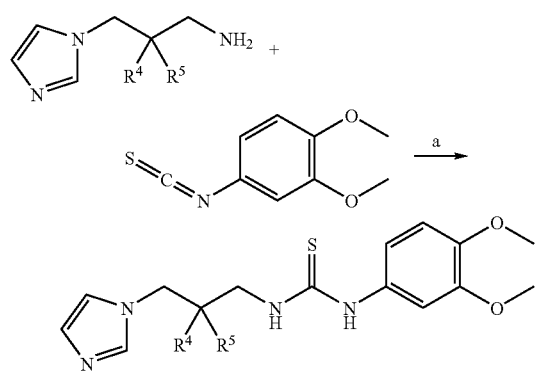

Reagents and conditions: (a) EtOH, 2 h, reflux

Synthesis scheme 5: Synthesis of the examples 110-112

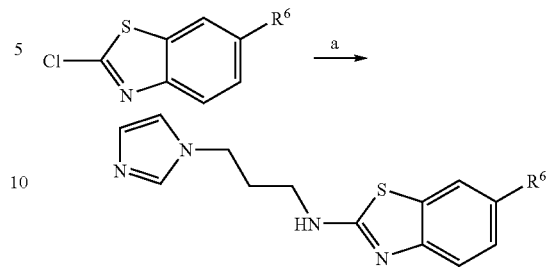

Reagents and conditions: (a) 1H-imidazole-1-propanamine, Triethylamine, Toluene, 12 h, reflux Synthesis scheme 6: Synthesis of the examples 113-132

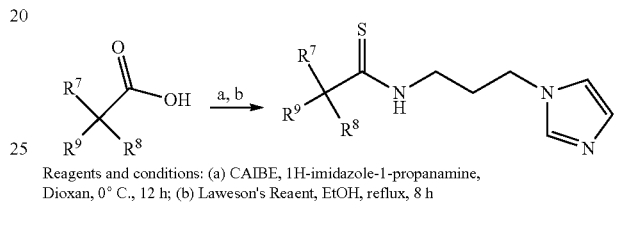

Reagents and conditions: (a) CAIBE, 1H-imidazole-1-propanamine, Dioxan, 0° C., 12 h; (b) Laweson's Reaent, EtOH, reflux, 8 h Synthesis scheme 7: Synthesis of the examples 133-135

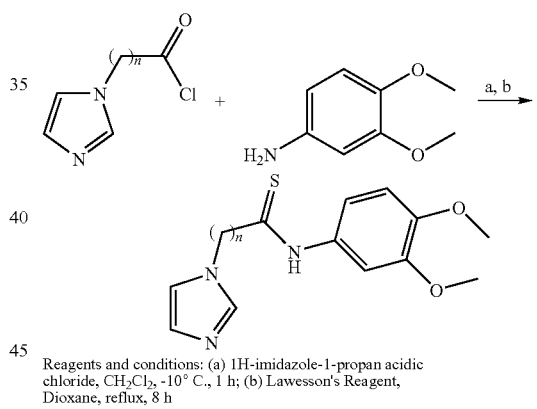

Reagents and conditions: (a) 1H-imidazole-1-propan acidic chloride, CH₂Cl₂, -10° C., 1 h; (b) Lawesson's Reagent, Dioxane, reflux, 8 h Synthesis scheme 8: Synthesis of the example 138

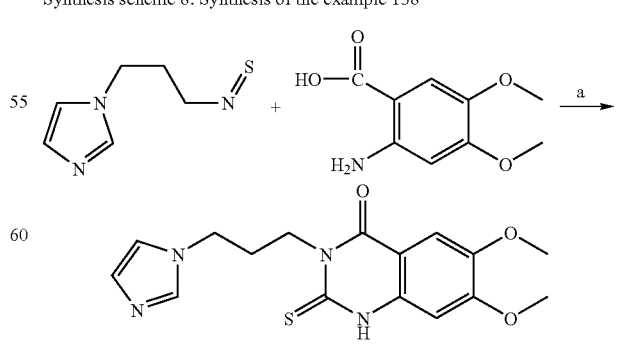

Reagents and conditions: (a) EtOH, reflux, 8 h

71

Synthesis scheme 9: Synthesis of the example 139

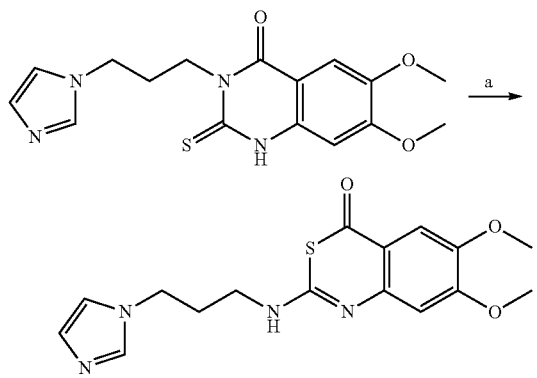

Reagents and conditions: (a) 75% conc. H₂SO₄, 4 h

Synthesis scheme 10: Synthesis of the example 140

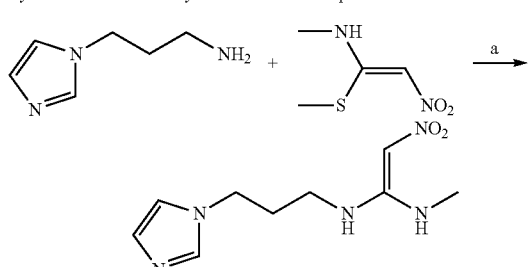

Reagents and conditions: (a) Acetonitrile, reflux 2 h

Synthesis scheme 11: Synthesis of the example 141

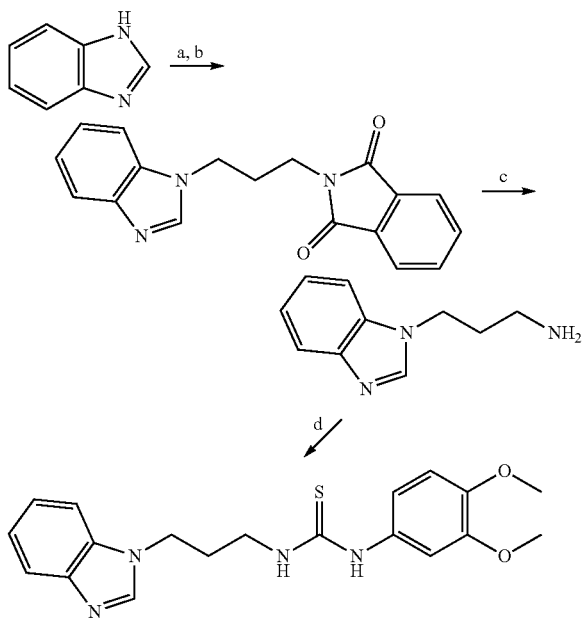

Reagents and conditions: (a) NaH, DMF, 4 h, rt.; (b), 8 h, 100° C.;
(c) H₂N—NH₂, EtOH, 8 h, reflux then 4N HCl, 6 h, reflux (d) 3, 4
dimethoxy-phenyl-isothiocyanate, EtOH, 6 h, reflux

72

Analytical Conditions

ESI-Mass spectra were obtained with a SCIEX API 365 spectrometer (Perkin Elmer). The $^1$H-NMR (500 MHz) data was recorded on a BRUKER AC 500, using DMSO-D$_6$ as solvent. Chemical shifts are expressed as parts per million downfield from tetramethylsilane. Splitting patterns have been designated as follows: s (singulet), d (doublet), dd (doublet of doublet), t (triplet), m (multiplet), and br (broad signal).

Detailed Synthesis Description

Examples 1-12 and 14-53

1H-imidazole-1-propanamine was reacted with the corresponding isothiocyanate in ethanol under reflux for 8 h. After that the solvent was removed and the remaining oil was dissolved in methylene chloride. The organic layer was washed twice with a saturated solution of NaHCO$_3$ followed by NaHSO$_4$ and brine, dried then evaporated. The remaining solid was re-crystallized from ethyl acetate, yielding the example thiourea in yields of 80-98%.

Example 13

1-(3-(1H-imidazol-1-yl)propyl)-3-(3,4-dimethoxyphenyl)thiourea 4.0 mmol of 3,4-dimethoxyphenyl isothiocyanate and 4.0 mmol of 3-(1H-imidazol-1-yl)alkyl-1-amine were dissolved in 10 mL of absolute ethanol. After stirring for 2 h under reflux, the solvent was evaporated and the resulting solid was recrystallized from ethanol.

Yield: 0.66 g (51.3%); mp: 160.0-161.0° C.

$^1$H NMR δ 1.8-2.0 (m, 2H), 3.4-3.5 (m, 2H), 3.75 (s, 6H), 3.9-4.0 (m, 2H), 6.7-6.8 (m, 1H), 6.9 (br m, 2H), 6.95 (s, 1H), 7.15 (s, 1H), 7.55 (br s, 1H), 7.6 (s, 1H), 9.3 (s, 1H); MS m/z 321.2 (M+H), 253.3 (M-C$_3$H$_3$N$_2$.)

Examples 96-102

1H-imidazole-1-propanamine was reacted with the corresponding isocyanate in ethanol under reflux for 8 h. After that the solvent was removed and the remaining oil was dissolved in methylene chloride. The organic layer was washed twice with a saturated solution of NaHCO$_3$ followed by NaHSO$_4$ and brine, dried then evaporated. The remaining solid was re-crystallized from ethyl acetate, yielding the example urea in yields of 85-90%.

Examples 136, 137

The 1H-imidazole-1-alkylamines were prepared according to the literature from □-brom-alkyl-phtalimides and imidazolium salt and. subsequent hydrazinolysis. The resulting products were transformed into the thioureas according to example 1-53 giving a 88% (example 136) and 95% (example 137) yield.

Examples 54-95

All examples were made from the corresponding thioureas by reacting with Water-soluble-carbodiimide (WSCD) and 1H-imidazole-1-propanamine in dry dimethyl formamide for 2 h at r.t. giving the trisubstituted guanidines with yields from 40-87%.

Examples 103-105

Imidazole was reacted with the corresponding brommethylphenylcyanide in DMF, utilizing 1 equivalent of NaH for 3 h under rt., giving the 1H-imidazole-1-methylphenylcyanides. The solvent was removed and the resulting oil was re-dissolved in dioxane. The cyanides were converted in the corresponding amines using 1 equivalent of LiAlH$_4$. After adding a saturated solution of KHSO$_4$, dioxane was evaporated and the aqueous layer was extracted by means of CHCl$_3$. The organic layer was concentrated in vacuo and the amine was converted in the corresponding thioureas according to example 1-53 giving a 78% (example 103) and 65% (example 104) and 81% (example 105) yield.

Examples 106-109

Starting from the corresponding methansulfonate-2-methylpropyl-phthalimides the amines were synthesized as described for the amines in example 136-137. The resulting products were transformed into the thioureas according to example 1-53 giving example 106-109 in total yields of 25-30%.

Examples 110-112

1H-imidazole-1-propanamine was reacted with the corresponding 2-chlorobenzo[d]thiazole in toluol for 24 h at a temperature of 130° C. After removing the solvent and recrystallization from methanol example 110-112 was yielded in an amount of 55-65%.

Examples 113-118, 120-124 and 126-132

1H-imidazole-1-propanamine was reacted with the corresponding 2-phenyl acetic acid in dry dioxane by adding one equivalent of CAIBE and N-methylmorpholine at a temperature of 0° C. After 2 h the mixture was allowed to warm to r.t. and the mixture was stirred for 12 h. After removing the solvent the resulting oil was redissolved in methylene chloride and the organic layer was washed by means of an aqueous solution of NaHCO$_3$ and water, dried and the solvent was evaporated. The remaining oil was dissolved in dioxane adding Laweson's Reagent. After stirring for 12 h a saturated solution of NaHCO$_3$ was added. Dioxane was evaporated and the aqueous layer was extracted by means of ethyl acetate. The organic layer was separated, dried and the solvent was evaporated. The remaining solid was crystallized from acetyl acetate/ether, giving 113-118, 120-124 and 126-132 with total yields of 62-85%.

Example 119

1 N-(3-(1H-imidazol-1-yl)propyl)-2-(3,4-dimethoxyphenyl)ethanethioamide

A mixture of 4.0 mmol triethylamine and 4.0 mmol of 3-(1H-imidazol-1-yl)alkyl-1-amine 20 mL of dioxane was added drop wise to an ice cooled, stirred solution of 4.0 mmol of 2-(3,4-dimethoxyphenyl)acetyl chloride in 30 mL of dioxane. The mixture was allowed to warm to r.t., and then stirred for 1 h. After removing the solvent by reduced pressure, the residue was redissolved in 50 mL of dichloromethane. The organic layer was washed by means of 30 mL of saturated aqueous solution of NaHCO$_3$, and water. The organic solution was dried, filtered, and the solvent was removed under reduced pressure. After redissolving in 50 mL of dry dioxane 2.2 mmol of Lawesson's reagent was added, and the mixture was heated to 90° C. and stirred for 8 h. The solvent was removed by reduced pressure, and the residue was redissolved in 50 mL of dichloromethane. The organic layer was washed three times by means of a saturated aqueous solution of NaHCO$_3$, followed three times by water, dried, filtered, and then the organic solvent was removed. The compound was purified by chromatography using a centrifugal-force-chromatography device, (Harrison Research Ltd.) utilizing silica plates of a layer thickness of 2 mm, and a CHCl$_3$/MeOH gradient as eluting system.

Yield: 0.14 g (10.6%); melting point: 148.0-150.0° C.

$^1$H NMR δ 2.0-2.15 (br m, 2H), 3.4-3.5 (m, 2H), 3.7 (s, 6H) 6.75-6.8 (m, 2H), 4.1-4.2 (m, 2H), 6.8-6.9 (m, 2H), 6.95-7.0 (m, 1H), 7.4 (s, 1H), 7.75-7.85 (br m, 1H), 8.6 (s, 1H) 10.2 (s, 1H); MS m/z 320.2 (M+H), 252.2 (M-C$_3$H$_3$N$_2$.)

Example 125

N-(3-(1H-imidazol-1-yl)propyl)-1-(3,4-dimethoxyphenyl)cyclopropanecarbothioamide 11.06 mmol of 3,4-dimethoxyphenyl acetonitrile, 34.8 mmol of 2-Bromo-1-chloroethanole an 1.16 mmol of triethylbenzylammonium Hydrochloride were dissolved in 10 mL of an aqueous solution of KOH (60%). The mixture was transferred into an ultrasonic bath and vigorously stirred for 3 h at room temperature. The resulting suspension was diluted with 40 mL of water and extracted three times by means of 20 mL of dichloromethane. The combined organic layers where washed by means of an aqueous solution of hydrochloric acid (1N), dried over Na$_2$SO$_4$ and the solvent was removed under reduced pressure. The remaining oil was purified by flash-chromatography using silica gel and ethyl acetate/heptane as eluting system, resulting in 0.81 g (34.4%) of 1-(3,4-dimethoxyphenyl)cyclopropanecarbonitrile 3.9 mmol of 1-(3,4-dimethoxyphenyl)cyclopropanecarbonitrile and 11.2 mmol of KOH were suspended in 80 mL of ethylene glycol. The mixture was stirred for 12 h under reflux. Then 80 mL of water were added and the aqueous layer was extracted two times with ether. After pH adjustment to a value of pH=4-5 using HCl (1N) the aqueous layer was extracted three times by means of ether, then the combined organic layers were dried over Na$_2$SO$_4$ and the solvent was removed, resulting in 0.81 g (93.5%) of 1-(3,4-dimethoxyphenyl)cyclopropanecarboxylic acid.

3.44 mmol of 1-(3,4-dimethoxyphenyl)cyclopropanecarboxylic acid, 3.5 mmol of N-Methyl morpholine, and 3.5 mmol of isobutyl chloroformiat were dissolved in dry tetrahydrofurane and stirred for 15 min at −15° C. Then 3.5 mmol of 3-(1H-imidazol-1-yl)alkyl-1-amine was added and the mixture was allowed to warm to 0° C. and was stirred for 12 h. The solvent was removed under reduced pressure and the remaining oil was redissolved in chloroform. Then the organic layer was washed two times by means of a saturated aqueous solution of NaHCO$_3$, then dried over Na$_2$SO$_4$ and the solvent was removed. Purification was performed by means of centrifugal forced chromatography using a Chromatotron® device (Harrison Research Ltd.) utilizing silica plates of a layer thickness of 2 mm, and a CHCl$_3$/MeOH gradient as eluting system resulting in 0.671 g (59.3%) of N-(3-(1H-imidazol-1-yl)propyl)-1-(3,4-dimethoxyphenyl)cyclopropane-carboxamide.

After redissolving in 30 mL of dry dioxane 1.43 mmol of Lawesson's reagent were added, and the mixture was heated to 90° C. and stirred for 8 h. The solvent was removed by reduced pressure, and the residue was remains were dissolved in 50 mL of dichloromethane. The organic layer was washed three times by means of a saturated aqueous solution of NaHCO$_3$, followed three times by water, dried, filtered, and then the organic solvent was removed. The compound was purified by chromatography using a centrifugal-force-chromatography device, (Harrison Research Ltd.) utilizing silica plates of a layer thickness of 2 mm, and a CHCl$_3$/MeOH gradient as eluting system.

Yield: 0.33 g (46.2%); melting point: 127.0-127.5° C.
$^1$H NMR δ 1.1-1.2 (t, 2H), 1.55-1.6 (t, 2H), 2.0-2.1 (m, 2H), 3.5-3.6 (m, 2H), 3.7-3.8 (s, 6H), 4.1-4.2 (t, 2H) 6.8-6.9 (m, 3H), 7.65 (s, 1H), 7.75 (s, 1H), 8.8 (m, 1H), 9.05 (s, 1H; MS m/z 346.0 (M+H), 278.2 (M-C$_3$H$_3$N$_2$.), 177.1 (M-C$_6$H$_8$N$_3$S.)

Examples 133-135

A mixture of 1 equivalent triethylamine and 3,4-dimethoxyaniline in dioxane was added to an stirred solution of the corresponding ω-bromoalkyl acidic chloride at a temperature of 0° C. The solution was allowed to warm to r.t. and stirred for 2 h. The solvent was evaporated, and the remaining oil was redissolved in dichloromethane. The organic layer was washed by means of water, dried, filtered, and the solvent was removed under reduced pressure.

Imidazole and sodium hydride were suspended in and the mixture was stirred under inert conditions at r.t. for 3 h. ω-Bromo-N-(3,4-dimethoxy-phenyl)alkylamide was added and the mixture was heated to 100° C. and stirred for 8 h. After that, the solvent was evaporated, hot toluene were added and the solution was filtered. Then the solvent was removed under reduced pressure. The transformation into the thioamides was performed as described for example 113-132 by means of Laweson's reagent, giving 133-135 in total yields of 13-20%.

The analytical data for further examples, which were synthesized according to the general synthesis schemes described above, are as follows:

Example 1

1-(3-(1H-imidazol-1-yl)propyl)-3-methylthiourea melting point: 122-122.5° C.
$^1$H NMR δ 1.85-1.95 (m, 2H), 2.8 (s, 3H), 3.2-3.5 (br d, 2H), 3.8-3.9 (m, 2H), 6.85 (d, 1H), 7.15 (d, 1H), 7.3-7.5 (br d, 2H), 7.65 (s, 1H); MS m/z 199.1 (M+H), 221.3 (M+Na), 131.0 (M-C$_3$H$_3$N$_2$.)

Example 2

1-(3-(1H-imidazol-1-yl)propyl)-3-tert-butylthiourea melting point: 147.0-147.5° C.
$^1$H NMR δ 1.3-1.4 (s, 9H), 1.85-1.95 (m, 2H), 3.5 (t, 2H), 3.8 (t, 2H), 6.85 (d, 1H), 7.15 (d, 1H), 7.3-7.5 (br d, 2H), 7.65 (s, 1H); MS m/z 241.1 (M+H), 173.1 (M-C$_3$H$_3$N$_2$.)

Example 3

1-(3-(1H-imidazol-1-yl)propyl)-3-benzylthiourea melting point: 127.0-128.0° C.
$^1$H NMR δ 1.85-1.95 (m, 2H), 3.2-3.5 (br d, 2H), 3.8-3.9 (m, 2H), 4.6 (s, 2H), 6.8 (d, 1H), 7.15 (d, 1H), 7.19-7.35 (m, 5H), 7.5-7.6 (br d, 2H), 7.85 (s, 1H); MS m/z 275.3 (M+H), 207.1 (M-C$_3$H$_3$N$_2$.)

Example 5

1-(3-(1H-imidazol-1-yl)propyl)-3-phenylthiourea melting point: 166.5-167.0° C.
$^1$H NMR δ 1.95-2.05 (m, 2H), 3.3-3.5 (br d, 2H), 3.9-4.0 (m, 2H), 6.85 (d, 1H), 7.05 (m, 1H) 7.15 (d, 1H), 7.25 (m, 2H), 7.35 (m, 2H), 7.6 (s, 1H), 7.8 (br s, 1H), 9.5 (br s, 1H); MS m/z 261.1 (M+H), 193.2 (M-C$_3$H$_3$N$_2$.)

Example 6

1-(3-(1H-imidazol-1-yl)propyl)-3-(4-fluorophenyl)thiourea melting point: 147.0-148.0° C.
$^1$H NMR δ 1.95-2.05 (m, 2H), 3.3-3.5 (br d, 2H), 3.9-4.05 (m, 2H), 6.85 (d, 1H), 7.05-7.15 (m, 3H), 7.3-7.4 (m, 2H), 7.6 (s, 1H), 7.7-7.8 (br s, 1H), 9.4 (br s, 1H); MS m/z 279.3 (M+H), 211.2 (M-C$_3$H$_3$N$_2$.)

Example 7

1-(3-(1H-imidazol-1-yl)propyl)-3-(4-ethylphenyl)thiourea melting point: 100.0-100.5° C.
$^1$H NMR δ 1.15-1.2 (t, 3H), 1.9-2.0 (m, 2H), 2.5-2.6 (m, 2H), 3.3-3.5 (br d, 2H), 3.9-4.05 (m, 2H), 6.85 (d, 1H), 7.1-7.2 (m, 3H), 7.25-7.3 (m, 2H), 7.6 (s, 1H), 7.7-7.8 (br s, 1H), 9.4 (br s, 1H); MS m/z 289.3 (M+H), 221.1 (M-C$_3$H$_3$N$_2$.)

Example 8

1-(3-(1H-imidazol-1-yl)propyl)-3-(4-(trifluoromethyl)phenyl)thiourea melting point: 154.5-155.0° C.
$^1$H NMR δ 1.9-2.1 (br m, 2H), 3.4-3.6 (br d, 2H), 3.95-4.1 (br m, 2H), 6.85 (d, 1H), 7.2 (d, 1H), 7.6-7.8 (m, 5H), 8.2 (br s, 1H), 9.9 (br s, 1H); MS m/z 329.3 (M+H), 261.2 (M-C$_3$H$_3$N$_2$.)

Example 10

1-(3-(1H-imidazol-1-yl)propyl)-3-(4-acetylphenyl)thiourea melting point: 170.0-171.0° C.
$^1$H NMR δ 1.9-2.1 (br m, 2H), 2.4-2.5 (s, 3H), 3.2-3.5 (br m, 2H), 3.9-4.1 (m, 2H), 6.85 (d, 1H), 7.15 (d, 1H), 7.5-7.65 (br m, 3H), 7.8-7.9 (m, 2H), 8.1 (m, 2H), 9.8 (br s, 1H)
MS m/z 303.2 (M+H), 235.1 (M-C$_3$H$_3$N$_2$.)

Example 11

1-(3-(1H-imidazol-1-yl)propyl)-3-(4-methoxyphenyl)thiourea melting point: 125.0-125.5° C.
$^1$H NMR δ 1.8-2.0 (br m, 2H), 3.2-3.5 (br m, 2H), 3.7 (s, 3H), 3.9-4.0 (m, 2H), 6.7-6.9 (m, 3H), 7.1-7.2 (m, 3H), 7.5 (s, 1H), 7.6 (s, 1H), 9.2 (s, 1H); MS m/z 291.1 (M+H), 223.2 (M-C$_3$H$_3$N$_2$.)

Example 14

1-(3-(1H-imidazol-1-yl)propyl)-3-(2,4-dimethoxyphenyl)thiourea melting point: 120.0-120.5° C.
$^1$H NMR δ 1.8-2.0 (br m, 2H), 3.4-3.5 (br m, 2H), 3.75 (s, 6H), 3.9-4.0 (m, 2H), 6.5 (d, 1H), 6.6 (s, 1H), 6.9 (s, 1H) 7.15 (s, 1H), 7.3 (d, 1H), 7.5 (br s, 1H), 7.6 (s, 1H), 9.75 (s, 1H); MS m/z 321.2 (M+H), 253.3 (M-C$_3$H$_3$N$_2$.)

Example 15

1-(3-(1H-imidazol-1-yl)propyl)-3-(3,5-dimethoxyphenyl)thiourea melting point: 142.0-143.0° C.
$^1$H NMR δ 1.8-2.0 (br m, 2H), 3.4-3.5 (br m, 2H), 3.6 (s, 6H), 3.95-4.0 (m, 2H), 6.25 (m, 1H), 6.6 (m, 2H), 6.9 (s, 1H), 7.2 (s, 1H), 7.6 (s, 1H), 7.8 (s, 1H), 9.5 (s, 1H); MS m/z 321.2 (M+H), 253.3 (M-C$_3$H$_3$N$_2$.)

Example 23

1-(3-(1H-imidazol-1-yl)propyl)-3-(2,3-dihydrobenzo[b][1,4]dioxin-7-yl)-thiourea melting point: 103.0-103.5° C.
$^1$H NMR δ 1.9-2.0 (br m, 2H), 3.3-3.5 (br d, 2H), 3.9-4.0 (m, 2H), 4.2-4.3 (m, 4H), 6.7 (m, 1H), 6.8-6.8 (m, 1H), 6.9 (m, 2H), 7.2 (s, 1H), 7.6 (m, 2H), 9.3 (s, 1H); MS m/z 319.3 (M+H), 251.3 (M-C$_3$H$_3$N$_2$.)

Example 24

1-(3-(1H-imidazol-1-yl)propyl)-3-(benzo[d][1,3]dioxol-6-yl)thiourea melting point: 115.0-115.6° C.
$^1$H NMR δ 1.9-2.1 (br m, 2H), 3.4-3.5 (br d, 2H), 4.05-4.15 (m, 2H), 6.0 (s, 2H), 6.7 (m, 1H), 6.8-6.85 (m, 1H), 6.95 (d, 1H), 7.25 (s, 1H), 7.45 (s, 1H), 7.7 (br s, 1H), 8.5 (br s, 1H), 9.4 (br s, 1H); MS m/z 305.2 (M+H), 237.2 (M-C$_3$H$_3$N$_2$.)

Example 25

1-(3-(1H-imidazol-1-yl)propyl)-3-(3,4,5-trimethoxyphenyl)thiourea melting point: 124.5-125.5° C.
$^1$H NMR δ 1.8-2.0 (m, 2H), 3.4-3.5 (br m, 2H), 3.6 (s, 3H) 3.7 (s, 6H), 3.9-4.0 (m, 2H), 6.65 (m, 2H), 6.85 (s, 1H), 7.2 (s, 1H), 7.6 (s, 1H), 7.7 (br s, 1H), 9.4 (s, 1H); MS m/z 351.3 (M+H), 283.2 (M-C$_3$H$_3$N$_2$.)

Example 26

1-(3-(1H-imidazol-1-yl)propyl)-3-(3-methoxyphenyl)thiourea melting point: 89.5-90.0° C.
$^1$H NMR δ 1.9-2.1 (br m, 2H), 3.4-3.5 (br m, 2H), 3.7 (s, 3H), 3.9-4.0 (m, 2H), 6.6-6.7 (m, 1H), 6.8-6.9 (m, 2H), 7.1 (m, 2H), 7.15-7.25 (br m, 1H), 7.6 (s, 1H), 7.8 (br s, 1H), 9.5 (s, 1H); MS m/z 291.1 (M+H), 223.2 (M-C$_3$H$_3$N$_2$.)

Example 27

1-(3-(1H-imidazol-1-yl)propyl)-3-(4-ethoxyphenyl)thiourea melting point: 126.0-126.5° C.
$^1$H NMR δ 1.5 (br m, 3H), 1.9-2.0 (br m, 2H), 3.4-3.5 (br m, 2H), 3.9-4.0 (br m, 4H), 6.8-6.9 (m, 2H), 6.95 (s, 1H), 7.15-7.2 (m, 2H), 7.25 (s, 1H), 7.55-7.6 (br s, 1H), 7.8 (s, 1H), 9.3 (s, 1H); MS m/z 305.2 (M+H), 237.2 (M-C$_3$H$_3$N$_2$.)

Example 33

1-(3-(1H-imidazol-1-yl)propyl)-3-(4-(methylthio)phenyl)thiourea melting point: 140.0-140.5° C.
$^1$H NMR δ 1.8-2.05 (br m, 2H), 2.5 (s, 3H), 3.3-3.5 (br m, 2H), 3.9-4.1 (m, 2H), 6.9 (m, 1H), 7.1-7.3 (br m, 5H), 7.6 (s, 1H), 7.75 (br s, 1H), 9.4 (s, 1H); MS m/z 307.2 (M+H), 239.2 (M-C$_3$H$_3$N$_2$.)

Example 42

1-(3-(1H-imidazol-1-yl)propyl)-3-(4-nitrophenyl)thiourea melting point: 165.0. 166.0° C.
$^1$H NMR δ 1.9-2.05 (m, 2H), 3.3-3.5 (br d, 2H), 3.95-4.05 (m, 2H), 6.85 (d, 1H), 7.15 (d, 1H), 7.6 (d, 1H), 7.7 (m, 2H) 8.1 (m, 2H), 8.3 (br s, 1H), 10.1 (br s, 1H); MS m/z 306.2 (M+H), 237.9 (M-C$_3$H$_3$N$_2$.)

Example 50

1-(3-(1H-imidazol-1-yl)propyl)-3-(4-(dimethylamino)phenyl)thiourea melting point: 146.5-147.0° C.
$^1$H NMR δ 1.9-2.0 (m, 2H), 2.9 (s, 6H), 3.4 (m, 2H), 3.9-4.0 (m, 2H), 6.7 (m, 2H), 6.9 (s, 1H), 7.05-7.1 (m, 2H), 7.15 (s, 1H), 7.4 (br s, 1H), 7.6 (s, 1H), 9.2 (s, 1H); MS m/z 304.2 (M+H), 236.0 (M-C$_3$H$_3$N$_2$.)

Example 102

1-(3-(1H-imidazol-1-yl)propyl)-3-(3,4-dimethoxyphenyl)urea melting point: 114.5-115.0° C.
$^1$H NMR δ 1.7-1.9 (m, 2H), 2.9-3.1 (m, 2H), 3.7 (2s, 6H), 3.9-4.0 (m, 2H), 6.1 (t, 1H), 6.7 (s, 2H), 6.8 (s, 1H), 7.15 (d, 2H), 7.6 (s, 1H), 8.2 (s, 1H); MS m/z 321.2 (M+H), 253.3 (M-C$_3$H$_3$N$_2$.)

Example 106

1-((S)-3-(1H-imidazol-1-yl)-2-methylpropyl)-3-(3,4-dimethoxyphenyl)-thiourea melting point: 150.5-151.5° C.
$^1$H NMR δ 0.9 (d, 3H), 2.3-2.4 (m, 2H), 2.5 (s, 1H), 3.7 (d, 6H), 4.0-4.1 (br m, 1H), 4.15-4.25 (br m, 1H), 6.75-6.8 (m, 1H), 6.85 (m, 1H), 6.9-7.0 (m, 1H), 7.65 (s, 1H), 7.75 (s, 2H), 9.1 (s, 1H), 9.5 (s, 1H); MS m/z 335.6 (M+H), 267.1 (M-C$_3$H$_3$N$_2$.)

Example 107

1-((R)-3-(1H-imidazol-1-yl)-2-methylpropyl)-3-(3,4-dimethoxyphenyl)-thiourea melting point: 155.0-157.5° C.
$^1$H NMR δ 0.9 (d, 3H), 2.3-2.4 (m, 2H), 2.5 (s, 1H), 3.7 (d, 6H), 4.0-4.1 (br m, 1H), 4.15-4.25 (br m, 1H), 6.75-6.8 (m, 1H), 6.85 (m, 1H), 6.9-7.0 (m, 1H), 7.65 (s, 1H), 7.75 (s, 2H), 9.1 (s, 1H), 9.5 (s, 1H); MS m/z 335.4 (M+H), 267.2 (M-$C_3H_3N_2$.)

Example 109

1-((1-((1H-imidazol-1-yl)methyl)cyclopropyl)methyl)-3-(3,4-dimethoxy-phenyl)thiourea melting point: 166.5-168.5° C.
$^1$H NMR δ 0.7-0.8 (br m, 2H), 1.85-1.9 (m, 1H), 2.15-2.2 (m, 1H), 2.2-2.3 (m, 1H), 3.4-3.5 (m, 1H), 3.7 (d, 6H), 4.2 (s, 1H), 4.95 (s, 1H), 6.75-6.8 (br m, 1H), 6.85-6.9 (br m, 1H), 7.0 (s, 1H), 7.5 (m, 1H), 7.6 (m, 1H), 7.7 (s, 0.5H), 7.8 (s, 0.5H), 8.85 (s, 0.5H), 9.1 (s, 0.5H), 9.35 (s, 0.5H), 9.45 (s, 0.5H); MS m/z 347.2 (M+H), 279.2 (M-$C_3H_3N_2$.), 137.5 (M-$C_9H_{13}N_4S$.)

Example 110

N-(3-(1H-imidazol-1-yl)propyl)benzo[d]thiazol-2-amine $^1$H NMR δ 1.95-2.15 (m, 2H), 3.25-3.35 (m, 2H), 4.0-4.1 (t, 2H), 6.9 (s, 1H), 6.95-7.05 (t, 1H), 7.15-7.2 (m, 2H), 7.35-7.4 (d, 1H), 7.60-7.70 (m, 2H), 8.0-8.1 (br s, 1H); MS m/z 259.4 (M+H), 191.3 (M-$C_3H_3N_2$.)

Example 111

N-(3-(1H-imidazol-1-yl)propyl)-6-chlorobenzo[d]thiazol-2-amine $^1$H NMR δ 1.95-2.15 (m, 2H), 3.25-3.35 (m, 2H), 4.0-4.1 (t, 2H), 6.9 (s, 1H), 7.1-7.2 (d, 2H), 7.3-7.4 (d, 1H), 7.65 (s, 1H), 7.8 (s, 1H), 8.2 (s, 1H); MS m/z 293.3 (M+H), 225.3 (M-$C_3H_3N_2$.)

Example 112

N-(3-(1H-imidazol-1-yl)propyl)-6-methoxybenzo[d]thiazol-2-amine $^1$H NMR δ 1.9-2.05 (m, 2H), 3.2-3.3 (m, 2H), 3.7 (s, 3H), 4.0-4.1 (t, 2H), 6.7-6.8 (d, 1H), 6.9 (s, 1H), 7.15-7.2 (s, 1H), 7.2-7.3 (m, 2H), 7.65 (s, 1H), 7.8 (s, 1H); MS m/z 289.1 (M+H), 221.4 (M-$C_3H_3N_2$.)

Example 115

(R)—N-(3-(1H-imidazol-1-yl)propyl)-2-phenylpropanethioamide melting point: 82.0-82.5° C.
$^1$H NMR δ 1.4-1.55 (d, 3H), 1.9-2.0 (m, 2H), 3.4-3.5 (m, 2H), 3.85-3.95 (m, 2H), 4.0-4.1 (q, 1H), 6.8-6.9 (s, 1H), 7.1 (s, 1H), 7.15-7.2 (m, 1H), 7.2-7.3 (m, 2H), 7.35-7.4 (m, 2H), 7.55 (s, 1H), 10.1 (s, 1H); MS m/z 274.4 (M+H), 206.3 (M-$C_3H_3N_2$.)

Example 116

(S)—N-(3-(1H-imidazol-1-yl)propyl)-2-phenylpropanethioamide melting point: 82.5-83.5° C.
$^1$H NMR δ 1.4-1.55 (d, 3H), 1.9-2.0 (m, 2H), 3.4-3.5 (m, 2H), 3.85-3.95 (m, 2H), 4.0-4.1 (q, 1H), 6.8-6.9 (s, 1H), 7.1 (s, 1H), 7.15-7.2 (m, 1H), 7.2-7.3 (m, 2H), 7.35-7.4 (m, 2H), 7.55 (s, 1H), 10.1 (s, 1H); MS m/z 274.4 (M+H), 206.3 (M-$C_3H_3N_2$.)

Example 121

N-(3-(1H-imidazol-1-yl)propyl)-1-(4-chlorophenyl)cyclobutanecarbo-thioamide melting point: 137.5-139.0° C.
$^1$H NMR δ 1.55-1.75 (br m, 2H), 1.85-1.95 (br m, 2H), 2.4-2.5 (br m, 2H), 2.7-2.85 (br m, 2H), 3.3-3.5 (br m, 2H), 3.8 (m, 2H), 6.9 (s, 1H), 7.0 (s, 1H), 7.3 (m, 2H), 7.45 (s, 1H) 7.5 (m, 2H), 9.6 (t, 1H); MS m/z 334.3 (M+H), 266.1 (M-$C_3H_3N_2$.)

Example 122

N-(3-(1H-imidazol-1-yl)propyl)-1-(4-chlorophenyl)cyclopentanecarbo-thioamide melting point: 140.0-141.0° C.
$^1$H NMR δ 1.5-1.65 (br m, 4H), 1.8-1.9 (m, 2H), 2.0-2.1 (m, 2H), 2.6 (m, 2H), 3.4-3.5 (m, 2H), 3.7-3.8 (m, 2H), 6.85 (s, 1H), 7.0 (s, 1H), 7.35 (m, 2H), 7.4 (m, 2H), 7.5 (s, 1H), 9.4 (t, 1H); MS m/z 348.2 (M+H), 280.2 (M-$C_3H_3N_2$.)

Example 123

N-(3-(1H-imidazol-1-yl)propyl)-1-(4-methoxyphenyl)cyclohexanecarbo-thioamide melting point: 162.5-164.0° C.
$^1$H NMR δ 1.2-1.3 (m, 1H), 1.35-1.5 (br m, 5H), 1.85-2.0 (br m, 4H), 2.4-2.6 (br m, 2H), 3.4-3.5 (m, 2H), 3.7 (s, 3H), 3.8 (m, 2H), 6.8 (m, 3H), 7.0 (s, 1H), 7.3 (m, 2H), 7.5 (s, 1H), 9.2 (t, 1H); MS m/z 358.3 (M+H), 290.3 (M-$C_3H_3N_2$.)

Example 124

N-(3-(1H-imidazol-1-yl)propyl)-1-(4-methoxyphenyl)cyclopropanecarbothioamide melting point: 129.0-129.5° C.
$^1$H NMR δ 1.0-1.1 (m, 2H), 1.5-1.6 (m, 2H), 1.9-2.0 (br m, 2H), 3.4-3.5 (m, 2H), 3.7 (s, 3H), 3.9 (m, 2H), 6.9 (m, 3H), 7.1 (s, 1H), 7.2-7.3 (m, 2H), 7.6 (s, 1H), 8.9 (br s, 1H); MS m/z 316.0 (M+H), 248.4 (M-$C_3H_3N_2$.)

Example 134

5-(1H-imidazol-1-yl)-N-(3,4-dimethoxyphenyl)pentanethioamide melting point: 128.0-128.5° C.
$^1$H NMR δ 1.65-1.70 (m, 2H), 1.75-1.80 (m, 2H), 2.7-2.75 (m, 2H), 3.7 (s, 3H), 3.75 (s, 3H), 4.0-4.05 (t, 2H), 6.9-7.0 (m, 2H), 7.2 (s, 1H), 7.3 (d, 1H), 7.5 (s, 1H), 7.75 (s, 1H) 11.0 (s, 1H); MS m/z 320.2 (M+H), 252.2 (M-$C_3H_3N_2$.)

Example 136

1-(2-(1H-imidazol-1-yl)ethyl)-3-(3,4-dimethoxyphenyl)thiourea melting point: 157.5-159.0° C.
$^1$H NMR δ 3.7 (2 s, 6H), 3.8 (m, 2H), 4.2 (m, 2H), 6.7 (m, 1H), 6.85 (m, 1H), 6.9 (m, 2H), 7.15 (s, 1H), 7.5 (br s, 1H), 7.6 (s, 1H), 9.5 (s, 1H); MS m/z 307.2 (M+H), 239.1 (M-$C_3H_3N_2$.)

What is claimed is:

1. A method of treating an inflammatory disease or condition, comprising:
   administering to a subject in need thereof a pharmaceutical composition comprising an effective amount of a glutaminyl cyclase (QC) inhibitor;
   wherein the QC inhibitor has a $K_i$ for QC inhibition of 1 µM or less.

2. The method of treating according to claim 1, wherein the disease is mild cognitive impairment (MCI).

3. The method of treating according to claim 2, wherein said pharmaceutical composition comprises a further agent, selected from the group consisting of nootropic agents, neuroprotectants, antiparkinsonian drugs, amyloid protein deposition inhibitors, beta amyloid synthesis inhibitors, antidepressants, anxiolytic drugs, antipsychotic drugs and anti-multiple sclerosis drugs.

4. The method of treating according to claim 1, wherein the disease is a chronic or acute inflammation, selected from rheumatoid arthritis, atherosclerosis, restenosis and pancreatitis.

5. The method of treating according to claim 4, wherein the disease is selected from restenosis and pancreatitis.

6. The method of treating according to claim 4, wherein the disease is restenosis.

7. The method of treating according to claim 4, wherein the disease is selected from rheumatoid arthritis and atherosclerosis.

8. The method of treating according to claim 4, wherein said pharmaceutical composition comprises a further agent, selected from the group consisting of inhibitors of the angiotensin converting enzyme (ACE); angiotensin II receptor blockers; diuretics; calcium channel blockers (CCB); beta-blockers; platelet aggregation inhibitors; cholesterol absorption modulators; HMG-Co-A reductase inhibitors; high density lipoprotein (HDL) increasing compounds; renin inhibitors; IL-6 inhibitors; antiinflammatory corticosteroids; antiproliferative agents; nitric oxide donors; inhibitors of extracellular matrix synthesis; growth factor or cytokine signal transduction inhibitors; MCP-1 antagonists and tyrosine kinase inhibitors.

9. The method of treating according to claim 1, wherein the disease and/or condition afflicts a human being.

10. The method of treating according to claim 1, wherein said QC inhibitor is a compound of formula I including pharmaceutically acceptable salts, solvates and stereoisomers thereof:

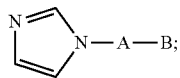

formula 1 wherein,
A is either
  (i) selected from an alkyl chain, alkenyl chain or alkynyl chain; or
  (ii) a group selected from

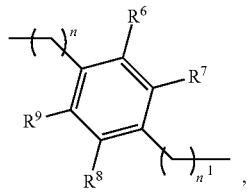

(I)

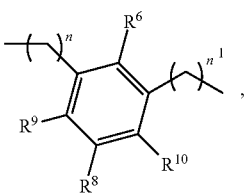

(II)

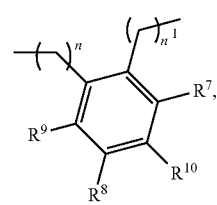

(III)

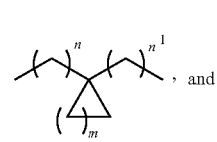

, and (IV)

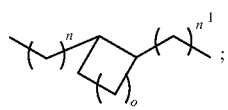

(V)

wherein,
  $R^6, R^7, R^8, R^9$ and $R^{10}$ are independently H or an alkyl chain, alkenyl chain, alkynyl chain, cycloalkyl, a carbocycle, aryl, heteroaryl, or a heterocycle;
  n and $n^1$ are independently 1-5;
  m is 1-5;
  o is 0-4; and
B is a group selected from

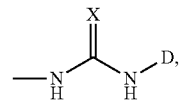

(VI)

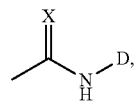

(VIa)

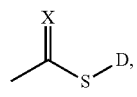

(VIb)

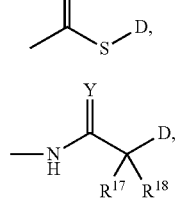

(VII)

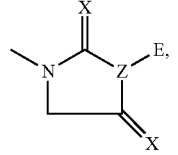

(VIII)

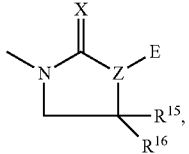

(IX)

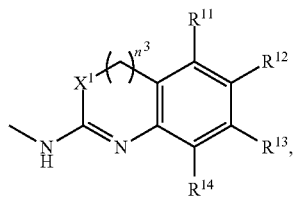

(X)

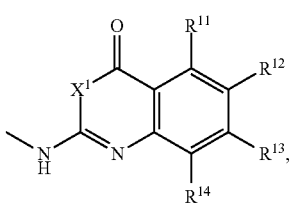

(XI)

93

-continued

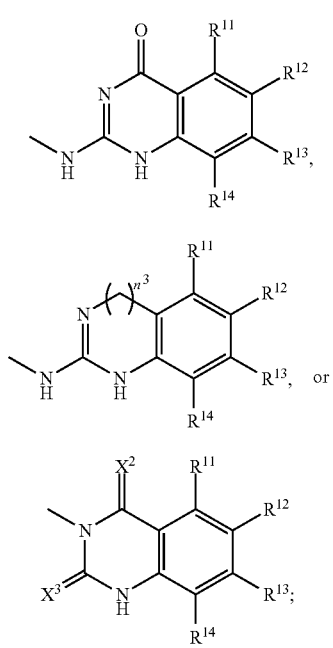

wherein,
D and E independently represent an alkyl chain, alkenyl chain, alkynyl chain, a cycloalkyl, carbocycle, aryl, -alkylaryl, heteroaryl, -alkylheteroaryl, acyl or a heterocycle;

Z is CH or N;

X represents $CR^{20}R^{21}$, O, S, $NR^{19}$, with the proviso for formulas (VIII) and (IX) that, if Z=CH, X is O or S;
  $R^{19}$ is selected from the group consisting of H, alkyl, cycloalkyl, aryl, heteroaryl, -oxyalkyl, -oxyaryl, carbonyl, amido, hydroxy, $NO_2$, $NH_2$, CN;
  $R^{20}$ and $R^{21}$ are independently selected from H, alkyl, cycloalkyl, heterocycle, aryl, heteroaryl, -oxyalkyl, -oxyaryl, carbonyl, amido, $NO_2$, $NH_2$, CN, $CF_3$;

$X^1$, $X^2$ and $X^3$ are independently O or S provided that $X^2$ and $X^3$ are not both O;

Y is O or S, with the proviso that Y may not by O, when the carbocycle formed by $R^{17}$ and $R^{18}$ has 3 members in the ring;

$R^{11}$, $R^{12}$, $R^{13}$ and $R^{14}$ can be independently selected from H, an alkyl chain, an alkenyl chain, an alkynyl chain, cycloalkyl, carbocycle, aryl, heteroaryl, a heterocycle, halo, alkoxy-, -thioalkyl, carboxyl, carboxylic acid ester, carbonyl, carbamide, carbimide, thiocarbamide, thiocarbonyl, $NH_2$, or $NO_2$;

$R^{15}$ and $R^{16}$ are independently of each other H or a branched alkyl chain, an unbranched alkyl chain, a branched alkenyl chain or an unbranched alkenyl chain;

$R^{17}$ and $R^{18}$ are independently selected from H, an alkyl chain, alkenyl chain, alkynyl chain, carbocycle, aryl, heteroaryl, or heteroalkyl, or can be connected to form a carbocycle with up to 6 ring atoms; and $n^3$ is 0 or 1.

11. The method of treating according to claim 1, wherein said QC inhibitor or a pharmaceutically acceptable salt, solvate or stereoisomer thereof is selected from:

94

(i) a compound of formula 1*,

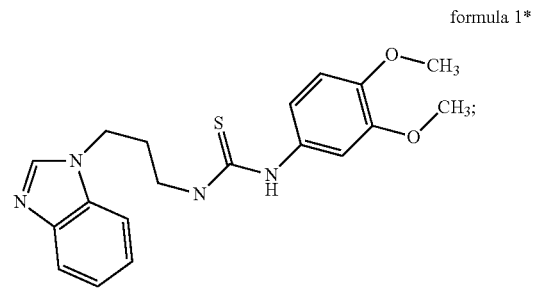

(ii) a compound of formula 1a,

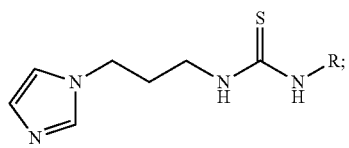

wherein R is selected from Methyl; tert-Butyl; Benzyl; Phenyl; 4-(fluoro)-phenyl; 4-(chloro)-phenyl; 4-(ethyl)-phenyl; 4-(trifluoromethyl)-phenyl; 4-(methoxy-carbonyl)-Phenyl; 4-(acetyl)-phenyl; 4-(methoxy)-phenyl; bicyclo[2.2.1]hept-5-en-2-yl; 3,4-(dimethoxy)-phenyl; 2,4-(dimethoxy)-phenyl; 3,5-(dimethoxy)-phenyl; 2-(methoxy-carbonyl)-Phenyl; 4-(oxazol-5-yl)-phenyl; 4-(pyrazol-1-yl)-phenyl; 4-(isopropyl)-phenyl; 4-(piperidine-1-sulfonyl)-Phenyl; 4-(morpholin-4-yl)-phenyl; 4-(cyano)-phenyl; 2,3-dihydro-benzo[1,4]benzo[1,3]dioxol-5-yl; 3,4,5(trimethoxy)-phenyl; 3-(methoxy)-phenyl; 4-(ethoxy)-phenyl; 4-(benzyloxy)-phenyl; 4-(methoxy)-benzyl; 3,4-(dimethoxy)-benzyl; 2-(methoxy-carbonyl)-thiophene-3-yl; 3-(ethoxy-carbonyl)-4,5,6,7-tetrahydrobenzo[b]thio-phene2-yl; 2-(methoxy-carbonyl)-4-(methyl)-thiophene-3-yl; Benzo[c][1,2,5]thiazol-4-yl; Benzo[c][1,2,5]thiazol-5-yl; 5-(methyl)-3-(phenyl)-isooxazol-4-yl; 3,5-(dimethyl)-isooxazol-4-yl; 4-(iodo)-phenyl; 4-(bromo)-phenyl; 4-(methyl)-phenyl; Naphthalen-1-yl; 4-(nitro)-phenyl; Butyl; Cyclooctyl; Furan-2-ylmethyl; Tetrahydrofuran-2-ylmethyl; Benzo[1,3]dioxol-5-ylmethyl; 2-(morpholin-4-yl)-ethyl; 4-(methylsulfanyl)-phenyl; 4-(dimethylamino)-phenyl; 4-(trifluoromethoxy)-phenyl; Benzoyl; or Pyridin-4-yl;

(iii) a compound of formula 1b,

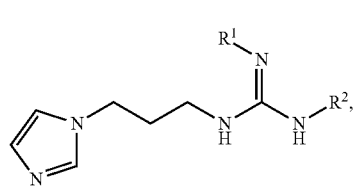

wherein
  $R^1$ is Cyano and $R^2$ is Methyl;
  $R^1$ is Cyano and $R^2$ is 3,4-(dimethoxy)-phenyl;
  $R^1$ is Cyano and $R^2$ is 2,4-(dimethoxy)-phenyl;

$R^1$ is Cyano and $R^2$ is 3,5-(dimethoxy)-phenyl;
$R^1$ is Cyano and $R^2$ is 2,3-dihydrobenzo[b][1,4]dioxin-7-yl;
$R^1$ is Cyano and $R^2$ is Benzo[d][1,3]dioxol-6-yl;
$R^1$ is Cyano and $R^2$ is 3,4,5-(trimethoxy)-phenyl;
$R^1$ is Cyano and $R^2$ is 3-(methoxy)-phenyl;
$R^1$ is Cyano and $R^2$ is 4-(ethoxy)-phenyl;
$R^1$ is Cyano and $R^2$ is 4-(benzyloxy)-phenyl;
$R^1$ is Cyano and $R^2$ is Phenyl;
$R^1$ is Cyano and $R^2$ is 4-(methoxy)-phenyl;
$R^1$ is Cyano and $R^2$ is 4-(acetyl)-phenyl;
$R^1$ is Cyano and $R^2$ is 4-(nitro)-phenyl;
$R^1$ is Cyano and $R^2$ is Benzyl;
$R^1$ is Cyano and $R^2$ is Naphthalen-1-yl;
$R^1$ is Cyano and $R^2$ is 4-(fluoro)-phenyl;
$R^1$ is Cyano and $R^2$ is 4-(iodo)-phenyl;
$R^1$ is Cyano and $R^2$ is 4-(bromo)-phenyl;
$R^1$ is Cyano and $R^2$ is Cyclooctyl;
$R^1$ is Cyano and $R^2$ is tert-butyl;
$R^1$ is Cyano and $R^2$ is 4-(methyl)-phenyl;
$R^1$ is Cyano and $R^2$ is 4-(methylthio)-phenyl;
$R^1$ is Cyano and $R^2$ is 4-(ethyl)-phenyl;
$R^1$ is Cyano and $R^2$ is 4-(dimethylamino)-phenyl;
$R^1$ is Cyano and $R^2$ is Butyl;
$R^1$ is Cyano and $R^2$ is Trityl;
$R^1$ is Cyano and $R^2$ is (Benzo[d][1,3]dioxol-6yl)methyl;
$R^1$ is Cyano and $R^2$ is (tetrahydrofuran-2-yl)methyl;
$R^1$ is Cyano and $R^2$ is 4-(trifluoromethyl)-phenyl;
$R^1$ is Cyano and $R^2$ is (furan-2-yl)methyl;
$R^1$ is Cyano and $R^2$ is 2-(morpholin-4-yl)-ethyl;
$R^1$ is Cyano and $R^2$ is 4-(oxazol-5-yl)-phenyl;
$R^1$ is Cyano and $R^2$ is Pyridin-3-yl;
$R^1$ is Cyano and $R^2$ is 4-(cyano)-phenyl;
$R^1$ is Cyano and $R^2$ is 4-(trifluoromethoxy)-phenyl;
$R^1$ is Cyano and $R^2$ is 4-(piperidinosulfonyl)-phenyl;
$R^1$ is Cyano and $R^2$ is 4-(1H-pyrazol-1-yl)phenyl;
$R^1$ is H and $R^2$ is 3,4-(dimethoxy)-phenyl;
$R^1$ is Methyl and $R^2$ is 3,4-(dimethoxy)-phenyl;
$R^1$ is Cyano and $R^2$ is 2,3,4-(trimethoxy)-phenyl; or
$R^1$ is Cyano and $R^2$ is Cycloheptyl;

(iv) a compound of formula 1c,

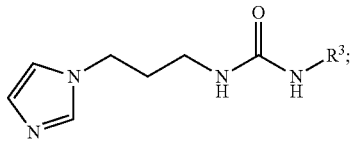

formual (1c)

wherein $R^3$ is selected from Ethyl; 6-fluoro-4H-benzo[d][1,3]dioxin-8-yll; 3-(cylopentyloxy)-4-(methoxy)-phenyll; 4-(heptyloxy)-phenyll; 3,4-dihydro-2H-benzo[b][1,4]dioxepin-7-yll; 4-(butoxy)-phenyll; or 3,4-(dimethoxy)-phenyll;

(v) a compound of formula 1d,

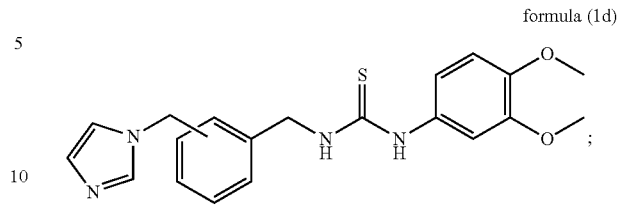

formula (1d)

wherein the substitution position on the benzyl ring is selected from 2, 3, or 4;

(vi) a compound of formula 1e,

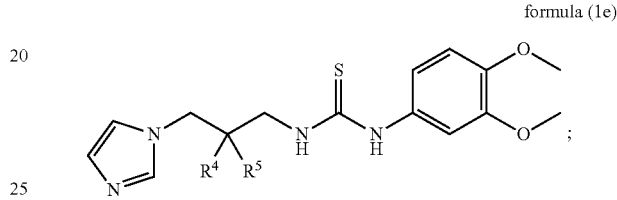

formula (1e)

wherein
$R^4$ is H and $R^5$ is Methyl;
$R^4$ is Methyl and $R^5$ is H;
$R^4$ is Methyl and $R^5$ is Methyl; or
$R^4$ is —$CH_2$—$CH_2$— and $R^5$ is —$CH_2$—$CH_2$—;

(vii) a compound of formula 1f,

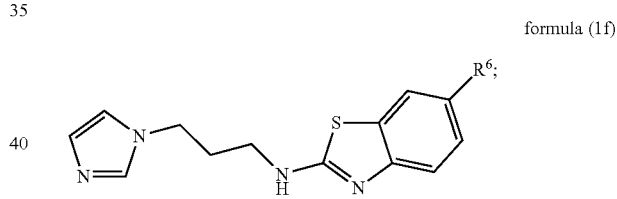

formula (1f)

wherein $R^6$ is selected from H, Chloro, or Methoxy;

(viii) a compound of formula 1g,

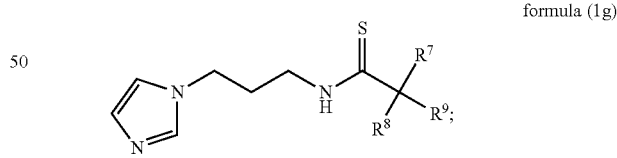

formula (1g)

wherein
$R^7$ is Phenyl, $R^8$ is H, and $R^9$ is H;
$R^7$ is Thiophen-2-yl, $R^8$ is H, and $R^9$ is H;
$R^7$ is Phenyl, $R^8$ is Methyl, and $R^9$ is H;
$R^7$ is Phenyl, $R^8$ is H, and $R^9$ is Methyl;
$R^7$ is Phenyl, $R^8$ is H, and $R^9$ is Ethyl;
$R^7$ is Phenyl, $R^8$ is H, and $R^9$ is Phenyl;
$R^7$ is 3,4-(dimethoxy)-Phenyl, $R^8$ is H, and $R^9$ is H;
$R^7$ is 3,4-(dimethoxy)-Phenyl, $R^8$ is Methyl, and $R^9$ is Methyl;
$R^7$ is 4-(chloro)-phenyl, $R^8$ is —$CH_2$—$CH_2$—$CH_2$—, and $R^9$ is —$CH_2$—$CH_2$—$CH_2$—;

R⁷ is 4-(chloro)-phenyl, R⁸ is —CH₂—C₂H₄—CH₂—, and R⁹ is —CH₂—C₂H₄—CH₂—;
R⁷ is 4-(methoxy)-phenyl, R⁸ is —CH₂—C₃H₆—CH₂—, and R⁹ is —CH₂—C₃H₆—CH₂—;
R⁷ is 4-(methoxy)-phenyl, R⁸ is —CH₂—CH₂—, and R⁹ is —CH₂—CH₂—;
R⁷ is 3,4-(dimethoxy)-Phenyl, R⁸ is —CH₂—CH₂—, and R⁹ is —CH₂—CH₂—;
R⁷ is 3,4,5-(trimethoxy)-Phenyl, R⁸ is —CH₂—CH₂—, and R⁹ is —CH₂—CH₂—;
R⁷ is 2,3,4-(trimethoxy)-Phenyl, R⁸ is —CH₂—CH₂—, and R⁹ is —CH₂—CH₂—;
R⁷ is 2-(methoxy)-phenyl, R⁸ is —CH₂—CH₂—, and R⁹ is —CH₂—CH₂—;
R⁷ is 3-(methoxy)-phenyl, R⁸ is —CH₂—CH₂—, and R⁹ is —CH₂—CH₂—;
R⁷ is 2,3-(dimethoxy)-Phenyl, R⁸ is —CH₂—CH₂—, and R⁹ is —CH₂—CH₂—;
R⁷ is 3,5-(dimethoxy)-Phenyl, R⁸ is —CH₂—CH₂—, and R⁹ is —CH₂—CH₂—; or
R⁷ is 2,5-(dimethoxy)-Phenyl, R⁸ is —CH₂—CH₂—, and R⁹ is —CH₂—CH₂—;

(ix) a compound of formula 1h,

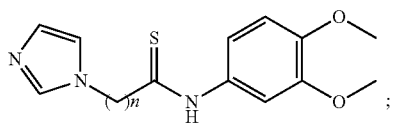

formula (1h)

wherein n is selected from 3, 4, or 5;

(x) a compound of formula 1i,

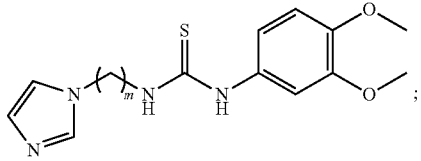

formula (1i)

wherein m is selected from 2 or 4; or (xi) a compound selected from

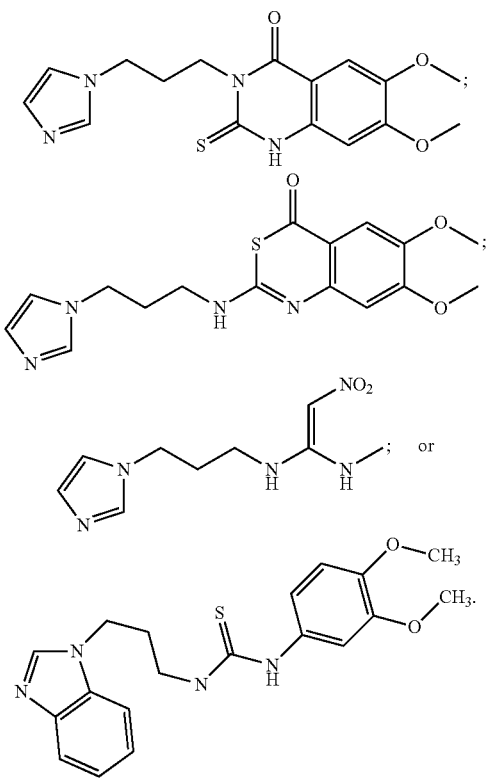

12. The method of treating according to claim 11, wherein said QC inhibitor is 1-(3-(1H-imidazole-1-yl)propyl)-3-(3,4-dimethoxy-phenyl)thiourea hydrochloride.

13. The method of treating according to claim 1, wherein administering said pharmaceutical composition comprises parenteral, enteral or oral administration.

14. The method of treating according to claim 12, wherein the disease is restenosis.

15. The method of treating according to claim 12, for the treatment of an inflammatory disease or condition.

16. The method of treating according to claim 1, wherein the QC inhibitor has a Ki for QC inhibition of 0.1 μM or less.

* * * * *

UNITED STATES PATENT AND TRADEMARK OFFICE
CERTIFICATE OF CORRECTION

| | | |
|---|---|---|
| PATENT NO. | : 8,338,120 B2 | Page 1 of 1 |
| APPLICATION NO. | : 12/039066 | |
| DATED | : December 25, 2012 | |
| INVENTOR(S) | : Stephan Schilling et al. | |

It is certified that error appears in the above-identified patent and that said Letters Patent is hereby corrected as shown below:

On the title page, item (75) "Torsten Hoffman"

should be item (75) --Torsten Hoffmann--

Signed and Sealed this
Nineteenth Day of February, 2013

Teresa Stanek Rea
*Acting Director of the United States Patent and Trademark Office*

SEQUENCE LISTING

<160> NUMBER OF SEQ ID NOS: 16

<210> SEQ ID NO 1
<211> LENGTH: 99
<212> TYPE: PRT
<213> ORGANISM: Homo sapiens

<400> SEQUENCE: 1

Met Lys Val Ser Ala Ala Leu Leu Cys Leu Leu Leu Ile Ala Ala Thr
1               5                   10                  15

Phe Ile Pro Gln Gly Leu Ala Gln Pro Asp Ala Ile Asn Ala Pro Val
            20                  25                  30

Thr Cys Cys Tyr Asn Phe Thr Asn Arg Lys Ile Ser Val Gln Arg Leu
        35                  40                  45

Ala Ser Tyr Arg Arg Ile Thr Ser Ser Lys Cys Pro Lys Glu Ala Val
    50                  55                  60

Ile Phe Lys Thr Ile Val Ala Lys Glu Ile Cys Ala Asp Pro Lys Gln
65                  70                  75                  80

Lys Trp Val Gln Asp Ser Met Asp His Leu Asp Lys Gln Thr Gln Thr
                85                  90                  95

Pro Lys Thr

<210> SEQ ID NO 2
<211> LENGTH: 300
<212> TYPE: DNA
<213> ORGANISM: Homo sapiens

<400> SEQUENCE: 2
atgaaagtct ctgccgccct tctgtgcctg ctgctcatag cagccacctt cattccccaa      60
gggctcgctc agccagatgc aatcaatgcc ccagtcacct gctgttataa cttcaccaat     120
aggaagatct cagtgcagag gctcgcgagc tatagaagaa tcaccagcag caagtgtccc     180
aaagaagctg tgatcttcaa gaccattgtg gccaaggaga tctgtgctga ccccaagcag     240
aagtgggttc aggattccat ggaccacctg gacaagcaaa cccaaactcc gaagacttga     300

<210> SEQ ID NO 3
<211> LENGTH: 1086
<212> TYPE: DNA
<213> ORGANISM: human

<400> SEQUENCE: 3
atggcaggcg aagacaccg gcgcgtcgtg ggcaccctcc acctgctgct gctggtggcc       60
gccctgccct gggcatccag gggggtcagt ccgagtgcct cagcctggcc agaggagaag     120
aattaccacc agccagccat tttgaattca tcggctcttc ggcaaattgc agaaggcacc     180
agtatctctg aaatgtggca aaatgactta cagccattgc tgatagagcg atacccggga     240
tcccctggaa gctatgctgc tcgtcagcac atcatgcagc gaattcagag gcttcaggct     300
gactgggtct tggaaataga caccttcttg agtcagacac cctatgggta ccggtctttc     360
tcaaatatca tcagcaccct caatcccact gctaaacgac atttggtcct cgcctgccac     420
tatgactcca gtatttttc ccactggaac aacagagtgt tgtaggagc cactgattca      480 gccgtgccat gtgcaatgat gttggaactt gctcgtgcct agacaagaa actcctttcc      540 ttaaagactg tttcagactc caagccagat tgtcactcc agctgatctt ctttgatggt      600
gaagaggctt tcttcactg gtctcctcaa gattctctct atgggtctcg acacttagct      660

```
gcaaagatgg catcgacccc gcacccacct ggagcgagag gcaccagcca actgcatggc    720
atggatttat tggtcttatt ggatttgatt ggagctccaa acccaacgtt tcccaatttt    780
tttccaaact cagccaggtg gttcgaaaga cttcaagcaa ttgaacatga acttcatgaa    840 ttgggttttgc tcaaggatca ctcttttggag gggcggtatt tccagaatta cagttatgga    900
ggtgtgattc aggatgacca tattccattt ttaagaagag gtgttccagt tctgcatctg    960
ataccgtctc ctttccctga agtctggcac accatggatg acaatgaaga aaatttggat   1020
gaatcaacca ttgacaatct aaacaaaatc ctacaagtct ttgtgttgga atatcttcat   1080
ttgtaa                                                               1086
```

<210> SEQ ID NO 4
<211> LENGTH: 361
<212> TYPE: PRT
<213> ORGANISM: human

<400> SEQUENCE: 4

```
Met Ala Gly Gly Arg His Arg Arg Val Val Gly Thr Leu His Leu
1               5                   10                  15

Leu Leu Val Ala Ala Leu Pro Trp Ala Ser Arg Gly Val Ser Pro Ser
            20                  25                  30

Ala Ser Ala Trp Pro Glu Glu Lys Asn Tyr His Gln Pro Ala Ile Leu
        35                  40                  45

Asn Ser Ser Ala Leu Arg Gln Ile Ala Glu Gly Thr Ser Ile Ser Glu
    50                  55                  60

Met Trp Gln Asn Asp Leu Gln Pro Leu Leu Ile Glu Arg Tyr Pro Gly
65                  70                  75                  80

Ser Pro Gly Ser Tyr Ala Ala Arg Gln His Ile Met Gln Arg Ile Gln
                85                  90                  95

Arg Leu Gln Ala Asp Trp Val Leu Glu Ile Asp Thr Phe Leu Ser Gln
            100                 105                 110

Thr Pro Tyr Gly Tyr Arg Ser Phe Ser Asn Ile Ile Ser Thr Leu Asn
        115                 120                 125

Pro Thr Ala Lys Arg His Leu Val Leu Ala Cys His Tyr Asp Ser Lys
    130                 135                 140

Tyr Phe Ser His Trp Asn Asn Arg Val Phe Val Gly Ala Thr Asp Ser
145                 150                 155                 160

Ala Val Pro Cys Ala Met Met Leu Glu Leu Ala Arg Ala Leu Asp Lys
                165                 170                 175

Lys Leu Leu Ser Leu Lys Thr Val Ser Asp Ser Lys Pro Asp Leu Ser
            180                 185                 190

Leu Gln Leu Ile Phe Phe Asp Gly Glu Glu Ala Phe Leu His Trp Ser
        195                 200                 205

Pro Gln Asp Ser Leu Tyr Gly Ser Arg His Leu Ala Ala Lys Met Ala
    210                 215                 220

Ser Thr Pro His Pro Pro Gly Ala Arg Gly Thr Ser Gln Leu His Gly
225                 230                 235                 240

Met Asp Leu Leu Val Leu Leu Asp Leu Ile Gly Ala Pro Asn Pro Thr
                245                 250                 255

Phe Pro Asn Phe Phe Pro Asn Ser Ala Arg Trp Phe Glu Arg Leu Gln
            260                 265                 270

Ala Ile Glu His Glu Leu His Glu Leu Gly Leu Leu Lys Asp His Ser
        275                 280                 285

Leu Glu Gly Arg Tyr Phe Gln Asn Tyr Ser Tyr Gly Gly Val Ile Gln
    290                 295                 300
```

```
Asp Asp His Ile Pro Phe Leu Arg Arg Gly Val Pro Val Leu His Leu
305                 310                 315                 320

Ile Pro Ser Pro Phe Pro Glu Val Trp His Thr Met Asp Asp Asn Glu
            325                 330                 335

Glu Asn Leu Asp Glu Ser Thr Ile Asp Asn Leu Asn Lys Ile Leu Gln
            340                 345                 350

Val Phe Val Leu Glu Tyr Leu His Leu
        355                 360

<210> SEQ ID NO 5
<211> LENGTH: 32
<212> TYPE: DNA
<213> ORGANISM: Artificial sequence
<220> FEATURE:
<223> OTHER INFORMATION: DNA primer

<400> SEQUENCE: 5
atataagctt atgaaagtct ctgccgccct tc                              32

<210> SEQ ID NO 6
<211> LENGTH: 32
<212> TYPE: DNA
<213> ORGANISM: Artificial sequence
<220> FEATURE:
<223> OTHER INFORMATION: DNA primer

<400> SEQUENCE: 6
atatgcggcc gctcaagtct tcggagtttg gg                              32

<210> SEQ ID NO 7
<211> LENGTH: 37
<212> TYPE: DNA
<213> ORGANISM: Artificial sequence
<220> FEATURE:
<223> OTHER INFORMATION: DNA primer

<400> SEQUENCE: 7
cattccccaa gggctcgctc cagatgcaat caatgcc                         37

<210> SEQ ID NO 8
<211> LENGTH: 37
<212> TYPE: DNA
<213> ORGANISM: Artificial sequence
<220> FEATURE:
<223> OTHER INFORMATION: DNA primer

<400> SEQUENCE: 8
ggcattgatt gcatctggag cgagcccttg gggaatg                         37

<210> SEQ ID NO 9
<211> LENGTH: 38
<212> TYPE: DNA
<213> ORGANISM: Artificial sequence
<220> FEATURE:
<223> OTHER INFORMATION: DNA primer

<400> SEQUENCE: 9
cattccccaa gggctcgctg atgcaatcaa tgccccag                        38

<210> SEQ ID NO 10
<211> LENGTH: 38
<212> TYPE: DNA
<213> ORGANISM: Artificial sequence
<220> FEATURE:
<223> OTHER INFORMATION: DNA primer
```

<400> SEQUENCE: 10

```
ctggggcatt gattgcatca gcgagccctt ggggaatg                                38
```

<210> SEQ ID NO 11
<211> LENGTH: 99
<212> TYPE: PRT
<213> ORGANISM: Homo sapiens

<400> SEQUENCE: 11

| Met | Lys | Val | Ser | Ala | Ala | Leu | Leu | Cys | Leu | Leu | Met | Ala | Ala | Thr |
|-----|-----|-----|-----|-----|-----|-----|-----|-----|-----|-----|-----|-----|-----|-----|
| 1   |     |     |     | 5   |     |     |     |     | 10  |     |     |     |     | 15  |

| Phe | Ser | Pro | Gln | Gly | Leu | Ala | Gln | Pro | Asp | Ser | Val | Ser | Ile | Pro | Ile |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Thr | Cys | Cys | Phe | Asn | Val | Ile | Asn | Arg | Lys | Ile | Pro | Ile | Gln | Arg | Leu |
|-----|-----|-----|-----|-----|-----|-----|-----|-----|-----|-----|-----|-----|-----|-----|-----|
|     |     |     | 35  |     |     |     |     | 40  |     |     |     |     | 45  |     |     |

| Glu | Ser | Tyr | Thr | Arg | Ile | Thr | Asn | Ile | Gln | Cys | Pro | Lys | Glu | Ala | Val |
|-----|-----|-----|-----|-----|-----|-----|-----|-----|-----|-----|-----|-----|-----|-----|-----|
|     |     | 50  |     |     |     |     | 55  |     |     |     |     | 60  |     |     |     |

| Ile | Phe | Lys | Thr | Gln | Arg | Gly | Lys | Glu | Val | Cys | Ala | Asp | Pro | Lys | Glu |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Arg | Trp | Val | Arg | Asp | Ser | Met | Lys | His | Leu | Asp | Gln | Ile | Phe | Gln | Asn |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

Leu Lys Pro

<210> SEQ ID NO 12
<211> LENGTH: 300
<212> TYPE: DNA
<213> ORGANISM: Homo sapiens

<400> SEQUENCE: 12

```
atgaaggttt ctgcagcgct tctgtgcctg ctgctcatgg cagccacttt cagccctcag      60
ggacttgctc agccagattc agtttccatt ccaatcacct gctgctttaa cgtgatcaat     120
aggaaaattc ctatccagag gctggagagc tacacaagaa tcaccaacat ccaatgtccc     180
aaggaagctg tgatcttcaa gacccaacgg ggcaaggagg tctgtgctga ccccaaggag     240
agatgggtca gggattccat gaagcatctg gaccaaatat ttcaaaatct gaagccatga     300
```

<210> SEQ ID NO 13
<211> LENGTH: 99
<212> TYPE: PRT
<213> ORGANISM: Homo sapiens

<400> SEQUENCE: 13

| Met | Lys | Ala | Ser | Ala | Ala | Leu | Leu | Cys | Leu | Leu | Thr | Ala | Ala | Ala |
|-----|-----|-----|-----|-----|-----|-----|-----|-----|-----|-----|-----|-----|-----|-----|
| 1   |     |     |     | 5   |     |     |     |     | 10  |     |     |     |     | 15  |

| Phe | Ser | Pro | Gln | Gly | Leu | Ala | Gln | Pro | Val | Gly | Ile | Asn | Thr | Ser | Thr |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Thr | Cys | Cys | Tyr | Arg | Phe | Ile | Asn | Lys | Lys | Ile | Pro | Lys | Gln | Arg | Leu |
|-----|-----|-----|-----|-----|-----|-----|-----|-----|-----|-----|-----|-----|-----|-----|-----|
|     |     |     | 35  |     |     |     |     | 40  |     |     |     |     | 45  |     |     |

| Glu | Ser | Tyr | Arg | Arg | Thr | Thr | Ser | Ser | His | Cys | Pro | Arg | Glu | Ala | Val |
|-----|-----|-----|-----|-----|-----|-----|-----|-----|-----|-----|-----|-----|-----|-----|-----|
|     |     | 50  |     |     |     |     | 55  |     |     |     |     | 60  |     |     |     |

| Ile | Phe | Lys | Thr | Lys | Leu | Asp | Lys | Glu | Ile | Cys | Ala | Asp | Pro | Thr | Gln |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Lys | Trp | Val | Gln | Asp | Phe | Met | Lys | His | Leu | Asp | Lys | Lys | Thr | Gln | Thr |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

Pro Lys Leu

-continued

```
<210> SEQ ID NO 14
<211> LENGTH: 300
<212> TYPE: DNA
<213> ORGANISM: Homo sapiens

<400> SEQUENCE: 14
atgaaagcct ctgcagcact tctgtgtctg ctgctcacag cagctgcttt cagcccccag      60
gggcttgctc agccagttgg gattaatact tcaactacct gctgctacag atttatcaat     120
aagaaaatcc ctaagcagag gctggagagc tacagaagga ccaccagtag ccactgtccc     180
cgggaagctg taatcttcaa gaccaaactg gacaaggaga tctgtgctga ccccacacag     240
aagtgggtcc aggactttat gaagcacctg gacaagaaaa cccaaactcc aaagctttga     300

<210> SEQ ID NO 15
<211> LENGTH: 98
<212> TYPE: PRT
<213> ORGANISM: Homo sapiens

<400> SEQUENCE: 15

Met Lys Val Ser Ala Val Leu Leu Cys Leu Leu Met Thr Ala Ala
1               5                   10                  15

Phe Asn Pro Gln Gly Leu Ala Gln Pro Asp Ala Leu Asn Val Pro Ser
                20                  25                  30

Thr Cys Cys Phe Thr Phe Ser Ser Lys Lys Ile Ser Leu Gln Arg Leu
            35                  40                  45

Lys Ser Tyr Val Ile Thr Thr Ser Arg Cys Pro Gln Lys Ala Val Ile
        50                  55                  60

Phe Arg Thr Lys Leu Gly Lys Glu Ile Cys Ala Asp Pro Lys Glu Lys
65                  70                  75                  80

Trp Val Gln Asn Tyr Met Lys His Leu Gly Arg Lys Ala His Thr Leu
                85                  90                  95

Lys Thr

<210> SEQ ID NO 16
<211> LENGTH: 297
<212> TYPE: DNA
<213> ORGANISM: Homo sapiens

<400> SEQUENCE: 16
atgaaagtct ctgcagtgct tctgtgcctg ctgctcatga cagcagcttt caaccccag       60 ggacttgctc agccagatgc actcaacgtc ccatctactt gctgcttcac atttagcagt     120
aagaagatct ccttgcagag gctgaagagc tatgtgatca ccaccagcag gtgtccccag     180
aaggctgtca tcttcagaac caaactgggc aaggagatct gtgctgaccc aaaggagaag     240
tgggtccaga attatatgaa acacctgggc cggaaagctc acaccctgaa gacttga       297
```